US008529913B2

(12) United States Patent
Grandi et al.

(10) Patent No.: US 8,529,913 B2
(45) Date of Patent: Sep. 10, 2013

(54) IMMUNOGENIC COMPOSITIONS FOR *STREPTOCOCCUS PYOGENES*

(75) Inventors: Guido Grandi, Segrate (IT); John Telford, Siena (IT); Giuliano Bensi, Florence (IT)

(73) Assignee: Novartis Vaccines and Diagnostics, SRL, Siena (IT)

(*) Notice: Subject to any disclaimer, the term of this patent is extended or adjusted under 35 U.S.C. 154(b) by 0 days.

(21) Appl. No.: 13/411,095

(22) Filed: Mar. 2, 2012

(65) Prior Publication Data
US 2012/0315292 A1 Dec. 13, 2012

Related U.S. Application Data

(60) Division of application No. 12/715,912, filed on Mar. 2, 2010, now Pat. No. 8,128,936, which is a continuation of application No. 10/565,126, filed as application No. PCT/US2007/024868 on Jul. 30, 2004.

(60) Provisional application No. 60/541,565, filed on Feb. 3, 2004, provisional application No. 60/491,822, filed on Jul. 31, 2003.

(51) Int. Cl.
*A61K 39/09* (2006.01)
*C07K 14/315* (2006.01)

(52) U.S. Cl.
USPC .............. 424/244.1; 424/184.1; 424/190.1; 435/69.7; 530/350

(58) Field of Classification Search
None
See application file for complete search history.

(56) References Cited

U.S. PATENT DOCUMENTS

| | | | |
|---|---|---|---|
| 4,281,061 A | 7/1981 | Zuk et al. |
| 4,454,121 A | 6/1984 | Beachey |
| 5,098,827 A | 3/1992 | Boyle et al. |
| 5,354,846 A | 10/1994 | Kehoe |
| 5,378,620 A | 1/1995 | Adams et al. |
| 5,391,712 A | 2/1995 | Adams et al. |
| 5,445,820 A | 8/1995 | Seidel et al. |
| 5,585,098 A | 12/1996 | Coleman |
| 5,700,648 A | 12/1997 | Kehoe |
| 5,821,088 A | 10/1998 | Darzins et al. |
| 5,846,547 A | 12/1998 | Cleary |
| 5,968,763 A | 10/1999 | Fischetti et al. |
| 6,174,528 B1 | 1/2001 | Cooper et al. |
| 6,372,222 B1 | 4/2002 | Michon et al. |
| 6,406,883 B1 | 6/2002 | Lutticken et al. |
| 6,420,152 B1 | 7/2002 | Adams et al. |
| 6,579,711 B1 | 6/2003 | Gaier et al. |
| 6,635,623 B1 | 10/2003 | Hoogeveen et al. |
| 6,669,703 B2 | 12/2003 | Shue |
| 6,737,521 B1 | 5/2004 | Fischetti et al. |
| 6,747,437 B2 | 6/2004 | Chiu |
| 6,777,547 B1 | 8/2004 | Podbielski |
| 6,833,356 B1 | 12/2004 | Koenig et al. |
| 6,936,252 B2 | 8/2005 | Gilbert et al. |
| 7,033,765 B1 | 4/2006 | Dime et al. |
| 7,041,814 B1 | 5/2006 | Weinstock et al. |
| 7,098,182 B2 | 8/2006 | Le Page et al. |
| 7,101,692 B2 | 9/2006 | Schneewind et al. |
| 7,128,918 B1 | 10/2006 | Hamel et al. |
| 7,128,919 B2 | 10/2006 | Adderson et al. |
| 7,169,902 B2 | 1/2007 | Podbielski |
| 7,247,308 B2 | 7/2007 | Martin et al. |
| 7,348,006 B2 | 3/2008 | Contorni et al. |
| 7,407,664 B2 | 8/2008 | Beall et al. |
| 7,438,912 B2 | 10/2008 | Meinke et al. |
| 7,485,710 B2 | 2/2009 | Reinscheid et al. |
| 8,128,936 B2 * | 3/2012 | Grandi et al. .............. 424/190.1 |
| 2002/0025516 A1 | 2/2002 | Black et al. |
| 2002/0045737 A1 | 4/2002 | Choi et al. |
| 2002/0061569 A1 | 5/2002 | Haselbeck et al. |
| 2002/0086023 A1 | 7/2002 | Dale |
| 2003/0035805 A1 | 2/2003 | Michel et al. |
| 2003/0109690 A1 | 6/2003 | Ruben et al. |
| 2003/0157122 A1 | 8/2003 | Dale |
| 2003/0171337 A1 | 9/2003 | Aylward et al. |
| 2004/0029129 A1 | 2/2004 | Wang et al. |
| 2004/0101536 A1 | 5/2004 | Teti et al. |
| 2004/0219639 A1 | 11/2004 | Potter et al. |
| 2004/0236072 A1 | 11/2004 | Olmsted et al. |

(Continued)

FOREIGN PATENT DOCUMENTS

| | | |
|---|---|---|
| EP | 0369825 | 5/1990 |
| EP | 0613947 | 1/1994 |

(Continued)

OTHER PUBLICATIONS

Azcarate-Peril et al., "Temporal gene expression and probiotic attributes of *Lactobacillus acidophilus* during growth in milk," J. Dairy Sci. 92, 870-86, 2009.
Lorenzen, 1993, Journal of General Virology, 74:623-630.
Abbas et al., *Cellular and Molecular Immunology*, 4th ed., Chapter 15, pp. 360-362, 2000.
Amara et al., "Molecular detection of methionine in rat brain using specific antibodies," Neurosci. Lett. 185, 147-50, Feb. 13, 1995.
Areschoug et al., "Group B *Streptococcal* surface proteins as targets for protective antibodies: identification of two novel proteins in strains of serotype V.," Inf. Immun. 67(12), 6350-57, Dec. 1999.
Banks et al., "Progress toward characterization of the Group A *Streptococcus metagenome*: Complete genome sequence of a macrolide-resistant serotype M6 strain," J. Infectious Diseases 190, 727-38, Aug. 15, 2004.

(Continued)

Primary Examiner — Padma V Baskar
(74) Attorney, Agent, or Firm — Banner & Witcoff, Ltd.

(57) ABSTRACT

The invention includes a GAS antigen, GAS 40, which is particularly suitable for use either alone or in combinations with additional GAS antigens, such as GAS 117, GAS 130, GAS 277, GAS 236, GAS 40, GAS 389, GAS 504, GAS 509, GAS 366, GAS 159, GAS 217, GAS 309, GAS 372, GAS 039, GAS 042, GAS 058, GAS 290, GAS 511, GAS 533, GAS 527, GAS 294, GAS 253, GAS 529, GAS 045, GAS 095, GAS 193, GAS 137, GAS 084, GAS 384, GAS 202, and GAS 057.

10 Claims, 14 Drawing Sheets

(56) References Cited

U.S. PATENT DOCUMENTS

| | | |
|---|---|---|
| 2005/0019345 A1 | 1/2005 | Podbielski |
| 2005/0020813 A1 | 1/2005 | Masignani et al. |
| 2005/0181388 A1 | 8/2005 | Edwards et al. |
| 2005/0214918 A1 | 9/2005 | Edwards et al. |
| 2005/0288866 A1 | 12/2005 | Sachdeva et al. |
| 2006/0039922 A1 | 2/2006 | Mizzen et al. |
| 2006/0041961 A1 | 2/2006 | Abad et al. |
| 2006/0073530 A1 | 4/2006 | Schneewind et al. |
| 2006/0115479 A1 | 6/2006 | Reinscheid et al. |
| 2006/0160121 A1 | 7/2006 | Mounts et al. |
| 2006/0165716 A1 | 7/2006 | Telford et al. |
| 2006/0194751 A1 | 8/2006 | Meinke et al. |
| 2006/0210579 A1 | 9/2006 | Telford et al. |
| 2006/0210580 A1 | 9/2006 | Telford et al. |
| 2006/0210581 A1 | 9/2006 | Telford et al. |
| 2006/0210582 A1 | 9/2006 | Telford et al. |
| 2006/0258849 A1 | 11/2006 | Telford et al. |
| 2006/0269541 A1 | 11/2006 | Meinke et al. |
| 2006/0275315 A1 | 12/2006 | Telford et al. |
| 2007/0036828 A1 | 2/2007 | Rappuoli et al. |
| 2007/0053924 A1 | 3/2007 | Tettelin et al. |
| 2007/0065464 A1 | 3/2007 | Grandi et al. |
| 2007/0098737 A1 | 5/2007 | Dale |
| 2007/0116712 A1 | 5/2007 | Hamel et al. |
| 2007/0128210 A1 | 6/2007 | Olmsted et al. |
| 2007/0128211 A1 | 6/2007 | Olmsted et al. |
| 2007/0128229 A1 | 6/2007 | Olmsted et al. |
| 2007/0141635 A1 | 6/2007 | James |
| 2008/0038268 A1 | 2/2008 | Martin et al. |
| 2008/0220010 A1 | 9/2008 | Telford et al. |
| 2009/0022753 A1 | 1/2009 | Olmsted et al. |

FOREIGN PATENT DOCUMENTS

| | | |
|---|---|---|
| EP | 0555438 | 1/1997 |
| EP | 0555439 | 10/1997 |
| EP | 1770171 | 4/2007 |
| GB | 2233977 | 1/1991 |
| WO | WO9006951 | 6/1990 |
| WO | WO9305155 | 3/1993 |
| WO | WO9305156 | 3/1993 |
| WO | WO9801561 | 1/1998 |
| WO | WO9818931 | 5/1998 |
| WO | WO9819689 | 5/1998 |
| WO | WO9823631 | 6/1998 |
| WO | WO9803677 | 8/1998 |
| WO | WO9913084 | 3/1999 |
| WO | WO9916882 | 4/1999 |
| WO | WO9926969 | 6/1999 |
| WO | WO9942588 | 8/1999 |
| WO | WO9954457 | 10/1999 |
| WO | WO0006736 | 2/2000 |
| WO | WO0006737 | 2/2000 |
| WO | WO0023456 | 4/2000 |
| WO | WO0062804 | 10/2000 |
| WO | WO0078787 | 12/2000 |
| WO | WO0132882 | 5/2001 |
| WO | WO0212294 | 2/2002 |
| WO | WO0234771 | 5/2002 |
| WO | WO02075507 | 9/2002 |
| WO | WO02077183 | 10/2002 |
| WO | WO02092818 | 11/2002 |
| WO | WO03068813 | 8/2003 |
| WO | WO03087353 | 10/2003 |
| WO | WO03093306 | 11/2003 |
| WO | WO2004018646 | 3/2004 |
| WO | WO2004035618 | 3/2004 |
| WO | WO2004041157 | 5/2004 |
| WO | WO2004078907 | 9/2004 |
| WO | WO2004099242 | 11/2004 |
| WO | WO2005013666 | 2/2005 |
| WO | WO2005028618 | 3/2005 |
| WO | WO2005076010 | 8/2005 |
| WO | WO2005108419 | 11/2005 |
| WO | WO2006035311 | 4/2006 |
| WO | WO2006042027 | 4/2006 |
| WO | WO2006069200 | 6/2006 |
| WO | WO2006078318 | 7/2006 |
| WO | WO2006082527 | 8/2006 |
| WO | WO2006082530 | 8/2006 |
| WO | WO2006130328 | 12/2006 |
| WO | WO2007018563 | 2/2007 |
| WO | WO2007039319 | 4/2007 |
| WO | WO2007052168 | 5/2007 |
| WO | WO2008020335 | 2/2008 |
| WO | WO2008108830 | 9/2008 |
| WO | WO2008003515 | 10/2008 |

OTHER PUBLICATIONS

Barnett & Scott, "Differential recognition of surface proteins in *Streptococcus pyogenes* by two sortase gene homologs," J. Bacteriol. 184, 2181-91, 2002.

Barnett et al., "A Novel Sortase, SrtC2, from *Streptococcus pyogenes* Anchors a Surface Protein Containing a QVPTGV Motif to the Cell Wall," *Journal of Bacteriology*, vol. 186, No. 17, pp. 5865-5875, Sep. 2004.

Beckmann et al., "Identification of Novel Adhesins from Group B *Streptococci* by Use of Phage Display Reveals that C5a Peptidase Mediates Fibronectin Binding," *Inf. Immun.* 70, 2869-76, Jun. 2002.

Bessen et al., "Genomic Localization of a T Serotype Locus to a Recombinatorial Zone Ending Extracellular Matrix-Binding Proteins in *Streptococcus pyogenes*," Infection and Immunity, vol. 70, No. 3, pp. 1159-1167, Mar. 2002.

Biswas et al., "Generation and Surface Localization of Intact M Protein in *Streptococcus pyogenes* Are Dependent on sagA," *Inf. Immun.* 69, 7029-38, Nov. 2001.

Black et al: "*Streptococcus pneumoniae* polypeptide coding region"; Genbank Accession No. AAV42990, Nov. 9, 1998.

Blackburn et al., "The end of the (DNA) line," Nature Structural Biology 7, 847-49, Oct. 2000.

Bork et al., "Powers and pitfalls in sequence analysis: the 70% hurdle," Genome Research 10, 398-400, 2000.

Borovec et al., "Synthesis and assembly of hepatitis A virus-specific proteins in BS-C-1 cells," J. Virol. 67, 3095-301, Jun. 1993.

Bowie et al., "Deciphering the message in protein sequences: tolerance to amino acid substitution," Science 257, 1306-10, 1990.

Brodeur et al., "Identification of group B streptococcal Sip protein, which elicits cross-protective immunity," Inf. Immun. 68(10), 5610-8, Oct. 2000.

Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111, 2129-38, 1990.

Chung et al., "Chlorosome protein," NCBI Accession No. 2115394F, Jul. 10, 1992.

Clancy et al., "Cloning and Characterization of a Novel Macrolide Efflux Gene, mreA, from *Streptococcus agalactiae*," Antimicrobial Agents and Chemotherapy 41, 2719-23, 1997.

Collins et al., "Mutation of the principal sigma factor causes loss of virulence in a strain of the *Mycobacterium tuberculosis* complex," Proc. Natl. Acad. Sci. USA 92, 8036-40, 1995.

Dale 1999 New vaccines and new vaccine technology, 13:227-243.

Dale et al., "New Protective Antigen of Group A *Streptococci*," J. Clin. Invest. 103, 1261-68, May 1999.

Dale et al., "Recombinant, octavalent group A streptococcal M protein vaccine," Vaccine 14, 944-48, 1996.

Dale, "Multivalent group A streptococcal vaccine designed to optimize the immunogenicity of six tandem M protein fragments," Vaccine 17, 193-200, 1999.

Database EMBL, Accession No. AAX13129, *Enterococcus faecalis* genome contig SEQ ID No. 192, Mar. 19, 1999.

Database EPO Proteins (Online), Feb. 2, 2004, "Sequence 7466 from Patent W00234771", XP002334316, Database accession No. CQ650509.

Database EPO Proteins, EBI Accession No. AX605513, "Sequence 3442 from WO0209818," Feb. 17, 2003.

Database Geneseq (Online), Dec. 2, 2004, "*Spyogenes* hyperimmune system reactive antigen Spy0269", XP002334513, Database accession No. ADR83896.

Database Geneseq (Online), Jul. 2, 2002, "*Streptococcus polypeptide* SEQ ID No. 9188", XP002334315, Database accession No. ABP300006.

Database Geneseq (Online), Jun. 19, 2003, "Protein encoded by Prokaryotic essential gene #319788", XP002334512, Database accession No. ABU46451.

Database Geneseq, "Fibrinogen-binding polypeptide, SEQ ID No. 17," EBI Accession No. GSP: ADS93952, Dec. 2, 2004; revised in 2007.

Database Geneseq, "Group B *Streptococcus* protein sequence SEQ ID No. 49," EBI Accession No. GSP:AAY91320, May 30, 2000.

Database Geneseq, "*Streptococcus agalactiae* protein, SEQ ID 2382," EBI Accession No. GSP:ADV81242, Feb. 24, 2005.

Database Geneseq, EBI Accession No. GSP: ABP27285, "*Streptococcus* polypeptide SEQ ID No. 3746," Jul. 2, 2002; revised in 2007.

Database Geneseq, EBI Accession No. GSP: ABP30134, "*Streptococcus polypeptide* SEQ ID No. 9444," Jul. 2, 2002.

Database Genseq, "Protein encoded by Prokaryotic essential gene #319788," Accession No. ABU46451, Jun. 13, 2003.

Database JPO Proteins, "Nucleic acid and protein originating in group B *Streptococcus*," EBI Accession No. JPOP:BD629260, Jul. 17, 2003.

Database Swissprot[Online] Oct. 1, 2002, accession No. EBI, Database accession No. Q9PGX9, Hypothetical protein XF0167.

Database UniProt [Online] Mar. 1, 2003, "Cell wall surface anchor family protein," retrieved from EBI accession No. UniProt: Q8DYR5, Database accession No. Q8DYR5, 872% identity with SEQ ID No. 20906.

Database UniProt [Online], Nov. 22, 2005, "Cell wall surface anchor family protein," retrieved from EBI accession No. UniProt: Q3D2D6; 100% identity with SEQ ID No. 20906; abstract.

De Boever et al., "*Enterococcus faecalis* conjugative plasmid pAM373. Complete nucleotide sequence and genetic analyses of sec phermone response," Mol. Microbiol. 37, 1327-41, 2000.

Dittmer et al., "Treatment of infectious diseases with immunostimulatory oligodeoxynucleotides containing CpG motifs," Curr. Opinion Microbiol. 6, 472-77, Oct. 2003.

Duez, "Enterococcus hirae mraR, pbp3s, mraY, murD, murG, ftsQ and ftsA genes, mraW, yllC and ftsZ partial genes," GENBANK Accesion No. Y13922, Apr. 18, 2005.

Ellis, *Vaccines*, Chapter 29, Plotkin et al., eds., W.B. Saunders Company (Philadelphia), pp. 568-575, 1988.

Examination Report for NZ 560966, Mar. 4, 2009, 2 pages.

Ferretti et al., "Putative surface exclusion protein," GENBANK Accession No. Q9A1H3, Oct. 31, 2006.

Ferretti et al: "*Streptococcus pyogenes* M1 GAS strain SF370, Section 87 of 167 of the complete genome" Database Accession No. AE006558, 2001.

Glaser et al., "Genome sequence of *Streptococcus agalactiae*, a pathogen causing invasive neonatal disease," Mol. Moicrobiol. 45, 1499-1513, 2002.

Grandi & Zagursky, "The impact of genomics in vaccine discovery: achievements and lessons," Expert. Rev. Vaccines 3, 621-23, 2004.

Grandi, "Genomics and Proteomics in Reverse Vaccines," in *Microbial Proteomics: Functional Biology of Whole Organisms*, Humphery-Smith & Hecker, eds., John Wiley & Sons, chapter 20, 2006.

Greenspan et al., "Defining epitopes: It's not as easy as it seems," Nature Biotechnol. 7, 936-37, 1999.

Gutekunst et al., "Analysis of RogB-Controlled Virulence Mechanisms and Gene Expression in *Streptococcus agalactiae*," Inf. Immun. 71, 5056-64, Sep. 2003.

Gutierrez et al., "insertional Mutagenesis and Recovery of Interrupted Genes of *Streptococcus mutans* by Using Transposon Tn917: Preliminary Characterization of Mutants Displaying Acid Sensitivity and Nutritional Requirements," J. Bacteriol. 178, 4166-75, Jul. 1996.

Guttierez et al., "*Streptococcus mutans* ProX (pouABC) gene, partial cds; YlxM (ylxM) gene, complete cds; Ffh (ffh) gene, complete cds, alternatively spliced; SatC (satC) and SatD (satD) gene, complete cds; and SatE (satE) gene, partical cds," GENBANK Accession No. U88582, Apr. 3, 2001.

Guzman et al., "Protective immune response against *Streptococcus pyogenes* in mice after intranasal vaccination with the fibronectin-binding protein Sfbl," J. Infectious Disease 179, 901-06, 1999.

Holmes, "PSMA specific antibodies and their diagnostic and therapeutic use," Exp. Opin. Invest. Drugs 10, 511-10, 2001.

Hong, "unnamed protein product [*Streptococcus pyogenes*]," NCBI Accession No. BAB1603, one page, Oct. 3, 2000.

Horvath et al., "Toward the development of a synthetic group a streptococcal vaccine of high purity and broad protective coverage," J Med Chem. Jul. 29, 2004;47(16):4100-4.

Hughs et al., "Identification of Major Outer surface Proteins of *Streptococcus agalactiae*," Inf. Immun. 70, 1254-59, Mar. 2002.

International Preliminary Examination Report for PCT/GB01/04789 (published as WO 02/34771) dated Feb. 17, 2003.

International Preliminary Examination Report for PCT/GB2003/001882 (published as WO 03/093306) dated Aug. 18, 2004.

International Preliminary Examination Report for PCT/IB2005/036009 (published as WO 06/042027) dated Apr. 11, 2007.

International Preliminary Examination Report for PCT/US2003/029167 (published as WO 04/041157) dated Mar. 5, 2005.

International Preliminary Examination Report for PCT/US2004/024868 (published as WO 05/032582) dated Feb. 6, 2006.

International Preliminary Examination Report for PCT/US2004/030032 (published as WO 05/028618) dated Mar. 16, 2006.

International Search Report for PCT/GB01/04789 (published as WO 02/34771) dated Aug. 27, 2002.

International Search Report for PCT/GB2003/001882 (published as WO 03/093306) dated Nov. 14, 2002.

International Search Report for PCT/IB2005/036009 (published as WO 06/042027) dated Jun. 20, 2006.

International Search Report for PCT/US05/046491 dated Jun. 26, 2007 (published as WO 2006/069200).

International Search Report for PCT/US2003/029167 (published as WO 04/041157) dated Aug. 2, 2004.

International Search Report for PCT/US2004/024868 (published as WO 05/032582) dated Oct. 28, 2005.

International Search Report for PCT/US2004/030032 (published as WO 05/028618) dated Dec. 6, 2005.

International Search Report for PCT/US2005/027239 (published as WO 06/078318) dated Aug. 25, 2008.

International Search Report for PCT/US2007/022838 (published as WO 08/108830) dated Oct. 9, 2008.

Jobling et al., "Analysis of structure and function of the B subunit of cholera toxin by the use of site-directed mutagenesis," Mol. Microbiol. 5, 1755-67, 1991.

Kalman et al., "Comparative genomes of *Chlamydia pneumoniae* and *C. trachomatis*," Nature Genetics 21, 385-89, Apr. 1999.

Kehoe et al., "Nucleotide Sequence of the Streptolysin O (SLO) Gene: Structural Homologies between SLO and Other Membrane-Damaging, Thiol-Activated Toxins," Inf. Immun. 55, 3228-32, Dec. 1987.

Koch et al., "Complexity and expression patterns of the desmosomal adherins," Proc. Natl. Acad. Sci. USA 89, 353-57, Jan. 1992.

Kunst et al., "The complete genome sequence of the Gram positive bacterium *Bacillus subtilis*," NCBI Accession No. CAB14964, Nov. 20, 1997.

Lachenauer et al., "A protective surface protein from the Type V Group B *Streptococcus* shares N-terminal sequence homology with the Alpha C Protein," Inf. Immun. 64, 4255-60, Oct. 1996.

Larsson et al., "Protection against experimental infection with group B *Streptococcus* by immunization with a bivalent protein vaccine," Vaccine 17, 454-58, 1999.

Lauer et al., "Genome Analysis Reveals Pili in Group B *Streptococcus*," Science 309, 105, Jul. 1, 2005.

Lazar et al., "Transforming growth factor alpha: mutation of aspartic acid 47 and leucine 48 results in different biological activities," Mol. Cell. Biol. 8, 1247-52, 1988.

Le Page et al., *Streptococcus agalactiae* sequence 217 from WO 01/32882, Genbank Accession No. AX134653, May 29, 2001.

Lei et al., "Identification and immunogenicity of group A *Streptococcus* culture supernatant proteins," Inf. Immunity 68, 6807-18, 2000.

Lewis, "Riddle of Biofilm Resistance," *Antimicrobial Agents and Chemotherapy*, vol. 45, No. 4, pp. 999-1007, Apr. 2001.

Lindahl et al., "Surface proteins of *Streptococcus agalactiae* and related proteins in other bacterial pathogens," Clinical Microbiol. Rev. 18(1), 102-07, Jan. 2005.

Madoff et al., "Maternal Immunization of Mice with Group B Streptococcal Type III Polysaccharide-Beta C Protein Conjugate Elicits Protective Antibody to Multiple Serotypes," J. Clinical Invest. 94, 286-92, 1994.

Maione et al., "Identification of a Universal Group B *Streptococcus* Vaccine by Multiple Genome Screen," *Science 309*, 148-50, Jul. 1, 2005.

McMillan et al., "Identification and assessment of new vaccine candidates for group A streptococcal infections," *Vaccine 22*, 2783-90, 2004.

McMillan et al., "Prospecting for new group A streptococcal vaccine candidates," *Indian J. Med. Res. 119*, 121-25, May 2004.

Meehan & Owen, "Sequence 1 from Patent WO9801561," GENBANK Accession No. A68631, May 6, 1999.

Michel et al: "Cloned alpha and beta C-protein antigens of group B Streptococci elicit protective immunity"; Infection and Immunity; vol. 59, No. 6, Jun. 1991; pp. 2023-2028.

Molling et al., "Naked DNA for vaccine or therapy," J. Mol. Med. 75, 242-46, 1997.

Mora et al., "Group A *Streptococcus* produce pilus-like structures containing protective antigens and Lancefield T antigens," Proc. Natl. Acad. Sci. USA 102, 15641-46, Oct. 25, 2005.

Musser, "The Next Chapter in Reverse Vaccinology," Nat. Biotechnol. 24, 157-58, 2006.

Nakagawa et- al., "Genome sequence of an M3 strain of *Streptococcus pyogenes* reveals a large-scale genomic rearrangement in invasive strains and new insights into phage evolution," *Genome Res. 13*, 1042-55, Jun. 2003.

Nakata et al., "MsmR, a specific positive regulator of the *Streptococcus pyogenes* FCT pathogenicity region and cytolysin-mediated translocation system genes," Mol. Microbiol. 57, 786-803, 2005.

Navarre et al., "Surface Proteins of Gram-Positive Bacteria and Mechanisms of Their Targeting to the Cell Wall Envelope," *Microbiology and Molecular Biology Reviews*, vol. 63, No. 1, pp. 174-229, Mar. 1999.

NCBI News, table on p. 4, "Microbial Genomes Available for BLAST Search," Jul. 1998.

Olive et al., "Protection of mice from group A streptococcal infection by intranasal immunisation with a peptide vaccine that contains a conserved M protein B cell epitope and lacks a T cell autoepitope," *Vaccine 20*, 2816-25, Jun. 21, 2002.

Orefici et al., "Possible virulence marker for *Streptococcus agalactiae* (Lancefiled Group B)," J. Clin. Microbiol. Infectious Diseases 7, 302-05, 1988.

Paoletti et al., "Neonatal mouse protection against infection with multiple group B streptococcal (GBS) serotypes by maternal immunization with a tetravalent GBS polysaccharide-tetanus toxoid conjugate vaccine," Inf. Immun. 62, 3236-43, 1994.

Paoletti, "Surface structure of group B *Streptoccoccus* important in human immunity," in *Gram Positive Pathogens*, Fischetti et al., eds., Chapter 14, pp. 137-153.

Pournaras et al., "Pheromone responses and high-level aminoglycoside resistance of conjugative plasmids of *Enterococcus faecalis* from Greece," J. Antimicrobial Chemotherapy 46, 1013-16, 2000.

Pritzlaff et al., "Genetic basis for the beta-haemolytic cytolitic activity of group B *Streptococcus*," Mol. Microbiol. 39, 236-48, 2001.

Pritzlaff et al., "*Streptococcus agalactiae* cyl gene cluster, partial sequence," GENBANK Accession No. AF157015, Feb. 8, 2001.

Proft et al., "Identification and Characterization of Novel Superantigens from *Streptococcus pyogenes*," J. Exp. Med. 189, 89-101, Jan. 4, 1999.

Pucci et al., "*Enterococcus faecalis* strain A24836 cell wall/cell division gene cluster, yllB, yllc, ylID, pbpC, mraY, murD, murG, divlB, ftsA and fitsZ genes, complete cds," GENBANK Accession No. U94707, Sep. 10, 1997.

Quinn, "The response of rheumatic and non-rheumatic children to streptolysin O concentrate," J. Clin. Invest. 36, 793-802, Jun. 1957.

Ramachandran et al., "Two Distinct Genotypes of *prtF2*, Encoding a Fibronectin Binding Protein, and Evolution of the Gene Family in *Streptococcus pyogenes*," *Journal of Bacteriology*, vol. 186, No. 22, pp. 7601-7609, Nov. 2004.

Rodewald et al., "Neonatal mouse model of group b streptococcal infection," J. Infectious Diseases 166, 635-39, 1992.

Rodriguez-Ortega et al., "Characterization and identification of vaccine candidate proteins through analysis of the group A *Streptococcus* surface proteome," Nature Biotechnol. 24, 191-97, 2006.

Roitt et al., Structure of Antigens, *Immunology*, 4th ed., Mosby, London, pp. 7.7 and 7.8, 1998.

Rosini et al., "Identification of novel genomic islands coding for antigenic pilus-like structures in *Streptococcus agalactiae*," Mol. Microbiol. 61, 126-41, 2006.

Rudenko et al., "Selection for activation of a new variant surface glycoprotein gene expression site in *Trypanosoma brucei* can result in deletion of the old one," Mol. Biochem. Parisitol. 95, 97-109, 1998; NCBI Accession No. CAD21770.

Rudinger et al., "Characteristics of the amino acids as components of a peptide hormone sequence," in *Peptide Hormones*, Parsons, ed., University Park Press, Jun. 1976, pp. 1-7.

Schneewind et al., "Sequence and Structural Characteristics of the Trypsin-Resistant T6 Surface Protein of Group A *Streptococci*," *Journal of Bacteriology*, vol. 172, No. 6, pp. 3310-3317, Jun. 1990.

Schneewind, "Structure of the Cell Wall anchor of Surface Proteins in *Staphylococcus aureus*," Science 268, 103-06, Apr. 7, 1995.

Segura et al., "*Streptococcus suis* and group B *Streptococcus* differ in their interactions with murine macrophages," FEMS Immunol. Med. Microbiol. 21, 189-95, 1998.

Seizen, "Multi-domain, cell envelope proteases of lactic acid bacteria," Antonie von Leeuwenhoek 76, 139-55, 1999.

Simpson et al., "*Xylella fastidiosa* 9a5c, section 136 of 229 of the complete genome," GENBANK Accession No. AE003990, Jun. 4, 2004.

Smoot et al., "Genome sequence and comparative microarray analysis of serotype M18 group A *Streptococcus* strains associated with acute rheumatic fever outbreaks," *Proc. Natl. Acad. Sci. USA 99*, 4668-73, Apr. 2, 2002.

Spellerberg et al., "*Streptococcus agalactiae* cyl gene cluster, complete sequence," GENBANK Accession No. AF093787, Jul. 31, 2000.

Spellerberg et al: "Identification of genetic determinants for the hemolytic activity of *Streptococcus agalactiae* by ISSI transposition"; J. Bacteriol.; vol. 181, No. 10, May 1999; pp. 3212-3219.

Stalhammar-Carlemalm et al: "The R28 Protein of *Streptococcus pyogenes* is related to several group B streptococcal surface proteins, confer protective immunity and promotes binding to human epithelial cells"; Mol. Microbiol. Jul. 1, 1999, pp. 208-219.

Stephenson et al., "The Fap1 fimbrial adhesin is a glycoprotein: antibodies specific for the glycan moiety block the adhesion of *Streptococcus parasanguis* in an in vitro tooth model," *Mol. Microbiol. 43*, 147-57, 2002.

Su et al., "Identification of a *Xenopus* cDNA that prevents mitotic catastrophe in the fission yeast *Schizosaccharomyces pombe*," Gene 145, 155-56, 1994.

Supplementary Search report for EP 03799822 (corresponding to WO 04/041157) dated Jan. 21, 2008.

Surovov & Ferretti, "Physical and Genetic Chromosomal Map of an M Type 1 Strain of *Streptococcus pyogenes*," J. Bacteriol. 178, 5546-49, Sep. 1996.

Takami et al., "Two component sensor histidine kinase involved in phosphate regulation," NCBI Accession No. NP_244022.1, Sep. 10, 2001.

Tettelin et al., "Complete genome sequence and comparative genomic analysis of an emerging human pathogen, serotype V *Streptococcus agalactiae*," Proc. Natl. Acad. Sci. USA 99, 12391-96, Sep. 17, 2002.

Tettelin et al., "Complete genome sequence of a virulent isolate of *Streptococcus pneumoniae*," Science 293, 498-506, 2001.

Tettelin et al., Database EMBL, Accession No. AE014193, *Streptococcus agalactiae* 2603V/R section 3 of 100 of the complete genome, Sep. 2, 2002.

Tettelin et al., Swiss-Prot Accession No. Q3DV91 for *Streptococcus agalactiae* strain 18R21, Nov. 22, 2005.

Tighe et al., "Gene vaccination: plasmid DNA is more than just a blueprint," Immunology Today 19, 89-97, Feb. 1998.

Todd, "Antigenic *Streptococcal hemolysin*," J. Exp. Med. 55, 267-80, 1932.

Ton-That & Schneewind, "Assembly of pili on the surface of *Corynebacterium diphtheriae*," Mol. Microbiol. 50, 1429-38, 2003.

Ton-That et al., "Sortases and pilin elements involved in pilus assembly of *Corynebacterium diphtheriae*," Mol. Microbiol. 53, 251-61, 2004.

UniProt Accession No. A7CNQ7, Jul. 5, 2004.

UniProt Accession No. Q5XEL1, Nov. 23, 2004.

UniProt Accession No. Q8P318, Oct. 1, 2002.

Vallet et al., "The chaperone/usher pathways of *Pseudomonas aeruginosa*: Identification of fimbrial gene clusters (cup) and their involvement in biofilm formation," *PNAS*, vol. 98, No. 12, pp. 6911-6916, Jun. 2001.

Watnick et al., "Steps in the development of a *Vibrio cholerae* El Tor biofilm," *Molecular Microbiology*, vol. 34, No. 3, pp. 586-595, 1999.

Wessels et al., "Stimulation of protective antibodies against type 1a and 1b group *B streptococci* by a type 1a polysaccharide-tetanus toxoid conjugate vaccine," Inf. Immun. 61, 4760-66, 1993.

Woodson et al., "Analysis of a ribose transport operon from *Bacillus subtilis*," Microbiology 140, 1829-38, 1994.

Zhong et al., "Hypothetical protein of *Arabidopsis thaliana*," NCBI Accession No. AAD29767, May 11, 1999.

\* cited by examiner

FIGURE 1: Annotation of GAS 40

Leader peptide

```
  1  MDLEQTKPNQ VKQKIALTST IALLSASVGV SHQVKADDRA SGETKASNTH
 51  DDSLPKPETI QEAKATIDAV EKTLSQQKAE LTELATALTK TTAEINHLKE
101  QQDNEQKALT SAQEIYTNTL ASSEETLLAQ GAEHQRELTA TETELHNAQA      coiled coil region
151  DQHSKETALS EQKASISAET TRAQDLVEQV KTSEQNIAKL NAMISNPDAI
201  TKAAQTANDN TKALSSELEK AKADLENQKA KVKKQLTEEL AAQKAALAEK
251  EAELSRLKSS APSTQDSIVG NNTMKAPQGY PLEELKKLEA SGYIGSASYN
301  NYYKEHADQI IAKASPGNQL NQYQDIPADR NRFVDPDNLT PEVQNELAQF
351  AAHMINSVRR QLGLPPVTVT AGSQEFARLL STSYKKTHGN TRPSFVYGQP
401  GVSGHYGVGP HDKTIIEDSA GASGLIRNDD NMYENIGAFN DVHTVNGIKR
451  GIYDSIKYML FTDHLHGNTY GHAINFLRVD KHNPNAPVYL GFSTSNVGSL
501  NEHFVMFPES NIANHQRFNK TPIKAVGSTK DYAQRVGTVS DTIAAIKGKV
551  SSLENRLSAI HQEADIMAAQ AKVSQLQGKL ASTLKQSDSL NLQVRQLNDT      coiled coil region
601  KGSLRTELLA AKAKQAQLEA TRDQSLAKLA SLKAALHQTE ALAEQAAARV
651  TALVAKKAHL QYLRDFKLNP NRLQVIRERI DNTKQDLAKT TSSLLNAQEA
701  LAALQAKQSS LEATIATTEH QLTLLKTLAN EKEYRHLDED IATVPDLQVA
751  PPLTGVKPLS YSKIDTTPLV QEMVKETKQL LEASARLAAE NTSLVAEALV      leucine zipper region
801  GQTSEMVASN AIVSKITSSI TQPSSKTSYG SGSSTTSNLI SDVDESTQRA
851  LKAGVVMLAA VGLTGFRFRK ESK
```

Transmembrane region

FIGURE 2 : Schematic of GAS40: putative surface exclusion protein prgA (873aa)
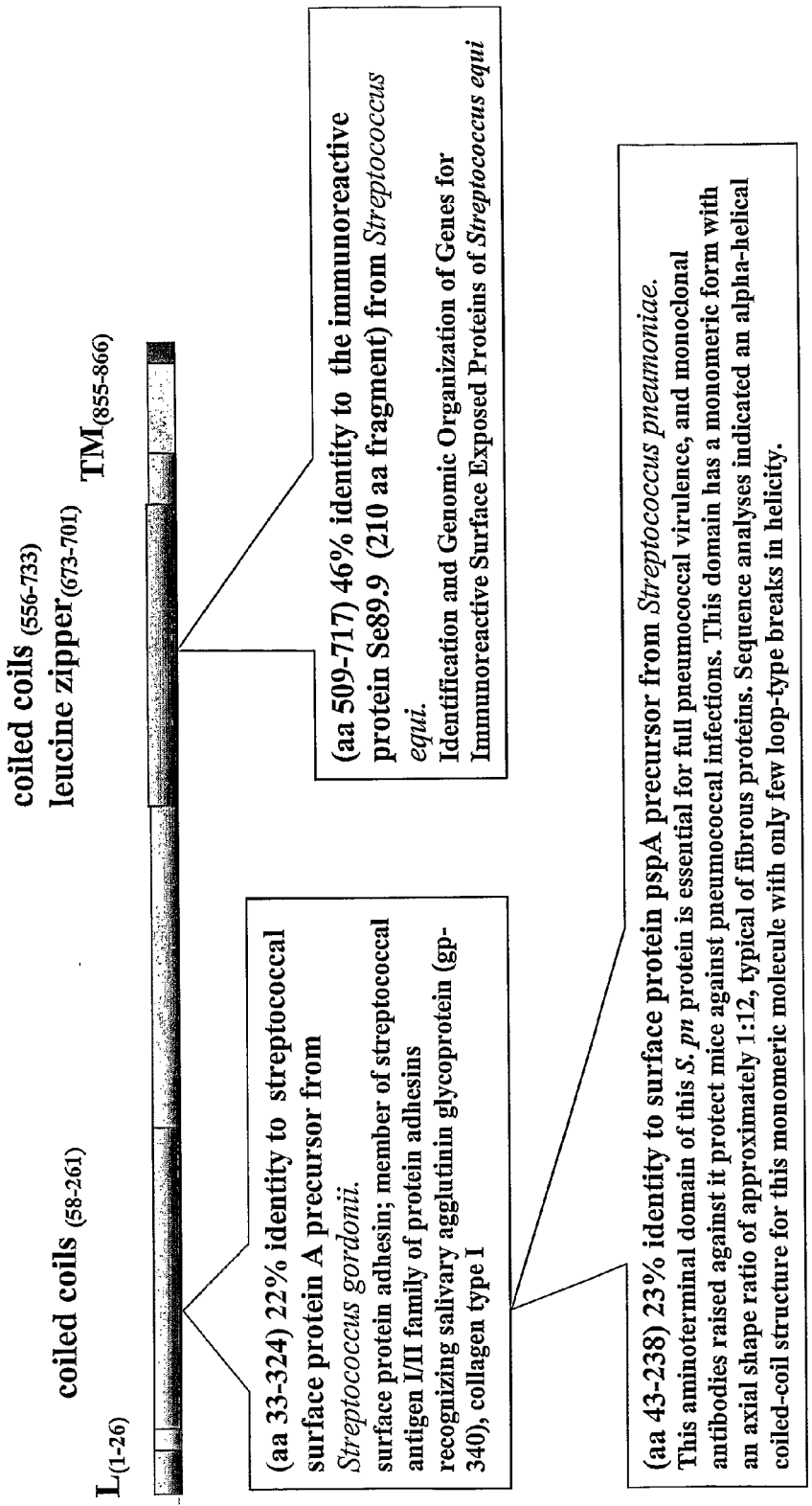

FIGURE 3. BLAST results of Coiled-Coil regions of GAS 40 with other Streptococcus bacteria

**3(a) BLAST alignment of amino acid sequence of GAS 40 including the first coiled-coil region with SpA precursor of *Streptococcus gordonii***

```
>gi|25990270|gb|AAC44101.3| streptococcal surface protein A precursor
[Streptococcus gordonii]
         Length = 1575
>ref|NP_268623.1| putative surface exclusion protein [Streptococcus pyogenes]
         Length = 873

Score = 63.2 bits (152), Expect = 5e-11
 Identities = 65/293 (22%), Positives = 124/293 (42%), Gaps = 13/293 (4%)

Query: 112  QDQTSDKGTATTAAENAQKQAEIKSDYAKQA----EEIKKTTEAYKKEVEAHQAETDKIN  167
            Q + D+ +  T A N    + K +  ++A       + ++KT   K E+         K
Sbjct: 33   QVKADDRASGETKASNTHDDSLPKPETIQEAKATIDAVEKTLSQQKAELTELATALTKTT 92

Query: 168  AENKAAEDKYQEDLKAHQAEVEKINTANATAKAEYEAKLAQYQKDLAAVQKANEDSQLDY  227
            AE    +++   + KA   + E        A+++     A+ A++Q++L A +    ++Q D
Sbjct: 93   AEINHLKEQQDNEQKALTSAQEIYTNTLASSEETLLAQGAEHQRELTATETELHNAQADQ 152

Query: 228  QNKLSAYQAELARVQKANAEAKEAYE--KAVKENTAKNAALQAENEAIKQRNETAKANYD  285
            +K +A  + A +     A++ E  K   ++N AK A+ +  +AI +   +TA  N
Sbjct: 153  HSKETALSEQKASISAETTRAQDLVEQVKTSEQNIAKLNAMISNPDAITKAAQTANDNTK 212

Query: 286  AAMKQYEADLAAIKKAKEDNDADYQAKLAAYQAELARVQKANADAKAAYEKAVEENTAKN  345
            A   + E   A  ++  K            +LAA +A LA  +   + K++    +    N
Sbjct: 213  ALSSELEKAKADLENQKAKVKKQLTEELAAQKAALAEKEAELSRLKSSAPSTQDSIVGNN 272

Query: 346  TAIQAEN---EAIKQRNAA---AKATYEAALKQYEADLAAAKKANEDSDADYQ  392
            T     +     E +K+ A+      A+Y   K++ AD   AK +  +   YQ
Sbjct: 273  TMKAPQGYPLEELKKLEASGYIGSASYNNYYKEH-ADQIIAKASPGNQLNQYQ 324
```

FIGURE 3, CONT. BLAST results of Coiled-Coil regions of GAS 40 with other Streptococcus bacteria

**3(b) BLAST alignment of amino acid sequence of GAS 40 including the first coiled-coil region with SpB precursor of *Streptococcus gordonii***

```
>gi|25055226|gb|AAC44102.3|    streptococcal surface protein B precursor
[Streptococcus gordonii]
         Length = 1499
>ref|NP_268623.1| putative surface exclusion protein [Streptococcus
pyogenes]
         Length = 873

Score = 54.3 bits (129), Expect = 2e-08
  Identities = 53/226 (23%), Positives = 98/226 (43%), Gaps = 13/226
  (5%)

Query: 111 QDQTSDKGTATTAAENAQKQAEIKSDYAKQA----EEIKKTTEAYKKEVEAHQAETDKIN 166
           Q + D+ +  T A N   + K +  ++A      + ++KT    K E+         K
Sbjct: 33  QVKADDRASGETKASNTHDDSLPKPETIQEAKATIDAVEKTLSQQKAELTELATALTKTT 92

Query: 167 AENKAAEDKYQEDLKAHQAEVEKINTANATAKAEYEAKLAQYQKDLAAVQKANEDSQLDY 226
           AE    +++   + KA + E        A+++     A+ A++Q++L A +      ++Q D
Sbjct: 93  AEINHLKEQQDNEQKALTSAQEIYTNTLASSEETLLAQGAEHQRELTATETELHNAQADQ 152

Query: 227 QNKLSAYQAELARV--QXXXXXXXXXXXXXXXXXNTAKNAALQAENEAIKQRNETAKANYD 284
           +K +A  + A +  +                  N AK A+ +  +AI + +TA  N
Sbjct: 153 HSKETALSEQKASISAETTRAQDLVEQVKTSEQNIAKLNAMISNPDAITKAAQTANDNTK 212

Query: 285 AAMKQYE---ADL----AAIKKAKEDNDADYQAKLAAYQAELARVQ 323
           A    + E     ADL        A  +KK   +   A  +A LA  +AEL+R++
Sbjct: 213 ALSSELEKAKADLENQKAKVKKQLTEELAAQKAALAEKEAELSRLK 258
```

FIGURE 3, CONT. BLAST results of Coiled-Coil regions of GAS 40 with other Streptococcus bacteria

**3(c) BLAST alignment of amino acid sequence of GAS 40 including the first coiled-coil region with Surface Protein PspA precursor of *Streptococcus pneumoniae***

```
>gi| 282335 |pir||A41971 surface protein pspA precursor - Streptococcus
pneumoniae
>ref|NP 268623.1| putative surface exclusion protein [Streptococcus
pyogenes]
          Length = 873

Score = 48.1 bits (113), Expect = 6e-07
 Identities = 46/200 (23%), Positives = 89/200 (44%), Gaps = 23/200
(11%)

Query: 139 KTKFNTVRAMVVPEPEQLAETK-------KKSEEAKQKAPELTKKLEEAKAKLEE-AEKK 190
           +TK +      +P+PE + E K        K   + K +  EL    L + A++     E++
Sbjct: 43  ETKASNTHDDSLPKPETIQEAKATIDAVEKTLSQQKAELTELATALTKTTAEINHLKEQQ 102

Query: 191 ATEAKQKVDAEEVAPQAKIAELENQVHRLEQELKEIDESESEDYAKEGFRAPLQSKLDAK 250
             E K    A+E+      + E +  +   +E+  +E+E + +  +    ++ L    +
Sbjct: 103 DNEQKALTSAQEIYTNTLASSEETLLAQGAEHQRELTATETELHNAQADQHSKETALSEQ 162

Query: 251 KAKLS----KLEELSDKIDELDAEIAKLEDQL-------KAAEENNNVEDYFKEGLEKTI 299
           KA +S    + ++L +++   +  IAKL   +       KAA+  N+            LEK
Sbjct: 163 KASISAETTRAQDLVEQVKTSEQNIAKLNAMISNPDAITKAAQTANDNTKALSSELEKA- 221

Query: 300 AAKKAELEKTEADLKKAVNE 319
              KA+LE  +A +KK + E
Sbjct: 222 ---KADLENQKAKVKKQLTE 238
```

FIGURE 3, CONT. BLAST results of Coiled-Coil regions of GAS 40 with other Streptococcus bacteria

**3(d) BLAST alignment of amino acid sequence of GAS 40 including the second coiled-coil region with SpB precursor of *Streptococcus gordonii***

```
>gi|23380384|gb|AAN18299.1|   immunoreactive protein Se89.9 (fragment)
[Streptococcus equi]
     Length = 210
>ref|NP_268623.1| putative surface exclusion protein [Streptococcus
pyogenes]
          Length = 873

Score =  173 bits (438), Expect = 4e-45
 Identities = 98/209 (46%), Positives = 144/209 (68%)

Query: 1    ESDIVDATRFSTTEIPKSGQVIDRSASIQALTNDIASIKGKIASLESRLADPSSEAEVTA 60
            ES+I +  RF+ T I  G   D + +   +++ IA+IKGK++SLE+RL+    EA++ A
Sbjct: 509  ESNIANHQRFNKTPIKAVGSTKDYAQRVGTVSDTIAAIKGKVSSLENRLSAIHQEADIMA 568

Query: 61   AQAKISQLQHQLEAAQAKSHKLDQQVEQLANTKDSLRTQLLAAKEEQAQLKANLDKALAL 120
            AQAK+SQLQ +L +   +S  L+ QV QL +TK SLRT+LLAAK +QAQL+A  D++LA
Sbjct: 569  AQAKVSQLQGKLASTLKQSDSLNLQVRQLNDTKGSLRTELLAAKAKQAQLEATRDQSLAK 628

Query: 121  LASSKATLHKLEAAMEEAKARVAGLASQKAQLEDLLAFEKNPNRIELAQEKVAAAKKALA 180
            LAS KA LH+ EA  E+A ARV  L ++KA L+ L  F+ NPNR+++ +E++   K+ LA
Sbjct: 629  LASLKAALHQTEALAEQAAARVTALVAKKAHLQYLRDFKLNPNRLQVIRERIDNTKQDLA 688

Query: 181  DTEDKLLAAQASLSDLQAQRARLQLSIAT 209
            T    LL AQ +L+ LQA+++ L+ +IAT
Sbjct: 689  KTTSSLLNAQEALAALQAKQSSLEATIAT 717
```

Figure 4: Secondary Structure Prediction of GAS 40

Figure 4(a) Secondary Structure prediction alignment with GAS 40 amino acid sequence

```
         10        20        30        40        50        60        70
          |         |         |         |         |         |         |
MDLEQTKPNQVKQKIALTSTIALLSASVGVSHQVKADDRASGETKASNTHDDSLPKPETIQEAKATIDAV
CCCCCCCChhhHHhhhhhhHHHHhhhccceeEEEecCCcCCCCCcCCCCCCCCCCCccHHHHHHHHHHH
EKTLSQQKAELTELATALTKTTAEINHLKEQQDNEQKALTSAQEIYTNTLASSEETLLAQGAEHQRELTA
HHHHHHHHHHHHHHHHHHHHHhHHHHHHHHHhhhHHHHHHHHHHHHHHHhcccchHHHHHHHHHHHHHHH
TETELHNAQADQHSKETALSEQKASISAETTRAQDLVEQVKTSEQNIAKLNAMISNPDAITKAAQTANDN
HHHHHHHHHHccccHHHHHhhhhccehhhhHHHHHHHHHhHHHHHHHHHHhhhcCcHHHHHHHHHHHhhc
TKALSSELEKAKADLENQKAKVKKQLTEELAAQKAALAEKEAELSRLKSSAPSTQDSIVGNNTMKAPQGY
cHHHHHHHHHHHHHHHHHHHHHHHHHHHHHHHHHHHHHHHHHHHHHHHHHHHHhcCCCCCCCCeEcCCCCCCCCC
PLEELKKLEASGYIGSASYNNYYKEHADQIIAKASPGNQLNQYQDIPADRNRFVDPDNLTPEVQNELAQF
CHHHHHHHHcCccceecCCHHHHHHHHHHHHHHHHCCchhhhhhccCccccCCCCCCCChHHHHHHHHHH
AAHMINSVRRQLGLPPVTVTAGSQEFARLLSTSYKKTHGNTRPSFVYGQPGVSGHYGVGPHDKTIIEDSA
HHHHHHHHHHcCCCCceecCCCHHHHHHHHhhccccCCCCceEEEcCCCceeeccceCcCCCeEEEEcC
GASGLIRNDDNMYENIGAFNDVHTVNGIKRGIYDSIKYMLFTDHLHGNTYGHAINFLRVDKHNPNAPVYL
CCCceecCCcHHHhhhcccccccccCccccHHHHHHHhheeecccCcchhHHheeeeecCCCCCCGEEE
GFSTSNVGSLNEHFVMFPESNIANHQRFNKTPIKAVGSTKDYAQRVGTVSDTIAAIKGKVSSLENRLSAI
EEEecCccCcccceeccccccchHHhhhCCCCCcccCCCHHHHHHchhHHHHHHHhcCcccHHHHHHHHH
HQEADIMAAQAKVSQLQGKLASTLKQSDSLNLQVRQLNDTKGSLRTELLAAKAKQAQLEATRDQSLAKLA
HHHHHHHHHHHHHHHHhHHHHHhccCCchhHHhhhhhcCcCHHHHHHHHHHHHHHHHHhhHHHHHHHH
SLKAALHQTEALAEQAAARVTALVAKKAHLQYLRDFKLNPNRLQVIRERIDNTKQDLAKTTSSLLNAQEA
HHHHHHHHHHHHHHHHHHHHHHHHHHHHHHHHHHHHHHHHHcCCcCHHHHHHHHHhHHHHHHHHHHHHHH
LAALQAKQSSLEATIATTEHQLTLLKTLANEKEYRHLDEDIATVPDLQVAPPLTGVKPLSYSKIDTTPLV
HHHHHHhhcCceeecccHHHHHHHHHHHHHhhhhhHHHhhhccCCCccCCCCCCcCCCceecCCCHHH
QEMVKETKQLLEASARLAAENTSLVAEALVGQTSEMVASNAIVSKITSSITQPSSKTSYGSGSSTTSNLI
HHHHHHHHHHHHHHHHHHHhHHHHHHHHHhcchhHHHHHhchhhhcceEEecCCCcccccccCccccCcce
SDVDESTQRALKAGVVMLAAVGLTGFRFRKESK
cCCchHHHHHHHhcceeeEeeccccceeeccCC
```

Sequence length : 873
PHD :
    Alpha helix    (Hh) : 525 is 60.14%
    3₁₀ helix      (Gg) :   0 is  0.00%
    Pi helix       (Ii) :   0 is  0.00%
    Beta bridge    (Bb) :   0 is  0.00%
    Extended strand (Ee) :  63 is  7.22%
    Beta turn     (Tt) :   0 is  0.00%
    Bend region   (Ss) :   0 is  0.00%
    Random coil   (Cc) : 285 is 32.65%
    Ambigous states (?)  :   0 is  0.00%

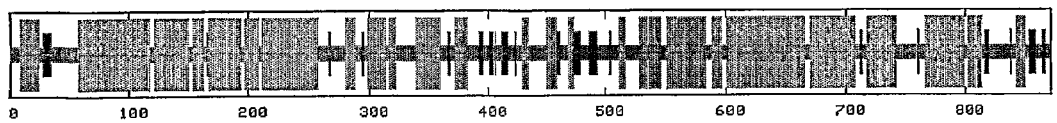

Figure 4(b): Secondary Structure prediction based on PairCoil Score

Paircoil score

Coiled coils found:

| | | | | | |
|---|---|---|---|---|---|
| positions | 58- 121 | initial register | 'f' | probability | 0.811 |
| positions | 156- 196 | initial register | 'e' | probability | 0.720 |
| positions | 198- 246 | initial register | 'e' | probability | 1.000 |
| positions | 247- 261 | initial register | 'a' | probability | 1.000 |
| positions | 556- 646 | initial register | 'e' | probability | 1.000 |
| positions | 671- 733 | initial register | 'f' | probability | 1.000 |

Figure 4(c): Secondary Structure prediction of Leucine Zipper within coiled coil.

```
              673                              701
QYLRDFKLNPNRLQVIRERIDNTKQDLAKTTSSLLNAQEALAALQAKQSSLEATIATTEH
             CCCCCCCCCCCCCCCCCCCCCCCCCCCCCCCCCCCCCCCCCCCCCCC
             L------I------L------L------L
             OOOOOOOOOOOOOOOOOOOOOOOOOOOOOOO
```

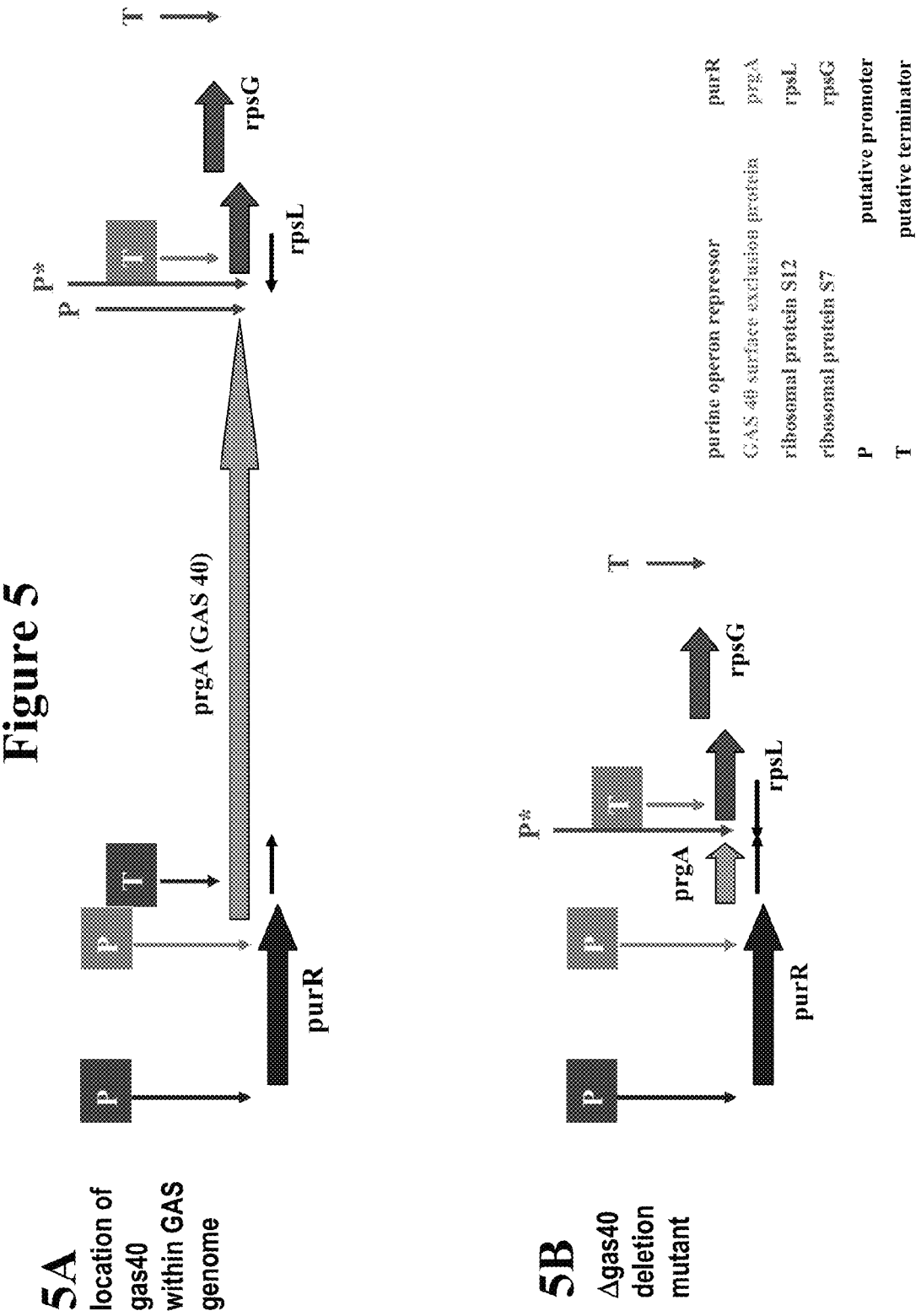

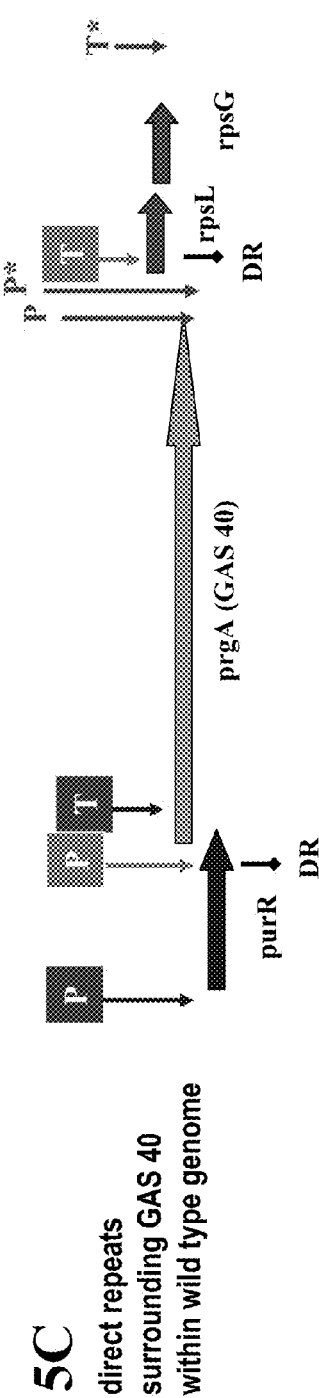
5C
direct repeats
surrounding GAS 40
within wild type genome
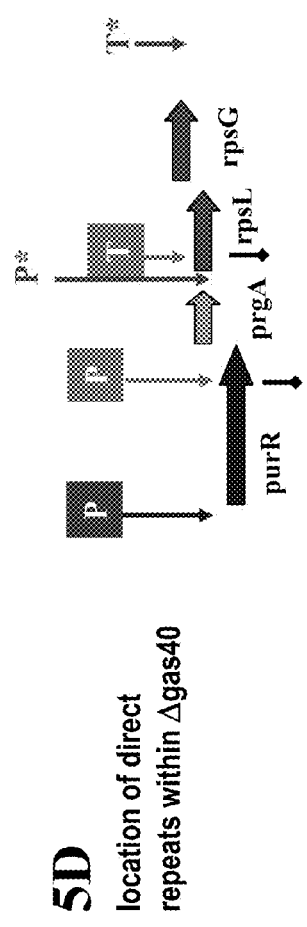
5D
location of direct
repeats within Δgas40
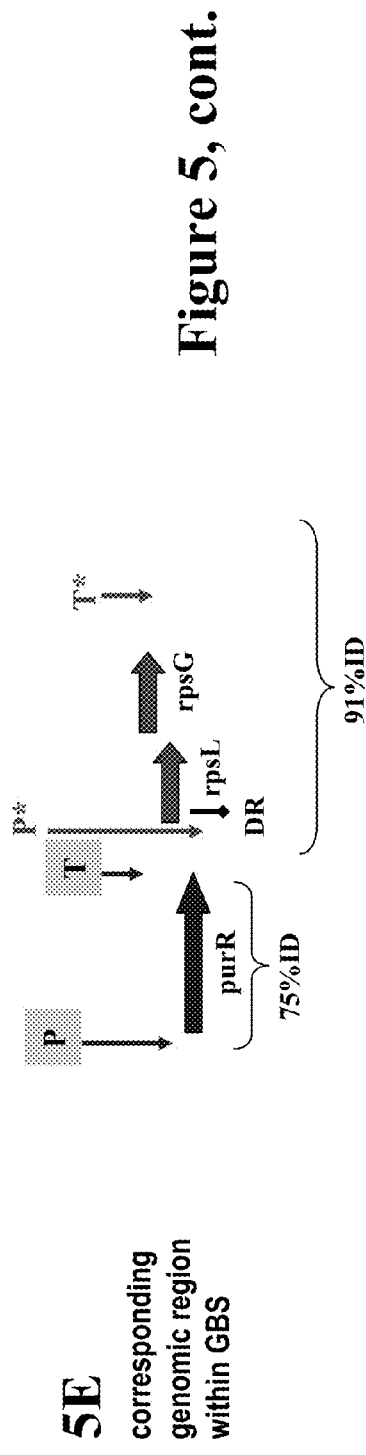
5E
corresponding
genomic region
within GBS
Figure 5, cont.

FIGURE 6: FACS Comparison of GAS 40 in wild type GAS and GAS 40 deletion mutant

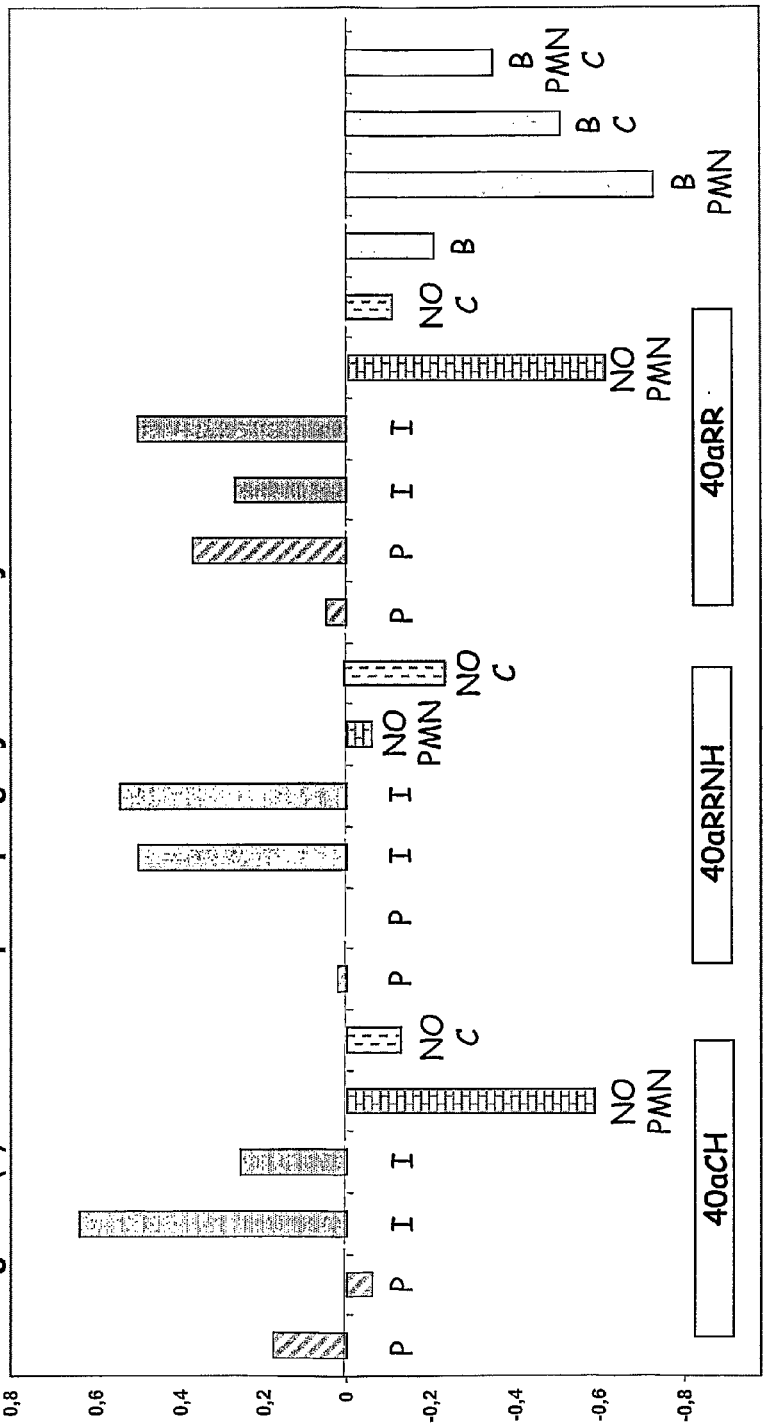

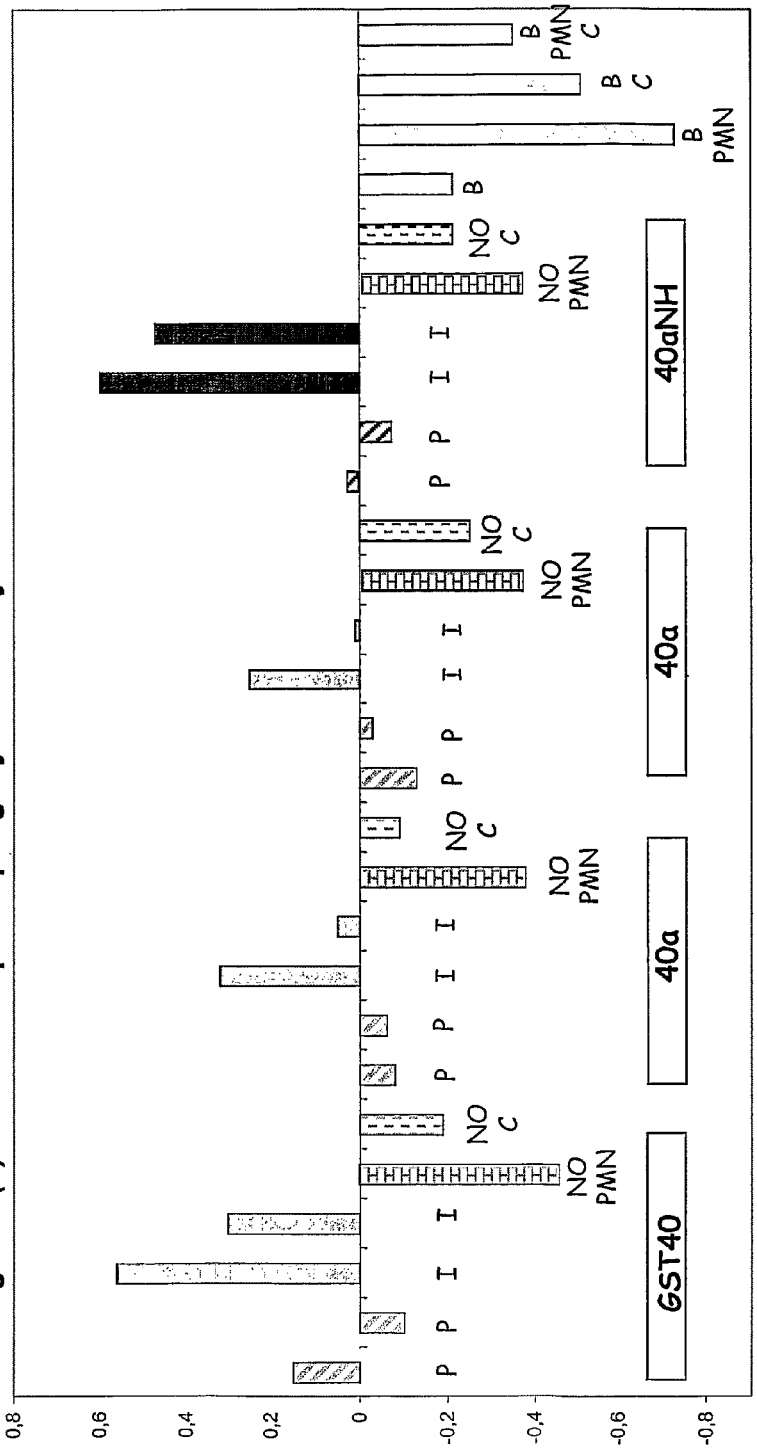

Figure 8: Immunization in Murine Mouse Model

| GAS antigen | Survival/Tested mice | | | Protection | pValue | Protein Purity |
|---|---|---|---|---|---|---|
| | alive | dead | tested | % | Chi-square | % |
| gst 40 | 67 | 63 | 130 | 51 | 0.000012 | |
| 253 | 14 | 36 | 50 | 28 | 0.006 | 15 |
| 253-urea | 2 | 8 | 10 | 20 | | 25 |
| 253-gst | 2 | 8 | 10 | 20 | | 30 |
| 39 | 9 | 31 | 40 | 22.5 | 0.09 | 20 |
| 39a | 13 | 37 | 50 | 26 | 0.016 | 10 |
| 39a | 10 | 30 | 40 | 25 | 0.039 | |
| 39a | 12 | 28 | 40 | 30 | 0.0046 | |
| urea 366 | 21 | 78 | 99 | 21.2 | 0.046 | 65 |
| 117 | 19 | 51 | 70 | 27 | 0.0036 | 15 |
| 117-urea | 1 | 9 | 10 | 10 | | 80 |
| 117-urea-2M | 7 | 23 | 30 | 23.3 | 0.1 | 80 |
| 117-urea-2M (prep 117) | 8 | 32 | 40 | 20 | 0.2 | |
| urea 504 | 9 | 31 | 40 | 22.5 | 0.09 | 50 |
| 504 | 14 | 26 | 40 | 35 | 0.0003 | 40 |
| 504 | 7 | 33 | 40 | 17.5 | 0.4 | 80 |
| urea 389 | 7 | 23 | 30 | 23 | 0.1 | 30 |
| 533 | 14 | 56 | 70 | 20 | 0.12 | 50 |
| new 533 | 4 | 16 | 20 | 20 | 0.34 | 30 |
| gst 57 | 12 | 48 | 60 | 20 | 0.14 | 60 |
| 57a | 0 | 20 | 20 | 0 | | 50 |
| 294 | 17 | 73 | 90 | 18.8 | 0.14 | 80 |
| 130 | 15 | 65 | 80 | 18.7 | 0.17 | 40 |
| 130 | 7 | 23 | 30 | 23.3 | 0.1 | 40 |
| 84 | 8 | 32 | 40 | 20 | 0.2 | 70 |
| urea 159 | 7 | 33 | 40 | 17.5 | 0.4 | 5 |
| 159a | 2 | 8 | 10 | 20 | | 65 |
| 527 | 10 | 40 | 50 | 20 | 0.17 | 50 |
| 527 | 3 | 17 | 20 | 15 | | 80 |
| 217 | 7 | 33 | 40 | 17.5 | 0.4 | 50 |
| 511 | 13 | 67 | 80 | 16.2 | 0.41 | 80 |
| 277 | 8 | 42 | 50 | 16 | 0.52 | 5 |
| 277a | 2 | 28 | 30 | 6.6 | | 50 |
| gst 202 | 3 | 17 | 20 | 10 | 0.75 | 5 |
| 202a | 5 | 25 | 30 | 16.6 | 0.53 | 5 |
| 45 | 5 | 25 | 30 | 16.6 | 0.53 | 80 |
| urea 309 | 5 | 25 | 30 | 20 | 0.53 | 8 |
| 290 | 6 | 34 | 40 | 15 | 0.67 | 50 |
| 529 | 6 | 34 | 40 | 15 | 0.67 | 5 |
| gst 58 | 10 | 60 | 70 | 14.2 | 0.71 | 30 |
| 384 | 7 | 43 | 50 | 14 | 0.78 | 80 |
| 384RR | 1 | 19 | 20 | 5 | | 80 |
| urea 509 | 7 | 53 | 60 | 11.6 | 0.84 | 50 |
| 509-NH | 2 | 8 | 10 | | | 75 |
| 509-CH | 0 | 10 | 10 | | | 75 |
| 193 | 7 | 53 | 60 | 11.6 | 0.84 | 65 |
| urea 372 | 4 | 25 | 29 | 13.7 | 0.85 | 20 |
| gst 42 | 4 | 26 | 30 | 13.3 | 0.9 | 50 |
| 95 | 5 | 35 | 40 | 12.5 | 1 | 55 |
| urea 236 | 5 | 35 | 40 | 12.5 | 1 | 80 |
| new 236 | 2 | 8 | 10 | 20 | | 70 |
| 137 | 5 | 35 | 40 | 12.5 | 1 | 75 |
| His-Stop | 29 | 201 | 230 | 12:06 | | |

IMMUNOGENIC COMPOSITIONS FOR *STREPTOCOCCUS PYOGENES*

All documents cited herein are incorporated by reference in their entirety.

This application is a division of Ser. No. 12/715,912 filed on Mar. 2, 2010, now U.S. Pat. No. 8,128,936, which is a continuation of Ser. No. 10/565,126 filed Sep. 18, 2006, now U.S. Pat. No. 7,709,009, which is a national stage entry of PCT/US04/24868 filed on Jul. 30, 2004, which claims the benefit and incorporates by reference in their entireties Ser. No. 60/491,822 filed on Jul. 31, 2003 and Ser. No. 60/541,565 filed on Feb. 3, 2004.

This application incorporates by reference the contents of a 436 kb text file created on Mar. 2, 2012 and named "PAT051962sequencelisting.txt," which is the sequence listing for this application.

FIELD OF THE INVENTION

This invention is in the fields of immunology and vaccinology. In particular, it relates to antigens derived from *Streptococcus pyogenes* and their use in immunisation. All documents cited herein are incorporated by reference in their entirety.

BACKGROUND OF THE INVENTION

Group A *streptococcus* ("GAS", *S. pyogenes*) is a frequent human pathogen, estimated to be present in between 5-15% of normal individuals without signs of disease. When host defences are compromised, or when the organism is able to exert its virulence, or when it is introduced to vulnerable tissues or hosts, however, an acute infection occurs. Related diseases include puerperal fever, scarlet fever, erysipelas, pharyngitis, impetigo, necrotising fasciitis, myositis and streptococcal toxic shock syndrome.

GAS is a gram positive, non-sporeforming coccus shaped bacteria that typically occurs in chains or in pairs of cells. Although *S. pyogenes* may be treated using antibiotics, a prophylactic vaccine to prevent the onset of disease is desired. Efforts to develop such a vaccine have been ongoing for many decades. While various GAS vaccine approaches have been suggested and some approaches are currently in clinical trials, to date, there are no GAS vaccines available to the public.

It is an object of the invention to provide further and improved compositions for providing immunity against GAS disease and/or infection. The compositions preferably include GAS 40, a GAS virulence factor identified by Applicants, which is particularly suitable for use in vaccines. In addition, the compositions are based on a combination of two or more (e.g. three or more) GAS antigens.

SUMMARY OF THE INVENTION

Applicants have discovered a group of thirty GAS antigens that are particularly suitable for immunisation purposes, particularly when used in combinations. In addition, Applicants have identified a GAS antigen (GAS 40) which is particularly immunogenic used either alone or in combinations with additional GAS antigens.

The invention therefore provides an immunogenic composition comprising GAS 40 (including fragments thereof or a polypeptide having sequence identity thereto). A preferred fragment of GAS 40 comprises one or more coiled-coil regions. The invention further includes an immunogenic composition comprising a combination of GAS antigens, said combination consisting of two to ten GAS antigens, wherein said combination includes GAS 40 or a fragment thereof or a polypeptide having sequence identity thereto. Preferably, the combination consists of three, four, five, six, or seven GAS antigens. Still more preferably, the combination consists of three, four, or five GAS antigens.

The invention also provides an immunogenic composition comprising a combination of GAS antigens, said combination consisting of two to thirty-one GAS antigens of a first antigen group, said first antigen group consisting of: GAS 117, GAS 130, GAS 277, GAS 236, GAS 40, GAS 389, GAS 504, GAS 509, GAS 366, GAS 159, GAS 217, GAS 309, GAS 372, GAS 039, GAS 042, GAS 058, GAS 290, GAS 511, GAS 533, GAS 527, GAS 294, GAS 253, GAS 529, GAS 045, GAS 095, GAS 193, GAS 137, GAS 084, GAS 384, GAS 202, and GAS 057. These antigens are referred to herein as the 'first antigen group'. Preferably, the combination of GAS antigens consists of three, four, five, six, seven, eight, nine, or ten GAS antigens selected from the first antigen group. Preferably, the combination of GAS antigens consists of three, four, or five GAS antigens selected from the first antigen group.

GAS 39, GAS 40, GAS 57, GAS 117, GAS 202, GAS 294, GAS 527, GAS 533, and GAS 511 are particularly preferred GAS antigens. Preferably, the combination of GAS antigens includes either or both of GAS 40 and GAS 117. Preferably, the combination includes GAS 40.

Representative examples of some of these antigen combinations are discussed below.

The combination of GAS antigens may consist of three GAS antigens selected from the first antigen group. Accordingly, in one embodiment, the combination of GAS antigens consists of GAS 40, GAS 117 and a third GAS antigen selected from the first antigen group. Preferred combinations include GAS 40, GAS 117 and a third GAS antigen selected from the group consisting of GAS 39, GAS 57, GAS 202, GAS 294, GAS 527, GAS 533, and GAS 511.

In another embodiment, the combination of GAS antigens consists of GAS 40 and two additional GAS antigens selected from the first antigen group. Preferred combinations include GAS 40 and two GAS antigens selected from the group consisting of GAS 39, GAS 57, GAS 117, GAS 202, GAS 294, GAS 527, GAS 533, and GAS 511. In another embodiment, the combination of GAS antigens consists of GAS 117 and two additional GAS antigens selected from the first antigen group.

The combination of GAS antigens may consist of four GAS antigens selected from the first antigen group. In one embodiment, the combination of GAS antigens consists of GAS 40, GAS 117 and two additional GAS antigens selected from the first antigen group. Preferred combinations include GAS 40, GAS 117, and two GAS antigens selected from the group consisting of GAS 39, GAS 57, GAS 202, GAS 294, GAS 527, GAS 533, and GAS 511.

In another embodiment, the combination of GAS antigens consists of GAS 40 and three additional GAS antigens selected from the first antigen group. Preferred combinations include GAS 40 and three additional GAS antigens selected from the group consisting of GAS 39, GAS 57, GAS 117, GAS 202, GAS 294, GAS 527, GAS 533, and GAS 511. In one embodiment, the combination of GAS antigens consists of GAS 117 and three additional antigens selected from the first antigen group.

The combination of GAS antigens may consist of five GAS antigens selected from the first antigen group. In one embodiment, the combination of GAS antigens consists of GAS 40, GAS 117 and three additional GAS antigens selected from the first antigen group. Preferred combinations include GAS 40, GAS 117 and three additional GAS antigens selected from the group consisting of GAS 39, GAS 57, GAS 202, GAS 294, GAS 527, GAS 533, and GAS 511. In another embodiment, the combination of GAS antigens consists of GAS 40 and four additional GAS antigens selected from the first antigen group. Preferred combinations include GAS 40 and four additional GAS antigens selected from the group consisting of GAS 39, GAS 57, GAS 117, GAS 202, GAS 294, GAS 527, GAS 533, and GAS 511. In one embodiment, the combination of GAS antigens consists of GAS 117 and four additional GAS antigens selected from the first antigen group.

The combination of GAS antigens may consist of eight GAS antigens selected from the first antigen group. In one embodiment, the combination of GAS antigens consists of GAS 40, GAS 117 and six additional GAS antigens selected from the first antigen group. In one embodiment, the combination of GAS antigens consists of GAS 40 and seven additional GAS antigens selected from the first antigen group. In one embodiment, the combination of GAS antigens consists of GAS 117 and seven additional GAS antigens selected from the first antigen group.

The combination of GAS antigens may consist of ten GAS antigens selected from the first antigen group. In one embodiment, the combination of GAS antigens consists of GAS 40, GAS 117 and eight additional GAS antigens selected from the first antigen group. In one embodiment, the combination of GAS antigens consists of GAS 40 and nine additional GAS antigens selected from the first antigen group. In one embodiment, the combination of GAS antigens consists of GAS 117 and nine additional GAS antigens selected from the first antigen group.

BRIEF DESCRIPTION OF THE FIGURES

FIG. 1 identifies a leader peptide sequence, two coiled-coil sequences, a leucine zipper sequence and a transmembrane sequence within a GAS 40 amino acid sequence (SEQ ID NO:1).

FIG. 2 depicts a schematic of GAS 40 identifying a leader peptide sequence, two coiled-coil sequences, a leucine zipper sequence and a transmembrane sequence, as well as coiled-coil regions of GAS 40 which have low level homology with other Streptococcal proteins of known or predicted function.

FIGS. 3A-3D include the BLAST alignment analysis of identified coiled-oil regions of GAS 40 (SEQ ID NO:1) with other *Streptococcus* bacteria. FIG. 3A, SpA precursor of *S. gordonii* (SEQ ID NO:15); FIG. 3B, SpB precursor of *S. gordonii* (SEQ ID NO:16); FIG. 3C, PspA precursor of *S. pneumoniae* (SEQ ID NO:17); FIG. 3D, SpB precursor of *S. gordonii* (SEQ ID NO:16).

FIG. 4 provides predicted secondary structure for an amino acid sequence of GAS 40 (SEQ ID NO:1).

FIG. 5 schematically depicts the location of GAS 40 within the GAS genome. It also includes comparison schematic depicting a GAS mutant with GAS 40 deleted. Further details on these schematics demonstrate the likelihood that GAS 40 was acquired by horizontal transfer through a transposon factor.

FIG. 6 provides comparison FACS analysis depicting the surface exposure of GAS 40 in a wild type strain (and no surface exposure in the GAS 40 deletion mutant).

FIG. 7 presents opsonophagocytosis data for GAS 40 (in various expression constructs).

FIG. 8 presents immunization and challenge data for several GAS antigens of the invention.

DETAILED DESCRIPTION OF THE INVENTION

As discussed above, the invention provides compositions comprising a combination of GAS antigens, wherein the combinations can be selected from groups of antigens which Applicants have identified as being particularly suitable for immunization purposes, particularly when used in combination. In particular, the invention includes compositions comprising GAS 40. GAS 40 and the other GAS antigens of the first antigen group are described in more detail below. Genomic sequences of at least three GAS strains are publicly available. The genomic sequence of an M1 GAS strain is reported at Ferretti et al, PNAS (2001) 98(8):4658-4663. The genomic sequence of an M3 GAS strain is reported at Beres et al., PNAS (2002) 99(15):10078-10083. The genomic sequence of an M18 GAS strain is reported at Smooet et al., PNAS (2002) 99(7):4668-4673. Preferably, the GAS antigens of the invention comprise polynucleotide or amino acid sequence of an M1, M3 or M18 GAS strains. More preferably, the GAS antigens of the invention comprise a polynucleotide or amino acid sequence of an M1 strain.

As there will be variance among the identified GAS antigens between GAS M types and GAS strain isolates, references to the GAS amino acid or polynucleotide sequences of the invention preferably include amino acid or polynucleotide sequences having sequence identity thereto. Preferred amino acid or polynucleotide sequences have 50% or more sequence identity (e.g., 60%, 65%, 70%, 75%, 80%, 85%, 90%, 91%, 92%, 93%, 94%, 95%, 96%, 97%, 98%, 99%, 99.5% or more). Similarly, references to the GAS amino acid or polynucleotide sequences of the invention preferably include fragments of those sequences, (i.e., fragments which retain or encode for the immunological properties of the GAS antigen). Preferred amino acid fragments include at least n consecutive amino acids, wherein n is 7 or more (e.g., 8, 10, 12, 14, 16, 18, 20, 25, 30, 35, 40, 50, 60, 70, 80, 90, 100, 150, 200, 250 or more). Preferred polynucleotide fragments include at least n consecutive polynucleotides, wherein n is 12 or more (e.g., 15, 16, 17, 18, 19, 20, 21, 22, 23, 24, 25, 26, 28, 30, 35, 40, 45, 50, 60, 70, 80, 90, 100, 150, 200, 250 or more). In one embodiment, the amino acid or polynucleotide fragments of the invention are not identical to amino acid or polynucleotide sequences from other (non-GAS) bacteria (e.g., the fragments are not identical to sequences in other *Streptococcus* bacteria).

(1) GAS 40

GAS 40 corresponds to M1 GenBank accession numbers GI: 13621545 and GI: 15674449, to M3 GenBank accession number GI: 21909733, to M18 GenBank accession number GI: 19745402, and is also referred to as 'Spy0269' (M1), 'SpyM3_0197' (M3), 'SpyM18_0256' (M18) and 'prgA'. GAS 40 has also been identified as a putative surface exclusion protein. Amino acid and polynucleotide sequences of GAS 40 from an M1 strain are set forth below and in the sequence listing as SEQ ID NOS: 1 and 2.

SEQ ID NO: 1

MDLEQTKPNQVKQKIALTSTIALLSASVGVSHQVKADDRASGETKASNTHDDSLPKPETIQEAKATIDAVEKTLSQQKAE

LTELATALTKTTAEINHLKEQQDNEQKALTSAQEIYTNTLASSEETLLAQGAEHQRELTATETELHNAQADQHSKETALSEQKASISA

ETTRAQDLVEQVKTSEQNIAKLNAMISNPDAITKAAQTANDNTKALSSELEKAKADLENQKAKVKKQLTEELAAQKAALAEKEAELSR

-continued

LKSSAPSTQDSIVGNNTMKAPQGYPLEELKKLEASGYIGSASYNNYYKEHADQIIAKASPGNQLNQYQDIPADRNRFVDPDNLTPEVQ
NELAQFAAHMINSVRRQLGLPPVTVTAGSQEFARLLSTSYKKTHGNTRPSFVYGQPGVSGHYGVGPHDKTIIEDSAGASGLIRNDDNM
YENIGAFNDVHTVNGIKRGIYDSIKYMLFTDHLHGNTYGHAINFLRVDKHNPNAPVYLGFSTSNVGSLNEHFVMFPESNIANHQRFNK
TPIKAVGSTKDYAQRVGTVSDTIAAIKGKVSSLENRLSAIHQEADIMAAQAKVSQLQGKLASTLKQSDSLNLQVRQLNDTKGSLRTEL
LAAKAKQAQLEATRDQSLAKLASLKAALHQTEALAEQAAARVTALVAKKAHLQYLRDFKLNPNRLQVIRERIDNTKQDLAKTTSSLLN
AQEALAALQAKQSSLEATIATTEHQLTLLKTLANEKEYRHLDEDIATVPDLQVAPPLTGVKPLSYSKIDTTPLVQEMVKETKQLLEAS
ARLAAENTSLVAEALVGQTSEMVASNAIVSKITSSITQPSSKTSYCSGSSTTSNLISDVDESTQR<u>ALKAGVVMLAAVGLTGFRFRKES
K</u>

SEQ ID NO: 2

<u>ATGGACTTAGAACAAACGAAGCCAAACCAAGTTAAGCAGAAAATTGCTTTAACCTCAACAATTGCTTTATTGAGTG</u>CCAGTGTAGGCG
TATCTCACCAAGTCAAAGCAGATGATAGAGCCTCAGGAGAAACGAAGGCGAGTAATACTCACGACGATAGTTTACCAAAACCAGAAAC
AATTCAAGAGGCAAAGGCAACTATTGATGCAGTTGAAAAAACTCTCAGTCAACAAAAAGCAGAACTGACAGAGCTTGCTACCGCTCTG
ACAAAAACTACTGCTGAAATCAACCACTTAAAAGAGCAGCAAGATAATGAACAAAAGCTTTAACCTCTGCACAAGAAATTTACACTA
ATACTCTTGCAAGTAGTGAGGAGACGCTATTAGCCCAAGGAGCCGAACATCAAAGAGAGTTAACAGCTACTGAAACAGAGCTTCATAA
TGCTCAAGCAGATCAACATTCAAAAGAGACTGCATTGTCAGAACAAAAAGCTAGCATTTCAGCAGAAACTACTCGAGCTCAAGATTTA
GTGGAACAAGTCAAAACGTCTGAACAAAATATTGCTAAGCTCAATGCTATGATTAGCAATCCTGATGCTATCACTAAAGCAGCTCAAA
CGGCTAATGATAATACAAAAGCATTAAGCTCAGAATTGGAGAAGGCTAAAGCTGACTTAGAAAATCAAAAAGCTAAAGTTAAAAAGCA
ATTGACTGAAGAGTTGGCAGCTCAGAAAGCTGCTCTAGCAGAAAAAGAGGCAGAACTTAGTCGTCTTAAATCCTCAGCTCCGTCTACT
CAAGATAGCATTGTGGGTAATAATACCATGAAAGCACCGCAAGGCTATCCTCTTGAAGAACTTAAAAAATTAGAAGCTAGTGGTTATA
TTGGATCAGCTAGTTACAATAATTATTACAAAGAGCATGCAGATCAAATTATTGCCAAAGCTAGTCCAGGTAATCAATTAAATCAATA
CCAAGATATTCCAGCAGATCGTAATCGCTTTGTTGATCCCGATAATTTGACACCAGAAGTGCAAAATGAGCTAGCGCAGTTTGCAGCT
CACATGATTAATAGTGTAAGAAGACAATTAGGTCTACCACCAGTTACTGTTACAGCAGGATCACAAGAATTTCCAAGATTACTTAGTA
CCAGCTATAAGAAAACTCATGGTAATACAAGACCATCATTTGTCTACGGACAGCCAGGGGTATCAGGGCATTATGGTGTTGGGCCTCA
TGATAAAACTATTATTGAAGACTCTGCCGGAGCGTCAGGGCTCATTCGAAATGATGATAACATGTACGAGAATATCGGTGCTTTTAAC
GATGTGCATACTGTGAATGGTATTAAACGTGGTATTTATGACAGTATCAAGTATATGCTCTTTACAGATCATTTACACGGAAATACAT
ACGGCCATGCTATTAACTTTTTACGTGTAGATAAACATAACCCTAATGCGCCTGTTTACCTTGGATTTTCAACCAGCAATGTAGGATC
TTTGAATGAACACTTTGTAATGTTTCCAGAGTCTAACATTGCTAACCATCAACGCTTTAATAAGACCCCTATAAAAGCCGTTGGAAGT
ACAAAAGATTATGCCCAAAGAGTAGGCACTGTATCTGATACTATTGCAGCGATCAAAGGAAAAGTAAGCTCATTAGAAAATCGTTTGT
CGGCTATTCATCAAGAAGCTGATATTATGGCAGCCCAAGCTAAAGTAAGTCAACTTCAAGGTAAATTAGCAAGCACACTTAAGCAGTC
AGACAGCTTAAATCTCCAAGTGAGACAATTAAATGATACTAAAGGTTCTTTGAGAACAGAATTACTAGCAGCTAAAGCAAAACAAGCA
CAACTCGAAGCTACTCGTGATCAATCATTAGCTAAGCTAGCATCGTTGAAAGCCGCACTGCACCAGACAGAAGCCTTAGCAGAGCAAG
CCGCAGCCAGAGTGACAGCACTGGTGGCTAAAAAAGCTCATTTGCAATATCTAAGGGACTTTAAATTGAATCCTAACCGCCTTCAAGT
GATACGTGAGCGCATTGATAATACTAAGCAAGATTTGGCTAAAACTACCTCATCTTTGTTAAATGCACAAGAAGCTTTAGCAGCCTTA
CAAGCTAAACAAAGCAGTCTAGAAGCTACTATTGCTACCACAGAACACCAGTTGACTTTGCTTAAAACCTTAGCTAACGAAAAGGAAT
ATCGCCACTTAGACGAAGATATAGCTACTGTGCCTGATTTGCAAGTAGCTCCACCTCTTACGGGCGTAAAACCGCTATCATATAGTAA
GATAGATACTACTCCGCTTGTTCAAGAAATGGTTAAAGAAACGAAACAACTATTAGAAGCTTCAGCAAGATTAGCTGCTGAAAATACA
AGTCTTGTAGCAGAAGCGCTTGTTGGCCAAACCTCTGAAATGGTAGCAAGTAATGCCATTGTGTCTAAAATCACATCTTCGATTACTC
AGCCCTCATCTAAGACATCTTATGGCTCAGGATCTTCTACAACGAGCAATCTCATTTCTGATGTTGATGAAAGTACTCAAAGA<u>GCTCT
TAAAGCAGGAGTCGTCATGTTGGCAGCTGTCGGCCTCACAGGATTTAGGTTCCGTAAGGAATCTAAGTGA</u>

Preferred GAS 40 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 1; and/or (b) which is a fragment of at least n consecutive amino acids of SEQ ID NO: 1, wherein n is 7 or more (e.g. 8, 10, 12, 14, 16, 18, 20, 25, 30, 35, 40, 50, 60, 70, 80, 90, 100, 150, 200, 250 or more). These GAS 40 proteins include variants (e.g. allelic variants, homologs, orthologs, paralogs, mutants, etc.) of SEQ ID NO: 1. Preferred fragments of (b) comprise an epitope from SEQ ID NO: 1. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 1.

For example, in one embodiment, the underlined amino acid sequence at the N-terminus (leader sequence) of SEQ ID NO: 1 is removed. (The amino acid and polynucleotide sequences for this N terminal leader sequence are listed in the sequence listing as SEQ ID NOS: 3 and 4. The amino acid and polynucleotide sequences for the remaining GAS 40 fragment are listed in the sequence listing as SEQ ID NOS: 5 and 6.)

As another example, in one embodiment, the underlined amino acid sequence at the C-terminus (transmembrane region) of SEQ ID NO: 1 is removed. (The amino acid and polynucleotide sequences for this transmembrane region are listed in the sequence listing as SEQ ID NOS: 7 and 8. The amino acid and polynucleotide sequences for the remaining GAS 40 fragment are listed in the sequence listing as SEQ ID NOS: 9 and 10).

Other fragments may omit one or more domains of the protein (e.g. omission of a signal peptide, of a cytoplasmic domain, of a transmembrane domain, or of an extracellular domain).

Further illustration of domains within GAS 40 is shown in FIGS. 1 and 2. As shown in these figures, an amino acid sequence for GAS 40 (SEQ ID NO: 1) contains a leader peptide sequence within amino acids 1-26 (for example SEQ ID NO: 3), a first coiled-coil region within amino acids 58-261 (SEQ ID NO: 12), a second coiled coil region generally within amino acids 556-733 (SEQ ID NO: 13), a leucine zipper region within amino acids 673-701 (SEQ ID NO: 14) and a transmembrane region within amino acids 855-866 (SEQ ID NO: 11). FIG. 1 depicts these regions within an amino acid sequence for GAS 40, while FIG. 2 depicts these regions schematically along the length of the GAS 40 protein.

The coiled-coil regions identified within GAS 40 are likely to form alpha helical coils. These structures are frequently involved in oligomerization interactions, for example between different regions of the protein or between regions of two separate proteins. The leucine zipper motif within the second coiled-coil region contains a series of leucine (or isoleucine) amino acid residues, spaced in such a way as to allow the protein to form a specialized oligomerization interaction between two alpha helices. In a leucine zipper motif, preferably, there are six amino acid residues interspaced between the repeating leucine residues. In a leucine zipper oligomeric structure, the alpha helices are thought to be held together by hydrophobic interactions between leucine residues, which are located on one side of each helix. Leucine zipper motifs are frequently involved in dimerization interactions. The location of the leucine zipper motif within the coiled-coil region further indicates the likelihood that this region of the GAS 40 protein is involved in an oligomerization interaction.

FIG. 2 also illustrates that there is low level homology between some of the identified regions of GAS 40 and other Streptococcal proteins with known or predicted two dimensional structures or surface localization. Such low level homology may indicate a similar secondary structures or even function. For example, amino acids 33 to 324 of GAS 40, including the first coiled-coil region, has approximately 22% sequence identity to a region (amino acids 112 to 392) of a protein from *Streptococcus gordonii* called streptococcal surface protein A ("SpA") precursor (Genbank reference GI 25990270, SEQ ID NO: 15). This protein is thought to be a surface protein adhesion, involved in the adhesion of that *Streptococcus* with mammalian host cell membranes. The *S. gordonii* SpA is a member of streptococcal antigen I/II family of protein adhesions and recognizes salivary agglutinin glycoprotein (gp-340) and type I collagen Amino acids 33 to 258 of GAS 40 also show low level sequence identify (23%) with another *S. gordonii* protein, Streptococcal surface protein B precursor (Genbank reference GI 25055226, SEQ ID NO: 16).

A similar region of GAS 40 which also overlaps with the first coiled-coil region (amino acids 43-238) demonstrates about 23% sequence identity to a region (amino acids 43-238) of a protein from *Streptococcus pneumoniae* called surface protein pspA precursor (Genbank reference GI 282335, SEQ ID NO: 17). The amino terminal domain of pspA is thought to be essential for full pneumococcal virulence, and monoclonal antibodies raised against it protect mice against pneumococcal infections. The pspA domain has a monomeric form with an axial shape ratio of approximately 1:12, typical of fibrous proteins. Sequence analyses indicates an alpha-helical coiled-coil structure for this monomeric molecule with only few loop-type breaks in helicity.

The second coiled-coil region of GAS 40 has about 46% sequence identity to a region (amino acids 509-717) of a protein from *Streptococcus equi* called immunoreactive protein Se89.9 (Genbank reference GI 2330384, SEQ ID NO: 18) (the full length sequence for Se89.9 is also available at http://pedant.gsf.de). This *Streptococcus equi* protein is predicted to be surface exposed. BLAST alignment of each of these Streptococcal sequences with GAS 40 is presented in FIG. 3.

Further illustration of the two dimensional structure of GAS 40 is shown in FIG. 4. First, FIG. 4(a) presents predicted secondary structure analysis aligned against the amino acid sequence for GAS 40. The predicted alpha helical regions in FIG. 4 generally correspond to the previously noted coiled-coil regions. In FIG. 4(b), PairCoil prediction is used to predict the location of putative coiled-coils. Here, two coil regions are identified, generally corresponding to the first and second coiled coil regions. FIG. 4(c) highlights the leucine zipper region and illustrates the regularly repeating leucine (or isoleucine) amino acid residues which are likely to participate in the leucine zipper.

Accordingly, the first coiled-coil region of GAS 40 comprises an amino acid sequence of at least ten (e.g., at least 10, 13, 15, 18, 20, 25, 30, 35, 40, 50, 70, 90, 100 or more) consecutive amino acid residues, selected from the N-terminal half of a full length GAS 40 sequence, and predicted to form an alpha-helical complex based on the functional characteristics of the amino acid residues in the sequence. SEQ ID NO: 12 is a preferred first coiled-coil region of GAS 40.

The second coiled-coil region of GAS 40 comprises an amino acid sequence of at least ten (e.g., at least 10, 13, 15, 18, 20, 25, 30, 35, 40, 50, 70, 90, 100 or more) consecutive amino acid residues, selected from the C-terminal half of a full length GAS 40 sequence, and predicted to form an alpha-helical complex based on the functional characteristics of the amino acid residues in the sequence. The second coiled-coil region preferably includes a leucine zipper motif. SEQ ID NO: 13 is a preferred second coiled-coil region of GAS 40.

The coiled-coil regions of GAS 40 are likely to be involved in the formation of oligomers such as dimers or trimers. Such oligomers could be homomers (containing two or more GAS 40 proteins oligomerized together) or heteromers (containing one or more additional GAS proteins oligomerized with GAS 40). Alternatively, the first and second coiled-coil regions may be interacting together within the GAS 40 protein to form oligomeric reactions between the first and second coiled-coil regions.

Accordingly, in one embodiment, the compositions of the invention include a GAS 40 antigen in the form of an oligomer. The oligomer may comprise two more GAS 40 antigens or fragments thereof, or it may comprise GAS 40 or a fragment thereof oligomerized to a second GAS antigen. Preferred GAS 40 fragments comprise an amino acid sequence selected from the group consisting of the first coiled-coil region and the second coiled-coil region. Such preferred GAS 40 fragments may be used alone or in the combinations of the invention.

The GAS polynucleotides and amino acid sequences of the invention may be manipulated to facilitate or optimise recombinant expression. For example, the N-terminal leader sequence may be replaced with a sequence encoding for a tag protein such as polyhistidine ("HIS") or glutathione S-transferase ("GST"). Such tag proteins may be used to facilitate purification, detection and stability of the expressed protein. Variations of such modifications for GAS 40 are discussed below. Such modifications can be applied to any of the GAS proteins of the invention.

An example of a GAS 40 sequence with both a GST and a HIS tag is denoted herein as "GST 40 HIS". This construct includes a GAS 40 sequence where the leader sequence is removed, a GST tag coding sequence is added to the N-terminus, and a HIS tag coding sequence is added to the C-terminus (using, for example, a pGEXNNH vector with NdeI and NotI restriction sites). Polynucleotide and amino acid sequences for the fused region of the GST tag, the GAS 40 sequence and the C-terminus HIS tag of GST 40 HIS are shown in SEQ ID NOS: 19 and 20.

Alternatively, a single tag sequence may be used. An example of a GAS 40 sequence with just a HIS tag is denoted as "40a-HIS". This construct includes a GAS 40 sequence where the N-terminus leader sequence and the C-terminus containing the transmembrane sequence is removed. In this construct, the HIS tag sequence is added to the C-terminus (using, for example, a cloning vector such as pET21b+ (Novagen) at the NdeI and NotI restriction sites). Polynucleotide and amino acid sequences for 40a-HIS are shown in SEQ ID NOS. 21 and 22.

In addition to the addition of purification tags, recombinant expression may also be facilitated by optimising coding sequences to those more abundant or accessible to the recombinant host. For example, the polynucleotide sequence AGA encodes an arginine amino acid residue. Arginine may also be encoded by the polynucleotide sequence CTG. This CTG codon is preferred by the translational enzymes in *E. coli*. In the 40a-HIS polynucleotide sequence SEQ ID NO 21, a C-terminus CTG coding for arginine has been replaced with CGT.

The following codons are generally underrepresented in *E. coli*: AGA, AGG and CGA. When these codons occur in a GAS polynucleotide sequence, they may be replaced with one of the other two optional codons encoding for the same amino acid residue.

A total of three ATG codons are optimised to CTG in the "40a-RR-HIS" construct, SEQ ID NOS 23 and 24. SEQ ID NO 23 is also shown below, with the optimised codons underlined. (other than the additional codon optimisation, 40a-RR-HIS is identical to 40a-HIS.)

SEQ ID N: 23

ATGAGTGTAGGCGTATCTCACCAAGTCAAAGCAGATGATAGAGCCTCAGGAGAAACGAAGGCGAGTAATACTCACGACGATAGTTTAC

CAAAACCAGAAACAATTCAAGAGGCAAAGGCAACTATTGATGCAGTTGAAAAAACTCTCAGTCAACAAAAAGCAGAACTGACAGAGCT

TGCTACCGCTCTGACAAAAACTACTGCTGAAATCAACCACTTAAAAGAGCAGCAAGATAATGAACAAAAAGCTTTAACCTCTGCACAA

GAAATTTACACTAATACTCTTGCAAGTAGTGAGGAGACGCTATTAGCCCAAGGAGCCGAACATCAAAGAGAGTTAACAGCTACTGAAA

CAGAGCTTCATAATGCTCAAGCAGATCAACATTCAAAAGAGACTGCATTGTCAGAACAAAAAGCTAGCATTTCAGCAGAAACTACTCG

AGCTCAAGATTTAGTGGAACAAGTCAAAACGTCTGAACAAAATATTGCTAAGCTCAATGCTATGATTAGCAATCCTGATGCTATCACT

AAAGCAGCTCAAACGGCTAATGATAATACAAAAGCATTAAGCTCAGAATTGGAGAAGGCTAAAGCTGACTTAGAAAATCAAAAAGCTA

AAGTTAAAAAGCAATTGACTGAAGAGTTGGCAGCTCAGAAAGCTGCTCTAGCAGAAAAAGAGGCAGAACTTAGTCGTCTTAAATCCTC

AGCTCCGTCTACTCAAGATAGCATTGTGGGTAATAATACCATGAAAGCACCGCAAGGCTATCCTCTTGAAGAACTTAAAAAATTAGAA

GCTAGTGGTTATATTGGATCAGCTAGTTACAATAATTATTACAAAGAGCATGCAGATCAAATTATTGCCAAAGCTAGTCCAGGTAATC

AATTAAATCAATACCAAGATATTCCAGCAGATCGTAATCGCTTTGTTGATCCCGATAATTTGACACCAGAAGTCCAAAATGAGCTAGC

GCAGTTTGCAGCTCACATGATTAATAGTGTA<u>cGtcGt</u>CAATTAGGTCTACCACCAGTTACTGTTACAGCAGGATCACAAGAATTTGCA

AGATTACTTAGTACCAGCTATAAGAAAACTCATGGTAATACAAGACCATCATTTGTCTACGGACAGCCAGGGGTATCAGGGCATTATG

GTGTTGGGCCTCATGATAAAACTATTATTGAAGACTCTGCCGGAGCGTCAGGGCTCATTCGAAATGATGATAACATGTACGAGAATAT

CGGTGCTTTTAACGATGTGCATACTGTGAATGGTATTAAACGTGGTATTTATGACAGTATCAAGTATATGCTCTTTACAGATCATTTA

CACGGAAATACATACGGCCATGCTATTAACTTTTTACGTGTAGATAAACATAACCCTAATGCGCCTGTTTACCTTGGATTTTCAACCA

GCAATGTAGGATCTTTGAATGAACACTTTGTAATGTTTCCAGAGTCTAACATTGCTAACCATCAACGCTTTAATAAGACCCCTATAAA

```
AGCCGTTGGAAGTACAAAAGATTATGCCCAAAGAGTAGGCACTGTATCTGATACTATTGCAGCGATCAAAGGAAAAGTAAGCTCATTA

GAAAATCGTTTGTCGGCTATTCATCAAGAAGCTGATATTATGGCAGCCCAAGCTAAAGTAAGTCAACTTCAAGGTAAATTAGCAAGCA

CACTTAAGCAGTCAGACAGCTTAAATCTCCAAGTGAGACAATTAAATGATACTAAAGGTTCTTTGAGAACAGAATTACTAGCAGCTAA

AGCAAAACAAGCACAACTCGAAGCTACTCGTGATCAATCATTAGCTAAGCTAGCATCGTTGAAAGCCGCACTGCACCAGACAGAAGCC

TTAGCAGAGCAAGCCGCAGCCAGAGTGACAGCACTGGTGGCTAAAAAAGCTCATTTGCAATATCTAAGGGACTTTAAATTGAATCCTA

ACCGCCTTCAAGTGATACGTGAGCGCATTGATAATACTAAGCAAGATTTGGCTAAAACTACCTCATCTTTGTTAAATGCACAAGAAGC

TTTAGCAGCCTTACAAGCTAAACAAAGCAGTCTAGAAGCTACTATTGCTACCACAGAACACCAGTTGACTTTGCTTAAAACCTTAGCT

AACGAAAAGGAATATCGCCACTTAGACGAAGATATAGCTACTGTGCCTGATTTGCAAGTAGCTCCACCTCTTACGGGCGTAAAACCGC

TATCATATAGTAAGATAGATACTACTCCGCTTGTTCAAGAAATGGTTAAAGAAACGAAACAACTATTAGAAGCTTCAGCAAGATTAGC

TGCTGAAAATACAAGTCTTGTAGCAGAAGCGCTTGTTGGCCAAACCTCTGAAATGGTAGCAAGTAATGCCATTGTGTCTAAAATCACA

TCTTCGATTACTCAGCCCTCATCTAAGACATCTTATGGCTCAGGATCTTCTACAACGAGCAATCTCATTTCTGATGTTGATGAAAGTA

CTCAAcGtGCGGCCGCACTCGAGCACCACCACCACCACCACCAC
```

Codon optimisation can also be used without a purification tag. Construct "40a-RR-Nat", SEQ ID NOS: 25 and 26, provides such an example. This construct comprises GAS 40 without the N-terminus leader sequence and the C-terminus transmembrane sequence, with three codon optimisations (and does not include a HIS tag sequence).

Different cloning vectors can be used to optimise expression in different host cells or under different culture conditions. The above discussed constructs used pET21b+ (Novagen) vector which includes an IPTG inducible promoter. As an alternative, an *E. coli/B. subtilis* expression shuttle vector such as pSM214gNH may be used. This vector uses a constitutive promoter instead of an IPTG inducible promoter. An example of a GAS 40 construct using this vector is denoted as "HIS-40a-NH", SEQ ID NOS 27 and 28. In this construct, both the N-terminus leader sequence and the C-terminus transmembrane sequence are removed, and a HIS tag is added to the N-terminus. Additional N-terminus amino acids are introduced with the cloning. In addition, two nucleotide changes which most likely occurred during PCR are indicated—neither of these changes results in amino acid changes.

As another alternative, the pSM214gCH shuttle vector may be used. An example of a GAS 40 construct using this vector is denoted as "HIS-40a-CH", SEQ ID NOS: 29 and 30. In this construct, the N-terminus leader sequence and the C-terminus transmembrane sequence are removed and the HIS tag is placed at the C-terminus Two additional amino acids are also introduced at the amino terminus. Three nucleotide changes introduced with the cloning are shown in the DNA sequence, with a resulting amino acid change indicated in the protein sequence (from amino acid F to S).

Codon optimisation can also be used with these alternative cloning vectors. GAS 40 construct "HIS-40a-RR-NH" comprises the "HIS-40a-NH" construct with three codon optimisations. HIS-40a-RR-NH is set forth in the sequence listing as SEQ ID NOS: 31 and 32.

Accordingly, the GAS antigens used in the invention may be produced recombinantly using expression constructs which facilitate their recombinant production. Preferred sequence modifications to facilitate expression may be selected from the group consisting of (1) the addition of a purification tag sequence and (2) codon optimisation.

As discussed above, Applicants have identified GAS 40 as being particularly suitable for use in immunogenic compositions, either alone or in combinations. The use of GAS 40 as a particularly effective GAS antigen is supported by its association with virulence, its surface localization, its effectiveness in bacterial opsonophagocytosis assays and in immunization challenge experiments. In addition, the potential horizontal acquisition of this virulence factor indicates that this antigen may be specific to GAS (relative to other Streptococcal bacteria). Further support for the antigenic properties of GAS 40 also includes the identification of coiled-coil regions within the GAS 40 two dimensional structure, and the low level homology of these regions with surface proteins of other Streptococcal bacteria, including some adhesion proteins.

Applicants' analysis of the location of GAS 40 within the Streptococcal pyogenes genome indicates that this virulence factor was likely acquired by GAS during evolution as a result of a horizontal gene transfer. FIG. 5A depicts GAS 40 within the GAS genome. It is preceded on the 5' end by a sequence designated "purine operon repressor" or "purR". It is followed on the 3' end by two sequences encoding ribosomal proteins designated "ribosomal protein S12", or "rpsL" and "ribosomal protein S7" or "rpsG". (Amino acid and polynucleotide sequences for these flanking genes are publicly available on GenBank. (PurR sequences can be found for example under Genbank reference GI: 15674250. RpsL sequences can be found for example under Genbank reference GI: 15674250. RpsG sequences can be found for example under Genbank reference GI: 15674250. Notably, there are two putative promoter sequences designated at the beginning of the rpsL sequence. FIG. 5B depicts a GAS mutant where a large portion of GAS 40 is deleted. The only portion of the GAS 40 sequence remaining corresponds to polynucleotides 1-97 of SEQ ID NO: 2. The deletion included one of the rpsL promoters, leaving the second, P*, intact. (The horizontal arrows underlining the schematic indicate the deleted region.)

FIG. 5C provides additional detail on the wildtype GAS sequence. Here, direct repeat sequences, designated "DR", are shown flanking the 5' and 3' ends of GAS 40. (The corresponding sequences in the GAS 40 deletion mutant are identified in FIG. 5D). These direct repeat sequences are approximately 8 basepairs. One example of such a basepair direct repeat comprises SEQ ID NO: 136. Such sequence motifs within a bacterial genome frequently indicate a horizontal gene transfer. In vivo infection experiments show that the GAS 40 deletion mutant is several logs less virulent than the wild type strain. (Details of this experiment are provided in Example 2).

The combination of the presence of the flanking direct repeat sequences and the virulence associated with GAS 40 strongly suggests that the GAS 40 sequence was horizontally acquired by *Streptococcus pyogenes* during evolution. Notably, while related purR and rpsL are present in related Streptococcal bacteria *Streptococcus agalactiae* and *Streptococcus mutants*, neither of these bacteria are known to have a GAS 40 homologue. (FIG. 5E schematically depicts the location of purR, rpsL, and rpsG homologues within *S. agalactiae* (Group B *Streptococcus*) and shows the percent homology of the GBS homologues with the GAS counterparts. Notably, GBS genomes generally only possess one of the direct repeat sequences—and do not contain a pair of the direct repeat sequences flanking the GAS 40 sequence.)

The surface location of GAS 40 is illustrated by the FACS diagram presented in FIG. 6. (Discussion of protocols relating to FACS analysis is presented in Example 1). FIG. 6 includes FACS diagrams for both the wild type GAS (designated DSM 2071, an M23 type of GAS) and the deletion mutant (designated DSM 2071.DELTA.40). The absorbance shift for the wild type strain indicates that GAS 40 is recognized on the surface of the bacteria by anti-GAS 40 antibodies (and that it is not recognized on the surface of the deletion mutant).

The surface exposure of GAS 40 is further demonstrated by a bacterial opsonophagocytosis assay illustrated in FIG. 7 and in Example 3. In this assay, GAS strains are incubated with preimmune and immune sera, polymorphonucleates and complement. (The immune sera is generated by mouse immunization with the indicated GAS protein.) Phagocytosis or growth of the bacteria are measured logarithmically. Positive histogram bars represent phagocytosis (or bacterial death). Negative histogram bars represent bacterial growth. As shown in FIG. 7, immune sera generated by each of the GAS 40 expressed proteins resulted in a reduction of bacteria (positive histogram bars).

Immunization challenge studies with GAS 40 are discussed in detail in Example 4. As shown in this example, GAS 40, as produced using various constructs, provides substantial protection in adult mice. Notably, most GAS 40 constructs provide almost as much protection as GAS M protein. (GAS M protein is used for comparison as it is known to be highly immunogenic. However, M protein is generally not regarded as a suitable GAS vaccine candidate as it varies widely among GAS strains and has epitopes with potential cross-reactivity with human tissues.) In addition, an N-terminus fragment of GAS 40 also provided significant protection in this model. The N-terminus fragment comprises about 292 amino acids from the N-terminus of GAS 40 overlaps with the first coiled-coil region. "40N-HIS" (SEQ ID NOS. 33 and 34) is an example of this GAS 40 fragment which comprises the coiled-coil region of GAS 40 and a C-terminus HIS tag.

(2) GAS 117

GAS 117 corresponds to M1 GenBank accession numbers GI: 13621679 and GI: 15674571, to M3 GenBank accession number GI: 21909852, to M18 GenBank accession number GI: 19745578, and is also referred to as 'Spy0448' (M1), 'SpyM3._0316' (M3), and 'SpyM18_0491' (M18). Examples of amino acid and polynucleotide sequences of GAS 117 of an M1 strain are set forth in the sequence listing as SEQ ID NOS: 35 and 36.

Preferred GAS 117 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5%, or more) to SEQ ED NO: 35; and/or (b) which is a fragment of at least n consecutive amino acids of SEQ ID NO: 35, wherein n is 7 or more (e.g. 8, 10, 12, 14, 16, 18, 20, 25, 30, 35, 40, 50, 60, 70, 80, 90, 100 or more). These GAS 117 proteins include variants (e.g. allelic variants, homologs, orthologs, paralogs, mutants, etc.) of SEQ ID NO: 35. Preferred fragments of (b) comprise an epitope from SEQ ID NO: 1. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 35. For example, in one embodiment, the underlined amino acid sequence at the N-terminus of SEQ ID NO: 35 (shown below) is removed. (SEQ ID NO: 37 comprises the removed N-terminal amino acid sequence. SEQ ID NO: 38 comprises a fragment of GAS 117 without the N-terminal amino acid sequence). Other fragments omit one or more domains of the protein (e.g. omission of a signal peptide, of a cytoplasmic domain, of a transmembrane domain, or of an extracellular domain).

SEQ ID NO: 35
<u>MTLKKHYYLLSLLALVTVGA</u>AFNTSQSVSAQVYSNEGYHQHLTDEKSH

LQYSKDNAQLQLRNILDGYQNDLGRHYSSYYYYNLRTVMGLSSEQDIE

KHYEELKNKLHDMYNHY (3) GAS 130

GAS 130 corresponds to M1 GenBank accession numbers GI: 13621794 and GI: 15674677, to M3 GenBank accession number GI: 21909954, to M18 GenBank accession number GI: 19745704, and is also referred to as 'Spy0591' (M1), 'SpyM3_0418' (M3), and 'SpyM18_0660' (M18). GAS 130 has potentially been identified as a putative protease. Examples of amino acid and polynucleotide sequences of GAS 130 of an M1 strain are set forth in the sequence listing as SEQ ID NOS: 39 and 40.

Preferred GAS 130 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 39; and/or (b) which is a fragment of at least n consecutive amino acids of SEQ ID NO: 39, wherein n is 7 or more (e.g. 8, 10, 12, 14, 16, 18, 20, 25, 30, 35, 40, 50, 60, 70, 80, 90, 100, 150, or more). These GAS 130 proteins include variants (e.g. allelic variants, homologs, orthologs, paralogs, mutants, etc.) of SEQ ID NO: 39. Preferred fragments of (b) comprise an epitope from SEQ ID NO: 39. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 39. Other fragments omit one or more domains of the protein (e.g. omission of a signal peptide, of a cytoplasmic domain, of a transmembrane domain, or of an extracellular domain).

(4) GAS 277

GAS 277 corresponds to M1 GenBank accession numbers GI: 13622962 and GI: 15675742, to M3 GenBank accession number GI: 21911206, to M18 GenBank accession number GI: 19746852, and is also referred to as 'Spy1939' (M1), 'SpyM3_1670' (M3), and 'SpyM18_2006' (M18). Amino acid and polynucleotide sequences of GAS 277 of an M1 strain are set forth in the sequence listing as SEQ ID NOS: 41 and 42.

Preferred GAS 277 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 41; and/or (b) which is a fragment of at least n consecutive amino acids of SEQ ID NO: 41, wherein n is 7 or more (e.g. 8, 10, 12, 14, 16, 18, 20, 25, 30, 35, 40, 50, 60, 70, 80, 90, 100, or more). These GAS 277 proteins include variants (e.g. allelic variants, homologs, orthologs, paralogs, mutants, etc.) of SEQ ID NO: 41. Preferred fragments of (b) comprise an epitope from SEQ ID NO: 41. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 41. For example, in one embodiment, the underlined amino acid sequence at the N-terminus of SEQ ID NO: 41 (shown below) is removed. (SEQ ID NO: 43 comprises the underlined N-terminal amino acid. SEQ ID NO: 44 comprises a fragment of GAS 277 with the N-terminal amino acid sequence removed). Other fragments omit one or more domains of the protein (e.g. omission of a signal peptide, of a cytoplasmic domain, of a transmembrane domain, or of an extracellular domain).

SEQ ID NO: 41
MTTMQKTISLLSLALLIGLLGTSGKAISVYAQDQHTDNVIAESTISQV

SVEASMRGTEPYIDATVTTDQPVRQPTQATITLKDASDNTINSWVYTM

AAQQRRFTAWFDLTGQKSGDYHVTVTVHTQEKAVTGQSGTVHFDQNKA

RKTPTNMQQKDTSKAMTNSVDVDTKAQTNQSANQEIDSTSNPFRSATN

HRSTSLKRSTKNEKLTPTASNSQKNGSNKTKMLVDKEEVKPTSKRGFP

WVLLGLVVSLAAGLFIAIQKVSRRK (5) GAS 236

GAS 236 corresponds to M1 GenBank accession numbers GI: 13622264 and GI: 15675106, M3 GenBank accession number GI: 21910321, and to M18 GenBank accession number GI: 19746075, and is also referred to as 'Spy1126' (M1), 'SpyM3_0785' (M3), and 'SpyM18_1087' (M18). Amino acid and polynucleotide sequences of GAS 236 from an M1 strain are set forth in the sequence listing as SEQ ID NOS: 45 and 46.

Preferred GAS 236 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 45; and/or (b) which is a fragment of at least n consecutive amino acids of SEQ ID NO: 45, wherein n is 7 or more (e.g. 8, 10, 12, 14, 16, 18, 20, 25, 30, 35, 40, 50, 60, 70, 80, 90, 100, 150 or more). These GAS 236 proteins include variants (e.g. allelic variants, homologs, orthologs, paralogs, mutants, etc.) of SEQ ID NO: 45. Preferred fragments of (b) comprise an epitope from SEQ ID NO: 45. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 45. For example, in one embodiment, the underlined amino acid sequence at the N-terminus of SEQ ID NO: 45 (shown below) is removed. (SEQ ID NO: 47 comprises the N-terminus amino acid sequence. SEQ ID NO: 48 comprises a fragment of GAS 236 with the N-terminus sequence removed). Other fragments omit one or more domains of the protein (e.g. omission of a signal peptide, of a cytoplasmic domain, of a transmembrane domain, or of an extracellular domain).

SEQ ID NO: 45
MTQMNYTGKVKRVAIIANGKYQSKRVASKLFSVFKDDPDFYLSKKNPD

IVISIGGDGMLLSAFHMYEKELDKVRFVGIHTGHLGFYTDYRDFEVDK

LIDNLRKDKGEQISYPILKVAITLDDGRVVKARALNEATVKRIEKTMV

ADVIINHVKFESFRGDGISVSTPTGSTAYNKSLGGAVLHPTIEALQLT

EISSLNNRVFRTLGSSIIIPKKDKIELVPKRLGIYTISIDNKTYQLKN

VTKVEYFIDDEKIHFVSSPSHTSFWERVKDAFIGEIDS (6) GAS 389

GAS 389 corresponds to M1 GenBank accession numbers GI: 13622996 and GI: 15675772, to M3 GenBank accession number GI: 21911237, to M18 GenBank accession number GI: 19746884, and is also referred to as 'Spy1981' (M1), 'SpyM3_1701' (M3), 'SpyM18_2045' (M18) and 'relA'. GAS 389 has also been identified as a (p)ppGpp synthetase. Amino acid and polynucleotide sequences of GAS 389 from an M1 strain are set forth in the sequence listing as SEQ ID NOS: 49 and 50.

Preferred GAS 389 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 49; and/or (b) which is a fragment of at least n consecutive amino acids of SEQ ID NO: 49, wherein n is 7 or more (e.g. 8, 10, 12, 14, 16, 18, 20, 25, 30, 35, 40, 50, 60, 70, 80, 90, 100, 150, 200, 250 or more). These GAS 389 proteins include variants (e.g. allelic variants, homologs, orthologs, paralogs, mutants, etc.) of SEQ ID NO: 49. Preferred fragments of (b) comprise an epitope from SEQ ID NO: 49. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 49. Other fragments omit one or more domains of the protein (e.g. omission of a signal peptide, of a cytoplasmic domain, of a transmembrane domain, or of an extracellular domain).

(7) GAS 504

GAS 504 corresponds to M1 GenBank accession numbers GI: 13622806 and GI: 15675600, to M3 GenBank accession number GI: 21911061, to M18 GenBank accession number GI: 19746708, and is also referred to as 'Spy1751' (M1), 'SpyM3_1525', 'SpyM18_1823' (M18) and 'fabK'. GAS 504 has also been identified as a putative trans-2-enoyl-ACP reductase II Amino acid and polynucleotide sequences of GAS 504 of an M1 strain are set forth below and in the sequence listing as SEQ ID NOS: 51 and 52.

Preferred GAS 504 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 51; and/or (b) which is a fragment of at least n consecutive amino acids of SEQ ID NO: 51, wherein n is 7 or more (e.g. 8, 10, 12, 14, 16, 18, 20, 25, 30, 35, 40, 50, 60, 70, 80, 90, 100, 150 or more). These GAS 504 proteins include variants (e.g. allelic variants, homologs, orthologs, paralogs, mutants, etc.) of SEQ ID NO: 51. Preferred fragments of (b) comprise an epitope from SEQ ID NO: 51. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 51. Other fragments omit one or more domains of the protein (e.g. omission of a signal peptide, of a cytoplasmic domain, of a transmembrane domain, or of an extracellular domain).

(8) GAS 509

GAS 509 corresponds to M1 GenBank accession numbers GI: 13622692 and GI: 15675496, to M3 GenBank accession number GI: 21910899, to M18 GenBank accession number GI: 19746544, and is also referred to as 'Spy1618' (M1), 'SpyM3_1363' (M3), 'SpyM18_1627' (M18) and 'cysM'. GAS 509 has also been identified as a putative O-acetylserine lyase Amino acid and polynucleotide sequences of GAS 509 of an M1 strain are set forth in the sequence listing as SEQ ID NOS: 53 and 54.

Preferred GAS 509 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 53; and/or (b) which is a fragment of at least n consecutive amino acids of SEQ ID NO: 53, wherein n is 7 or more (e.g. 8, 10, 12, 14, 16, 18, 20, 25, 30, 35, 40, 50, 60, 70, 80, 90, 100, or more). These GAS 509 proteins include variants (e.g. allelic variants, homologs, orthologs, paralogs, mutants, etc.) of SEQ ID NO: 53. Preferred fragments of (b) comprise an epitope from SEQ ID NO: 53. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 53. For example, in one embodiment, the underlined amino acid sequence at the C-terminus of SEQ ID NO: 53 (shown below) is removed. (SEQ ID NO: 55 comprises the C-terminus amino acid sequence. SEQ ID NO: 56 comprises a fragment of GAS 509 with the C-terminus sequence removed). Other fragments omit one or more domains of the protein (e.g. omission of a signal peptide, of a cytoplasmic domain, of a transmembrane domain, or of an extracellular domain).

SEQ ID NO: 53
MTKIYKTITELVGQTPIIKLNRLIPNEAADVYVKLEAFNPGSSVKDRI

ALSMIEAAEAEGLISPGDVIIEFTSGNTGIGLAWVGAAKGYRVIIVMP

ETMSLERRQIIQAYGAELVLTPGAEGMKGAIAKAETLAIELGAWMPMQ

FNNPANPSIHEKTTAQEILEAFKEISLDAFVSGVGTGGTLSGVSHVLK

KANPETVIYAVEAEESAVLSGQEPGPHKIQGISAGFIPNTLDTKAYDQ

IIRVKSKDALETARLTGAKEG<u>FLVGISSGAALYAAIEVAKQLGKGKHV</u>

<u>LTILPDNGERYLSTELYDVPVIKTK</u>

(9) GAS 366

GAS 366 corresponds to M1 GenBank accession numbers GI: 13622612, GI: 15675424 and GI: 30315979, to M3 GenBank accession number GI: 21910712, to M18 GenBank accession number GI: 19746474, and is also referred to as 'Spy1525' (M1), 'SpyM3_1176' (M3), 'SpyM18_1542' (M18) and 'murD'. GAS 366 has also been identified as a UDP-N-acetylemuramoylalanine-D-glutamate ligase or a D-glutamic acid adding enzyme Amino acid and polynucleotide sequences of GAS 366 of an M1 strain are set forth in the sequence listing as SEQ ID NOS: 57 and 58.

Preferred GAS 366 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 57; and/or (b) which is a fragment of at least n consecutive amino acids of SEQ ID NO: 57, wherein n is 7 or more (e.g. 8, 10, 12, 14, 16, 18, 20, 25, 30, 35, 40, 50, 60, 70, 80, 90, 100, 150 or more). These GAS 366 proteins include variants (e.g. allelic variants, homologs, orthologs, paralogs, mutants, etc.) of SEQ ID NO: 57. Preferred fragments of (b) comprise an epitope from SEQ ID NO: 57. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 57. For example, in one embodiment, the underlined amino acid sequence at the N-terminus of SEQ ID NO: 57 (shown below) is removed. (SEQ ID NO: 59 comprises the N-terminus leader sequence. SEQ ID NO: 60 comprises a fragment of GAS 366 where the N-terminus sequence is removed). Other fragments omit one or more domains of the protein (e.g. omission of a signal peptide, of a cytoplasmic domain, of a transmembrane domain, or of an extracellular domain).

SEQ ID NO: 57
<u>MKVISNFQNKKILILGLAKSGEAAAKLLTKLGALVTVNDSKPFDQNPA</u>

AQALLEEGIKVICGSHPVELLDENFEYMVKNPGIPYDNPMVKRALAKE

IPILTEVELAYFVSEAPIIGITGSNGKTTTTTMIADVLNAGGQSALLS

GNIGYPASKVVQKAIAGDTLVMELSSFQLVGVNAFRPHIAVITNLMPT

HLDYHGSFEDYVAAKWMIQAQMTESDYLILNANQEISATLAKTTKATV

IPFSTQKVVDGAYLKDGILYFKEQAIIAATDLGVPGSHNIENALATIA

VAKLSGIADDIIAQCLSHFGGVKHRLQRVGQIKDITFYNDSKSTNILA

TQKALSGFDNSRLILIAGGLDRGNEFDDLVPDLLGLKQMIILGESAER

MKRAANKAEVSYLEARNVAEATELAFKLAQTGDTILLSRANASWDMYP

NFEVRGDEFLATFDCLRGDA

(10) GAS 159

GAS 159 corresponds to M1 GenBank accession numbers GI: 13622244 and GI: 15675088, to M3 GenBank accession number GI: 21910303, to M18 GenBank accession number GI: 19746056, and is also referred to as 'Spy1105' (M1), 'SpyM3_0767' (M3), 'SpyM18_1067' (M18) and 'potD'. GAS 159 has also been identified as a putative spermidine/putrescine ABC transporter (a periplasmic transport protein). Amino acid and polynucleotide sequences of GAS 159 of an M1 strain are set forth below and in the sequence listing as SEQ ID NOS: 61 and 62.

SEQ ID NO: 61
M<u>RKLYSFLAGVLGVIVILTSLSFI</u>LQKKSGSGSQSDKLVIYNWGDYID

PALLKKFTKETGIEVQYETFDSNEAMYTKIKQGGTTYDIAVPSDYTID

KMIKENLLNKLDKSKLVGMDNIGKEFLGKSFDPQNDYSLPYFWGTVGI

VYNDQLVDKAPMHWEDLWRPEYKNSIMLIDGAREMLGVGLTTFGYSVN

SKNLEQLQAAERKLQQLTPNVKAIVADEMKGYMIQGDAAIGITFSGEA

SEMLDSNEHLHYIVPSEGSNLWFDNLVLPKTMKHEKEAYAPLNFINRP

ENAAQNAAYIGYATPNKKAKALLPDEIKNDPAFYPTDDIIKKLEVYDN

LGSR<u>WLGIYNDLYLQFKMYRK</u>

-continued

SEQ ID NO: 62

ATGCGTAAACTTTATTCCTTTCTAGCAGGAGTTTTGGGTGTTATTGTT

ATTTTAACAAGTCTTTCTTTCATCTTGCAGAAAAGCAGGGCGGAACCA

CTTACGACATTGCTGTTCCTAGTGATTACACCATTGATAAAATGATCA

AAGAAAACCTACTCAATAAGCTTGATAAGTCAAAATTAGTTGGCATGG

ATAATATCGGGAAGAATTTTTAGGGAAAAGCTTTGACCCACAAAACG

ACTATTCTTTGCCTTATTTCTGGGGAACCGTTGGGATTGTTTATAATG

ATCAATTAGTTGATAAGGCGCCTATGCACTGGGAAGATCTGTGGCGTC

CAGAATATAAAAATAGTATTATGCTGATTGATGGAGCGCGTGAAATGC

TAGGGGTTGGTTTAACAACTTTTGGTTATAGTGTGAATTCTAAAAATC

TAGAGCAGTTGCAGGCAGCCGAGAGAAAACTGCAGCAGTTGACGCCGA

ATGTTAAAGCCATTGTAGCAGATGAGATGAAAGGCTACATGATTCAAG

GTGACGCTGCTATTGGAATTACCTTTTCTGGTGAAGCCAGTGAGATGT

TAGATAGTAACGAACACCTTCACTACATCGTGCCTTCAGAAGGGTCTA

ACCTTTGGTTTGATAATTTGGTACTACCAAAAACCATGAAACACGAAA

AAGAAGCTTATGCTTTTTTGAACTTTATCAATCGTCCTGAAAATGCTG

CGCAAAATGCTGCATATATTGGTTATGCGACACCAAATAAAAAAGCCA

AGGCCTTACTTCCAGATGAGATAAAAAATGATCCTGCTTTTTATCCAA

CAGATGACATTATCAAAAAATTGGAAGTTTATGACAATTTAGGGTCAA

GATGGTTGGGGATTTATAATGATTTATACCTCCAATTTAAAATGTATC

GCAAATAA

Preferred GAS 159 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 61; and/or (b) which is a fragment of at least n consecutive amino acids of SEQ ID NO: 61, wherein n is 7 or more (e.g. 8, 10, 12, 14, 16, 18, 20, 25, 30, 35, 40, 50, 60, 70, 80, 90, 100, 150 or more). These GAS 159 proteins include variants (e.g. allelic variants, homologs, orthologs, paralogs, mutants, etc.) of SEQ ID NO: 61. Preferred fragments of (b) comprise an epitope from SEQ ID NO: 61. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 61. For example, in one embodiment, the underlined amino acid sequence at the N-terminus of SEQ ID NO: 61 (shown below) is removed. (SEQ ID NO: 63 comprises the N-terminus leader amino acid sequence. SEQ ID NO: 64 comprises a fragment of GAS 159 where the N-terminus leader amino acid sequence is removed). In another example, the underlined amino acid sequence at the C-terminus of SEQ ID NO: 61 is removed. (SEQ ID NO: 65 comprises the C-terminus hydrophobic region. SEQ ID NO: 66 comprises a fragment of GAS 159 where the C-terminus hydrophobic region is removed. SEQ ID NO: 67 comprises a fragment of GAS 159 where both the N-terminus leader sequence and C-terminus hydrophobic region are removed.) Other fragments omit one or more domains of the protein (e.g. omission of a signal peptide, of a cytoplasmic domain, of a transmembrane domain, or of an extracellular domain).

SEQ ID NO: 61

MRKLYSFLAGVLGVIVILTSLSFILQKKSGSGSQSDKLVIYNWGDYID

PALLKKFTKETGIEVQYETFDSNEAMYTKIKQGGTTYDIAVPSDYTID

KMIKENLLNKLDKSKLVGMDNIGKEFLGKSFDPQNDYSLPYFWGTVGI

VYNDQLVDKAPMHWEDLWRPEYKNSIMLIDGAREMLGVGLTTFGYSVN

SKNLEQLQAAERKLQQLTPNVKAIVADEMKGYMIQGDAAIGITFSGEA

SEMLDSNEHLHYIVPSEGSNLWFDNLVLPKTMKHEKEAYAFLNFINRP

ENAAQNAAYIGYATPNKKAKALLPDEIKNDPAFYPTDDIIKKLEVYDN

LGSRWLGIYNDLYLQFKMYRK

(11) GAS 217

GAS 217 corresponds to M1 GenBank accession numbers GI: 13622089 and GI: 15674945, to M3 GenBank accession number GI: 21910174, to M18 GenBank accession number GI: 19745987, and is also referred to as 'Spy0925' (M1), 'SpyM3_0638' (M3), and 'SpyM18_0982' (M8). GAS 217 has also been identified as a putative oxidoreductase. Amino acid and polynucleotide sequences of GAS 217 of an M1 strain are set forth in the sequence listing as SEQ ID NOS: 68 and 69.

Preferred GAS 217 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 68; and/or (b) which is a fragment of at least n consecutive amino acids of SEQ ID NO: 68, wherein n is 7 or more (e.g. 8, 10, 12, 14, 16, 18, 20, 25, 30, 35, 40, 50, 60, 70, 80, 90, 100, or more). These GAS 217 proteins include variants (e.g. allelic variants, homologs, orthologs, paralogs, mutants, etc.) of SEQ ID NO: 68. Preferred fragments of (b) comprise an epitope from SEQ ID NO: 68. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 68. Other fragments omit one or more domains of the protein (e.g. omission of a signal peptide, of a cytoplasmic domain, of a transmembrane domain, or of an extracellular domain).

(12) GAS 309

GAS 309 corresponds to M1 GenBank accession numbers GI: 13621426 and GI: 15674341, to M3 GenBank accession number GI: 21909633, to M18 GenBank accession number GI: 19745363, and is also referred to as 'Spy0124' (M1), 'SpyM3_0097' (M3), 'SpyM18_0205' (M18), 'nra' and 'rofA'. GAS 309 has also been identified as a regulatory protein and a negative transcriptional regulator Amino acid and polynucleotide sequences of GAS 309 of an M1 strain are set forth in the sequence listing as SEQ ID NOS: 70 and 71.

Preferred GAS 309 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 70; and/or (b) which is a fragment of at least n consecutive amino acids of SEQ ID NO: 70, wherein n is 7 or more (e.g. 8, 10, 12, 14, 16, 18, 20, 25, 30, 35, 40, 50, 60, 70, 80, 90, 100, or more). These GAS 309 proteins include variants (e.g. allelic variants, homologs, orthologs, paralogs, mutants, etc.) of SEQ ID NO: 70. Preferred fragments of (b) comprise an epitope front SEQ ID NO: 70. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 70. Other fragments omit one or more domains of the protein (e.g. omission of a signal peptide, of a cytoplasmic domain, of a transmembrane domain, or of an extracellular domain).

(13) GAS 372

GAS 372 corresponds to M1 GenBank accession numbers GI: 13622698 and GI: 15675501, to M3 GenBank accession number GI: 21910905, to M18 GenBank accession number GI: 19746500 and is also referred to as 'Spy1625' (M1), 'SpyM3_1369' (M3), and 'SpyM18_1634' (M18). GAS 372 has also been identified as a putative protein kinase or a putative eukaryotic-type serine/threonine kinase. Amino acid and polynucleotide sequences of GAS 372 of an M1 strain are set forth in the sequence listing as SEQ ID NOS: 72 and 73.

Preferred GAS 372 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 72; and/or (b) which is a fragment of at least n consecutive amino acids of SEQ ID NO: 72, wherein n is 7 or more (e.g. 8, 10, 12, 14, 16, 18, 20, 25, 30, 35, 40, 50, 60, 70, 80, 90, 100, 150, 200, 250 or more). These GAS 372 proteins include variants (e.g. allelic variants, homologs, orthologs, paralogs, mutants, etc.) of SEQ ID NO: 72. Preferred fragments of (b) comprise an epitope from SEQ ID NO: 72. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 72. Other fragments omit one or more domains of the protein (e.g. omission of a signal peptide, of a cytoplasmic domain, of a transmembrane domain, or of an extracellular domain).

(14) GAS 039

GAS 039 corresponds to M1 GenBank accession numbers GI: 13621542 and GI: 15674446, to M3 GenBank accession number GI: 21909730, to M18 GenBank accession number GI: 19745398 and is also referred to as 'Spy0266' (M1), 'SpyM3_0194' (M3), and 'SpyM18_0250' (M18). Amino acid and polynucleotide sequences of GAS 039 of an M1 strain are set forth in the sequence listing as SEQ ID NOS: 74 and 75.

Preferred GAS 039 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 74; and/or (b) which is a fragment of at least n consecutive amino acids of SEQ ID NO: 74, wherein n is 7 or more (e.g. 8, 10, 12, 14, 16, 18, 20, 25, 30, 35, 40, 50, 60, 70, 80, 90, 100, 150, or more). These GAS 039 proteins include variants (e.g. allelic variants, homologs, orthologs, paralogs, mutants, etc.) of SEQ ID NO: 74. Preferred fragments of (b) comprise an epitope from SEQ ID NO: 74. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 74. Other fragments omit one or more domains of the protein (e.g. omission of a signal peptide, of a cytoplasmic domain, of a transmembrane domain, or of an extracellular domain).

(15) GAS 042

GAS 042 corresponds to M1 GenBank accession numbers GI: 13621559 and GI: 15674461, to M3 GenBank accession number GI: 21909745, to M18 GenBank accession number GI: 19745415, and is also referred to as 'Spy0287' (M1), 'SpyM3_0209' (M3), and 'SpyM18_0275' (M18). Amino acid and polynucleotide sequences of GAS 042 of an M1 strain are set forth in the sequence listing as SEQ ID NOS: 76 and 77.

Preferred GAS 042 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 76; and/or (b) which is a fragment of at least n consecutive amino acids of SEQ ID NO: 76, wherein n is 7 or more (e.g. 8, 10, 12, 14, 16, 18, 20, 25, 30, 35, 40, 50, 60, 70, 80, 90, 100, 150, or more). These GAS 042 proteins include variants (e.g. allelic variants, homologs, orthologs, paralogs, mutants, etc.) of SEQ ID NO: 76. Preferred fragments of (b) comprise an epitope from SEQ ID NO: 76. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 76. Other fragments omit one or more domains of the protein (e.g. omission of a signal peptide, of a cytoplasmic domain, of a transmembrane domain, or of an extracellular domain).

(16) GAS 058

GAS 058 corresponds to M1 GenBank accession numbers GI: 13621663 and GI: 15674556, to M3 GenBank accession number GI: 21909841, to M18 GenBank accession number GI: 19745567 and is also referred to as 'Spy0430' (M1), 'SpyM3_0305' (M3), and 'SpyM18_0477' (M18). Amino acid and polynucleotide sequences of GAS 058 of an M1 strain are set forth in the sequence listing as SEQ ID NOS: 78 and 79.

Preferred GAS 058 proteins for use with the invention comprise an amino acid sequence: (a) having 50% or more identity (e.g. 60%, 65%, 70%, 75%, 80%, 85%, 90%, 91%, 92%, 93%, 98%, 99%, 99.5% or more) to SEQ ID NO: 78; and/or (b) which is a fragment of at least it consecutive amino acids of SEQ ID NO: 78, wherein n is 7 or more (e.g. 8, 10, 12, 14, 16, 18, 20, 25, 30, 35, 40, 50, 60, 70, 80, 90, 100, 150, or more). These GAS 058 proteins include variants (e.g. allelic variants, homologs, orthologs, paralogs, mutants, etc.) of SEQ ID NO: 78. Preferred fragments of (b) comprise an epitope from SEQ ID NO: 78. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 78. For example, in one embodiment, the underlined amino acid sequence at the N-terminus of SEQ ID NO: 78 (shown below) is removed. (SEQ ID NO: 80 comprises the N-terminal leader sequence. SEQ ID NO: 81 comprises a fragment of GAS 58 where the N-terminal leader sequence is removed.) Other fragments omit one or more domains of the protein (e.g. omission of a signal peptide, of a cytoplasmic domain, of a transmembrane domain, or of an extracellular domain).

```
                                         SEQ ID NO: 78
MKWSGFMKTKSKRFLNLATLCLALLGTTLLMAHPVQAEVISKRDYMTR

FGLGDLEDDSANYPSNLEARYKGYLEGYEKGLKGDDIPERPKIQVPED

VQPSDHGDYRDGYEEGFGEGQHKRDPLETEAEDDSQGGRQEGRQGHQE

GADSSDLNVEESDGLSVIDEVVGVIYQAFSTIWTYLSGLF
```

(17) GAS 290

GAS 290 corresponds to M1 GenBank accession numbers GI: 13622978 and GI: 15675757, to M3 GenBank accession number GI: 21911221, to M18 GenBank accession number GI: 19746869 and is also referred to as 'Spy1959' (M1), 'SpyM3_1685' (M3), and 'SpyM18_2026' (M18). Amino acid and polynucleotide sequences of GAS 290 of an M1 strain are set forth in the sequence listing as SEQ ID NOS: 82 and 83.

Preferred GAS 290 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 82; and/or (b) which is a fragment of at least n consecutive amino acids of SEQ ID NO: 82, wherein n is 7 or more (e.g. 8, 10, 12, 14, 16, 18, 20, 25, 30, 35, 40, 50, 60, 70, 80, 90, 100 or more). These GAS 290 proteins include variants (e.g. allelic variants, homologs, orthologs, paralogs, mutants, etc.) of SEQ ID NO: 82. Preferred fragments of (b) comprise an epitope from SEQ ID NO: 82. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 82. Other fragments omit one or more domains of the protein (e.g. omission of a signal peptide, of a cytoplasmic domain, of a transmembrane domain, or of an extracellular domain).

(18) GAS 511

GAS 511 corresponds to M1 GenBank accession numbers GI: 13622798 and GI: 15675592, to M3 GenBank accession number GI: 21911053, to M18 GenBank accession number GI: 19746700 and is also referred to as 'Spy1743' (M1), 'SpyM3_1517' (M3), 'SpyM18_1815' (M18) 'accA' Amino acid and polynucleotide sequences of GAS 511 of an M1 strain are set forth in the sequence listing as SEQ ID NOS: 84 and 85.

Preferred GAS 511 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 84; and/or (b) which is a fragment of at least n consecutive amino acids of SEQ ID NO: 84, wherein n is 7 or more (e.g. 8, 10, 12, 14, 16, 18, 20, 25, 30, 35, 40, 50, 60, 70, 80, 90, 100 or more). These GAS 511 proteins include variants (e.g. allelic variants, homologs, orthologs, paralogs, mutants, etc.) of SEQ ID NO: 84. Preferred fragments of (b) comprise an epitope from SEQ ID NO: 84. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 84. Other fragments omit one or more domains of the protein (e.g. omission of a signal peptide, of a cytoplasmic domain, of a transmembrane domain, or of an extracellular domain).

(19) GAS 533

GAS 533 corresponds to M1 GenBank accession numbers GI: 13622912 and GI: 15675696, to M3 GenBank accession number GI: 21911157, to M18 GenBank accession number GI: 19746804 and is also referred to as 'Spy1877' (M1), 'SpyM3_1621' (M3), 'SpyM18_1942' (M18) and 'glnA'. GAS 533 has a been identified as a putative glutamine synthetase. Amino acid and polynucleotide sequences of GAS 533 of an M1 strain are set forth in the sequence listing as SEQ ID NOS: 86 and 87.

Preferred GAS 533 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 86; and/or (b) which is a fragment of at least n consecutive amino acids of SEQ ID NO: 86, wherein n is 7 or more (e.g. 8, 10, 12, 14, 16, 18, 20, 25, 30, 35, 40, 50, 60, 70, 80, 90, 100, 150, 200 or more). These GAS 533 proteins include variants (e.g. allelic variants, homologs, orthologs, paralogs, mutants, etc.) of SEQ ID NO: 86. Preferred fragments of (b) comprise an epitope from SEQ ID NO: 86. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 86. Other fragments omit one or more domains of the protein (e.g. omission of a signal peptide, of a cytoplasmic domain, of a transmembrane domain, or of an extracellular domain).

(20) GAS 527

GAS 527 corresponds to M1 GenBank accession numbers GI: 13622332, GI: 15675169, and GI: 24211764, to M3 GenBank accession number GI: 21910381, to M18 GenBank accession number GI: 19746136, and is also referred to as 'Spy1204' (M1), 'SpyM3_0845' (M3), 'SpyM18_1155' (M18) and 'guaA'. GAS 527 has also been identified as a putative GMP synthetase (glutamate hydrolyzing) (glutamate amidotransferase) Amino acid and polynucleotide sequences of GAS 527 of an M1 strain are set forth in the sequence listing as SEQ ID NOS: 88 and 89.

Preferred GAS 527 proteins for use with the invention comprise an amino acid sequence: (a) having 50% or more identity (e.g. 60%, 65%, 70%, 75%, 80%, 85%, 90%, 91%, 92%, 93%, 98%, 99%, 99.5% or more) to SEQ ID NO: 88; and/or (b) which is a fragment of at least n consecutive amino acids of SEQ ID NO: 88, wherein n is 7 or more (e.g. 8, 10, 12, 14, 16, 18, 20, 25, 30, 35, 40, 50, 60, 70, 80, 90, 100, 150, 200 or more). These GAS 527 proteins include variants (e.g. allelic variants, homologs, orthologs, paralogs, mutants, etc.) of SEQ ID NO: 88. Preferred fragments of (b) comprise an epitope from SEQ ID NO: 88. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 88. Other fragments omit one or more domains of the protein (e.g. omission of a signal peptide, of a cytoplasmic domain, of a transmembrane domain, or of an extracellular domain).

(21) GAS 294

GAS 294 corresponds to M1 GenBank accession numbers GI: 13622306, GI: 15675145, and GI: 26006773, to M3 GenBank accession number GI: 21910357, to M18 GenBank accession number GI: 19746111 and is also referred to as 'Spy1173' (M1), 'SpyM3_0821' (M3), 'SpyM18_1125' (M18) and 'gid'. GAS 294 has also been identified as a putative glucose-inhibited division protein. Amino acid and polynucleotide sequences of GAS 294 of an M1 strain are set forth in the sequence listing as SEQ ID NOS: 90 and 91.

Preferred GAS 294 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 90; and/or (b) which is a fragment of at least n consecutive amino acids of SEQ ID NO: 90, wherein n is 7 or more (e.g. 8, 10, 12, 14, 16, 18, 20, 25, 30, 35, 40, 50, 60, 70, 80, 90, 100, 150, 200 or more). These GAS 294 proteins include variants (e.g. allelic variants, homologs, orthologs, paralogs, mutants, etc.) of SEQ ID NO: 90. Preferred fragments of (b) comprise an epitope from SEQ ID NO: 90. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 90. Other fragments omit one or more domains of the protein (e.g. omission of a signal peptide, of a cytoplasmic domain, of a transmembrane domain, or of an extracellular domain).

(22) GAS 253

GAS 253 corresponds to M1 GenBank accession numbers GI: 13622611, GI: 15675423, and GI: 21362716, to M3 GenBank accession number GI: 21910711, to M18 GenBank accession number GI: 19746473 and is also referred to as 'Spy1524' (M1), 'SpyM3_1175' (M3), 'SpyM18_1541' (M18) and 'murG'. GAS 253 has also been identified as a putative undecaprenyl-PP-MurNAc-pentapeptide-UDPG1cNAc GlcNAc transferase Amino acid and polynucleotide sequences of GAS 253 of an M1 strain are set forth in the sequence listing as SEQ ID NOS: 92 and 93.

Preferred GAS 253 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 92; and/or (b) which is a fragment of at least n consecutive amino acids of SEQ ID NO: 92, wherein n is 7 or more (e.g. 8, 10, 12, 14, 16, 18, 20, 25, 30, 35, 40, 50, 60, 70, 80, 90, 100, 150, 200 or more). These GAS 253 proteins include variants (e.g. allelic variants, homologs, orthologs, paralogs, mutants, etc.) of SEQ ID NO: 92. Preferred fragments of (b) comprise an epitope from SEQ ID NO: 92. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 92. Other fragments omit one or more domains of the protein (e.g. omission of a signal peptide, of a cytoplasmic domain, of a transmembrane domain, or of an extracellular domain).

(23) GAS 529

GAS 529 corresponds to M1 GenBank accession numbers GI: 13622403, GI: 15675233, and GI: 21759132, to M3 GenBank accession number GI: 21910446, to M18 GenBank accession number GI: 19746203 and is also referred to as 'Spy1280' (M1), 'SpyM3_0910' (M3), 'SpyM18_1228' (M18) and 'glmS'. GAS 529 has also been identified as a putative L-glutamine-D-fructose-6-phosphate aminotransferase (Glucosamine-6-phosphate synthase) Amino acid and polynucleotide sequences of GAS 529 of an M1 strain are set forth below and in the sequence listing as SEQ ID NOS: 94 and 95.

Preferred GAS 529 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 94; and/or (b) which is a fragment of at least it consecutive amino acids of SEQ ID NO: 94, wherein n is 7 or more (e.g. 8, 10, 12, 14, 16, 18, 20, 25, 30, 35, 40, 50, 60, 70, 80, 90, 100, 150, 200 or more). These GAS 529 proteins include variants (e.g. allelic variants, homologs, orthologs, paralogs, mutants, etc.) of SEQ ID NO: 94. Preferred fragments of (b) comprise an epitope from SEQ ID NO: 94. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 94. Other fragments omit one or more domains of the protein (e.g. omission of a signal peptide, of a cytoplasmic domain, of a transmembrane domain, or of an extracellular domain).

(24) GAS 045

GAS 045 corresponds to M3 GenBank accession number GI: 21909751, M18 GenBank accession number GI: 19745421 and is referred to as 'SpyM3_0215' (M3), 'SpyM18_oppA' (M18) and 'oppA'. GAS 045 has been identified as an oligopeptide permease Amino acid and polynucleotide sequences of GAS 045 from an M1 strain are set forth in the sequence listing as SEQ ID NOS: 96 and 97.

Preferred GAS 045 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 96; and/or (b) which is a fragment of at least n consecutive amino acids of SEQ ID NO: 96, wherein n is 7 or more (e.g. 8, 10, 12, 14, 16, 18, 20, 25, 30, 35, 40, 50, 60, 70, 80, 90, 100, 150, 200 or more). These GAS 045 proteins include variants (e.g. allelic variants, homologs, orthologs, paralogs, mutants, etc.) of SEQ ID NO: 96. Preferred fragments of (b) comprise an epitope from SEQ ID NO: 96. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 96. For example, in one embodiment, the underlined amino acid sequence at the N-terminus of SEQ ID NO: 96 (shown below) is removed. (SEQ ID NO: 98 comprises the underlined N-terminal leader sequence. SEQ ID NO: 99 comprises a fragment of GAS 45 where the N-terminal leader sequence is removed). Other fragments omit one or more domains of the protein (e.g. omission of a signal peptide, of a cytoplasmic domain, of a transmembrane domain, or of an extracellular domain).

```
                                               SEQ ID NO: 96
VTFMKKKSKWLAAVSVAILSVSALAACGNKNASGGSEATKTYKYVFVND

PKSLDYILTNGGGTTDVITQMVDGLLENDEYGNLVPSLAKDWKVSKDG

LTYTYTLRDGVSWYTADGEEYAPVTAEDFVTGLKHAVDDKSDALYVVE

DSIKNLKAYQNGEVDFKEVGVKALDDKTVQYTLNKPESYWNSKTTYSV

LFPVNAKFLKSKGKDFGTTDPSSILVNGAYFLSAFTSKSSMEFHKNEN

YWDAKNVGIESVKLTYSDGSDPGSFYKNFDKGEFSVARLYPNDPTYKS

AKKNYADNITYGMLTGDIRHLTWNLNRTSFKNTKKDPAQQDAGKKALN

NKDFRQAIQFAFDRASFQAQTAGQDAKTKALRNMLVPPTFVTIGESDF

GSEVEKEMAKLGDEWKDVNLADAQDGFYNPEKAKAEFAKAKEALTAEG

VTFPVQLDYPVDQANAATVQEAQSFKQSVEASLGKENVIVNVLETETS

THEAQGFYAETPEQQDYDIISSWWGPDYQDPRTYLDIMSPVGGGSVIQ

KLGIKAGQNKDVVAAAGLDTYQTLLDEAAAITDDNDARYKAYAKAQAY

LTDNAVDIPVVALGGTPRVTKAVPFSGGFSWAGSKGPLAYKGMKLQDK

PVTVKQYEKAKEKWMKAKAKSNAKYAEKLADHVEK
```

(25) GAS 095

GAS 095 corresponds to M1 GenBank accession numbers GI: 13622787 and GI: 15675582, to M3 GenBank accession number GI: 21911042, to M18 GenBank accession number GI: 19746634 and is also referred to as 'Spy 1733' (M1), 'SpyM3_1506' (M3), 'SpyM18_1741' (M18). GAS 095 has also identified as a putative transcription regulator. Amino acid and polynucleotide sequences of GAS 095 of an M1 strain are set forth in the sequence listing as SEQ ID NOS: 100 and 101.

Preferred GAS 095 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 100; and/or (b) which is a fragment of at least n consecutive amino acids of SEQ ID NO: 100, wherein n is 7 or more (e.g. 8, 10, 12, 14, 16, 18, 20, 25, 30, 35, 40, 50, 60, 70, 80, 90, 100, 150, 200 or more). These GAS 095 proteins include variants (e.g. allelic variants, homologs, orthologs, paralogs, mutants, etc.) of SEQ ID NO: 100. Preferred fragments of (b) comprise an epitope from SEQ ID NO: 100. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 100. For example, in one embodiment, the underlined amino acid sequence at the N-terminus of SEQ ID NO: 100 (shown below) is removed. (SEQ ID NO: 102 comprises the amino acid sequence of the underlined N-terminal leader sequence. SEQ ID NO: 103 comprises a fragment of GAS 95 where the N-terminal leader sequence is removed.) Other fragments omit one or more domains of the protein (e.g. omission of a signal peptide, of a cytoplasmic domain, of a transmembrane domain, or of an extracellular domain).

SEQ ID NO: 100
MKIGKKIVLMFTAIVLTTVLALGVYLTSAYTFSTGELSKTFKDFSTSS

NKSDAIKQTRAFSILLMGVDTGSSERASKWEGNSDSMILVTVNPKTKK

TTMTSLERDTLTTLSGPKNNENNGVEAKLNAAYAAGGAQMAIMTVQDL

LNITIDNYVQINMQGLIDLVNAVGGITVTNEFDFPISIAENEPEYQAT

VAPGTHKINGEQALVYARMRYDDPEGDYGRQKRQREVIQKVLKKILAL

DSISSYRKILSAVSSNMQTNIEISSRTIPSLLGYRDALRTIKTYQLKG

EDATLSDGGSYQIVTSNHLLEIQNRIRTELGLHKVNQLKTNATVYENL

YGSTKSQTVNNNYDSSGQAPSYSDSHSSYANYSSGVDTGQSASTDQDS

TASSHRPATPSSSSDALAADESSSSGSGSLVPPANINPQT

(26) GAS 193

GAS 193 corresponds to M1 GenBank accession numbers GI: 13623029 and GI: 15675802, to M3 GenBank accession number GI: 21911267, to M18 GenBank accession number GI: 19746914 and is also referred to as 'Spy2025' (M1), 'SpyM3_1731' (M3), 'SpyM18_2082' (M18) and 'isp'. GAS 193 has also been identified as an immunogenic secreted protein precursor. Amino acid and polynucleotide sequences of GAS 193 of an M1 strain are set forth in the sequence listing as SEQ ID NOS: 104 and 105.

Preferred GAS 193 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 104; and/or (b) which is a fragment of at least n consecutive amino acids of SEQ ID NO: 104, wherein n is 7 or more (e.g. 8, 10, 12, 14, 16, 18, 20, 25, 30, 35, 40, 50, 60, 70, 80, 90, 100, 150, 200 or more). These GAS 193 proteins include variants (e.g. allelic variants, homologs, orthologs, paralogs, mutants, etc.) of SEQ ID NO: 104. Preferred fragments of (b) comprise an epitope from SEQ ID NO: 104. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 104. Other fragments omit one or more domains of the protein (e.g. omission of a signal peptide, of a cytoplasmic domain, of a transmembrane domain, or of an extracellular domain).

(27) GAS 137

GAS 137 corresponds to M1 GenBank accession numbers GI: 13621842, GI: 15674720 and GI: 30173478, to M3 GenBank accession number GI: 21909998, to M18 GenBank accession number GI: 19745749 and is also referred to as 'Spy0652' (M1), 'SpyM3_0462', and 'SpyM18_0713' (M18) Amino acid and polynucleotide sequences of GAS 137 of an M1 strain are set forth in the sequence listing as SEQ ID NOS: 106 and 107.

Preferred GAS 137 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 106; and/or (b) which is a fragment of at least n consecutive amino acids of SEQ ID NO: 106, wherein it is 7 or more (e.g. 8, 10, 12, 14, 16, 18, 20, 25, 30, 35, 40, 50, 60, 70, 80, 90, 100, 150, 200 or more). These GAS 137 proteins include variants (e.g. allelic variants, homologs, orthologs, paralogs, mutants, etc.) of SEQ ID NO: 106. Preferred fragments of (b) comprise an epitope from SEQ ID NO: 106. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 106. Other fragments omit one or more domains of the protein (e.g. omission of a signal peptide, of a cytoplasmic domain, of a transmembrane domain, or of an extracellular domain).

(28) GAS 084

GAS 084 corresponds to M1 GenBank accession numbers GI: 13622398 and GI: 15675229, to M3 GenBank accession number GI: 21910442, to M18 GenBank accession number GI: 19746199 and is also referred to as 'Spy1274' (M1), 'SpyM3_0906' and 'SpyM18_1223' (M18). GAS 084 has also been identified as a putative amino acid ABC transporter/periplasmic amino acid binding protein. Amino acid and polynucleotide sequences of GAS 084 of an M1 strain are set forth in the sequence listing as SEQ ID NOS: 108 and 109.

Preferred GAS 084 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 108; and/or (b) which is a fragment of at least n consecutive amino acids of SEQ ID NO: 108, wherein n is 7 or more (e.g. 8, 10, 12, 14, 16, 18, 20, 25, 30, 35, 40, 50, 60, 70, 80, 90, 100, 150, 200 or more). These GAS 084 proteins include variants (e.g. allelic variants, homologs, orthologs, paralogs, mutants, etc.) of SEQ ID NO: 108. Preferred fragments of (b) comprise an epitope from SEQ ID NO: 108. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 108. For example, in one embodiment, the underlined amino acid sequence at the N-terminus of SEQ ID NO: 108 (shown below) is removed. (SEQ ID NO: 110 comprises an amino acid sequence comprising the underlined N-terminal leader sequence of GAS 84. SEQ ID NO: 111 comprises a fragment of GAS 84 where the N-terminal leader sequence is removed). Other fragments omit one or more domains of the protein (e.g. omission of a signal peptide, of a cytoplasmic domain, of a transmembrane domain, or of an extracellular domain).

SEQ ID NO: 108
MIIKKRTVAILAIASSFFLVACQATKSLKSGDAWGVYQKQKSITVGFD

NTFVPMGYKDESGRCKGFDIDLAKEVFHQYGLKVNFQAINWDMKEAEL

NNGKIDVIWNGYSITKERQDKVAFTDSYMRNEQIIVVKKRSDIKTISD

```
MKHKVLGAQSASSGYDSLLRTPKLLKDFIKNKDANQYETFTQAFIDLK

SDRIDGILIDKVYANYYLAKEGQLENYRMIPTTFENEAFSVGLRKEDK

TLQAKINRAFRVLYQNGKFQAISEKWFGDDVATANIKS
```

(29) GAS 384

GAS 384 corresponds to M1 GenBank accession numbers GI: 13622908 and GI: 15675693, to M3 GenBank accession number GI: 21911154, to M18 GenBank accession number GI: 19746801 and is also referred to as 'Spy1874' (M1), 'SpyM3_1618' (M3), and 'SpyM18_1939' (M18). GAS 384 has also been identified as a putative glycoprotein endopeptidase. Amino acid and polynucleotide sequences of GAS 384 of an M1 strain are set forth in the sequence listing as SEQ ID NOS: 112 and 113.

Preferred GAS 384 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 112; and/or (b) which is a fragment of at least n consecutive amino acids of SEQ ID NO: 112, wherein it is 7 or more (e.g. 8, 10, 12, 14, 16, 18, 20, 25, 30, 35, 40, 50, 60, 70, 80, 90, 100, 150, 200 or more). These GAS 384 proteins include variants (e.g. allelic variants, homologs, orthologs, paralogs, mutants, etc.) of SEQ ID NO: 112. Preferred fragments of (b) comprise an epitope from SEQ ID NO: 112. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 112. Other fragments omit one or more domains of the protein (e.g. omission of a signal peptide, of a cytoplasmic domain, of a transmembrane domain, or of an extracellular domain).

(30) GAS 202

GAS 202 corresponds to M1 GenBank accession numbers GI: 13622431 and GI: 15675258, to M3 GenBank accession number GI: 21910527, to M18 GenBank accession number GI: 19746290 and is also referred to as 'Spy1309' (M1), 'SpyM3_0991' (M3), 'SpyM18_1321' (M18) and 'dltD'. GAS 202 has also been identified as a putative extramembranal protein. Amino acid and polynucleotide sequences of GAS 202 of an M1 strain are set forth in the sequence listing as SEQ ID NOS: 114 and 115.

Preferred GAS 202 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 114; and/or (b) which is a fragment of at least n consecutive amino acids of SEQ ID NO: 114, wherein n is 7 or more (e.g. 8, 10, 12, 14, 16, 18, 20, 25, 30, 35, 40, 50, 60, 70, 80, 90, 100, 150, 200 or more). These GAS 202 proteins include variants (e.g. allelic variants, homologs, orthologs, paralogs, mutants, etc.) of SEQ ID NO: 114. Preferred fragments of (b) comprise an epitope from SEQ ID NO: 114. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 114. Other fragments omit one or more domains of the protein (e.g. omission of a signal peptide, of a cytoplasmic domain, of a transmembrane domain, or of an extracellular domain).

(31) GAS 057

GAS 057 corresponds to M1 GenBank accession numbers GI: 13621655 and GI: 15674549, to M3 GenBank accession number GI: 21909834, to M18 GenBank accession number GI: 19745560 and is also referred to as 'Spy0416' (M1), 'SpyM3_0298' (M3), 'SpyM18_0464' (M18) and 'prtS'. GAS 057 has also been identified as a putative cell envelope proteinase Amino acid and polynucleotide sequences of GAS 057 of an M1 strain are set forth in the sequence listing as SEQ ID NOS: 116 and 117.

Preferred GAS 057 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 116; and/or (b) which is a fragment of at least n consecutive amino acids of SEQ ID NO: 116, wherein n is 7 or more (e.g. 8, 10, 12, 14, 16, 18, 20, 25, 30, 35, 40, 50, 60, 70, 80, 90, 100, 150, 200 or more). These GAS 057 proteins include variants (e.g. allelic variants, homologs, orthologs, paralogs, mutants, etc.) of SEQ ID NO: 116. Preferred fragments of (1)) comprise an epitope from SEQ ID NO: 116. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 116. For example, in one embodiment, the underlined amino acid sequence at the N-terminus of SEQ ID NO: 116 (shown below) is removed. (SEQ ID NO: 118 comprises the underlined N-terminal leader sequence. SEQ ID NO: 119 comprises a fragment of GAS 57 where the N-terminal leader sequence is removed.) In another example, the underlined amino acid sequence at the C-terminus of SEQ ID NO: 116 is removed. (SEQ ID NO: 120 comprises the underlined C-terminal hydrophobic region. SEQ ID NO: 121 comprises a fragment of GAS 57 where the C-terminal hydrophobic region is removed. SEQ ID NO: 122 comprises a fragment of GAS 57 where both the N-terminal leader sequence and the C-terminal hydrophobic region are removed.) Other fragments omit one or more domains of the protein (e.g. omission of a signal peptide, of a cytoplasmic domain, of a transmembrane domain, or of an extracellular domain).

```
                                                                            SEQ ID NO: 116
MEKKQRFSLRKYKSGTFSVLIGSVFLVMTTTVAADELSTMSEPTITNHAQQQAQHLTNTELSSAESKSQDTSQITLKTNREKEQSQDL

VSEPTTTELADTDAASMANTGSDATQKSASLPPVNTDVHDWVKTKGAWDKGYKGQGKVVAVIDTGIDPAHQSMRISDVSTAKVKSKED

MLARQKAAGINYGSWINDKVVFAHNYVENSDNIKENQFEDFDEDWENFEFDAEAEPKAIKKHKIYRPQSTQAPKETVIKTEETDGSHD

IDWTQTDDDTKYESHGMHVTGIVAGNSKEAAATGARFLGIAPEAQVMFMRVFANDIMGSAESLFIKAIEDAVALGADVINLSLGTANG

AQLSGSKPLMEAIEKAKKAGVSVVVAAGNERVYGSDHDDPLATNPDYGLVGSPSTGRTPTSVAAINSKWVIQRLMTVKELENRADLNH

GKAIYSESVDFKDIKDSLGYDKSHQFAYVKESTDAGYNAQDVKGKTALIERDPNKTYDEMIALAKKHGALGVLIFNNKPGQSNRSMRL

TANGMGIPSAFISHEFGKAMSQLNGNGTGSLEFDSVVSKAPSQKGNEMNHFSNWGLTSDGYLKPDITAPGGDIYSTYNDNHYGSQTGT
```

-continued

```
SMASPQIAGASLLVKQYLEKTQPNLPKEKIADIVKNLLMSNAQIHVNPETKTTTSPRQQGAGLLNIDGAVTSGLYVTGKDNYGSISLG

NITDTMTFDVTVHNLSNKDKTLRYDTELLTDHVDPQKGRFTLTSHSLKTYQGGEVTVPANGKVTVRVTMDVSQFTKELTKQMPNGYYL

EGFVRFRDSQDDQLNRVNIPFVGFKGQFENLAVAEESIYRLKSQGKTGFYFDESGPKDDIYVGKHFTGLVTLGSETNVSTKTISDNGL

HTLGTFKNADGKFILEKNAQGNPVLAISPNGDNNQDFAAFKGVFLRKYQGLKASVYHASDKEHKNPLWVSPESFKGDKNFNSDIRFAK

STTLLGTAFSGKSLTGAELPDGHYHYVVSYYPDVVGAKRQEMTFDMILDRQKPVLSQATFDPETNRFKPEPLKDRGLAGVRKDSVFLY

ERKDNKPYTVTINDSYKYVSVEDNKTFVERQADGSFILPLDKAKLGDFYYMVEDFAGNVAIAKLGDHLPQTLGKTPIKLKLTDGNYQT

KETLKDNLEMTQSDTGLVTNQAQLAVVHRNQPQSQLTKMNQDFFISPNEDGNKDFVAFKGLKNNVYNDLTVNVYAKDDHQKQTPIWSS

QAGASVSAIESTAWYGITARGSKVMPGDYQYVVTYRDEHGKEHQKQYTISVNDKKPMITQGRFDTINGVDHFTPDKTKALDSSGIVRE

EVFYLAKKNGRKFDVTEGKDGITVSDNKVYIPKNPDGSYTISKRDGVTLSDYYYLVEDRAGNVSFATLRDLKAVGKDKAVVNFGLDLP

VPEDKQIVNFTYLVRDADGKPIENLEYYNNSGNSLILPYGKYTVELLTYDTNAAKLESDKIVSFTLSADNNFQQVTFKITMLATSQIT

AHFDHLLPEGSRVSLKTAQDQLIPLEQSLYVPKAYGKTVQEGTYEVVVSLPKGYRIEGNTKVNTLPNEVHELSLRLVKVGDASDSTGD

HKVMSKNNSQALTASATPTKSTTSATAKALPSTGEKMGLKLRIVGLVLLGLTCVFSRKKSTKD
```

Representative examples of immunization with GAS antigens of the invention in the murine mouse model discussed above are summarized in FIG. 8. The first column identifies the GAS antigen used in the experiment. In some instances purification aspects are referenced in this list. Also, modifications to the polynucleotide sequence which have been made to facilitate the recombinant expression of the antigen are denoted in the chart with the following annotations: "a", indicates that N or C terminal hydrophobic regions have been removed; RR indicates codon optimisation; "NH" and "CH" correspond to the expression vectors similar to those indicated in the GAS 40 construct examples. Where a p value is given, it was calculated based on the control HIS stop values at the bottom of the chart.

Mice immunized with GAS 40 yielded substantially improved survival rates on challenge—in a collection of over 100 mice immunizations, immunization with GAS 40 yielded over 50% survival. The other GAS antigens in the chart offered an amount of protection that, for example if combined with GAS 40, could offer improved protection.

The immunogenicity of other known GAS antigens may be improved by combination with two or more GAS the first antigen group. Such other known GAS antigens include a second antigen group consisting of (1) one or more variants of the M surface protein or fragments thereof, (2) fibronectin-binding protein, (3) streptococcal heme-associated protein, or (4) SagA. These antigens are referred to herein as the "second antigen group".

The invention thus includes an immunogenic composition comprising a combination of GAS antigens, said combination consisting of two to thirty-one GAS antigens of the first antigen group and one, two, three, or four GAS antigens of the second antigen group. Preferably, the combination consists of three, four, five, six, seven, eight, nine, or ten GAS antigens from the first antigen group. Still more preferably, the combination consists of three, four or five GAS antigens from the first antigen group. Preferably, the combination of GAS antigens includes either or both of GAS 40 and GAS 117. Preferably, the combination of GAS antigens includes one or more variants of the M surface protein.

Each of the GAS antigens of the second antigen group are described in more detail below.

(1) M Surface Protein

The M protein is a GAS virulence factor which has been associated with both colonization and resistance to phagocytosis. Over 100 different type variants of the M protein have been identified on the basis of antigenic specificity and M protein is thought to be the major cause of antigenic shift and antigenic drift in GAS. The M protein also binds fibrinogen from serum and blocks the binding of complement to the underlying peptidoglycan. This action is thought to increase GAS survival within a mammalian host by inhibiting phagocytosis.

Unfortunately, the GAS M protein contains some epitopes which mimic those of mammalian muscle and connective tissue. Certain GAS M proteins may be rheumatogenic since they contain epitopes related to heart muscle, and may lead to autoimmune rheumatic carditis (rheumatic fever) following an acute infection.

Epitopes having increased bactericidal activity and having decreased likelihood of cross-reacting with human tissues have been identified in the amino terminal region and combined into fusion proteins containing approximately six, seven, or eight M protein fragments linked in tandem. See Hu et al., Infection & Immunity (2002) 70(4):2171-2177; Dale, Vaccine (1999) 17:193-200; Dale et al., Vaccine 14(10):944-948; WO 02/094851 and WO 94/06465. (Each of the M protein variants, fragments and fusion proteins described in these references are specifically incorporated herein by reference.)

Accordingly, the compositions of the invention may further comprise a GAS M surface protein or a fragment or derivative thereof. One or more GAS M surface protein fragments may be combined together in a fusion protein. Alternatively, one or more GAS M surface protein fragments are combined with a GAS antigen or fragment thereof of the first antigen group. One example of a GAS M protein is set forth in the sequence listing as SEQ ID NO: 123.

Preferred GAS M proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to a known M protein such as SEQ ID NO: 123; and/or (b) which is a fragment of at least n consecutive amino acids of a known M protein such as SEQ ID NO: 123, wherein n is 7 or more (e.g. 8, 10, 12, 14, 16, 18, 20, 25, 30, 35, 40, 50, 60, 70, 80, 90, 100, 150 or more). These GAS M proteins include variants (e.g. allelic variants, homologs, orthologs, paralogs, mutants, etc.) of SEQ ID NO: 123. Preferred fragments of (b) comprise an epitope from a known M protein, such as SEQ ID NO: 123.

Preferably, the fragment is one of those described in the references above. Preferably, the fragment is constructed in a fusion protein with one or more additional M protein fragments. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of a known M protein such as SEQ ID NO: 123. Other fragments omit one or more domains of the protein (e.g. omission of a signal peptide, of a cytoplasmic domain, of a transmembrane domain, or of an extracellular domain).

(2) Fibronectin-Binding Protein

GAS fibronectin-binding protein ('SfbI') is a multifunctional bacterial protein thought to mediate attachment of the bacteria to host cells, facilitate bacterial internalization into cells and to bind to the Fc fragment of human IgG, thus interfering with Fc-receptor mediated phagocytosis and antibody-dependent cell cytotoxicity Immunization of mice with SfbI and an 'H12 fragment' (encoded by positions 1240-1854 of the SfbI gene) are discussed in Schulze et al., Vaccine (2003) 21:1958-1964; Schulze et al., Infection and Immunity (2001) 69(1):622-625 and Guzman et al., Journal of Infectious Diseases (1999) 179:901-906. One example of an amino acid sequence for GAS SfbI is shown in the sequence listing as SEQ ID NO: 124.

Preferred SfbI proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 124; and/or (b) which is a fragment of at least n consecutive amino acids of SEQ ID NO: 124, wherein n is 7 or more (e.g. 8, 10, 12, 14, 16, 18, 20, 25, 30, 35, 40, 50, 60, 70, 80, 90, 100, or more). These SfbI proteins include variants (e.g. allelic variants, homologs, orthologs, paralogs, mutants, etc.) of SEQ ID NO: 124. Preferred fragments of (b) comprise an epitope from SEQ ID NO: 124. Preferably, the fragment is one of those described in the references above. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 124. Other fragments omit one or more domains of the protein (e.g. omission of a signal peptide, of a cytoplasmic domain, of a transmembrane domain, or of an extracellular domain).

(3) Streptococcal Heme-Associated Protein

The GAS streptococcal heme-associated protein ('Shp') has been identified as a GAS cell surface protein. It is thought to be cotranscribed with genes encoding homologues of an ABC transporter involved in iron uptake in gram-negative bacteria. The Shp protein is further described in Lei et al., "Identification and Characterization of a Novel Heme-Associated Cell Surface Protein Made by *Streptococcus pyogenes*", Infection and Immunity (2002) 70(8):4494-4500. One example of a Shp protein is shown in the sequence listing as SEQ ID NO: 125.

Preferred Shp proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 125; and/or (b) which is a fragment of at least n consecutive amino acids of SEQ ID NO: 125, wherein n is 7 or more (e.g. 8, 10, 12, 14, 16, 18, 20, 25, 30, 35, 40, 50, 60, 70, 80, 90, 100 or more). These Shp proteins include variants (e.g. allelic variants, homologs, orthologs, paralogs, mutants, etc.) of SEQ ID NO: 125. Preferred fragments of (b) comprise an epitope from SEQ ID NO: 125. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 125. Other fragments omit one or more domains of the protein (e.g. omission of a signal peptide, of a cytoplasmic domain, of a transmembrane domain, or of an extracellular domain).

(4) SagA

Streptolysin S (SLS), also known as 'SagA', is thought to be produced by almost all GAS colonies. This cytolytic toxin is responsible for the beta-hemolysis surrounding colonies of GAS grown on blood agar and is thought to be associated with virulence. While the full SagA peptide has not been shown to be immunogenic, a fragment of amino acids 10-30 (SagA 10-30) has been used to produce neutralizing antibodies. See Dale et al., "Antibodies against a Synthetic Peptide of SagA Neutralize the Cytolytic Activity of Streptolysin S from Group A Streptococci", Infection and Immunity (2002) 70(4):2166-2170. The amino acid sequence of SagA 10-30 is shown in the sequence listing as SEQ ID NO: 126.

Preferred SagA 10-30 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 126; and/or (b) which is a fragment of at least n consecutive amino acids of SEQ ID NO: 126, wherein it is 7 or more (e.g. 8, 10, 12, 14, 16, 18, or 20). These SagA 10-30 proteins include variants (e.g. allelic variants, homologs, orthologs, paralogs, mutants, etc.) of SEQ ID NO: 126.

There is an upper limit to the number of GAS antigens which will be in the compositions of the invention. Preferably, the number of GAS antigens in a composition of the invention is less than 20, less than 19, less than 18, less than 17, less than 16, less than 15, less than 14, less than 13, less than 11, less than 10, less than 9, less than 8, less than 7, less than 6, less than 5, less than 4, or less than 3. Still more preferably, the number of GAS antigens in a composition of the invention is less than 6, less than 5, or less than 4. Still more preferably, the number of GAS antigens in a composition of the invention is 3. The GAS antigens used in the invention are preferably isolated, i.e., separate and discrete, from the whole organism with which the molecule is found in nature or, when the polynucleotide or polypeptide is not found in nature, is sufficiently free of other biological macromolecules so that the polynucleotide or polypeptide can be used for its intended purpose.

Fusion Proteins

The GAS antigens used in the invention may be present in the composition as individual separate polypeptides, but it is preferred that at least two (i.e. 2, 3, 4, 5, 6, 7, 8, 9, 10, 11, 12, 13, 14, 15, 16, 17, 18, 19 or 20) of the antigens are expressed as a single polypeptide chain (a 'hybrid' polypeptide). Hybrid polypeptides offer two principal advantages: first, a polypeptide that may be unstable or poorly expressed on its own can be assisted by adding a suitable hybrid partner that overcomes the problem; second, commercial manufacture is simplified as only one expression and purification need be employed in order to produce two polypeptides which are both antigenically useful.

The hybrid polypeptide may comprise two or more polypeptide sequences from the first antigen group. Accordingly, the invention includes a composition comprising a first amino acid sequence and a second amino acid sequence, wherein said first and second amino acid sequences are selected from a GAS antigen or a fragment thereof of the first antigen group. Preferably, the first and second amino acid sequences in the hybrid polypeptide comprise different epitopes.

The hybrid polypeptide may comprise one or more polypeptide sequences from the first antigen group and one or more polypeptide sequences from the second antigen group. Accordingly, the invention includes a composition comprising a first amino acid sequence and a second amino acid sequence, said first amino acid sequence selected from a GAS antigen or a fragment thereof from the first antigen group and said second amino acid sequence selected from a GAS antigen or a fragment thereof from the second antigen group. Preferably, the first and second amino acid sequences in the hybrid polypeptide comprise different epitopes.

Hybrids consisting of amino acid sequences from two, three, four, five, six, seven, eight, nine, or ten GAS antigens are preferred. In particular, hybrids consisting of amino acid sequences from two, three, four, or five GAS antigens are preferred.

Different hybrid polypeptides may be mixed together in a single formulation. Within such combinations, a GAS antigen may be present in more than one hybrid polypeptide and/or as a non-hybrid polypeptide. It is preferred, however, that an antigen is present either as a hybrid or as a non-hybrid, but not as both.

Hybrid polypeptides can be represented by the formula NH$_2$-A-{-X-L-}$_n$-B—COOH, wherein: X is an amino acid sequence of a GAS antigen or a fragment thereof from the first antigen group or the second antigen group; L is an optional linker amino acid sequence; A is an optional N-terminal amino acid sequence; B is an optional C-terminal amino acid sequence; and n is 2, 3, 4, 5, 6, 7, 8, 9, 10, 11, 12, 13, 14 or 15.

If a —X— moiety has a leader peptide sequence in its wild-type form, this may be included or omitted in the hybrid protein. In some embodiments, the leader peptides will be deleted except for that of the —X-moiety located at the N-terminus of the hybrid protein i.e. the leader peptide of X$_1$ will be retained, but the leader peptides of X$_2$ ... X$_n$ will be omitted. This is equivalent to deleting all leader peptides and using the leader peptide of X$_1$ as moiety -A-.

For each n instances of {—X-L-}, linker amino acid sequence -L- may be present or absent. For instance, when n=2 the hybrid may be NH$_2$—X$_1$-L$_1$-X$_2$-L$_2$-COOH, NH$_2$—X$_1$—X$_2$—COOH, NH$_2$—X$_1$-L$_1$-X$_2$—COOH NH$_2$—X$_1$—X$_2$-L$_2$-COOH, etc. Linker amino acid sequence(s) -L- will typically be short (e.g. 20 or fewer amino acids i.e. 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising Gly, where n=2, 3, 4, 5, 6, 7, 8, 9, 10 or more), and histidine tags (i.e. His$_n$ where n=3, 4, 5, 6, 7, 8, 9, 10 or more). Other suitable linker amino acid sequences will be apparent to those skilled in the art. A useful linker is GSGGGG, with the Gly-Ser dipeptide being formed from a BamHI restriction site, thus aiding cloning and manipulation, and the (Gly)$_4$ tetrapeptide being a typical poly-glycine linker.

-A- is an optional N-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. His$_n$ where n=3, 4, 5, 6, 7, 8, 9, 10 or more). Other suitable N-terminal amino acid sequences will be apparent to those skilled in the art. If X$_1$ lacks its own N-terminus methionine, -A- is preferably an oligopeptide (e.g. with 1, 2, 3, 4, 5, 6, 7 or 8 amino acids) which provides a N-terminus methionine.

—B— is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. H is where n=3, 4, 5, 6, 7, 8, 9, 10 or more), or sequences which enhance protein stability. Other suitable C-terminal amino acid sequences will be apparent to those skilled in the art.

Most preferably, n is 2 or 3.

The fusion constructs of the invention may include a combination of two or more GAS antigens, wherein said combination includes GAS 40 or a fragment thereof or a polypeptide having sequence identity thereto.

The fusion constructs of the invention may include a combination of GAS antigens, said combination consisting of two to thirty-one GAS antigens of the first antigen group, said first antigen group consisting of: GAS 117, GAS 130, GAS 277, GAS 236, GAS 40, GAS 389, GAS 504, GAS 509, GAS 366, GAS 159, GAS 217, GAS 309, GAS 372, GAS 039, GAS 042, GAS 058, GAS 290, GAS 511, GAS 533, GAS 527, GAS 294, GAS 253, GAS 529, GAS 045, GAS 095, GAS 193, GAS 137, GAS 084, GAS 384, GAS 202, and GAS 057. Preferably, the combination of GAS antigens consists of three, four, five, six, seven, eight, nine, or ten GAS antigens selected from the first antigen group. Preferably, the combination of GAS antigens consists of three, four, or five GAS antigens selected from the first antigen group.

GAS 39, GAS 40, GAS 57, GAS 117, GAS 202, GAS 294, GAS 527, GAS 533, and GAS 511 are particularly preferred GAS antigens for use in the fusion constructs of the invention. Preferably, the combination of GAS antigens includes either or both of GAS 40 and GAS 117. Preferably, the combination includes GAS 40.

Recombinant expression of the fusion constructs of the invention may be improved or optimised by the same methods described for the expression of the GAS antigens alone (discussed above). Fusion constructs of GAS 40 and GAS 117 are exemplified below.

In the first example, GAS 117 is linked to GAS 40a-RR. (As discussed above, GAS 40a-RR is a codon optimised GAS 40 sequence where the N-terminal leader sequence and the C-terminal transmembrane sequence are removed). In this construct a GAS 117 fragment (where the N-terminal leader sequence is removed) is placed to the N-terminus of the GAS 40 sequence and a HIS tag is added to the C-terminus of the GAS 40 sequence. This construct is designated "117-40a-RR" Amino acid and polynucleotide sequences for this construct are shown in the sequence listing as SEQ ID NOS: 127 and 128.

The GAS 117 and GAS 40 sequences are preferably linked by a linker sequence comprising multiple Glycine residues. For example, the linker used in 117-40a-RR fusion construct, a linker sequence of SEQ ID NO: 129 (YASGGGS) is used.

In a second example, the relative locations of the GAS 40 and GAS 117 sequences can be exchanged. In this construct, designated "40a-RR-117", the GAS 40a-RR sequence is placed to the N-terminus of the GAS 117 sequence and the HIS tag is added to the C-terminus of the GAS 117 sequence. Amino acid and polynucleotide sequences for this fusion construct are shown in the sequence listing as SEQ ID NOS: 130 and 131.

Alternatively, the fusion constructs may be designed without codon optimisations. For example, polynucleotide and amino acid sequences for fusion construct "117-40a" is shown in the sequence listing as SEQ ID NOS: 132 and 133. (While no codon optimisations were used, three point mutations apparently occurred during the cloning, only one of which involved a conservative amino acid change (Glucine to Glycine). In the murine immunization model (previously discussed above), immunization with "11740a" has yielded up to 80% survival upon challenge.

A preferred GAS 40 fusion sequence comprises a fragment of GAS 40 comprising one or more of the coiled-coil regions. For example, the fusion construct may comprise a GAS 40 sequence comprising the first coiled-coil region. "117-40N" is an example of this type of construct Amino acid and polynucleotide sequences for this construct are shown in the sequence listing as SEQ ID NOS; 132 and 133.

The invention also provides nucleic acids encoding hybrid polypeptides of the invention. Furthermore, the invention provides nucleic acid which can hybridise to this nucleic acid, preferably under "high stringency" conditions (e.g. 65.degree. C. in a 0.1.times.SSC, 0.5% SDS solution).

The GAS antigens of the invention may also be used to prepare antibodies specific to the GAS antigens. The antibodies are preferably specific to the first or second coiled-coil regions of GAS 40. The invention also includes the use of combination of two or more types of antibodies selected from the group consisting of antibodies specific to GBS 80, GAS 117, GAS 130, GAS 277, GAS 236, GAS 40, GAS 389, GAS 504, GAS 509, GAS 366, GAS 159, GAS 217, GAS 309, GAS 372, GAS 039, GAS 042, GAS 058, GAS 290, GAS 511, GAS 533, GAS 527, GAS 294, GAS 253, GAS 529, GAS 045, GAS 095, GAS 193, GAS 137, GAS 084, GAS 384, GAS 202, and GAS 057. Preferably, the combination includes an antibody specific to GAS 40, or a fragment thereof.

The GAS specific antibodies of the invention include one or more biological moieties that, through chemical or physical means, can bind to or associate with an epitope of a GAS polypeptide. The antibodies of the invention include antibodies which specifically bind to a GAS antigen, preferably GAS 80. The invention includes antibodies obtained from both polyclonal and monoclonal preparations, as well as the following: hybrid (chimeric) antibody molecules (see, for example, Winter et al. (1991) *Nature* 349: 293-299; and U.S. Pat. No. 4,816,567; F(ab')$_2$ and F(ab) fragments; F$_v$ molecules (non-covalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, for example, Huston et al. (1988) *Proc Natl Acad Sci USA* 85:5897-5883); dimeric and trimeric antibody fragment constructs; minibodies (see, e.g., Pack et al. (1992) *Biochem* 31:1579-1584; Cumber et al. (1992) *J Immunology* 149B: 120-126); humanized antibody molecules (see, for example, Riechmann et al. (1988) *Nature* 332:323-327; Verhoeyan et al. (1988) *Science* 239:1534-1536; and U.K. Patent Publication No. GB 2,276,169, published 21 Sep. 1994); and, any functional fragments obtained from such molecules, wherein such fragments retain immunological binding properties of the parent antibody molecule. The invention further includes antibodies obtained through non-conventional processes, such as phage display.

Preferably, the GAS specific antibodies of the invention are monoclonal antibodies. Monoclonal antibodies of the invention include an antibody composition having a homogeneous antibody population. Monoclonal antibodies of the invention may be obtained from murine hybridomas, as well as human monoclonal antibodies obtained using human rather than murine hybridomas. See, e.g., Cote, et al. *Monoclonal Antibodies and Cancer Therapy*, Alan R. Liss, 1985, p 77.

Polypeptides of the invention can be prepared by various means (e.g. recombinant expression, purification from cell culture, chemical synthesis, etc.) and in various forms (e.g. native, fusions, non-glycosylated, lipidated, etc.). They are preferably prepared in substantially pure form (i.e. substantially free from other GAS or host cell proteins).

Nucleic acid according to the invention can be prepared in many ways (e.g. by chemical synthesis, from genomic or cDNA libraries, from the organism itself, etc.) and can take various forms (e.g. single stranded, double stranded, vectors, probes, etc.). They are preferably prepared in substantially pure form (i.e. substantially free from other GAS or host cell nucleic acids).

The term "nucleic acid" includes DNA and RNA, and also their analogues, such as those containing modified backbones (e.g. phosphorothioates, etc.), and also peptide nucleic acids (PNA), etc. The invention includes nucleic acid comprising sequences complementary to those described above (e.g. for antisense or probing purposes).

The invention also provides a process for producing a polypeptide of the invention, comprising the step of culturing a host cell transformed with nucleic acid of the invention under conditions which induce polypeptide expression.

The invention provides a process for producing a polypeptide of the invention, comprising the step of synthesising at least part of the polypeptide by chemical means.

The invention provides a process for producing nucleic acid of the invention, comprising the step of amplifying nucleic acid using a primer-based amplification method (e.g. PCR).

The invention provides a process for producing nucleic acid of the invention, comprising the step of synthesising at least part of the nucleic acid by chemical means.

Strains

Preferred polypeptides of the invention comprise an amino acid sequence found in an M1, M3 or M18 strain of GAS. The genomic sequence of an M1 GAS strain is reported at Ferretti et al, PNAS (2001) 98(8):4658-4663. The genomic sequence of an M3 GAS strain is reported at Beres et al., PNAS (2002) 99(15):10078-10083. The genomic sequence of an M18 GAS strain is reported at Smooet et al., PNAS (2002) 99(7):4668-4673.

Where hybrid polypeptides are used, the individual antigens within the hybrid (i.e. individual —X— moieties) may be from one or more strains. Where n=2, for instance, $X_2$ may be from the same strain as $X_1$ or from a different strain. Where n=3, the strains might be (i) $X_1=X_2=X_3$ (ii) $X_1=X_2 \neq X_3$ (iii) $X_1 \neq X_2=X_3$ (iv) $X_1 \neq X_2 \neq X_3$ or (v) $X_1=X_3 \neq X_2$, etc.

Purification and Recombinant Expression

The GAS antigens of the invention may be isolated from a *Streptococcus pyogenes*, or they may be recombinantly produced, for instance, in a heterologous host. Preferably, the GAS antigens are prepared using a heterologous host. The heterologous host may be prokaryotic (e.g. a bacterium) or eukaryotic. It is preferably *E. coli*, but other suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), yeasts, etc.

Recombinant production of polypeptides is facilitated by adding a tag protein to the GAS antigen to be expressed as a fusion protein comprising the tag protein and the GAS antigen. Such tag proteins can facilitate purification, detection and stability of the expressed protein. Tag proteins suitable for use in the invention include a polyarginine tag (Arg-tag), polyhistidine tag (His-tag), FLAG-tag, Strep-tag, c-myc-tag, S-tag, calmodulin-binding peptide, cellulose-binding domain, SBP-tag, chitin-binding domain, glutathione S-transferase-tag (GST), maltose-binding protein, transcription termination anti-termination factor (NusA), *E. coli* thioredoxin (TrxA) and protein disulfide isomerase I (DsbA).

Preferred tag proteins include His-tag and GST. A full discussion on the use of tag proteins can be found at Terpe et al., Appl Microbiol Biotechnol (2003) 60:523-533.

After purification, the tag proteins may optionally be removed from the expressed fusion protein, i.e., by specifically tailored enzymatic treatments known in the art. Commonly used proteases include enterokinase, tobacco etch virus (TEV), thrombin, and factor $X_a$.

Immunogenic Compositions and Medicaments

Compositions of the invention are preferably immunogenic compositions, and are more preferably vaccine compositions. The pH of the composition is preferably between 6 and 8, preferably about 7. The pH may be maintained by the use of a buffer. The composition may be sterile and/or pyrogen-free. The composition may be isotonic with respect to humans.

Vaccines according to the invention may either be prophylactic (i.e. to prevent infection) or therapeutic (i.e. to treat infection), but will typically be prophylactic. Accordingly, the invention includes a method for the therapeutic or prophylactic treatment of a Streptococcus pyogenes infection in an animal susceptible to streptococcal infection comprising administering to said animal a therapeutic or prophylactic amount of the immunogenic compositions of the invention. Preferably, the immunogenic composition comprises a combination of GAS antigens, said combination consisting of two to thirty-one GAS antigens of the first antigen group. Preferably, the combination of GAS antigens consists of three, four, five, six, seven, eight, nine, or ten GAS antigens selected from the first antigen group. Preferably, the combination of GAS antigens consists of three, four, or five GAS antigens selected from the first antigen group. Preferably, the combination of GAS antigens includes either or both of GAS 40 and GAS 117.

Alternatively, the invention includes an immunogenic composition comprising a combination of GAS antigens, said combination consisting of two to thirty-one GAS antigens of the first antigen group and one, two, three, or four GAS antigens of the second antigen group. Preferably, the combination consists of three, four, five, six, seven, eight, nine, or ten GAS antigens from the first antigen group. Still more preferably, the combination consists of three, four or five GAS antigens from the first antigen group. Preferably, the combination of GAS antigens includes either or both of GAS 40 and GAS 117. Preferably, the combination of GAS antigens includes one or more variants of the M surface protein.

The invention also provides a composition of the invention for use as a medicament. The medicament is preferably able to raise an immune response in a mammal (i.e. it is an immunogenic composition) and is more preferably a vaccine.

The invention also provides the use of the compositions of the invention in the manufacture of a medicament for raising an immune response in a mammal. The medicament is preferably a vaccine. The invention also provides for a kit comprising a first component comprising a combination of GAS antigens. In one embodiment, the combination of GAS antigens consists of a mixture of two to thirty-one GAS antigens selected from the first antigen group. Preferably, the combination consists of three, four, five, six, seven, eight, nine, or ten GAS antigens from the first antigen group. Preferably, the combination consists of three, four, or five GAS antigens from the first antigen group. Preferably, the combination includes either or both of GAS 117 and GAS 040.

In another embodiment, the kit comprises a first component comprising a combination of GAS antigens consisting of a mixture of two to thirty-one GAS antigens of the first antigen group and one, two, three, or four GAS antigens of the second antigen group. Preferably, the combination consists of three, four, five, six, seven, eight, nine, or ten GAS antigens from the first antigen group. Still more preferably, the combination consists of three, four or five GAS antigens from the first antigen group. Preferably, the combination of GAS antigens includes either or both of GAS 40 and GAS 117. Preferably, the combination of GAS antigens includes one or more variants of the M surface protein.

The invention also provides a delivery device pre-filled with the immunogenic compositions of the invention.

The invention also provides a method for raising an immune response in a mammal comprising the step of administering an effective amount of a composition of the invention. The immune response is preferably protective and preferably involves antibodies and/or cell-mediated immunity The method may raise a booster response.

The mammal is preferably a human. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

These uses and methods are preferably for the prevention and/or treatment of a disease caused by Streptococcus pyogenes (e.g. pharyngitis (such as streptococcal sore throat), scarlet fever, impetigo, erysipelas, cellulitis, septicemia, toxic shock syndrome, necrotizing fasciitis (flesh eating disease) and sequelae (such as rheumatic fever and acute glomerulonephritis)). The compositions may also be effective against other streptococcal bacteria.

One way of checking efficacy of therapeutic treatment involves monitoring GAS infection after administration of the composition of the invention. One way of checking efficacy of prophylactic treatment involves monitoring immune responses against the GAS antigens in the compositions of the invention after administration of the composition.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral (e.g. tablet, spray), vaginal, topical, transdermal (e.g. see WO99/27961) or transcutaneous (e.g. see WO02/074244 and WO02/064162), intranasal (e.g. see WO03/028760), ocular, aural, pulmonary or other mucosal administration. The invention may be used to elicit systemic and/or mucosal immunity.

Dosage treatment can be a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc.

The compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. Such kits may comprise one or more antigens in liquid form and one or more lyophilised antigens. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Further Components of the Composition

The composition of the invention will typically, in addition to the components mentioned above, comprise one or more 'pharmaceutically acceptable carriers', which include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. A thorough discussion of pharmaceutically acceptable excipients is available in Gennaro (2000) *Remington: The Science and Practice of Pharmacy*. 20th ed., ISBN: 0683306472.

Vaccines of the invention may be administered in conjunction with other immunoregulatory agents. In particular, compositions will usually include an adjuvant.

Preferred further adjuvants include, but are not limited to, one or more of the following set forth below:

A. Mineral Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. {e.g. see chapters 8 & 9 of *Vaccine design: the subunit and adjuvant approach* (1995) Powell & Newman. ISBN 0-306-44867-X}), or mixtures of different mineral compounds, with the compounds taking any suitable form (e.g. gel, crystalline, amorphous, etc.), and with adsorption being preferred. The mineral containing compositions may also be formulated as a particle of metal salt. See WO00/23105.

B. Oil-Emulsions

Oil-emulsion compositions suitable for use as adjuvants in the invention include squalene-water emulsions, such as MF59 (5% Squalene, 0.5% TWEEN® 80, and 0.5% SPAN® 85, formulated into submicron particles using a microfluidizer). See WO90/14837. See also, Podda, "The adjuvanted influenza vaccines with novel adjuvants: experience with the MF59-adjuvanted vaccine", Vaccine (2001) 19: 2673-2680; Frey et al., "Comparison of the safety, tolerability, and immunogenicity of a MF59-adjuvanted influenza vaccine and a non-adjuvanted influenza vaccine in non-elderly adults", Vaccine (2003) 21:4234-4237. MF59 is used as the adjuvant in the FLUAD™ influenza virus trivalent subunit vaccine.

Particularly preferred adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v TWEEN® 80 (polyoxyethylenesorbitan monooleate), and/or 0.25-1.0% SPAN® 85 (sorbitan trioleate), and, optionally, N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), for example, the submicron oil-in-water emulsion known as "MP59" (International Publication No. WO90/14837; U.S. Pat. Nos. 6,299,884 and 6,451,325, incorporated herein by reference in their entireties; and Ott et al., "MP59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277-296). MF59 contains 4-5% w/v Squalene (e.g. 4.3%), 0.25-0.5% w/v TWEEN® and 0.5% w/v SPAN® 85 and optionally contains various amounts of MTP-PE, formulated into submicron particles using a microfluidizer such as Model 110Y microfluidizer (Microfluidics, Newton, Mass.). For example, MMP-PE may be present in an amount of about 0-500 μg/dose, more preferably 0-250 μg/dose and most preferably, 0-100 μg/dose. As used herein, the term "MF59-0" refers to the above submicron oil-in-water emulsion lacking MTP-PE, while the term MF59-MTP denotes a formulation that contains MTP-PE. For instance, "M59-100" contains 100 μg MTP-PE per dose, and so on. MF69, another submicron oil-in-water emulsion for use herein, contains 4.3% w/v squalene, 0.25% w/v TWEEN® 80, and 0.75% w/v SPAN® 85 and optionally MTP-PE. Yet another submicron oil-in-water emulsion is MF75, also known as SAF, containing 10% squalene, 0.4% TWEEN® 80, 5% pluronic-blocked polymer L121, and thr-MDP, also microfluidized into a submicron emulsion. M5-MTP denotes an M75 formulation that includes MTP, such as from 100-400 μg MTP-PE per dose. Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325, incorporated herein by reference in their entireties.

Complete Freund's adjuvant (CFA) and incomplete Freund's adjuvant (IFA) may also be used as adjuvants in the invention.

C. Saponin Formulations

Saponin formulations, may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from Smilax ornata (sarsaprilla), *Gypsophilla paniculata* (brides veil), and *Saponaria officianalis* (soap root). Saponin adjuvant formulations include purified formulations, such as QS21, as well as lipid formulations, such as ISCOMs. Saponin compositions have been purified using High Performance Thin Layer Chromatography (HP-LC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO 96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP 0 109 942, WO 96/11711 and WO 96/33739. Optionally, the ISCOMS may be devoid of additional detergent. See WO00107621.

A review of the development of saponin based adjuvants can be found at Barr, et al., Advanced Drug Delivery Reviews (1998) 32:247-271. See also Sjolander, et al., Advanced Drug Delivery Reviews (1998) 32:321-338.

D. Virosomes and Virus Like Particles (VLPs)

Virosomes and Virus Like Particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in WO 03/024480, WO 03/024481, and Niikura et al., Virology (2002) 293:273-280, Lenz et al., Journal of Immunology (2001) 5246-5355; Pinto, et al. Journal of Infectious Diseases (2003) 188:327-338 and Gerber et al., Journal of Virology (2001) 75(10):4752-4760. Virosomes are discussed further in, for example, Gluck et al., Vaccine (2002) 20:B10-B16.

E. Bacterial or Microbial Derivatives

Adjuvants suitable for use in the invention include bacterial or microbial derivatives such as:

(1) Non-Toxic Derivatives of Enterobacterial Lipopolysaccharide (LPS)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g. RC-529. See Johnson et al. (1999) *Bioorg Med Chem Lett* 9:2273-2278.

(2) Lipid A Derivatives

Lipid A derivatives include derivatives of lipid A from *Escherichia coli* such as OM-174. OM-174 is described for example in Meraldi et al., Vaccine (2003) 21:2485-2491 and Pajak, et al., Vaccine (2003) 21:836-842.

(3) Immunostimulatory Oligonucleotides

Immunostimulatory oligonucleotides suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpGs can include nucleotide modifications/analogs such as phosphorothioate modifications and can be double-stranded or single-stranded. Optionally, the guanosine may be replaced with an analog such as 2'-deoxy-7-deazaguanosine. See Kandimalla, et al., Nucleic Acids Research (2003) 31(9): 2393-2400; WO 02/26757 and WO 99/62923 for examples of possible analogue substitutions. The adjuvant effect of CpG oligonucleotides is further discussed in Krieg, Nature Medicine (2003) 9(7): 831-835; McCluskie, et al., FEMS Immunology and Medical Microbiology (2002) 32:179-185; WO 98/40100, U.S. Pat. No. 6,207,646, U.S. Pat. No. 6,239,116, and U.S. Pat. No. 6,429,199.

The CpG sequence may be directed to TLR9, such as the motif GTCGTT or TTCGTT. See Kandimalla, et al., Biochemical Society Transactions (2003) 31 (part 3): 654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell, et al., J. Immunol. (2003) 170(8):4061-4068; Krieg, TRENDS in Immunology (2002) 23(2): 64-65 and WO 01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla, et al., BBRC (2003) 306:948-953; Kandimalla, et al., Biochemical Society Transactions (2003) 31(part 3):664-658; Bhagat et al., BBRC (2003) 300:853-861 and WO 03/035836.

(4) ADP-Ribosylating Toxins and Detoxified Derivatives Thereof

Bacterial ADP-ribosylating toxins and detoxified derivatives thereof may be used as adjuvants in the invention. Preferably, the protein is derived from *E. coli* (i.e., *E. coli* heat labile enterotoxin "LT"), cholera ("Cr"), or pertussis ("PT"). The use of detoxified ADP-ribosylating toxins as mucosal adjuvants is described in WO 95/17211 and as parenteral adjuvants in WO 98/42375. Preferably, the adjuvant is a detoxified LT mutant such as LT-K63.

F. Human Immunomodulators

Human immunomodulators suitable for use as adjuvants in the invention include cytokines, such as interleukins (e.g. IL-1, IL-2, IL-4, IL-5, IL-6, IL-7, IL-12, etc.), interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres (Singh et al. (2001) *J. Cont. Rele.* 70:267-276) or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention. E.g., WO99/27960.

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes

Examples of liposome formulations suitable for use as adjuvants are described in U.S. Pat. No. 6,090,406, U.S. Pat. No. 5,916,588, and EP 0 626 169.

J. Polyoxyethylene Ether and Polyoxyethylene Ester Formulations

Adjuvants suitable for use in the invention include polyoxyethylene ethers and polyoxyethylene esters. WO99/52549. Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152).

Preferred polyoxyethylene ethers are selected from the following group: polyoxyethylene-9-lauryl ether (laureth 9), polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in Andrianov et al., "Preparation of hydrogel microspheres by coacervation of aqueous polyphophazene solutions", Biomaterials (1998) 19(1-3):109-115 and Payne et al., "Protein Release from Polyphosphazene Matrices", Adv. Drug. Delivery Review (1998) 31(3):185-196.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues, described further in Stanley, "Imiquimod and the imidazoquinolones: mechanism of action and therapeutic potential" Clin Exp Dermatol (2002) 27(7):571-577 and Jones, "Resiquimod 3M", Curr Opin Investig Drugs (2003) 4(2):214-218.

The invention may also comprise combinations of aspects of one or more of the adjuvants identified above. For example, the following adjuvant compositions may be used in the invention:

(1) a saponin and an oil-in-water emulsion (WO99/11241);

(2) a saponin (e.g., QS21)+a non-toxic LPS derivative (e.g., 3dMPL) (see WO 94/00153);

(3) a saponin (e.g., QS21)+a non-toxic LPS derivative (e.g., 3dMPL)+a cholesterol;

(4) a saponin (e.g. QS21)+3dMPL+IL-12 (optionally+a sterol) (WO98/57659);

(5) combinations of 3dMPL with, for example, QS21 and/or oil-in-water emulsions (European patent applications 0835318, 0735898 and 0761231);

(6) SAF, containing 10% Squalane, 0.4% TWEEN® 80, 5% pluronic-block polymer L121, and thr-MDP, either microfluidized into a submicron emulsion or vortexed to generate a larger particle size emulsion.

(7) RIBI™ adjuvant system (RAS), (Ribi Immunochem) containing 2% Squalene, 0.2% TWEEN® 80, and one or more bacterial cell wall components from the group consisting of monophosphorylipid A (MPL), trehalose dimycolate (TDM), and cell wall skeleton (CWS), preferably MPL+CWS (DETOX™); and (8) one or more mineral salts (such as an aluminum salt)+a non-toxic derivative of LPS (such as 3dPML).

(9) one or more mineral salts (such as an aluminum salt)+ an immunostimulatory oligonucleotide (such as a nucleotide sequence including a CpG motif).

Aluminium salts and MF59 are preferred adjuvants for parenteral immunisation. Mutant bacterial toxins are preferred mucosal adjuvants.

The composition may include an antibiotic.

Further Antigens

The compositions of the invention may further comprise one or more additional non-GAS antigens, including additional bacterial, viral or parasitic antigens.

In one embodiment, the GAS antigen combinations of the invention are combined with one or more additional, non-GAS antigens suitable for use in a paediatric vaccine. For example, the GAS antigen combinations may be combined with one or more antigens derived from a bacteria or virus selected from the group consisting of *N. meningitidis* (including serogroup A, B, C, W135 and/or Y), *Streptococcus pneumoniae, Bordetella pertussis, Moraxella catarrhalis, Tetanus, Diphtheria*, Respiratory Syncytial virus ('RSV'), polio, measles, mumps, rubella, and rotavirus.

In another embodiment, the GAS antigen combinations of the invention are combined with one or more additional, non-GAS antigens suitable for use in a vaccine designed to protect elderly or immunocomprised individuals. For example, the GAS antigen combinations may be combined with an antigen derived from the group consisting of *Enterococcus faecalis, Staphylococcus aureus, Staphylococcus epidermis, Pseudomonas aeruginosa, Legionella pneumophila, Listeria monocytogenes*, influenza, and Parainfluenza virus ('PIV').

Where a saccharide or carbohydrate antigen is used, it is preferably conjugated to a carrier protein in order to enhance immunogenicity {e.g. Ramsay et al. (2001) *Lancet* 357(9251):195-196; Lindberg (1999) *Vaccine* 17 Suppl 2:S28-36; Buttery & Moxon (2000) *J R Coll Physicians Lond* 34:163-168; Ahmad & Chapnick (1999) *Infect Dis Clin North Am* 13:113-133, vii. Goldblatt (1998) *J. Med. Microbiol.* 47:563-567; European patent 0 477 508; U.S. Pat. No. 5,306, 492; WO98/42721; *Conjugate Vaccines* (eds. Cruse et al.) ISBN 3805549326, particularly vol. 10:48-114; Hermanson (1996) *Bioconjugate Techniques* ISBN: 0123423368 or 012342335X}. Preferred carrier proteins are bacterial toxins or toxoids, such as diphtheria or tetanus toxoids. The CRM$_{197}$ diphtheria toxoid is particularly preferred {*Research Disclosure*, 453077 (January 2002)}. Other carrier polypeptides include the *N. meningitidis* outer membrane protein {EP-A-0372501}, synthetic peptides {EP-A-0378881 and EP-A-0427347}, heat shock proteins {WO93/17712 and WO94/03208}, pertussis proteins {WO98/58668 and EP-A-0471177}, protein D from *H. influenzae* {WO00/56360}, cytokines {WO91/01146}, lymphokines, hormones, growth factors, toxin A or B from *C. difficile* {WO00/61761}, iron-uptake proteins {WO01/72337}, etc. Where a mixture comprises capsular saccharides from both serogroups A and C, it may be preferred that the ratio (w/w) of MenA saccharide: MenC saccharide is greater than 1 (e.g. 2:1, 3:1, 4:1, 5:1, 10:1 or higher). Different saccharides can be conjugated to the same or different type of carrier protein. Any suitable conjugation reaction can be used, with any suitable linker where necessary.

Toxic protein antigens may be detoxified where necessary e.g. detoxification of pertussis toxin by chemical and/or genetic means.

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens in the composition will typically be present at a concentration of at least 1 µg/ml each. In general, the concentration of any given antigen will be sufficient to elicit an immune response against that antigen.

As an alternative to using protein antigens in the composition of the invention, nucleic acid encoding the antigen may be used {e.g. Robinson & Torres (1997) *Seminars in Immunology* 9:271-283; Donnelly et al. (1997) *Annu Rev Immunol* 15:617-648; Scott-Taylor & Dalgleish (2000) *Expert Opin Investig Drugs* 9:471-480; Apostolopoulos & Plebanski (2000) *Curr Opin Mol Ther* 2:441-447; Ilan (1999) *Curr Opin Mol Ther* 1:116-12 Dubensky et al. (2000) *Mol Med* 6:723-732; Robinson & Pertmer (2000) *Adv Virus Res* 55:1-74 Donnelly et al. (2000) *Am J Respir Crit. Care Med* 162(4 Pt 2):S190-193 Davis (1999) *Mt. Sinai J. Med.* 66:84-90}. Protein components of the compositions of the invention may thus be replaced by nucleic acid (preferably DNA e.g. in the form of a plasmid) that encodes the protein.

DEFINITIONS

The term "comprising" means "including" as well as "consisting" e.g. a composition "comprising" X may consist exclusively of X or may include something additional e.g. X+Y.

The term "about" in relation to a numerical value x means, for example, x±10%.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of *Current Protocols in Molecular Biology* (F. M. Ausubel et al., eds., 1987) Supplement 30. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in Smith & Waterman (1981) Adv. Appl. Math. 2:482-489. Similar sequence identity methods can be used to determine sequence homology between two polynucleotide sequences.

The following example demonstrates one way of preparing recombinant GAS antigens of the invention and testing their efficacy in a murine model.

Example 1

Preparation of Recombinant GAS Antigens of the Invention and Demonstration of Efficacy in Murine Model Recombinant GAS proteins corresponding to two or more of the GAS antigens of the first antigen group are expressed as follows.

1. Cloning of GAS Antigens for Expression in *E. coli*

The selected GAS antigens were cloned in such a way to obtain two different kinds of recombinant proteins: (1) proteins having an hexa-histidine tag at the carboxy-terminus (Gas-His) and (2) proteins having the hexa-histidine tag at the carboxy-terminus and GST at the amino-terminus (Gst-Gas-His). Type (1) proteins were obtained by cloning in a pET21b+vector (available from Novagen). The type (2) proteins were obtained by cloning in a pGEX-NNH vector. This cloning strategy allowed for the GAS genomic DNA to be used to amplify the selected genes by PCR, to perform a single restriction enzyme digestion of the PCR products and to clone then simultaneously into both vectors.

(a) Construction of pGEX-NNH Expression Vectors

Two pairs of complementary oligodeoxyribonucleotides are synthesised using the DNA synthesiser ABI394 (Perkin Elmer) and reagents from Cruachem (Glasgow, Scotland). Equimolar amounts of the oligo pairs (50 ng each oligo) are annealed in T4 DNA ligase buffer (New England Biolabs) for 10 mm in a final volume of 50 µl and then left to cool slowly at room temperature. With the described procedure the following DNA linkers are obtained:

```
gexNN linker
                                                    (SEQ ID NOS: 137 and 138)
           NdeI NheI XmaI    EcoRI   NcoI      SalI     XhoI      SacI

GATCCCATATGGCTAGCCCGGGGAATTCGTCCATGGAGTGAGTCGACTGACTCGAGTGATCGAGCTC

GGTATACCGATCGGGCCCCTTAAGCAGGTACCTCACTCAGCTGACTGAGCTCACTAGCTCGAG

NotI

CTGAGCGGCCGCATGAA

GACTCGCCGGCGTACTTTCGA gexNNH linker
                                                    (SEQ ID NOS: 139 and 140)
        HindIII NotI   XhoI     Hexa-Histidine

TCGACAAGCTTGCGGCCGCACTCGAGCATCACCATCACCATCACTGAT

GTTCGAACGCCGGCGTGAGCACGTAGAGGTAGTGGTAGTGACTATCGA
```

The plasmid pGEX-KG [K. L. Guan and J. E. Dixon, Anal. Biochem. 192, 262 (1991)] is digested with BamHI and HindIII and 100 ng is ligated overnight at 16.degree. C. to the linker gexNN with a molar ratio of 3:1 linker/plasmid using 200 units of T4 DNA ligase (New england Biolabs). After transformation of the ligation product in *E. coli* DH5, a clone containing the pGEX-NN plasmid, having the correct linker, is selected by means of restriction enzyme analysis and DNA sequencing. The new plasmid pGEX-NN is digested with SalI and HindIII and ligated to the linker gexNNH. After transformation of the ligation product in *E. coli* DHS, a clone containing the pGEX-NNH plasmid, having the correct linker, is selected by means of restriction enzyme analysis and DNA sequencing.

(b) Chromosomal DNA Preparation

GAS SF370 strain is grown in THY medium until OD.sub.600 is 0.6-0.8. Bacteria are then centrifuged, suspended in TES buffer with lysozyme (10 mg/ml) and mutanolysine (10 U/µl) and incubated 1 hr at 37° C.

Following treatment of the bacterial suspension with RNAase, Proteinase K and 10% Sarcosyl/EDTA, protein extraction with saturated phenol and phenol/chloroform is carried out. The resulting supernatant is precipitated with Sodium Acetate/Ethanol and the extracted DNA is pelletted by centrifugation, suspended in Tris buffer and kept at −20° C.

(c) Oligonucleotide Design

Synthetic oligonucleotide primers are designed on the basis of the coding sequence of each GAS antigen using the sequence of *Streptococcus pyogenes* SF370 M1 strain. Any predicted signal peptide is omitted, by deducing the 5' end amplification primer sequence immediately downstream from the predicted leader sequence. For most GAS antigens, the 5' tail of the primers (see Table 1, below) include only one restriction enzyme recognition site (NdeI or NheI, or SpeI depending on the gene's own restriction pattern); the 3' primer tails (see Table 1) include a XhoI or a NotI or a HindIII restriction site.

TABLE 1

Oligonucleotide tails of the primers used to amplify genes encoding selected GAS antigens.

| 5' tails | 3' tails |
|---|---|
| NdeI 5' GTGCGTCATATG 3' (SEQ ID NO: 141) | XhoI 5' GCGTCTGAG 3' (SEQ ID NO: 144) |
| NheI 5' GTGCGTGCTAGC 3' (SEQ ID NO: 142) | NotI 5' ACTCGCTAGCGGCCGC 3' (SEQ ID NO: 145) |
| SpeI 5' GTGCGTACTAGT 3' (SEQ ID NO: 143) | HindIII 5' GCGTAAGCTT 3' (SEQ ID NO: 146) |

As well as containing the restriction enzyme recognition sequences, the primers include nucleotides which hybridize to the sequence to be amplified. The number of hybridizing nucleotides depends on the melting temperature of the primers which can be determined as described [(Breslauer et al., Proc. Nat. Acad. Sci. 83, 3746-50 (1986)]. The average melting temperature of the selected oligos is 50-55° C. for the hybridizing region alone and 65-75° C. for the whole oligos. Oligos can be purchased from MWG-Biotech S.p.A. (Firenze, Italy).

(d) PCR Amplification

The standard PCR protocol is as follows: 50 ng genomic DNA are used as template in the presence of 0.2 µM each primer, 200 µM each dNTP, 1.5 mM MgCl$_2$, 1×PCR buffer minus Mg (Gibco-BRL), and 2 units of Taq DNA polymerase (Platinum Taq, Gibco-BRL) in a final volume of 100 µl. Each sample undergoes a double-step amplification: the first 5 cycles are performed using as the hybridizing temperature of one of the oligos excluding the restriction enzyme tail, followed by 25 cycles performed according to the hybridization temperature of the whole length primers. The standard cycles are as follows:

one cycle:
denaturation: 94° C., 2 min,
5 cycles:
denaturation: 94° C., 30 seconds,
hybridization: 51° C., 50 seconds,
elongation: 72° C., 1 min or 2 mM and 40 sec,
25 cycles:
denaturation: 94° C., 30 seconds,
hybridization: 70° C., 50 seconds,
elongation: 72° C., 1 min or 2 mM and 40 sec,
72° C., 7 min,
4° C.

The elongation time is 1 min for GAS antigens encoded by ORFs shorter than 2000 bp, and 2 min and 40 seconds for ORFs longer than 2000 bp. The amplifications are performed using a Gene Amp PCR system 9600 (Perkin Elmer).

To check the amplification results, 4 µl of each PCR product is loaded onto 1-1.5 agarose gel and the size of amplified fragments compared with DNA molecular weight standards (DNA markers III or IX, Roche). The PCR products are loaded on agarose gel and after electrophoresis the right size bands are excised from the gel. The DNA is purified from the agarose using the Gel Extraction Kit (Qiagen) following the instruction of the manufacturer. The final elution volume of the DNA is 50 µl TE (10 mM Tris-HCl, 1 mM EDTA, pH 8). One µl of each purified DNA is loaded onto agarose gel to evaluate the yield.

(e) Digestion of PCR Fragments

One-two µg of purified PCR products are double digested overnight at 37° C. with the appropriate restriction enzymes (60 units of each enzyme) using the appropriate restriction buffer in 100 µl final volume. The restriction enzymes and the digestion buffers are from New England Biolabs. After purification of the digested DNA (PCR purification Kit, Qiagen) and elution with 30 µl TE, 1 µl is subjected to agarose gel electrophoresis to evaluate the yield in comparison to titrated molecular weight standards (DNA markers III or IX, Roche).

(f) Digestion of the Cloning Vectors (pET21b+ and pGEX-NNH)

10 µg of plasmid is double digested with 100 units of each restriction enzyme in 400 µl reaction volume in the presence of appropriate buffer by overnight incubation at 37° C. After electrophoresis on a 1% agarose gel, the band corresponding to the digested vector is purified from the gel using the Qiagen Qiaex II Gel Extraction Kit and the DNA was eluted with 50 µl TE. The DNA concentration is evaluated by measuring OD$_{260}$ of the sample.

(g) Cloning of the PCR Products

Seventy five ng of the appropriately digested and purified vectors and the digested and purified fragments corresponding to each selected GAS antigen are ligated in final volumes of 10-20 µl with a molar ratio of 1:1 fragment/vector, using 400 units T4 DNA ligase (New England Biolabs) in the presence of the buffer supplied by the manufacturer. The reactions are incubated overnight at 16° C.

Transformation of *E. coli* BL21 (Novagen) and *E. coli* BL21-DE3 (Novagen) electrocompetent cells is performed using pGEX-NNH ligations and pET21b+ ligations respectively. The transformation procedure is as follows: 1-2 µL$_1$ the ligation reaction is mixed with 50 µL$_1$ of ice cold competent cells, then the cells are poured in a gene pulser 0.1 cm electrode cuvette (Biorad). After pulsing the cells in a Micro-Pulser electroporator (Biorad) following the manufacturer instructions the cells are suspended in 0.95 ml of SOC medium and incubated for 45 min at 37° C. under shaking. 100 and 900 µl of cell suspensions are plated on separate plates of agar LB 100 µg/ml Ampicillin and the plates are incubated overnight at 37° C. The screening of the transformants is done by PCR: randomly chosen transformants are picked and suspended in 30 µl of PCR reaction mix containing the PCR buffer, the 4 dNTPs, 1.5 mM $MgCl_2$, Taq polymerase and appropriate forward and reverse oligonucleotide primers that are able to hybridize upstream and downstream from the polylinker of pET21b+ or pGEX-NNH vectors. After 30 cycles of PCR, 5 µl of the resulting products are run on agarose gel electrophoresis in order to select for positive clones from which the expected PCR band is obtained. PCR positive clones are chosen on the basis of the correct size of the PCR product, as evaluated by comparison with appropriate molecular weight markers (DNA markers III or IX, Roche).

2. Protein Expression

PCR positive colonies are inoculated in 3 ml LB 100 µg/ml Ampicillin and grown at 37° C. overnight. 70 µ$L_1$ of the overnight culture is inoculated in 2 ml LB/Amp and grown at 37.degree. C. until $OD_{600}$ of the pET clones reached the 0.4-0.8 value or until $OD_{600}$ of the pGEX clones reached the 0.8-1 value. Protein expression is then induced by adding 1 mM IPTG (Isopropyl 13-D thio-galacto-piranoside) to the mini-cultures. After 3 hours incubation at 37° C. the final $OD_{600}$ is checked and the cultures are cooled on ice. After centrifugation of 0.5 ml culture, the cell pellet is suspended in 50 µl of protein Loading Sample Buffer (60 mM Tris HCl pH 6.8, 5% w/v SDS, 10% w/v glycerin, 0.1% w/v Bromophenol Blue, 100 mM DTT) and incubated at 100° C. for 5 min. A volume of boiled sample corresponding to 0.1 $OD_{600}$ culture is analysed by SDS-PAGE and Coomassie Blue staining to verify the presence of induced protein band.

3. Purification of the Recombinant Proteins

Single colonies are inoculated in 25 ml LB 100 µg/ml Ampicillin and grown at 37° C. overnight. The overnight culture is inoculated in 500 ml LB/Amp and grown under shaking at 25° C. until $OD_{600}$ 0.4-0.7. Protein expression is then induced by adding 1 mM IPTG to the cultures. After 3.5 hours incubation at 25° C. the final $OD_{600}$ is checked and the cultures are cooled on ice. After centrifugation at 6000 rpm (JA10 rotor, Beckman), the cell pellet is processed for purification or frozen at −20° C.

(a) Procedure for the Purification of Soluble His-Tagged Proteins from *E. coli*

(1) Transfer the pellets from −20° C. to ice bath and reconstitute with 10 ml 50 mM $NaHPO_4$ buffer, 300 mM NaCl, pH 8.0, pass in 40-50 ml centrifugation tubes and break the cells as per the following outline.

(2) Break the pellets in the French Press performing three passages with in-line washing.

(3) Centrifuge at about 30-40000×g per 15-20 min. If possible use rotor JA 25.50 (21000 rpm, 15 min.) or JA-20 (18000 rpm, 15 min.)

(4) Equilibrate the Poly-Prep columns with 1 ml Fast Flow Chelating SEPHAROSE® resin with 50 mM phosphate buffer, 300 mM NaCl, pH 80.

(5) Store the centrifugation pellet at −20° C., and load the supernatant in the columns.

(6) Collect the flow through.

(7) Wash the columns with 10 ml (2 ml+2 ml+4 ml) 50 mM phosphate buffer, 300 mM NaCl, pH 8.0.

(8) Wash again with 10 ml 20 mM imidazole buffer, 50 mM phosphate, 300 mM NaCl, pH 8.0.

(9) Elute the proteins bound to the columns with 4.5 ml (1.5 ml+1.5 ml+1.5 ml) 250 mM imidazole buffer, 50 mM phosphate, 300 mM NaCl, pH 8.0 and collect the 3 corresponding fractions of 1.5 ml each. Add to each tube 15 µl DTT 200 mM (final concentration 2 mM)

(10) Measure the protein concentration of the first two fractions with the Bradford method, collect a 10 µg aliquot of proteins from each sample and analyse by SDS-PAGE. (N.B.: should the sample be too diluted, load 21 µl+7 µl loading buffer).

(11) Store the collected fractions at +4° C. while waiting for the results of the SDS-PAGE analysis.

(12) For immunisation prepare 4-5 aliquots of 100 µg each in 0.5 ml in 40% glycerol. The dilution buffer is the above elution buffer, plus 2 mM DTT. Store the aliquots at −20° C. until immunisation.

(b) Purification of His-Tagged Proteins from Inclusion Bodies

Purifications are carried out essentially according the following protocol:

(1) Bacteria are collected from 500 ml cultures by centrifugation. If required store bacterial pellets at −20° C. For extraction, resuspend each bacterial pellet in 10 ml 50 mM Tris—HCl buffer, pH 8.5 on an ice bath.

(2) Disrupt the resuspended bacteria with a French Press, performing two passages.

(3) Centrifuge at 35000×g for 15 min and collect the pellets. Use a Beckman rotor JA 25.50 (21000 rpm, 15 min.) or JA-20 (18000 rpm, 15 min.).

(4) Dissolve the centrifugation pellets with 50 mM Tris HCl, 1 mM TCEP (Tris(2-carboxyethyl)-phosphine hydrochloride, Pierce), 6M guanidium chloride, pH 8.5. Stir for ~10 min. with a magnetic bar.

(5) Centrifuge as described above, and collect the supernatant.

(6) Prepare an adequate number of Poly-Prep (Bio-Rad) columns containing 1 ml of Fast Flow Chelating SEPHAROSE® (Pharmacia) saturated with Nichel according to manufacturer recommendations. Wash the columns twice with 5 ml of $H_2O$ and equilibrate with 50 mM Tris HCl, 1 mM TCEP, 6M guanidinium chloride, pH 8.5.

(7) Load the supernatants from step 5 onto the columns, and wash with 5 ml of 50 mM Tris HCl buffer, 1 mM TCEP, 6M urea, pH 8.5

(8) Wash the columns with 10 ml of 20 mM imidazole, 50 mM TRIS-HCl, 6M urea, 1 mM TCEP, pH 8.5. Collect and set aside the first 5 ml for possible further controls.

(9) Elute the proteins bound to the columns with 4.5 ml of a buffer containing 250 mM imidazole, 50 mM Tris HCl, 6M urea, 1 mM TCEP, pH 8.5. Add the elution buffer in three 1.5 ml aliquots, and collect the corresponding 3 fractions. Add to each fraction 15 µl DTT (final concentration 2 mM).

(10) Measure eluted protein concentration with the Bradford method, and analyse aliquots of ca 10 µgof protein by SDS-PAGE.

(11) Store proteins at −20° C. in 40% (v/v) glycerol, 50 mM Tris HCl, 2M urea, 0.5 M arginine, 2 mM DTT, 0.3 mM TCEP, 83.3 mM imidazole, pH 8.5.

(c) Procedure for the Purification of GST-Fusion Proteins from *E. coli*

(1) Transfer the bacterial pellets from −20.degree. C. to an ice bath and suspend with 7.5 ml PBS, pH 7.4 to which a mixture of protease inhibitors (COMPLETE™-Boehringer Mannheim, 1 tablet every 25 ml of buffer) has been added.

(2) Transfer to 40-50 ml centrifugation tubes and sonicate according to the following procedure:

a. Position the probe at about 0.5 cm from the bottom of the tube b. Block the tube with the clamp c. Dip the tube in an ice bath d. Set the sonicator as follows: Timer→Hold, Duty Cycle→55, Out. Control→>6.

e. perform 5 cycles of 10 impulses at a time lapse of 1 minute (i.e. one cycle=10 impulses+~45" hold; b. 10 impulses+~45" hold; c. 10 impulses+~45" hold; d. 10 impulses+~45" hold; e. 10 impulses+~45" hold).

(3) Centrifuge at about 30-40000×g for 15-20 min. E.g.: use rotor Beckman JA 25.50 at 21000 rpm, for 15 min.

(4) Store the centrifugation pellets at −20° C., and load the supernatants on the chromatography columns, as follows (5) Equilibrate the Poly-Prep (Bio-Rad) columns with 0.5 ml (~=1 ml suspension) of Glutathione-SEPHAROSE® 4B resin, wash with 2 ml (1+1) $H_2O$, and then with 10 ml (2+4+4) PBS, pH 7.4.

(6) Load the supernatants on the columns and discard the flow through.

(7) Wash the columns with 10 ml (2+4+4) PBS, pH 7.4.

(8) Elute the proteins bound to the columns with 4.5 ml of 50 mM Tris buffer, 10 mM reduced glutathione, pH 8.0, adding 1.5 ml+1.5 ml+1.5 ml and collecting the respective 3 fractions of ~1.5 ml each.

(9) Measure the protein concentration of the first two fractions with the Bradford method, analyse a 10 µg aliquot of proteins from each sample by SDS-PAGE. (N.B.: if the sample is too diluted load 21 µl (+7 µl loading buffer).

(10) Store the collected fractions at +4° C. while waiting for the results of the SDS-PAGE analysis.

(11) For each protein destined to the immunisation prepare 4-5 aliquots of 100 µg each in 0.5 ml of 40% glycerol. The dilution buffer is 50 mM Tris HCl, 2 mM DTT, pH 8.0. Store the aliquots at −20° C. until immunisation.

4. Murine Model of Protection from GAS Infection (a) Immunization Protocol

Groups of 10 CD 1 female mice aged between 6 and 7 weeks are immunized with two or more GAS antigens of the invention, (20 µg of each recombinant GAS antigen), suspended in 100 µl of suitable solution. Each group receives 3 doses at days 0, 21 and 45 Immunization is performed through intraperitoneal injection of the protein with an equal volume of Complete Freund's Adjuvant (CFA) for the first dose and Incomplete Freund's Adjuvant (IFA) for the following two doses. In each immunization scheme negative and positive control groups are used.

For the negative control group, mice are immunized with E. coli proteins eluted from the purification columns following processing of total bacterial extract from a E. coli strain containing either the pET21b or the pGEX-NNH vector (thus expressing GST only) without any cloned GAS ORF (groups can be indicated as H is Stop or GSTStop respectively).

For the positive control groups, mice are immunized with purified GAS M cloned from either GAS SF370 or GAS DSM 2071 strains (groups indicated as 192SP and 192DSM respectively).

Pooled sera from each group is collected before the first immunization and two weeks after the last one. Mice are infected with GAS about a week after.

Immunized mice are infected using a GAS strain different from that used for the cloning of the selected proteins. For example, the GAS strain can be DSM 2071 M23 type, obtainable from the German Collection of Microorganisms and Cell Cultures (DSMZ).

For infection experiments, DSM 2071 is grown at 37° C. in THY broth until $OD_{600}$ 0.4. Bacteria are pelleted by centrifugation, washed once with PBS, suspended and diluted with PBS to obtain the appropriate concentration of bacteria/ml and administered to mice by intraperitoneal injection. Between 50 and 100 bacteria are given to each mouse, as determined by plating aliquots of the bacterial suspension on 5 THY plates. Animals are observed daily and checked for survival.

5. Analysis of Immune Sera (a) Preparation of GAS Total Protein Extracts

Total protein extracts are prepared by incubating a bacterial culture grown to $OD_{600}$ 0.4-0.5 in Tris 50 mM pH 6.8/mutanolysin (20 units/ml) for 2 hr at 37° C., followed by incubation for ten minutes on ice in 0.24 N NaOH and 0.96% (3-mercaptoethanol. The extracted proteins are precipitated by addition of trichloroacetic acid, washed with ice-cold acetone and suspended in protein loading buffer.

(b) Western Blot Analysis

Aliquots of total protein extract mixed with SDS loading buffer (1x: 60 mM Tris HCl HCl pH 6.8, 5% w/v SDS, 10% v/v glycerin, 0.1% Bromophenol Blue, 100 mM DTT) and boiled 5 minutes at 95° C., were loaded on a 12.5% SDS-PAGE precast gel (Biorad). The gel is run using a SDS-PAGE running buffer containing 250 mM Tris, 2.5 mM Glycine and 0.1% SDS. The gel is electroblotted onto nitrocellulose membrane at 200 mA for 60 minutes. The membrane is blocked for 60 minutes with PBS/0.05% TWEEN® 20 (Sigma), 10% skimmed milk powder and incubated O/N at 4° C. with PBS/0.05% TWEEN® 20, 1% skimmed milk powder, with the appropriate dilution of the sera. After washing twice with PBS/0.05% TWEEN®, the membrane is incubated for 2 hours with peroxidase-conjugated secondary anti-mouse antibody (Amersham) diluted 1:4000. The nitrocellulose is washed three times for 10 minutes with PBS/0.05% TWEEN® and once with PBS and thereafter developed by Opti-4CN Substrate Kit (Biorad).

(c) Preparation of Paraformaldehyde Treated GAS Cultures

A bacterial culture grown to $OD_{600}$ 0.4-0.5 is washed once with PBS and concentrated four times in PBS/0.05% Paraformaldehyde. Following 1 hr incubation at 37° C. with shacking, the treated culture is kept overnight at 4° C. and complete inactivation of bacteria is then controlled by plating aliquots on THY blood agar plates.

(d) FACS analysis of Paraformaldehyde Treated GAS Cultures with Mouse Immune Sera About $10^5$ Paraformaldehyde inactivated bacteria are washed with 200 µl of PBS in a 96 wells U bottom plate and centrifuged for 10 min. at 3000 g, at 4° C. The supernatant is discarded and the bacteria are suspended in 20 µl of PBS-0.1% BSA. Eighty µl of either pre-immune or immune mouse sera diluted in PBS-0.1% BSA are added to the bacterial suspension to a final dilution of either 1:100, 1:250 or 1:500, and incubated on ice for 30 min. Bacteria are washed once by adding 100 µL$_1$ of PBS-0.1% BSA, centrifuged for 10 min. at 3000 g, 4° C., suspended in 200 µl of PBS-0.1% BSA, centrifuged again and suspended in 10 µl of Goat Anti-Mouse IgG, F(ab')$_2$ fragment specific-R-Phycoerythrin-conjugated (Jackson Immunoresearch Laboratories Inc., cat. N$_o$ 115-116-072) in PBS-0.1% BSA to a final dilution of 1:100, and incubated on ice for 30 min. in the dark. Bacteria are washed once by adding 180 µl of PBS-0.1% BSA and centrifuged for 10 min. at 3000 g, 4.degree. C. The supernatant is discarded and the bacteria were suspended in 200 µl of PBS. Bacterial suspension is passed through a cytometric chamber of a FACS Calibur (Becton Dikinson, Mountain View, Calif. USA) and 10,000 events are acquired. Data are analysed using Cell Quest Software (Becton Dikinson, Mountain View, Calif. USA) by drawing a morphological dot plot (using forward and side scatter parameters) on bacterial signals. An histogram plot is then created on FL2 intensity of fluorescence log scale recalling the morphological region of bacteria.

Example 2

Comparison of Virulence of Wild Type Gas Strain (Including GAS 40) and Gas 40 Deletion Mutant The following example provides a comparison between the virulence of a wild type GAS strain and a GAS 40 deletion mutant. Mutant GAS strains where a majority of the GAS 40 sequence is removed were prepared by standard methods. Immunization groups of ten mice per group were injected with either the wild type or mutant GAS strains. As shown below, injection of a range of concentrations of the wild type isolate resulted in mouse fatalities, while injection with the GAS 440 mutant did not.

| GAS strain | concentration | number of fatalities |
|---|---|---|
| wild type | $2 \times 10^5$ | 10 |
| wild type | $2 \times 10^6$ | 9 |
| wild type | $2 \times 10^7$ | 5 |
| GASΔ40 | $2 \times 10^2$ | 0 |
| GASΔ40 | $2 \times 10^3$ | 0 |
| GASΔ40 | $2 \times 10^4$ | 0 |
| GASΔ40 | $2 \times 10^5$ | 0 |
| GASΔ40 | $2 \times 10^6$ | 0 |
| GASΔ40 | $2 \times 10^7$ | 0 |

Example 3

Bacterial Opsonophagocytosis Assay of GAS 40 Constructs

The following example demonstrates the surface exposure of GAS 40 by use in a bacterial opsonophagocytosis assay. The following GAS constructs, each of which is described in detail above, were used in the assay: 40a-CH, 40a-RR-NH, 40a-RR, GST-40, 40a, 40a and 40a-NH. (The two references to "40a" in FIG. 7 refer to sera prepared on different days.

The assay was performed as follows.
1. Preparation of Bacterial Inoculum.

GAS bacteria are grown in THY medium until they reach the middle exponential phase ($OD_{600}$ 0.4) at 37° C. Bacteria are washed twice in chilled saline solution and are suspended in HBSS medium with the volume being adjusted for each strain depending on the amount of bacteria which will be used. Bacterial cells are kept in ice until use.
2. Preparation of PMN.

PMN are prepared from buffy coats of heparinized blood from healthy volunteers. The buffy coat is incubated for 30 minutes in a solution containing dextran, NaCl and Heparin (rate 1:1). After incubation the supernatant, rich of leukocytes, is removed, transferred in a clean tube and centrifuged at 700×g for 20 minutes. A short wash in water is performed to break red blood cells and then a solution of NaCl is added to restore the appropriate salt concentration. After this step cells are centrifuged, washed and suspended in MEM at a suitable concentration.
3. Opsonophagocytosis Assay.

GAS strains (prepared as described) are incubated with heat inactivated immune mice serum derived from immunization with the indicated GAS antigen (or preimmune for the control), human PMN and baby rabbit complement. 1 hour of incubation at 37° C. Samples taken immediately before and after the incubation are plated on THY blood agar plates. Phagocytosis is evaluated comparing the difference in the number of colonies at the two times for the preimmune and the immune serum. Data are reported as logarithm number of grown colonies at t=0-logarithm number of grown colonies at t=60

The results of the assay are shown in FIG. 7. The Y axis reports the difference between the logarithm of colony counts at time 0 and the logarithm of the colony counts after 60 seconds: log(CFU@T0)-log(CFU@T60'). If there has been growth (i.e., the bacteria are not actively killed), negative numbers (negative bars) result. If bacteria are killed, positive numbers (positive histogram bars) result. As shown in FIG. 7, positive histogram bars are reported for each of the GAS constructs. The last four yellow bars in FIG. 7 represent controls: B=bacteria alone, B PMN=bacteria+polymorphonucleates, B C=Bacteria+complement, P PMN C=bacteria+polymorphonucleates+complement (no serum).

Example 4

GAS 40 Immunization Challenge Experiments in Murine Mouse Model of Protection A sample of the percent survival results from numerous murine mouse model experiments using the GAS 40 antigen are listed below. Annotations indicate where construct used to express the recombinant GAS 40 antigen was modified to facilitate expression.

| GAS antigen | % Survival in Mouse Challenge Model |
|---|---|
| 40a | 55 |
| 40a-RR | 70 |
| 40a-RR-NH | 60 |

It will be understood that the invention has been described by way of example only and modifications may be made whilst remaining within the scope and spirit of the invention.

The invention claimed is:

1. An immunogenic composition comprising a combination of *Streptococcus pyogenes* (GAS) antigens in substantially pure form, said combination consisting of two to ten GAS antigens, wherein said combination includes:
   (A) a Spy0269 antigen which comprises a fragment of 200 or more consecutive amino acids of SEQ ID NO:1; and
   (B) a Spy0448 antigen which comprises a fragment of 25 or more consecutive amino acids of SEQ ID NO:35.

2. The immunogenic composition of claim 1 wherein the Spy0269 antigen comprises amino acids 27-849 of SEQ ID NO:1.

3. The immunogenic composition of claim 1 wherein the Spy0269 antigen lacks amino acids 2-26 of SEQ ID NO:1.

4. The immunogenic composition of claim 2 wherein the Spy0269 antigen lacks amino acids 2-26 of SEQ ID NO:1.

5. The immunogenic composition of claim 1 wherein the Spy0269 antigen lacks amino acids 850-873 of SEQ ID NO:1.

6. The immunogenic composition of claim 2 wherein the Spy0269 antigen lacks amino acids 850-873 of SEQ ID NO:1.

7. The immunogenic composition of claim 3 wherein the Spy0269 antigen lacks amino acids 850-873 of SEQ ID NO:1.

8. The immunogenic composition of claim 1 wherein the Spy0448 antigen comprises SEQ ID NO:38.

9. The immunogenic composition of claim 1 further comprising an adjuvant.

10. A method of raising an immune response against *Streptococcus pyogenes*, comprising administering to an animal in need thereof an effective amount of the immunogenic composition of claim 1.

* * * * *

SEQUENCE LISTING

<160> NUMBER OF SEQ ID NOS: 146

<210> SEQ ID NO 1
<211> LENGTH: 873
<212> TYPE: PRT
<213> ORGANISM: Streptococcus pyogenes

<400> SEQUENCE: 1

Met Asp Leu Glu Gln Thr Lys Pro Asn Gln Val Lys Gln Lys Ile Ala
 1               5                   10                  15

-continued

Leu Thr Ser Thr Ile Ala Leu Leu Ser Ala Ser Val Gly Val Ser His
        20                  25                  30

Gln Val Lys Ala Asp Asp Arg Ala Ser Gly Glu Thr Lys Ala Ser Asn
        35                  40                  45

Thr His Asp Asp Ser Leu Pro Lys Pro Glu Thr Ile Gln Glu Ala Lys
        50                  55                  60

Ala Thr Ile Asp Ala Val Glu Lys Thr Leu Ser Gln Gln Lys Ala Glu
65                  70                  75                  80

Leu Thr Glu Leu Ala Thr Ala Leu Thr Lys Thr Thr Ala Glu Ile Asn
                85                  90                  95

His Leu Lys Glu Gln Gln Asp Asn Glu Gln Lys Ala Leu Thr Ser Ala
            100                 105                 110

Gln Glu Ile Tyr Thr Asn Thr Leu Ala Ser Ser Glu Glu Thr Leu Leu
            115                 120                 125

Ala Gln Gly Ala Glu His Gln Arg Glu Leu Thr Ala Thr Glu Thr Glu
130                 135                 140

Leu His Asn Ala Gln Ala Asp Gln His Ser Lys Glu Thr Ala Leu Ser
145                 150                 155                 160

Glu Gln Lys Ala Ser Ile Ser Ala Glu Thr Thr Arg Ala Gln Asp Leu
            165                 170                 175

Val Glu Gln Val Lys Thr Ser Glu Gln Asn Ile Ala Lys Leu Asn Ala
            180                 185                 190

Met Ile Ser Asn Pro Asp Ala Ile Thr Lys Ala Ala Gln Thr Ala Asn
            195                 200                 205

Asp Asn Thr Lys Ala Leu Ser Ser Glu Leu Glu Lys Ala Lys Ala Asp
            210                 215                 220

Leu Glu Asn Gln Lys Ala Lys Val Lys Lys Gln Leu Thr Glu Glu Leu
225                 230                 235                 240

Ala Ala Gln Lys Ala Ala Leu Ala Glu Lys Glu Ala Glu Leu Ser Arg
            245                 250                 255

Leu Lys Ser Ser Ala Pro Ser Thr Gln Asp Ser Ile Val Gly Asn Asn
            260                 265                 270

Thr Met Lys Ala Pro Gln Gly Tyr Pro Leu Glu Glu Leu Lys Lys Leu
            275                 280                 285

Glu Ala Ser Gly Tyr Ile Gly Ser Ala Ser Tyr Asn Asn Tyr Tyr Lys
            290                 295                 300

Glu His Ala Asp Gln Ile Ile Ala Lys Ala Ser Pro Gly Asn Gln Leu
305                 310                 315                 320

Asn Gln Tyr Gln Asp Ile Pro Ala Asp Arg Asn Arg Phe Val Asp Pro
            325                 330                 335

Asp Asn Leu Thr Pro Glu Val Gln Asn Glu Leu Ala Gln Phe Ala Ala
            340                 345                 350

His Met Ile Asn Ser Val Arg Arg Gln Leu Gly Leu Pro Pro Val Thr
            355                 360                 365

Val Thr Ala Gly Ser Gln Glu Phe Ala Arg Leu Leu Ser Thr Ser Tyr
            370                 375                 380

Lys Lys Thr His Gly Asn Thr Arg Pro Ser Phe Val Tyr Gly Gln Pro
385                 390                 395                 400

Gly Val Ser Gly His Tyr Gly Val Gly Pro His Asp Lys Thr Ile Ile
            405                 410                 415

Glu Asp Ser Ala Gly Ala Ser Gly Leu Ile Arg Asn Asp Asp Asn Met
            420                 425                 430

Tyr Glu Asn Ile Gly Ala Phe Asn Asp Val His Thr Val Asn Gly Ile

-continued

```
            435                 440                 445
Lys Arg Gly Ile Tyr Asp Ser Ile Lys Tyr Met Leu Phe Thr Asp His
450                 455                 460

Leu His Gly Asn Thr Tyr Gly His Ala Ile Asn Phe Leu Arg Val Asp
465                 470                 475                 480

Lys His Asn Pro Asn Ala Pro Val Tyr Leu Gly Phe Ser Thr Ser Asn
                485                 490                 495

Val Gly Ser Leu Asn Glu His Phe Val Met Phe Pro Glu Ser Asn Ile
                500                 505                 510

Ala Asn His Gln Arg Phe Asn Lys Thr Pro Ile Lys Ala Val Gly Ser
                515                 520                 525

Thr Lys Asp Tyr Ala Gln Arg Val Gly Thr Val Ser Asp Thr Ile Ala
530                 535                 540

Ala Ile Lys Gly Lys Val Ser Ser Leu Glu Asn Arg Leu Ser Ala Ile
545                 550                 555                 560

His Gln Glu Ala Asp Ile Met Ala Ala Gln Ala Lys Val Ser Gln Leu
                565                 570                 575

Gln Gly Lys Leu Ala Ser Thr Leu Lys Gln Ser Asp Ser Leu Asn Leu
                580                 585                 590

Gln Val Arg Gln Leu Asn Asp Thr Lys Gly Ser Leu Arg Thr Glu Leu
595                 600                 605

Leu Ala Ala Lys Ala Lys Gln Ala Gln Leu Glu Ala Thr Arg Asp Gln
610                 615                 620

Ser Leu Ala Lys Leu Ala Ser Leu Lys Ala Ala Leu His Gln Thr Glu
625                 630                 635                 640

Ala Leu Ala Glu Gln Ala Ala Ala Arg Val Thr Ala Leu Val Ala Lys
                645                 650                 655

Lys Ala His Leu Gln Tyr Leu Arg Asp Phe Lys Leu Asn Pro Asn Arg
                660                 665                 670

Leu Gln Val Ile Arg Glu Arg Ile Asp Asn Thr Lys Gln Asp Leu Ala
                675                 680                 685

Lys Thr Thr Ser Ser Leu Leu Asn Ala Gln Glu Ala Leu Ala Ala Leu
690                 695                 700

Gln Ala Lys Gln Ser Ser Leu Glu Ala Thr Ile Ala Thr Thr Glu His
705                 710                 715                 720

Gln Leu Thr Leu Leu Lys Thr Leu Ala Asn Glu Lys Glu Tyr Arg His
                725                 730                 735

Leu Asp Glu Asp Ile Ala Thr Val Pro Asp Leu Gln Val Ala Pro Pro
                740                 745                 750

Leu Thr Gly Val Lys Pro Leu Ser Tyr Ser Lys Ile Asp Thr Thr Pro
                755                 760                 765

Leu Val Gln Glu Met Val Lys Glu Thr Lys Gln Leu Leu Glu Ala Ser
                770                 775                 780

Ala Arg Leu Ala Ala Glu Asn Thr Ser Leu Val Ala Glu Ala Leu Val
785                 790                 795                 800

Gly Gln Thr Ser Glu Met Val Ala Ser Asn Ala Ile Val Ser Lys Ile
                805                 810                 815

Thr Ser Ser Ile Thr Gln Pro Ser Ser Lys Thr Ser Tyr Gly Ser Gly
                820                 825                 830

Ser Ser Thr Thr Ser Asn Leu Ile Ser Asp Val Asp Glu Ser Thr Gln
                835                 840                 845

Arg Ala Leu Lys Ala Gly Val Val Met Leu Ala Ala Val Gly Leu Thr
850                 855                 860
```

Gly Phe Arg Phe Arg Lys Glu Ser Lys
865                 870

<210> SEQ ID NO 2
<211> LENGTH: 2622
<212> TYPE: DNA
<213> ORGANISM: S. pyogenes

<400> SEQUENCE: 2

| | | | | | |
|---|---|---|---|---|---|
| atggacttag | aacaaacgaa | gccaaaccaa | gttaagcaga | aaattgcttt | aacctcaaca | 60 |
| attgctttat | tgagtgccag | tgtaggcgta | tctcaccaag | tcaaagcaga | tgatagagcc | 120 |
| tcaggagaaa | cgaaggcgag | taatactcac | gacgatagtt | accaaaaacc | agaaacaatt | 180 |
| caagaggcaa | aggcaactat | tgatgcagtt | gaaaaaactc | tcagtcaaca | aaaagcagaa | 240 |
| ctgacagagc | ttgctaccgc | tctgacaaaa | actactgctg | aaatcaacca | cttaaaagag | 300 |
| cagcaagata | tgaacaaaaa | agctttaacc | tctgcacaag | aaatttacac | taatactctt | 360 |
| gcaagtagtg | aggagacgct | attagcccaa | ggagccgaac | atcaaagaga | gttaacagct | 420 |
| actgaaacag | agcttcataa | tgctcaagca | gatcaacatt | caaaagagac | tgcattgtca | 480 |
| gaacaaaaag | ctagcatttc | agcagaaact | actcgagctc | aagatttagt | ggaacaagtc | 540 |
| aaaacgtctg | aacaaaatat | tgctaagctc | aatgctatga | ttagcaatcc | tgatgctatc | 600 |
| actaaagcag | ctcaaacggc | taatgataat | acaaaagcat | taagctcaga | attggagaag | 660 |
| gctaaagctg | acttagaaaa | tcaaaaagct | aaagttaaaa | agcaattgac | tgaagagttg | 720 |
| gcagctcaga | aagctgctct | agcagaaaaa | gaggcagaac | ttagtcgtct | aaatcctca | 780 |
| gctccgtcta | ctcaagatag | cattgtgggt | aataatacca | tgaaagcacc | gcaaggctat | 840 |
| cctcttgaag | aacttaaaaa | attagaagct | agtggtata | ttggatcagc | tagttacaat | 900 |
| aattattaca | agagcatgc | agatcaaatt | attgccaaag | ctagtccagg | taatcaatta | 960 |
| aatcaataccc | aagatattcc | agcagatcgt | aatcgctttg | ttgatcccga | aatttgaca | 1020 |
| ccagaagtgc | aaaatgagct | agcgcagttt | gcagctcaca | tgattaatag | tgtaagaaga | 1080 |
| caattaggtc | taccaccagt | tactgttaca | gcaggatcac | aagaatttgc | aagattactt | 1140 |
| agtaccagct | ataagaaaac | tcatggtaat | acaagaccat | catttgtcta | cggacagcca | 1200 |
| ggggtatcag | gcattatgg | tgttgggcct | catgataaaa | ctattattga | agactctgcc | 1260 |
| ggagcgtcag | gctcattcg | aaatgatgat | aacatgtacg | agaatatcgg | tgcttttaac | 1320 |
| gatgtgcata | ctgtgaatgg | tattaaacgt | ggtatttatg | acagtatcaa | gtatatgctc | 1380 |
| tttacagatc | atttacacgg | aaatacatac | ggccatgcta | ttaactttt | acgtgtagat | 1440 |
| aaacataacc | ctaatgcgcc | tgtttacctt | ggattttcaa | ccagcaatgt | aggatctttg | 1500 |
| aatgaacact | ttgtaatgtt | tccagagtct | aacattgcta | accatcaacg | ctttaataag | 1560 |
| accctatata | agccgttgg | aagtacaaaa | gattatgccc | aaagagtagg | cactgtatct | 1620 |
| gatactattg | cagcgatcaa | aggaaaagta | agctcattag | aaaatcgttt | gtcggctatt | 1680 |
| catcaagaag | ctgatattat | ggcagcccaa | gctaaagtaa | gtcaacttca | aggtaaatta | 1740 |
| gcaagcacac | ttaagcagtc | agacagctta | aatctccaag | tgacacaatt | aaatgatact | 1800 |
| aaaggttctt | tgagaacaga | attactagca | gctaaagcaa | acaagcaca | actcgaagct | 1860 |
| actcgtgatc | aatcattagc | taagctagca | tcgttaaag | ccgcactgca | ccagacagaa | 1920 |
| gccttagcag | agcaagccgc | agccagagtg | acagcactgg | tggctaaaaa | agctcatttg | 1980 |
| caatatctaa | gggactttaa | attgaatcct | aaccgcttc | aagtgatacg | tgagcgcatt | 2040 |
| gataatacta | agcaagattt | ggctaaaact | acctcatctt | tgttaaatgc | acaagaagct | 2100 |

```
ttagcagcct acaagctaa acaaagcagt ctagaagcta ctattgctac cacagaacac    2160
cagttgactt tgcttaaaac cttagctaac gaaaaggaat atcgccactt agacgaagat    2220
atagctactg tgcctgattt gcaagtagct ccacctctta cgggcgtaaa accgctatca    2280
tatagtaaga tagatactac tccgcttgtt caagaaatgg ttaaagaaac gaaacaacta    2340
ttagaagctt cagcaagatt agctgctgaa aatacaagtc ttgtagcaga agcgcttgtt    2400
ggccaaacct ctgaaatggt agcaagtaat gccattgtgt ctaaaatcac atcttcgatt    2460
actcagccct catctaagac atcttatggc tcaggatctt ctacaacgag caatctcatt    2520
tctgatgttg atgaaagtac tcaaagagct cttaaagcag gagtcgtcat gttggcagct    2580
gtcggcctca caggatttag gttccgtaag gaatctaagt ga                      2622
```

<210> SEQ ID NO 3
<211> LENGTH: 26
<212> TYPE: PRT
<213> ORGANISM: S. pyogenes

<400> SEQUENCE: 3

Met Asp Leu Glu Gln Thr Lys Pro Asn Gln Val Lys Gln Lys Ile Ala
 1               5                  10                  15

Leu Thr Ser Thr Ile Ala Leu Leu Ser Ala
             20                  25

<210> SEQ ID NO 4
<211> LENGTH: 78
<212> TYPE: DNA
<213> ORGANISM: Streptococcus pyogenes

<400> SEQUENCE: 4
atggacttag aacaaacgaa gccaaaccaa gttaagcaga aaattgcttt aacctcaaca    60
attgctttat tgagtgcc                                                  78

<210> SEQ ID NO 5
<211> LENGTH: 847
<212> TYPE: PRT
<213> ORGANISM: Streptococcus pyogenes

<400> SEQUENCE: 5

Ser Val Gly Val Ser His Gln Val Lys Ala Asp Asp Arg Ala Ser Gly
 1               5                  10                  15

Glu Thr Lys Ala Ser Asn Thr His Asp Asp Ser Leu Pro Lys Pro Glu
             20                  25                  30

Thr Ile Gln Glu Ala Lys Ala Thr Ile Asp Ala Val Glu Lys Thr Leu
         35                  40                  45

Ser Gln Gln Lys Ala Glu Leu Thr Glu Leu Ala Thr Ala Leu Thr Lys
     50                  55                  60

Thr Thr Ala Glu Ile Asn His Leu Lys Glu Gln Gln Asp Asn Glu Gln
 65                  70                  75                  80

Lys Ala Leu Thr Ser Ala Gln Glu Ile Tyr Thr Asn Thr Leu Ala Ser
                 85                  90                  95

Ser Glu Glu Thr Leu Leu Ala Gln Gly Ala Glu His Gln Arg Glu Leu
            100                 105                 110

Thr Ala Thr Glu Thr Glu Leu His Asn Ala Gln Ala Asp Gln His Ser
        115                 120                 125

Lys Glu Thr Ala Leu Ser Glu Gln Lys Ala Ser Ile Ser Ala Glu Thr
    130                 135                 140

```
Thr Arg Ala Gln Asp Leu Val Glu Gln Val Lys Thr Ser Glu Gln Asn
145                 150                 155                 160

Ile Ala Lys Leu Asn Ala Met Ile Ser Asn Pro Asp Ala Ile Thr Lys
            165                 170                 175

Ala Ala Gln Thr Ala Asn Asp Asn Thr Lys Ala Leu Ser Ser Glu Leu
        180                 185                 190

Glu Lys Ala Lys Ala Asp Leu Glu Asn Gln Lys Ala Lys Val Lys Lys
    195                 200                 205

Gln Leu Thr Glu Glu Leu Ala Ala Gln Lys Ala Ala Leu Ala Glu Lys
210                 215                 220

Glu Ala Glu Leu Ser Arg Leu Lys Ser Ser Ala Pro Ser Thr Gln Asp
225                 230                 235                 240

Ser Ile Val Gly Asn Asn Thr Met Lys Ala Pro Gln Gly Tyr Pro Leu
            245                 250                 255

Glu Glu Leu Lys Lys Leu Glu Ala Ser Gly Tyr Ile Gly Ser Ala Ser
        260                 265                 270

Tyr Asn Asn Tyr Tyr Lys Glu His Ala Asp Gln Ile Ala Lys Ala
    275                 280                 285

Ser Pro Gly Asn Gln Leu Asn Gln Tyr Gln Asp Ile Pro Ala Asp Arg
290                 295                 300

Asn Arg Phe Val Asp Pro Asp Asn Leu Thr Pro Glu Val Gln Asn Glu
305                 310                 315                 320

Leu Ala Gln Phe Ala Ala His Met Ile Asn Ser Val Arg Arg Gln Leu
                325                 330                 335

Gly Leu Pro Pro Val Thr Val Thr Ala Gly Ser Gln Glu Phe Ala Arg
            340                 345                 350

Leu Leu Ser Thr Ser Tyr Lys Lys Thr His Gly Asn Thr Arg Pro Ser
        355                 360                 365

Phe Val Tyr Gly Gln Pro Gly Val Ser Gly His Tyr Gly Val Gly Pro
370                 375                 380

His Asp Lys Thr Ile Ile Glu Asp Ser Ala Gly Ala Ser Gly Leu Ile
385                 390                 395                 400

Arg Asn Asp Asp Asn Met Tyr Glu Asn Ile Gly Ala Phe Asn Asp Val
                405                 410                 415

His Thr Val Asn Gly Ile Lys Arg Gly Ile Tyr Asp Ser Ile Lys Tyr
            420                 425                 430

Met Leu Phe Thr Asp His Leu His Gly Asn Thr Tyr Gly His Ala Ile
        435                 440                 445

Asn Phe Leu Arg Val Asp Lys His Asn Pro Asn Ala Pro Val Tyr Leu
450                 455                 460

Gly Phe Ser Thr Ser Asn Val Gly Ser Leu Asn Glu His Phe Val Met
465                 470                 475                 480

Phe Pro Glu Ser Asn Ile Ala Asn His Gln Arg Phe Asn Lys Thr Pro
                485                 490                 495

Ile Lys Ala Val Gly Ser Thr Lys Asp Tyr Ala Gln Arg Val Gly Thr
            500                 505                 510

Val Ser Asp Thr Ile Ala Ile Lys Gly Lys Val Ser Ser Leu Glu
        515                 520                 525

Asn Arg Leu Ser Ala Ile His Gln Glu Ala Asp Ile Met Ala Ala Gln
530                 535                 540

Ala Lys Val Ser Gln Leu Gln Gly Lys Leu Ala Ser Thr Leu Lys Gln
545                 550                 555                 560

Ser Asp Ser Leu Asn Leu Gln Val Arg Gln Leu Asn Asp Thr Lys Gly
                565                 570                 575
```

```
Ser Leu Arg Thr Glu Leu Leu Ala Ala Lys Ala Lys Gln Ala Gln Leu
            580                 585                 590

Glu Ala Thr Arg Asp Gln Ser Leu Ala Lys Leu Ala Ser Leu Lys Ala
        595                 600                 605

Ala Leu His Gln Thr Glu Ala Leu Ala Glu Gln Ala Ala Arg Val
    610                 615                 620

Thr Ala Leu Val Ala Lys Lys Ala His Leu Gln Tyr Leu Arg Asp Phe
625                 630                 635                 640

Lys Leu Asn Pro Asn Arg Leu Gln Val Ile Arg Glu Arg Ile Asp Asn
                645                 650                 655

Thr Lys Gln Asp Leu Ala Lys Thr Thr Ser Ser Leu Leu Asn Ala Gln
            660                 665                 670

Glu Ala Leu Ala Ala Leu Gln Ala Lys Gln Ser Ser Leu Glu Ala Thr
        675                 680                 685

Ile Ala Thr Thr Glu His Gln Leu Thr Leu Lys Thr Leu Ala Asn
    690                 695                 700

Glu Lys Glu Tyr Arg His Leu Asp Glu Asp Ile Ala Thr Val Pro Asp
705                 710                 715                 720

Leu Gln Val Ala Pro Pro Leu Thr Gly Val Lys Pro Leu Ser Tyr Ser
                725                 730                 735

Lys Ile Asp Thr Thr Pro Leu Val Gln Glu Met Val Lys Glu Thr Lys
            740                 745                 750

Gln Leu Leu Glu Ala Ser Ala Arg Leu Ala Ala Glu Asn Thr Ser Leu
        755                 760                 765

Val Ala Glu Ala Leu Val Gly Gln Thr Ser Glu Met Val Ala Ser Asn
    770                 775                 780

Ala Ile Val Ser Lys Ile Thr Ser Ile Thr Gln Pro Ser Ser Lys
785                 790                 795                 800

Thr Ser Tyr Gly Ser Gly Ser Ser Thr Thr Ser Asn Leu Ile Ser Asp
                805                 810                 815

Val Asp Glu Ser Thr Gln Arg Ala Leu Lys Ala Gly Val Val Met Leu
            820                 825                 830

Ala Ala Val Gly Leu Thr Gly Phe Arg Phe Arg Lys Glu Ser Lys
        835                 840                 845

<210> SEQ ID NO 6
<211> LENGTH: 2544
<212> TYPE: DNA
<213> ORGANISM: Streptococcus pyogenes

<400> SEQUENCE: 6
agtgtaggcg tatctcacca agtcaaagca gatgatagag cctcaggaga acgaaggcg      60 agtaatactc acgacgatag tttaccaaaa ccagaaacaa ttcaagaggc aaaggcaact    120
attgatgcag ttgaaaaaac tctcagtcaa caaaaagcag aactgacaga gcttgctacc    180
gctctgacaa aaactactgc tgaaatcaac cacttaaaag agcagcaaga taatgaacaa    240
aaagctttaa cctctgcaca agaaatttac actaatactc ttgcaagtag tgaggagacg    300
ctattagccc aaggagccga acatcaaaga gagttaacag ctactgaaac agagcttcat    360
aatgctcaag cagatcaaca ttcaaaagag actgcattgt cagaacaaaa agctagcatt    420
tcagcagaaa ctactcgagc tcaagattta gtggaacaag tcaaaacgtc tgaacaaaat    480
attgctaagc tcaatgctat gattagcaat cctgatgcta tcactaaagc agctcaaacg    540
gctaatgata tacaaaagc attaagctca gaattggaga aggctaaagc tgacttagaa    600
```

```
aatcaaaaag ctaaagttaa aaagcaattg actgaagagt tggcagctca gaaagctgct    660
ctagcagaaa aagaggcaga acttagtcgt cttaaatcct cagctccgtc tactcaagat    720
agcattgtgg gtaataatac catgaaagca ccgcaaggct atcctcttga agaacttaaa    780
aaattagaag ctagtggtta tattggatca gctagttaca ataattatta caagagcat    840
gcagatcaaa ttattgccaa agctagtcca ggtaatcaat taaatcaata ccaagatatt    900
ccagcagatc gtaatcgctt tgttgatccc gataatttga caccagaagt gcaaaatgag    960
ctagcgcagt ttgcagctca catgattaat agtgtaagaa gacaattagg tctaccacca   1020
gttactgtta cagcaggatc acaagaattt gcaagattac ttagtaccag ctataagaaa   1080
actcatggta atacaagacc atcatttgtc tacggacagc caggggtatc agggcattat   1140
ggtgttgggc ctcatgataa aactattatt gaagactctg ccggagcgtc agggctcatt   1200
cgaaatgatg ataacatgta cgagaatatc ggtgctttta acgatgtgca tactgtgaat   1260
ggtattaaac gtggtatttta tgacagtatc aagtatatgc tctttacaga tcatttacac   1320
ggaaatacat acggccatgc tattaacttt ttacgtgtag ataaacataa ccctaatgcg   1380
cctgtttacc ttggattttc aaccagcaat gtaggatctt tgaatgaaca ctttgtaatg   1440
tttccagagt ctaacattgc taaccatcaa cgctttaata agaccccatt aaaagccgtt   1500
ggaagtacaa aagattatgc ccaaagagta ggcactgtat ctgatactat tgcagcgatc   1560
aaaggaaaag taagctcatt agaaaatcgt ttgtcggcta ttcatcaaga agctgatatt   1620
atggcagccc aagctaaagt aagtcaactt caaggtaaat tagcaagcac acttaagcag   1680
tcagacagct taaatctcca agtgagacaa ttaaatgata ctaaaggttc tttgagaaca   1740
gaattactag cagctaaagc aaaacaagca caactcgaag ctactcgtga tcaatcatta   1800
gctaagctag catcgttgaa agccgcactg caccagacag aagccttagc agagcaagcc   1860
gcagccagag tgacagcact ggtggctaaa aaagctcatt tgcaatatct aagggacttt   1920
aaattgaatc ctaaccgcct tcaagtgata cgtgagcgca ttgataatac taagcaagat   1980
ttggctaaaa ctacctcatc tttgttaaat gcacaagaag cttttagcagc cttacaagct   2040
aaacaaagca gtctagaagc tactattgct accacagaac accagttgac tttgcttaaa   2100
accttagcta cgaaaaggaa atatcgccac ttagacgaag atatagctac tgtgcctgat   2160
ttgcaagtag ctccacctct tacgggcgta aaaccgctat catatagtaa gatagatact   2220
actccgcttg ttcaagaaat ggttaaagaa acgaaacaac tattagaagc ttcagcaaga   2280
ttagctgctg aaaatacaag tcttgtagca gaagcgcttg ttggccaaac ctctgaaatg   2340
gtagcaagta atgccattgt gtctaaaatc acatcttcga ttactcagcc ctcatctaag   2400
acatcttatg gctcaggatc ttctacaacg agcaatctca tttctgatgt tgatgaaagt   2460
actcaaagag ctcttaaagc aggagtcgtc atgttggcag ctgtcggcct cacaggattt   2520
aggttccgta aggaatctaa gtga                                         2544
```

<210> SEQ ID NO 7
<211> LENGTH: 24
<212> TYPE: PRT
<213> ORGANISM: Streptococcus pyogenes

<400> SEQUENCE: 7

Ala Leu Lys Ala Gly Val Val Met Leu Ala Ala Val Gly Leu Thr Gly
 1               5                  10                  15

Phe Arg Phe Arg Lys Glu Ser Lys
            20

-continued

```
<210> SEQ ID NO 8
<211> LENGTH: 75
<212> TYPE: DNA
<213> ORGANISM: Streptococcus pyogenes

<400> SEQUENCE: 8
gctcttaaag caggagtcgt catgttggca gctgtcggcc tcacaggatt taggttccgt    60
aaggaatcta agtga                                                    75

<210> SEQ ID NO 9
<211> LENGTH: 849
<212> TYPE: PRT
<213> ORGANISM: Streptococcus pyogenes

<400> SEQUENCE: 9
```

Met Asp Leu Glu Gln Thr Lys Pro Asn Gln Val Lys Gln Lys Ile Ala
1               5                   10                  15

Leu Thr Ser Thr Ile Ala Leu Leu Ser Ala Ser Val Gly Val Ser His
            20                  25                  30

Gln Val Lys Ala Asp Asp Arg Ala Ser Gly Glu Thr Lys Ala Ser Asn
        35                  40                  45

Thr His Asp Asp Ser Leu Pro Lys Pro Glu Thr Ile Gln Glu Ala Lys
    50                  55                  60

Ala Thr Ile Asp Ala Val Glu Lys Thr Leu Gln Gln Lys Ala Glu
65                  70                  75                  80

Leu Thr Glu Leu Ala Thr Ala Leu Thr Lys Thr Ala Glu Ile Asn
            85                  90                  95

His Leu Lys Glu Gln Gln Asp Asn Glu Gln Lys Ala Leu Thr Ser Ala
            100                 105                 110

Gln Glu Ile Tyr Thr Asn Thr Leu Ala Ser Ser Glu Glu Thr Leu Leu
        115                 120                 125

Ala Gln Gly Ala Glu His Gln Arg Glu Leu Thr Ala Thr Glu Thr Glu
    130                 135                 140

Leu His Asn Ala Gln Ala Asp Gln His Ser Lys Glu Thr Ala Leu Ser
145                 150                 155                 160

Glu Gln Lys Ala Ser Ile Ser Ala Glu Thr Thr Arg Ala Gln Asp Leu
            165                 170                 175

Val Glu Gln Val Lys Thr Ser Glu Gln Asn Ile Ala Lys Leu Asn Ala
        180                 185                 190

Met Ile Ser Asn Pro Asp Ala Ile Thr Lys Ala Ala Gln Thr Ala Asn
    195                 200                 205

Asp Asn Thr Lys Ala Leu Ser Ser Glu Leu Glu Lys Ala Lys Ala Asp
    210                 215                 220

Leu Glu Asn Gln Lys Ala Lys Val Lys Lys Gln Leu Thr Glu Glu Leu
225                 230                 235                 240

Ala Ala Gln Lys Ala Ala Leu Ala Glu Lys Glu Ala Glu Leu Ser Arg
            245                 250                 255

Leu Lys Ser Ser Ala Pro Ser Thr Gln Asp Ser Ile Val Gly Asn Asn
            260                 265                 270

Thr Met Lys Ala Pro Gln Gly Tyr Pro Leu Glu Glu Leu Lys Lys Leu
        275                 280                 285

Glu Ala Ser Gly Tyr Ile Gly Ser Ala Ser Tyr Asn Asn Tyr Tyr Lys
    290                 295                 300

Glu His Ala Asp Gln Ile Ile Ala Lys Ala Ser Pro Gly Asn Gln Leu
305                 310                 315                 320

```
Asn Gln Tyr Gln Asp Ile Pro Ala Asp Arg Asn Arg Phe Val Asp Pro
                325                 330                 335

Asp Asn Leu Thr Pro Glu Val Gln Asn Glu Leu Ala Gln Phe Ala Ala
            340                 345                 350

His Met Ile Asn Ser Val Arg Arg Gln Leu Gly Leu Pro Pro Val Thr
        355                 360                 365

Val Thr Ala Gly Ser Gln Glu Phe Ala Arg Leu Leu Ser Thr Ser Tyr
    370                 375                 380

Lys Lys Thr His Gly Asn Thr Arg Pro Ser Phe Val Tyr Gly Gln Pro
385                 390                 395                 400

Gly Val Ser Gly His Tyr Gly Val Gly Pro His Asp Lys Thr Ile Ile
                405                 410                 415

Glu Asp Ser Ala Gly Ala Ser Gly Leu Ile Arg Asn Asp Asp Asn Met
            420                 425                 430

Tyr Glu Asn Ile Gly Ala Phe Asn Asp Val His Thr Val Asn Gly Ile
        435                 440                 445

Lys Arg Gly Ile Tyr Asp Ser Ile Lys Tyr Met Leu Phe Thr Asp His
    450                 455                 460

Leu His Gly Asn Thr Tyr Gly His Ala Ile Asn Phe Leu Arg Val Asp
465                 470                 475                 480

Lys His Asn Pro Asn Ala Pro Val Tyr Leu Gly Phe Ser Thr Ser Asn
                485                 490                 495

Val Gly Ser Leu Asn Glu His Phe Val Met Phe Pro Glu Ser Asn Ile
            500                 505                 510

Ala Asn His Gln Arg Phe Asn Lys Thr Pro Ile Lys Ala Val Gly Ser
        515                 520                 525

Thr Lys Asp Tyr Ala Gln Arg Val Gly Thr Val Ser Asp Thr Ile Ala
    530                 535                 540

Ala Ile Lys Gly Lys Val Ser Ser Leu Glu Asn Arg Leu Ser Ala Ile
545                 550                 555                 560

His Gln Glu Ala Asp Ile Met Ala Ala Gln Ala Lys Val Ser Gln Leu
                565                 570                 575

Gln Gly Lys Leu Ala Ser Thr Leu Lys Gln Ser Asp Ser Leu Asn Leu
            580                 585                 590

Gln Val Arg Gln Leu Asn Asp Thr Lys Gly Ser Leu Arg Thr Glu Leu
        595                 600                 605

Leu Ala Ala Lys Ala Lys Gln Ala Gln Leu Glu Ala Thr Arg Asp Gln
    610                 615                 620

Ser Leu Ala Lys Leu Ala Ser Leu Lys Ala Ala Leu His Gln Thr Glu
625                 630                 635                 640

Ala Leu Ala Glu Gln Ala Ala Ala Arg Val Thr Ala Leu Val Ala Lys
                645                 650                 655

Lys Ala His Leu Gln Tyr Leu Arg Asp Phe Lys Leu Asn Pro Asn Arg
            660                 665                 670

Leu Gln Val Ile Arg Glu Arg Ile Asp Asn Thr Lys Gln Asp Leu Ala
        675                 680                 685

Lys Thr Thr Ser Ser Leu Leu Asn Ala Gln Glu Ala Leu Ala Ala Leu
    690                 695                 700

Gln Ala Lys Gln Ser Ser Leu Glu Ala Thr Ile Ala Thr Thr Glu His
705                 710                 715                 720

Gln Leu Thr Leu Leu Lys Thr Leu Ala Asn Glu Lys Glu Tyr Arg His
                725                 730                 735

Leu Asp Glu Asp Ile Ala Thr Val Pro Asp Leu Gln Val Ala Pro Pro
            740                 745                 750
```

| | | | | | | | | | | | | |
|---|---|---|---|---|---|---|---|---|---|---|---|---|
|Leu|Thr|Gly|Val|Lys|Pro|Leu|Ser|Tyr|Ser|Lys|Ile|Asp|Thr|Thr|Pro|
| | |755| | | |760| | | |765| | | | | |

Leu Val Gln Glu Met Val Lys Glu Thr Lys Gln Leu Leu Glu Ala Ser
          770              775              780

Ala Arg Leu Ala Ala Glu Asn Thr Ser Leu Val Ala Glu Ala Leu Val
785              790              795              800

Gly Gln Thr Ser Glu Met Val Ala Ser Asn Ala Ile Val Ser Lys Ile
              805              810              815

Thr Ser Ser Ile Thr Gln Pro Ser Ser Lys Thr Ser Tyr Gly Ser Gly
          820              825              830

Ser Ser Thr Thr Ser Asn Leu Ile Ser Asp Val Asp Glu Ser Thr Gln
          835              840              845

Arg

<210> SEQ ID NO 10
<211> LENGTH: 2547
<212> TYPE: DNA
<213> ORGANISM: Streptococcus pyogenes

<400> SEQUENCE: 10

```
atggacttag aacaaacgaa gccaaaccaa gttaagcaga aaattgcttt aacctcaaca        60
attgctttat tgagtgccag tgtaggcgta tctcaccaag tcaaagcaga tgatagagcc       120
tcaggagaaa cgaaggcgag taatactcac gacgatagtt taccaaaacc agaaacaatt       180
caagaggcaa aggcaactat tgatgcagtt gaaaaaactc tcagtcaaca aaagcagaa        240
ctgacagagc ttgctaccgc tctgacaaaa actactgctg aaatcaacca cttaaaagag       300
cagcaagata tgaacaaaaa agctttaacc tctgcacaag aaatttacac taatactctt       360
gcaagtagtg aggagacgct attagcccaa ggagccgaac atcaaagaga gttaacagct       420
actgaaacag agcttcataa tgctcaagca gatcaacatt caaagagac tgcattgtca        480
gaacaaaaag ctagcatttc agcagaaact actcgagctc aagatttagt ggaacaagtc       540
aaaacgtctg aacaaaatat tgctaagctc aatgctatga ttagcaatcc tgatgctatc       600
actaaagcag ctcaaacggc taatgataat acaaaagcat taagctcaga attggagaag       660
gctaaagctg acttagaaaa tcaaaaagct aaagttaaaa agcaattgac tgaagagttg       720
gcagctcaga aagctgctct agcagaaaaa gaggcagaac ttagtcgtct aaatcctca        780
gctccgtcta ctcaagatag cattgtgggt aataatacca tgaaagcacc gcaaggctat       840
cctcttgaag aacttaaaaa attagaagct agtggttata ttggatcagc tagttacaat       900
aattattaca aagagcatgc agatcaaatt attgccaaag ctagtccagg taatcaatta       960
aatcaatacc aagatattcc agcagatcgt aatcgctttg ttgatcccga aatttgaca       1020
ccagaagtgc aaaatgagct agcgcagttt gcagctcaca tgattaatag tgtaagaaga      1080
caattaggtc taccaccagt tactgttaca gcaggatcac aagaatttgc aagattactt      1140
agtaccagct ataagaaaac tcatggtaat acaagaccat catttgtcta cggacagcca      1200
ggggtatcag ggcattatgg tgttgggcct catgataaaa ctattattga agactctgcc      1260
ggagcgtcag ggctcattcg aaatgatgat aacatgtacg agaatatcgg tgcttttaac      1320
gatgtgcata ctgtgaatgg tattaaacgt ggtatttatg acagtatcaa gtatatgctc      1380
tttacagatc atttcacgg aaatacatac ggccatgcta ttaacttttt acgtgtagat      1440
aaacataacc ctaatgcgcc tgtttacctt ggattttcaa ccagcaatgt aggatctttg      1500
aatgaacact tgtaatgtt tccagagtct aacattgcta accatcaacg ctttaataag      1560
```

```
accccctataa aagccgttgg aagtacaaaa gattatgccc aaagagtagg cactgtatct    1620
gatactattg cagcgatcaa aggaaaagta agctcattag aaaatcgttt gtcggctatt    1680
catcaagaag ctgatattat ggcagcccaa gctaaagtaa gtcaacttca aggtaaatta    1740
gcaagcacac ttaagcagtc agacagctta aatctccaag tgagacaatt aaatgatact    1800
aaaggttctt tgagaacaga attactagca gctaaagcaa acaagcaca actcgaagct     1860 actcgtgatc aatcattagc taagctagca tcgttgaaag ccgcactgca ccagacagaa    1920
gccttagcag agcaagccgc agccagagtg acagcactgg tggctaaaaa agctcatttg    1980
caatatctaa gggactttaa attgaatcct aaccgccttc aagtgatacg tgagcgcatt    2040
gataatacta agcaagattt ggctaaaact acctcatctt tgttaaatgc acaagaagct    2100
ttagcagcct acaagctaa acaaagcagt ctagaagcta ctattgctac cacagaacac    2160
cagttgactt tgcttaaaac cttagctaac gaaaaggaat atcgccactt agacgaagat    2220
atagctactg tgcctgattt gcaagtagct ccacctctta cgggcgtaaa accgctatca    2280
tatagtaaga tagatactac tccgcttgtt caagaaatgg ttaaagaaac gaaacaacta    2340
ttagaagctt cagcaagatt agctgctgaa atacaagtc ttgtagcaga agcgcttgtt     2400 ggccaaaacct ctgaaatggt agcaagtaat gccattgtgt ctaaaatcac atcttcgatt   2460
actcagccct catctaagac atcttatggc tcaggatctt ctacaacgag caatctcatt    2520
tctgatgttg atgaaagtac tcaaaga                                        2547
```

<210> SEQ ID NO 11
<211> LENGTH: 16
<212> TYPE: PRT
<213> ORGANISM: Streptococcus pyogenes

<400> SEQUENCE: 11

Ala Leu Lys Ala Gly Val Val Met Leu Ala Ala Val Gly Leu Thr Gly
 1               5                  10                  15

<210> SEQ ID NO 12
<211> LENGTH: 204
<212> TYPE: PRT
<213> ORGANISM: Streptococcus pyogenes

<400> SEQUENCE: 12

Glu Thr Ile Gln Glu Ala Lys Ala Thr Ile Asp Ala Val Glu Lys Thr
 1               5                  10                  15

Leu Ser Gln Gln Lys Ala Glu Leu Glu Leu Ala Thr Ala Leu Thr
        20                  25                  30

Lys Thr Thr Ala Glu Ile Asn His Leu Lys Glu Gln Gln Asp Asn Glu
    35                  40                  45

Gln Lys Ala Leu Thr Ser Ala Gln Glu Ile Tyr Thr Asn Thr Leu Ala
50                  55                  60

Ser Ser Glu Glu Thr Leu Leu Ala Gln Gly Ala Glu His Gln Arg Glu
65                  70                  75                  80

Leu Thr Ala Thr Glu Thr Glu Leu His Asn Ala Gln Ala Asp Gln His
                85                  90                  95

Ser Lys Glu Thr Ala Leu Ser Glu Gln Lys Ala Ser Ile Ser Ala Glu
            100                 105                 110

Thr Thr Arg Ala Gln Asp Leu Val Glu Gln Val Lys Thr Ser Glu Gln
        115                 120                 125

Asn Ile Ala Lys Leu Asn Ala Met Ile Ser Asn Pro Asp Ala Ile Thr
    130                 135                 140

```
Lys Ala Ala Gln Thr Ala Asn Asp Asn Thr Lys Ala Leu Ser Ser Glu
145                 150                 155                 160

Leu Glu Lys Ala Lys Ala Asp Leu Glu Asn Gln Lys Ala Lys Val Lys
                165                 170                 175

Lys Gln Leu Thr Glu Leu Ala Ala Gln Lys Ala Ala Leu Ala Glu
            180                 185                 190

Lys Glu Ala Glu Leu Ser Arg Leu Lys Ser Ser Ala
        195                 200
```

<210> SEQ ID NO 13
<211> LENGTH: 178
<212> TYPE: PRT
<213> ORGANISM: Streptococcus pyogenes

<400> SEQUENCE: 13

```
Arg Leu Ser Ala Ile His Gln Glu Ala Asp Ile Met Ala Ala Gln Ala
1               5                   10                  15

Lys Val Ser Gln Leu Gln Gly Lys Leu Ala Ser Thr Leu Lys Gln Ser
            20                  25                  30

Asp Ser Leu Asn Leu Gln Val Arg Gln Leu Asn Asp Thr Lys Gly Ser
        35                  40                  45

Leu Arg Thr Glu Leu Leu Ala Ala Lys Ala Lys Gln Ala Gln Leu Glu
50                  55                  60

Ala Thr Arg Asp Gln Ser Leu Ala Lys Leu Ala Ser Leu Lys Ala Ala
65                  70                  75                  80

Leu His Gln Thr Glu Ala Leu Ala Glu Gln Ala Ala Arg Val Thr
                85                  90                  95

Ala Leu Val Ala Lys Lys Ala His Leu Gln Tyr Leu Arg Asp Phe Lys
                100                 105                 110

Leu Asn Pro Asn Arg Leu Gln Val Ile Arg Glu Arg Ile Asp Asn Thr
            115                 120                 125

Lys Gln Asp Leu Ala Lys Thr Thr Ser Ser Leu Leu Asn Ala Gln Glu
130                 135                 140

Ala Leu Ala Ala Leu Gln Ala Lys Gln Ser Ser Leu Glu Ala Thr Ile
145                 150                 155                 160

Ala Thr Thr Glu His Gln Leu Thr Leu Leu Lys Thr Leu Ala Asn Glu
                165                 170                 175

Lys Glu
```

<210> SEQ ID NO 14
<211> LENGTH: 31
<212> TYPE: PRT
<213> ORGANISM: Streptococcus pyogenes

<400> SEQUENCE: 14

```
Gln Val Ile Arg Glu Arg Ile Asp Asn Thr Lys Gln Asp Leu Ala Lys
1               5                   10                  15

Thr Thr Ser Ser Leu Leu Asn Ala Gln Glu Ala Leu Ala Ala Leu
            20                  25                  30
```

<210> SEQ ID NO 15
<211> LENGTH: 1575
<212> TYPE: PRT
<213> ORGANISM: Streptococcus gordonii

<400> SEQUENCE: 15

```
Met Asn Lys Arg Lys Glu Val Phe Gly Phe Arg Lys Ser Lys Val Ala
1               5                   10                  15
```

-continued

```
Lys Thr Leu Cys Gly Ala Val Leu Gly Ala Ala Leu Ile Ala Ile Ala
             20                  25                  30

Asp Gln Gln Val Leu Ala Asp Glu Val Thr Glu Thr Asn Ser Thr Ala
             35                  40                  45

Asn Val Ala Val Thr Thr Gly Asn Pro Ala Thr Asn Leu Pro Glu
 50                  55                  60

Ala Gln Gly Glu Ala Thr Glu Ala Ala Ser Gln Ser Gln Ala Gln Ala
 65                  70                  75                  80

Gly Ser Lys Glu Gly Ala Leu Pro Val Glu Val Ser Ala Asp Asp Leu
                 85                  90                  95

Asn Gln Ala Val Thr Asp Ala Lys Ala Ala Gly Val Asn Val Val Gln
             100                 105                 110

Asp Gln Thr Ser Asp Lys Gly Thr Ala Thr Thr Ala Ala Glu Asn Ala
             115                 120                 125

Gln Lys Gln Ala Glu Ile Lys Ser Asp Tyr Ala Lys Gln Ala Glu Glu
 130                 135                 140

Ile Lys Lys Thr Thr Glu Ala Tyr Lys Lys Glu Val Glu Ala His Gln
145                 150                 155                 160

Ala Glu Thr Asp Lys Ile Asn Ala Glu Asn Lys Ala Ala Glu Asp Lys
             165                 170                 175

Tyr Gln Glu Asp Leu Lys Ala His Gln Ala Glu Val Gly Lys Ile Asn
             180                 185                 190

Thr Ala Asn Ala Thr Ala Lys Ala Glu Tyr Glu Ala Lys Leu Ala Gln
             195                 200                 205

Tyr Gln Lys Asp Leu Ala Ala Val Gln Lys Ala Asn Glu Asp Ser Gln
 210                 215                 220

Leu Asp Tyr Gln Asn Lys Leu Ser Ala Tyr Gln Ala Glu Leu Ala Arg
225                 230                 235                 240

Val Gln Lys Ala Asn Ala Glu Ala Lys Glu Ala Tyr Glu Lys Ala Val
             245                 250                 255

Lys Glu Asn Thr Ala Lys Asn Ala Ala Leu Gln Ala Glu Asn Glu Ala
             260                 265                 270

Ile Lys Gln Arg Asn Glu Thr Ala Lys Ala Asn Tyr Asp Ala Ala Met
             275                 280                 285

Lys Gln Tyr Glu Ala Asp Leu Ala Ala Ile Lys Lys Ala Lys Glu Asp
 290                 295                 300

Asn Asp Ala Asp Tyr Gln Ala Lys Leu Ala Ala Tyr Gln Ala Glu Leu
305                 310                 315                 320

Ala Arg Val Gln Lys Ala Asn Ala Asp Ala Lys Ala Ala Tyr Glu Lys
             325                 330                 335

Ala Val Glu Glu Asn Thr Ala Lys Asn Thr Ala Ile Gln Ala Glu Asn
             340                 345                 350

Glu Ala Ile Lys Gln Arg Asn Ala Ala Ala Lys Ala Thr Tyr Glu Ala
             355                 360                 365

Ala Leu Lys Gln Tyr Glu Ala Asp Leu Ala Ala Ala Lys Lys Ala Asn
             370                 375                 380

Glu Asp Ser Asp Ala Asp Tyr Gln Ala Lys Leu Ala Ala Tyr Gln Thr
385                 390                 395                 400

Glu Leu Ala Arg Val Gln Lys Ala Asn Ala Asp Ala Lys Ala Ala Tyr
                 405                 410                 415

Glu Lys Ala Val Glu Asp Asn Lys Ala Lys Asn Ala Ala Leu Gln Ala
             420                 425                 430

Glu Asn Glu Glu Ile Lys Gln Arg Asn Ala Ala Ala Lys Thr Asp Tyr
```

-continued

```
                435                 440                 445
Glu Ala Lys Leu Ala Lys Tyr Glu Ala Asp Leu Ala Lys Tyr Lys Lys
450                 455                 460

Glu Leu Ala Glu Tyr Pro Ala Lys Leu Lys Ala Tyr Glu Asp Glu Gln
465                 470                 475                 480

Ala Gln Ile Lys Ala Ala Leu Val Glu Leu Glu Lys Asn Lys Asn Gln
                485                 490                 495

Asp Gly Tyr Leu Ser Lys Pro Ser Ala Gln Ser Leu Val Tyr Asp Ser
                500                 505                 510

Glu Pro Asn Ala Gln Leu Ser Leu Thr Thr Asn Gly Lys Met Leu Lys
515                 520                 525

Ala Ser Ala Val Asp Glu Ala Phe Ser His Asp Thr Ala Gln Tyr Ser
530                 535                 540

Lys Lys Ile Leu Gln Pro Asp Asn Leu Asn Val Ser Tyr Leu Gln Gln
545                 550                 555                 560

Ala Asp Asp Val Thr Ser Ser Met Glu Leu Tyr Gly Asn Phe Gly Asp
                565                 570                 575

Lys Ala Gly Trp Thr Thr Thr Val Gly Asn Asn Thr Glu Val Lys Phe
                580                 585                 590

Ala Ser Val Leu Leu Glu Arg Gly Gln Ser Val Thr Ala Thr Tyr Thr
                595                 600                 605

Asn Leu Glu Lys Ser Tyr Tyr Asn Gly Lys Lys Ile Ser Lys Ala Val
610                 615                 620

Phe Lys Tyr Ser Leu Asp Ser Asp Ser Lys Phe Lys Asn Val Asp Lys
625                 630                 635                 640

Ala Trp Leu Gly Val Leu Pro Asp Pro Thr Leu Gly Val Phe Ala Ser
                645                 650                 655

Ala Tyr Thr Gly Gln Glu Glu Lys Asp Thr Ser Ile Phe Ile Lys Asn
                660                 665                 670

Glu Phe Thr Phe Tyr Asp Glu Asn Asp Gln Pro Ile Asn Phe Asp Asn
                675                 680                 685

Ala Leu Leu Ser Val Ala Ser Leu Asn Arg Glu Asn Asn Ser Ile Glu
690                 695                 700

Met Ala Lys Asp Tyr Ser Gly Thr Phe Val Lys Ile Ser Gly Ser Ser
705                 710                 715                 720

Val Gly Glu Lys Asp Gly Lys Ile Tyr Ala Thr Glu Thr Leu Asn Phe
                725                 730                 735

Lys Gln Gly Gln Gly Gly Ser Arg Trp Thr Met Tyr Lys Asn Ser Gln
                740                 745                 750

Pro Gly Ser Gly Trp Asp Ser Asp Ala Pro Asn Ser Trp Tyr Gly
                755                 760                 765

Ala Gly Ala Ile Ser Met Ser Gly Pro Thr Asn His Val Thr Val Gly
770                 775                 780

Ala Ile Ser Ala Thr Gln Val Val Pro Ser Asp Pro Val Met Ala Val
785                 790                 795                 800

Ala Thr Gly Lys Arg Pro Asn Ile Trp Tyr Ser Leu Asn Gly Lys Ile
                805                 810                 815

Arg Ala Val Asn Val Pro Lys Ile Thr Lys Glu Lys Pro Thr Pro Pro
                820                 825                 830

Val Ala Pro Thr Glu Pro Gln Ala Pro Thr Tyr Glu Val Glu Lys Pro
                835                 840                 845

Leu Glu Pro Ala Pro Val Ala Pro Thr Tyr Glu Asn Glu Pro Thr Pro
850                 855                 860
```

-continued

```
Pro Val Lys Thr Pro Asp Gln Pro Glu Pro Ser Lys Pro Glu Glu Pro
865                 870                 875                 880

Thr Tyr Glu Thr Glu Lys Pro Leu Glu Pro Ala Pro Val Val Pro Thr
            885                 890                 895

Tyr Glu Asn Glu Pro Thr Pro Pro Val Lys Thr Pro Asp Gln Pro Glu
        900                 905                 910

Pro Ser Lys Pro Glu Glu Pro Thr Tyr Glu Thr Glu Lys Pro Leu Glu
            915                 920                 925

Pro Ala Pro Val Ala Pro Thr Tyr Glu Asn Glu Pro Thr Pro Pro Val
        930                 935                 940

Lys Thr Pro Asp Gln Pro Glu Pro Ser Lys Pro Glu Glu Pro Thr Tyr
945                 950                 955                 960

Asp Pro Leu Pro Thr Pro Pro Val Ala Pro Thr Pro Lys Gln Leu Pro
            965                 970                 975

Thr Pro Pro Val Val Pro Thr Val His Phe His Tyr Ser Ser Leu Leu
        980                 985                 990

Ala Gln Pro Gln Ile Asn Lys Glu Ile Lys Asn Glu Asp Gly Val Asp
            995                1000                1005

Ile Asp Arg Thr Leu Val Ala Lys Gln Ser Ile Val Lys Phe Glu Leu
1010                1015                1020

Lys Thr Glu Ala Leu Thr Ala Gly Arg Pro Lys Thr Thr Ser Phe Val
1025                1030                1035                1040

Leu Val Asp Pro Leu Pro Thr Gly Tyr Lys Phe Asp Leu Asp Ala Thr
            1045                1050                1055

Lys Ala Ala Ser Thr Gly Phe Asp Thr Thr Tyr Asp Glu Ala Ser His
            1060                1065                1070

Thr Val Thr Phe Lys Ala Thr Asp Glu Thr Leu Ala Thr Tyr Asn Ala
        1075                1080                1085

Asp Leu Thr Lys Pro Val Glu Thr Leu His Pro Thr Val Val Gly Arg
        1090                1095                1100

Val Leu Asn Asp Gly Ala Thr Tyr Ile Asn Asn Phe Thr Leu Thr Val
1105                1110                1115                1120

Asn Asp Ala Tyr Gly Ile Lys Ser Asn Val Val Arg Val Thr Thr Pro
            1125                1130                1135

Gly Lys Pro Asn Asp Pro Asp Asn Pro Asn Asn Asn Tyr Ile Lys Pro
            1140                1145                1150

Thr Lys Val Asn Lys Asn Lys Glu Gly Leu Asn Ile Asp Gly Lys Glu
        1155                1160                1165

Val Leu Ala Gly Ser Thr Asn Tyr Tyr Glu Leu Thr Trp Asp Leu Asp
1170                1175                1180

Gln Tyr Lys Gly Asp Lys Ser Ser Lys Glu Ala Ile Gln Asn Gly Phe
1185                1190                1195                1200

Tyr Tyr Val Asp Asp Tyr Pro Glu Glu Ala Leu Asp Val Arg Pro Asp
            1205                1210                1215

Leu Val Lys Val Ala Asp Glu Lys Gly Asn Gln Val Ser Gly Val Ser
            1220                1225                1230

Val Gln Gln Tyr Asp Ser Leu Glu Ala Ala Pro Lys Lys Val Gln Asp
        1235                1240                1245

Leu Leu Lys Lys Ala Asn Ile Thr Val Lys Gly Ala Phe Gln Leu Phe
        1250                1255                1260

Ser Ala Asp Asn Pro Glu Glu Phe Tyr Lys Gln Tyr Val Ser Thr Gly
1265                1270                1275                1280

Thr Ser Leu Val Ile Thr Asp Pro Met Thr Val Lys Ser Glu Phe Gly
            1285                1290                1295
```

-continued

Lys Thr Gly Gly Lys Tyr Glu Asn Lys Ala Tyr Gln Ile Asp Phe Gly
              1300                1305                1310

Asn Gly Tyr Ala Thr Glu Val Val Asn Asn Val Pro Lys Ile Thr
        1315                1320                1325

Pro Lys Lys Asp Val Thr Val Ser Leu Asp Pro Thr Ser Glu Asn Leu
        1330                1335                1340

Asp Gly Gln Thr Val Gln Leu Tyr Gln Thr Phe Asn Tyr Arg Leu Ile
1345                1350                1355                1360

Gly Gly Phe Ile Pro Gln Asn His Ser Glu Glu Leu Glu Asp Tyr Ser
            1365                1370                1375

Phe Val Asp Asp Tyr Asp Gln Ala Gly Asp Gln Tyr Thr Gly Asn Tyr
        1380                1385                1390

Lys Thr Phe Ser Ser Leu Asn Leu Thr Met Lys Asp Gly Ser Val Ile
        1395                1400                1405

Lys Ala Gly Thr Asp Leu Thr Ser Gln Thr Thr Ala Glu Thr Asp Ala
        1410                1415                1420

Ala Asn Gly Ile Val Thr Val Arg Ser Lys Glu Asp Ser Leu Gln Lys
1425                1430                1435                1440

Ile Ser Leu Asp Ser Pro Phe Gln Ala Glu Thr Tyr Leu Gln Met Arg
            1445                1450                1455

Arg Ile Ala Ile Gly Thr Phe Glu Asn Thr Tyr Val Asn Thr Val Asn
        1460                1465                1470

Lys Val Ala Tyr Ala Ser Asn Thr Val Arg Thr Thr Pro Ile Pro
        1475                1480                1485

Arg Thr Pro Asp Lys Pro Thr Pro Ile Pro Thr Pro Lys Pro Lys Asp
    1490                1495                1500

Pro Asp Lys Pro Glu Thr Pro Lys Glu Pro Lys Val Pro Ser Pro Lys
1505                1510                1515                1520

Val Glu Asp Pro Ser Ala Pro Ile Pro Val Ser Val Gly Lys Glu Leu
            1525                1530                1535

Thr Thr Leu Pro Lys Thr Gly Thr Asn Asp Ser Ser Tyr Met Pro Tyr
        1540                1545                1550

Leu Gly Leu Ala Ala Leu Val Gly Val Leu Gly Leu Gly Gln Leu Lys
        1555                1560                1565

Arg Lys Glu Asp Glu Ser Asn
    1570                1575

<210> SEQ ID NO 16
<211> LENGTH: 1499
<212> TYPE: PRT
<213> ORGANISM: Streptococcus gordonii

<400> SEQUENCE: 16

Met Gln Lys Arg Glu Val Phe Gly Phe Arg Lys Ser Lys Val Ala Lys
1               5                   10                  15

Thr Leu Cys Gly Ala Val Leu Gly Ala Ala Leu Ile Ala Ile Ala Asp
            20                  25                  30

Gln Gln Val Leu Ala Asp Glu Val Thr Glu Thr Asn Ser Thr Ala Asn
        35                  40                  45

Val Ala Val Thr Thr Thr Gly Asn Pro Ala Thr Asn Leu Pro Glu Ala
    50                  55                  60

Gln Gly Glu Ala Thr Glu Ala Ala Ser Gln Ser Gln Ala Gln Ala Gly
65                  70                  75                  80

Ser Lys Asp Gly Ala Leu Pro Val Glu Val Ser Ala Asp Asp Leu Asn
                85                  90                  95

```
Lys Ala Val Thr Asp Ala Lys Ala Ala Gly Val Asn Val Gln Asp
            100                 105                 110
Gln Thr Ser Asp Lys Gly Thr Ala Thr Ala Ala Glu Asn Ala Gln
            115                 120                 125
Lys Gln Ala Glu Ile Lys Ser Asp Tyr Ala Lys Gln Ala Glu Ile
            130                 135                 140
Lys Lys Thr Thr Glu Ala Tyr Lys Lys Val Glu Ala His Gln Ala
145                 150                 155                 160
Glu Thr Asp Lys Ile Asn Ala Glu Asn Lys Ala Ala Glu Asp Lys Tyr
                165                 170                 175
Gln Glu Asp Leu Lys Ala His Gln Ala Glu Val Glu Lys Ile Asn Thr
                180                 185                 190
Ala Asn Ala Thr Ala Lys Ala Glu Tyr Glu Ala Lys Leu Ala Gln Tyr
                195                 200                 205
Gln Lys Asp Leu Ala Ala Val Gln Lys Ala Asn Glu Asp Ser Gln Leu
                210                 215                 220
Asp Tyr Gln Asn Lys Leu Ser Ala Tyr Gln Ala Glu Leu Ala Arg Val
225                 230                 235                 240
Gln Lys Ala Asn Ala Glu Ala Lys Glu Ala Tyr Glu Lys Ala Val Lys
                245                 250                 255
Glu Asn Thr Ala Lys Asn Ala Ala Leu Gln Ala Glu Asn Glu Ala Ile
                260                 265                 270
Lys Gln Arg Asn Glu Thr Ala Lys Ala Asn Tyr Asp Ala Ala Met Lys
                275                 280                 285
Gln Tyr Glu Ala Asp Leu Ala Ala Ile Lys Lys Ala Lys Glu Asp Asn
                290                 295                 300
Asp Ala Asp Tyr Gln Ala Lys Leu Ala Ala Tyr Gln Ala Glu Leu Ala
305                 310                 315                 320
Arg Val Gln Lys Ala Asn Ala Asp Ala Lys Ala Ala Tyr Glu Lys Ala
                325                 330                 335
Val Glu Glu Asn Thr Ala Lys Asn Thr Ala Ile Gln Ala Glu Asn Glu
                340                 345                 350
Ala Ile Lys Gln Arg Asn Glu Thr Ala Lys Ala Thr Tyr Glu Ala Ala
                355                 360                 365
Val Lys Gln Tyr Glu Ala Asp Leu Ala Ala Val Lys Gln Ala Asn Ala
                370                 375                 380
Thr Asn Glu Ala Asp Tyr Gln Ala Lys Leu Ala Ala Tyr Gln Thr Glu
385                 390                 395                 400
Leu Ala Arg Val Gln Lys Ala Asn Ala Asp Ala Lys Ala Thr Tyr Glu
                405                 410                 415
Lys Ala Val Glu Asp Asn Lys Ala Lys Asn Ala Ala Leu Gln Ala Glu
                420                 425                 430
Asn Glu Glu Ile Lys Gln Arg Asn Ala Ala Lys Thr Asp Tyr Glu
                435                 440                 445
Ala Lys Leu Ala Lys Tyr Glu Ala Asp Leu Ala Lys Tyr Lys Lys Asp
                450                 455                 460
Phe Ala Ala Tyr Thr Ala Ala Leu Ala Glu Ala Glu Ser Lys Lys Lys
465                 470                 475                 480
Gln Asp Gly Tyr Leu Ser Glu Pro Arg Ser Gln Ser Leu Asn Phe Lys
                485                 490                 495
Ser Glu Pro Asn Ala Ile Arg Thr Ile Asp Ser Ser Val His Gln Tyr
                500                 505                 510
Gly Gln Gln Glu Leu Asp Ala Leu Val Lys Ser Trp Gly Ile Ser Pro
```

-continued

```
            515                 520                 525
Thr Asn Pro Asp Arg Lys Lys Ser Thr Ala Tyr Ser Tyr Phe Asn Ala
        530                 535                 540
Ile Asn Ser Asn Asn Thr Tyr Ala Lys Leu Val Leu Glu Lys Asp Lys
545                 550                 555                 560
Pro Val Asp Val Thr Tyr Thr Gly Leu Lys Asn Ser Ser Phe Asn Gly
                565                 570                 575
Lys Lys Ile Ser Lys Val Val Tyr Thr Tyr Thr Leu Lys Glu Thr Gly
                580                 585                 590
Phe Asp Asp Gly Thr Lys Met Thr Met Phe Ala Ser Ser Asp Pro Thr
            595                 600                 605
Val Thr Ala Trp Tyr Asn Asp Tyr Phe Thr Ser Thr Asn Ile Asn Val
        610                 615                 620
Lys Val Lys Phe Tyr Asp Glu Glu Gly Gln Leu Met Asn Leu Thr Gly
625                 630                 635                 640
Gly Leu Val Asn Phe Ser Ser Leu Asn Arg Gly Asn Gly Ser Gly Ala
                645                 650                 655
Ile Asp Lys Asp Ala Ile Glu Ser Val Arg Asn Phe Asn Gly Arg Tyr
                660                 665                 670
Ile Pro Ile Ser Gly Ser Ser Ile Lys Ile His Glu Asn Asn Ser Ala
                675                 680                 685
Tyr Ala Asp Ser Ser Asn Ala Glu Lys Ser Arg Gly Ala Arg Trp Asp
            690                 695                 700
Thr Ser Glu Trp Asp Thr Thr Ser Ser Pro Asn Asn Trp Tyr Gly Ala
705                 710                 715                 720
Ile Val Gly Glu Ile Thr Gln Ser Glu Ile Ser Phe Asn Met Ala Ser
                725                 730                 735
Ser Lys Ser Gly Asn Ile Trp Phe Ala Phe Asn Ser Asn Ile Asn Ala
            740                 745                 750
Ile Gly Val Pro Thr Lys Pro Val Ala Pro Thr Ala Pro Thr Gln Pro
            755                 760                 765
Met Tyr Glu Thr Glu Lys Pro Leu Glu Pro Ala Pro Val Val Pro Thr
        770                 775                 780
Tyr Glu Asn Glu Pro Thr Pro Val Lys Thr Pro Asp Gln Pro Glu
785                 790                 795                 800
Pro Ser Lys Pro Glu Glu Pro Thr Tyr Glu Thr Lys Pro Leu Glu
                805                 810                 815
Pro Ala Pro Val Ala Pro Thr Tyr Glu Asn Glu Pro Thr Pro Pro Val
                820                 825                 830
Lys Ile Pro Asp Gln Pro Glu Pro Ser Lys Pro Glu Glu Pro Thr Tyr
            835                 840                 845
Glu Thr Glu Lys Pro Leu Glu Pro Ala Pro Val Ala Pro Thr Tyr Glu
        850                 855                 860
Asn Glu Pro Thr Pro Pro Val Lys Thr Pro Asp Gln Pro Glu Pro Ser
865                 870                 875                 880
Lys Pro Glu Glu Pro Thr Tyr Asp Pro Leu Pro Thr Pro Pro Leu Ala
                885                 890                 895
Pro Thr Pro Lys Gln Leu Pro Thr Pro Pro Val Val Pro Thr Val His
            900                 905                 910
Phe His Tyr Ser Ser Leu Leu Ala Gln Pro Gln Ile Asn Lys Glu Ile
        915                 920                 925
Lys Asn Glu Asp Gly Val Asp Ile Asp Arg Thr Leu Val Ala Lys Gln
930                 935                 940
```

-continued

```
Ser Ile Gly Lys Phe Glu Leu Lys Thr Glu Ala Leu Thr Ala Gly Arg
945                 950                 955                 960

Pro Lys Thr Thr Ser Phe Val Leu Val Asp Pro Leu Pro Thr Gly Tyr
                965                 970                 975

Lys Phe Asp Leu Asp Ala Thr Lys Ala Ala Ser Thr Gly Phe Asp Thr
            980                 985                 990

Thr Tyr Asp Glu Ala Ser His Thr Val Thr Phe Lys Ala Thr Asp Glu
        995                 1000                1005

Thr Leu Ala Thr Tyr Asn Ala Asp Leu Thr Lys Pro Val Glu Thr Leu
    1010                1015                1020

His Pro Thr Val Val Gly Arg Val Leu Asn Asp Gly Ala Thr Tyr Thr
1025                1030                1035                1040

Asn Asn Phe Thr Leu Thr Val Asn Asp Ala Tyr Gly Ile Lys Ser Asn
                1045                1050                1055

Val Val Arg Val Thr Thr Pro Gly Lys Pro Asn Asp Pro Asp Asn Pro
            1060                1065                1070

Asn Asn Asn Tyr Ile Lys Pro Thr Lys Val Asn Lys Asn Lys Glu Gly
        1075                1080                1085

Leu Asn Ile Asp Gly Lys Glu Val Leu Ala Gly Ser Thr Asn Tyr Tyr
    1090                1095                1100

Glu Leu Thr Trp Asp Leu Asp Gln Tyr Lys Gly Asp Lys Ser Ser Lys
1105                1110                1115                1120

Glu Ala Ile Gln Asn Gly Phe Tyr Tyr Val Asp Tyr Pro Glu Glu
                1125                1130                1135

Ala Leu Asp Val Arg Pro Asp Leu Val Lys Val Ala Asp Glu Lys Gly
            1140                1145                1150

Asn Gln Val Ser Gly Val Ser Val Gln Gln Tyr Asp Ser Leu Glu Ala
        1155                1160                1165

Ala Pro Lys Lys Val Gln Asp Leu Leu Lys Lys Ala Asn Ile Thr Val
    1170                1175                1180

Lys Gly Ala Phe Gln Leu Phe Ser Ala Asp Asn Pro Glu Glu Phe Tyr
1185                1190                1195                1200

Lys Gln Tyr Val Ser Thr Gly Thr Ser Leu Val Ile Thr Asp Pro Met
                1205                1210                1215

Thr Val Lys Ser Glu Phe Gly Lys Thr Gly Lys Tyr Glu Asn Lys
            1220                1225                1230

Ala Tyr Gln Ile Asp Phe Gly Asn Gly Tyr Ala Thr Glu Val Val Val
        1235                1240                1245

Asn Asn Val Pro Lys Ile Thr Pro Lys Lys Asp Val Thr Val Ser Leu
    1250                1255                1260

Asp Pro Thr Ser Glu Asn Leu Asp Gly Gln Thr Val Gln Leu Tyr Gln
1265                1270                1275                1280

Thr Phe Asn Tyr Arg Leu Ile Gly Gly Phe Ile Pro Gln Asn His Ser
                1285                1290                1295

Glu Glu Leu Glu Asp Tyr Ser Phe Val Asp Asp Tyr Asp Gln Ala Gly
            1300                1305                1310

Asp Gln Tyr Thr Gly Asn Tyr Lys Thr Phe Ser Ser Leu Asn Leu Thr
        1315                1320                1325

Met Lys Asp Gly Ser Val Ile Lys Ala Gly Thr Asp Leu Thr Ser Gln
    1330                1335                1340

Thr Thr Ala Glu Thr Asp Ala Thr Asn Gly Ile Val Thr Val Arg Phe
1345                1350                1355                1360

Lys Glu Asp Phe Leu Gln Lys Ile Ser Leu Asp Ser Pro Phe Gln Ala
                1365                1370                1375
```

-continued

```
Glu Thr Tyr Leu Gln Met Arg Arg Ile Ala Ile Gly Thr Phe Glu Asn
            1380                1385                1390

Thr Tyr Val Asn Thr Val Asn Lys Val Ala Tyr Ala Ser Asn Thr Val
        1395                1400                1405

Arg Thr Thr Pro Ile Pro Arg Thr Pro Asp Lys Pro Thr Pro Ile
    1410                1415                1420

Pro Thr Pro Lys Pro Lys Asp Pro Asp Lys Pro Glu Thr Pro Lys Glu
1425                1430                1435                1440

Pro Lys Val Pro Ser Pro Lys Val Glu Asp Pro Ser Ala Pro Ile Pro
                1445                1450                1455

Val Ser Val Gly Lys Glu Leu Thr Thr Leu Pro Lys Thr Gly Thr Asn
            1460                1465                1470

Asp Ala Thr Tyr Met Pro Tyr Leu Gly Leu Ala Ala Leu Val Gly Phe
        1475                1480                1485

Leu Gly Leu Gly Leu Ala Lys Arg Lys Glu Asp
    1490                1495

<210> SEQ ID NO 17
<211> LENGTH: 619
<212> TYPE: PRT
<213> ORGANISM: Streptococcus pneumoniae

<400> SEQUENCE: 17

Met Asn Lys Lys Met Ile Leu Thr Ser Leu Ala Ser Val Ala Ile
1               5                   10                  15

Leu Gly Ala Gly Phe Val Ala Ser Gln Pro Thr Val Val Arg Ala Glu
            20                  25                  30

Glu Ser Pro Val Ala Ser Gln Ser Lys Ala Glu Lys Asp Tyr Asp Ala
        35                  40                  45

Ala Lys Lys Asp Ala Lys Asn Ala Lys Lys Ala Val Glu Asp Ala Gln
    50                  55                  60

Lys Ala Leu Asp Asp Ala Lys Ala Ala Gln Lys Lys Tyr Asp Glu Asp
65                  70                  75                  80

Gln Lys Lys Thr Glu Glu Lys Ala Ala Leu Glu Lys Ala Ala Ser Glu
                85                  90                  95

Glu Met Asp Lys Ala Val Ala Ala Val Gln Gln Ala Tyr Leu Ala Tyr
            100                 105                 110

Gln Gln Ala Thr Asp Lys Ala Ala Lys Asp Ala Ala Asp Lys Met Ile
        115                 120                 125

Asp Glu Ala Lys Lys Arg Glu Glu Ala Lys Thr Lys Phe Asn Thr
    130                 135                 140

Val Arg Ala Met Val Val Pro Glu Pro Glu Gln Leu Ala Glu Thr Lys
145                 150                 155                 160

Lys Lys Ser Glu Glu Ala Lys Gln Lys Ala Pro Glu Leu Thr Lys Lys
                165                 170                 175

Leu Glu Glu Ala Lys Ala Lys Leu Glu Glu Ala Glu Lys Lys Ala Thr
            180                 185                 190

Glu Ala Lys Gln Lys Val Asp Ala Glu Glu Val Ala Pro Gln Ala Lys
        195                 200                 205

Ile Ala Glu Leu Glu Asn Gln Val His Arg Leu Glu Gln Glu Leu Lys
    210                 215                 220

Glu Ile Asp Glu Ser Glu Ser Glu Asp Tyr Ala Lys Glu Gly Phe Arg
225                 230                 235                 240

Ala Pro Leu Gln Ser Lys Leu Asp Ala Lys Lys Ala Lys Leu Ser Lys
                245                 250                 255
```

Leu Glu Glu Leu Ser Asp Lys Ile Asp Glu Leu Asp Ala Glu Ile Ala
                260                 265                 270

Lys Leu Glu Asp Gln Leu Lys Ala Ala Glu Glu Asn Asn Asn Val Glu
            275                 280                 285

Asp Tyr Phe Lys Glu Gly Leu Glu Lys Thr Ile Ala Ala Lys Lys Ala
        290                 295                 300

Glu Leu Glu Lys Thr Glu Ala Asp Leu Lys Lys Ala Val Asn Glu Pro
305                 310                 315                 320

Glu Lys Pro Ala Pro Ala Pro Glu Thr Pro Ala Pro Glu Ala Pro Ala
                325                 330                 335

Glu Gln Pro Lys Pro Ala Pro Ala Pro Gln Pro Ala Pro Ala Pro Lys
            340                 345                 350

Pro Glu Lys Pro Ala Glu Gln Pro Lys Pro Glu Lys Thr Asp Asp Gln
        355                 360                 365

Gln Ala Glu Glu Asp Tyr Ala Arg Arg Ser Glu Glu Glu Tyr Asn Arg
    370                 375                 380

Leu Thr Gln Gln Gln Pro Pro Lys Ala Glu Lys Pro Ala Pro Ala Pro
385                 390                 395                 400

Lys Thr Gly Trp Lys Gln Glu Asn Gly Met Trp Tyr Phe Tyr Asn Thr
                405                 410                 415

Asp Gly Ser Met Ala Thr Gly Trp Leu Gln Asn Asn Gly Ser Trp Tyr
            420                 425                 430

Tyr Leu Asn Ser Asn Gly Ala Met Ala Thr Gly Trp Leu Gln Tyr Asn
        435                 440                 445

Gly Ser Trp Tyr Tyr Leu Asn Ala Asn Gly Ala Met Ala Thr Gly Trp
    450                 455                 460

Ala Lys Val Asn Gly Ser Trp Tyr Tyr Leu Asn Ala Asn Gly Ala Met
465                 470                 475                 480

Ala Thr Gly Trp Leu Gln Tyr Asn Gly Ser Trp Tyr Tyr Leu Asn Ala
                485                 490                 495

Asn Gly Ala Met Ala Thr Gly Trp Ala Lys Val Asn Gly Ser Trp Tyr
            500                 505                 510

Tyr Leu Asn Ala Asn Gly Ala Met Ala Thr Gly Trp Leu Gln Tyr Asn
        515                 520                 525

Gly Ser Trp Tyr Tyr Leu Asn Ala Asn Gly Ala Met Ala Thr Gly Trp
    530                 535                 540

Ala Lys Val Asn Gly Ser Trp Tyr Tyr Leu Asn Ala Asn Gly Ala Met
545                 550                 555                 560

Ala Thr Gly Trp Val Lys Asp Gly Asp Thr Trp Tyr Tyr Leu Glu Ala
                565                 570                 575

Ser Gly Ala Met Lys Ala Ser Gln Trp Phe Lys Val Ser Asp Lys Trp
            580                 585                 590

Tyr Tyr Val Asn Gly Leu Gly Ala Leu Ala Val Asn Thr Thr Val Asp
        595                 600                 605

Gly Tyr Lys Val Asn Ala Asn Gly Glu Trp Val
    610                 615

<210> SEQ ID NO 18
<211> LENGTH: 210
<212> TYPE: PRT
<213> ORGANISM: Streptococcus equii

<400> SEQUENCE: 18

Glu Ser Asp Ile Val Asp Ala Thr Arg Phe Ser Thr Thr Glu Ile Pro
1               5                   10                  15

```
Lys Ser Gly Gln Val Ile Asp Arg Ser Ala Ser Ile Gln Ala Leu Thr
            20                  25                  30

Asn Asp Ile Ala Ser Ile Lys Gly Lys Ile Ala Ser Leu Glu Ser Arg
        35                  40                  45

Leu Ala Asp Pro Ser Ser Glu Ala Glu Val Thr Ala Ala Gln Ala Lys
    50                  55                  60

Ile Ser Gln Leu Gln His Gln Leu Glu Ala Ala Gln Ala Lys Ser His
65                  70                  75                  80

Lys Leu Asp Gln Gln Val Glu Gln Leu Ala Asn Thr Lys Asp Ser Leu
                85                  90                  95

Arg Thr Gln Leu Leu Ala Ala Lys Glu Glu Gln Ala Gln Leu Lys Ala
            100                 105                 110

Asn Leu Asp Lys Ala Leu Ala Leu Leu Ala Ser Ser Lys Ala Thr Leu
        115                 120                 125

His Lys Leu Glu Ala Ala Met Glu Gly Ala Lys Ala Arg Val Ala Gly
    130                 135                 140

Leu Ala Ser Gln Lys Ala Gln Leu Glu Asp Leu Leu Ala Phe Glu Lys
145                 150                 155                 160

Asn Pro Asn Arg Ile Glu Leu Ala Gln Glu Lys Val Ala Ala Ala Lys
                165                 170                 175

Lys Ala Leu Ala Asp Thr Glu Asp Lys Leu Leu Ala Ala Gln Ala Ser
            180                 185                 190

Leu Ser Asp Leu Gln Ala Gln Arg Ala Arg Leu Gln Leu Ser Ile Ala
        195                 200                 205

Thr Ile
    210

<210> SEQ ID NO 19
<211> LENGTH: 2601
<212> TYPE: DNA
<213> ORGANISM: Streptococcus equi

<400> SEQUENCE: 19
ctggttccgc gtggatccca tatgagtgta ggcgtatctc accaagtcaa agcagatgat      60
agagcctcag gagaaacgaa ggcgagtaat actcacgacg atagtttacc aaaaccagaa     120
acaattcaag aggcaaaggc aactattgat gcagttgaaa aaactctcag tcaacaaaaa     180
gcagaactga cagagcttgc taccgctctg acaaaaacta ctgctgaaat caaccactta     240
aaagagcagc aagataatga acaaaaagct ttaacctctg cacaagaaat ttacactaat     300
actcttgcaa gtagtgagga gacgctatta gcccaaggag ccgaacatca aagagagtta     360
acagctactg aaacagagct tcataatgct caagcagatc aacattcaaa agagactgca     420
ttgtcagaac aaaaagctag catttcagca gaaactactc gagctcaaga tttagtggaa     480
caagtcaaaa cgtctgaaca aaatattgct aagctcaatg ctatgattag caatcctgat     540
gctatcacta agcagctca acggctaat gataatacaa aagcattaag ctcagaattg      600
gagaaggcta agctgacttt agaaaatcaa aaagctaaag ttaaaaagca attgactgaa     660
gagttggcag ctcagaaagc tgctctagca gaaaagagg cagaacttag tcgtcttaaa      720
tcctcagctc cgtctactca agatagcatt gtgggtaata ataccatgaa agcaccgcaa     780
ggctatcctc ttgaagaact taaaaaatta gaagctagtg gttatattgg atcagctagt     840
tacaataatt attacaaaga gcatgcagat caaattattg ccaaagctag tccaggtaat     900
caattaaatc aataccaaga tattccagca gatcgtaatc gctttgttga tcccgataat     960
```

-continued

```
ttgacaccag aagtgcaaaa tgagctagcg cagtttgcag ctcacatgat taatagtgta    1020
agaagacaat taggtctacc accagttact gttacagcag gatcacaaga atttgcaaga    1080
ttacttagta ccagctataa gaaaactcat ggtaatacaa gaccatcatt tgtctacgga    1140
cagccagggg tatcagggca ttatggtgtt gggcctcatg ataaaactat tattgaagac    1200
tctgccggag cgtcagggct cattcgaaat gatgataaca tgtacgagaa atcggtgct    1260 tttaacgatg tgcatactgt gaatggtatt aaacgtggta tttatgacag tatcaagtat    1320
atgctcttta cagatcattt acacggaaat acatacggcc atgctattaa cttttacgt    1380 gtagataaac ataaccctaa tgcgcctgtt taccttggat tttcaaccag caatgtagga    1440
tctttgaatg aacactttgt aatgtttcca gagtctaaca ttgctaacca tcaacgcttt    1500
aataagaccc ctataaaagc cgttggaagt acaaaagatt atgcccaaag agtaggcact    1560
gtatctgata ctattgcagc gatcaaagga aaagtaagct cattagaaaa tcgtttgtcg    1620
gctattcatc aagaagctga tattatggca gcccaagcta agtaagtca acttcaaggt    1680 aaattagcaa gcacacttaa gcagtcagac agcttaaatc tccaagtgag acaattaaat    1740
gatactaaag gttcttttgag aacagaatta ctagcagcta agcaaaaca agcacaactc    1800 gaagctactc gtgatcaatc attagctaag ctagcatcgt tgaaagccgc actgcaccag    1860
acagaagcct tagcagagca agccgcagcc agagtgacag cactggtggc taaaaaagct    1920
catttgcaat atctaaggga ctttaaattg aatcctaacc gccttcaagt gatacgtgag    1980
cgcattgata atactaagca agatttggct aaaactacct catctttgtt aaatgcacaa    2040
gaagctttag cagccttaca agctaaacaa agcagtctag aagctactat tgctaccaca    2100
gaacaccagt tgactttgct taaaaccta gctaacgaaa aggaatatcg ccacttagac    2160
gaagatatag ctactgtgcc tgatttgcaa gtagctccac ctcttacggg cgtaaaaccg    2220
ctatcatata gtaagataga tactactccg cttgttcaag aaatggttaa agaaacgaaa    2280
caactattag aagcttcagc aagattagct gctgaaaata caagtcttgt agcagaagcg    2340
cttgttggcc aaacctctga aatggtagca agtaatgcca ttgtgtctaa aatcacatct    2400
tcgattactc agccctcatc taagacatct tatggctcag gatcttctac aacgagcaat    2460
ctcatttctg atgttgatga agtactcaa agagctctta agcaggagt cgtcatgttg    2520 gcagctgtcg gcctcacagg atttaggttc cgtaaggaat ctaaggcggc cgcactcgag    2580
caccaccacc accaccacca c                                              2601
```

<210> SEQ ID NO 20
<211> LENGTH: 866
<212> TYPE: PRT
<213> ORGANISM: Streptococcus pyogenes

<400> SEQUENCE: 20

```
Leu Val Pro Arg Gly Ser His Met Ser Val Gly Val Ser His Gln Val
 1               5                  10                  15

Lys Ala Asp Asp Arg Ala Ser Gly Glu Thr Lys Ala Ser Asn Thr His
            20                  25                  30

Asp Asp Ser Leu Pro Lys Pro Glu Thr Ile Gln Glu Ala Lys Ala Thr
        35                  40                  45

Ile Asp Ala Val Glu Lys Thr Leu Ser Gln Gln Lys Ala Glu Leu Thr
    50                  55                  60

Glu Leu Ala Thr Ala Leu Thr Lys Thr Ala Glu Ile Asn His Leu
65                  70                  75                  80

Lys Glu Gln Gln Asp Asn Glu Gln Lys Ala Leu Thr Ser Ala Gln Glu
```

-continued

```
                    85                  90                  95
Ile Tyr Thr Asn Thr Leu Ala Ser Ser Glu Glu Thr Leu Leu Ala Gln
                100                 105                 110

Gly Ala Glu His Gln Arg Glu Leu Thr Ala Thr Glu Thr Glu Leu His
            115                 120                 125

Asn Ala Gln Ala Asp Gln His Ser Lys Glu Thr Ala Leu Ser Glu Gln
        130                 135                 140

Lys Ala Ser Ile Ser Ala Glu Thr Thr Arg Ala Gln Asp Leu Val Glu
145                 150                 155                 160

Gln Val Lys Thr Ser Glu Gln Asn Ile Ala Lys Leu Asn Ala Met Ile
                165                 170                 175

Ser Asn Pro Asp Ala Ile Thr Lys Ala Ala Gln Thr Ala Asn Asp Asn
            180                 185                 190

Thr Lys Ala Leu Ser Ser Glu Leu Glu Lys Ala Lys Ala Asp Leu Glu
        195                 200                 205

Asn Gln Lys Ala Lys Val Lys Lys Gln Leu Thr Glu Glu Leu Ala Ala
    210                 215                 220

Gln Lys Ala Ala Leu Ala Glu Lys Glu Ala Glu Leu Ser Arg Leu Lys
225                 230                 235                 240

Ser Ser Ala Pro Ser Thr Gln Asp Ser Ile Val Gly Asn Asn Thr Met
                245                 250                 255

Lys Ala Pro Gln Gly Tyr Pro Leu Glu Leu Lys Lys Leu Glu Ala
            260                 265                 270

Ser Gly Tyr Ile Gly Ser Ala Ser Tyr Asn Asn Tyr Lys Glu His
        275                 280                 285

Ala Asp Gln Ile Ile Ala Lys Ala Ser Pro Gly Asn Gln Leu Asn Gln
    290                 295                 300

Tyr Gln Asp Ile Pro Ala Asp Arg Asn Arg Phe Val Asp Pro Asp Asn
305                 310                 315                 320

Leu Thr Pro Glu Val Gln Asn Glu Leu Ala Gln Phe Ala Ala His Met
                325                 330                 335

Ile Asn Ser Val Arg Arg Gln Leu Gly Leu Pro Pro Val Thr Val Thr
            340                 345                 350

Ala Gly Ser Gln Glu Phe Ala Arg Leu Leu Ser Thr Ser Tyr Lys Lys
        355                 360                 365

Thr His Gly Asn Thr Arg Pro Ser Phe Val Tyr Gly Gln Pro Gly Val
    370                 375                 380

Ser Gly His Tyr Gly Val Gly Pro His Asp Lys Thr Ile Ile Glu Asp
385                 390                 395                 400

Ser Ala Gly Ala Ser Gly Leu Ile Arg Asn Asp Asp Asn Met Tyr Glu
                405                 410                 415

Asn Ile Gly Ala Phe Asn Asp Val His Thr Val Asn Gly Ile Lys Arg
            420                 425                 430

Gly Ile Tyr Asp Ser Ile Lys Tyr Met Leu Phe Thr Asp His Leu His
        435                 440                 445

Gly Asn Thr Tyr Gly His Ala Ile Asn Phe Leu Arg Val Asp Lys His
    450                 455                 460

Asn Pro Asn Ala Pro Val Tyr Leu Gly Phe Ser Thr Ser Asn Val Gly
465                 470                 475                 480

Ser Leu Asn Glu His Phe Val Met Phe Pro Glu Ser Asn Ile Ala Asn
                485                 490                 495

His Gln Arg Phe Asn Lys Thr Pro Ile Lys Ala Val Gly Ser Thr Lys
            500                 505                 510
```

```
Asp Tyr Ala Gln Arg Val Gly Thr Val Ser Asp Thr Ile Ala Ala Ile
    515                 520                 525

Lys Gly Lys Val Ser Ser Leu Glu Asn Arg Leu Ser Ala Ile His Gln
530                 535                 540

Glu Ala Asp Ile Met Ala Ala Gln Ala Lys Val Ser Gln Leu Gln Gly
545                 550                 555                 560

Lys Leu Ala Ser Thr Leu Lys Gln Ser Asp Ser Leu Asn Leu Gln Val
                565                 570                 575

Arg Gln Leu Asn Asp Thr Lys Gly Ser Leu Arg Thr Glu Leu Leu Ala
            580                 585                 590

Ala Lys Ala Lys Gln Ala Gln Leu Glu Ala Thr Arg Asp Gln Ser Leu
        595                 600                 605

Ala Lys Leu Ala Ser Leu Lys Ala Ala Leu His Gln Thr Glu Ala Leu
    610                 615                 620

Ala Glu Gln Ala Ala Ala Arg Val Thr Ala Leu Val Ala Lys Lys Ala
625                 630                 635                 640

His Leu Gln Tyr Leu Arg Asp Phe Lys Leu Asn Pro Asn Arg Leu Gln
                645                 650                 655

Val Ile Arg Glu Arg Ile Asp Asn Thr Lys Gln Asp Leu Ala Lys Thr
            660                 665                 670

Thr Ser Ser Leu Leu Asn Ala Gln Glu Ala Leu Ala Ala Leu Gln Ala
        675                 680                 685

Lys Gln Ser Ser Leu Glu Ala Thr Ile Ala Thr Glu His Gln Leu
    690                 695                 700

Thr Leu Leu Lys Thr Leu Ala Asn Glu Lys Glu Tyr Arg His Leu Asp
705                 710                 715                 720

Glu Asp Ile Ala Thr Val Pro Asp Leu Gln Val Ala Pro Pro Leu Thr
                725                 730                 735

Gly Val Lys Pro Leu Ser Tyr Ser Lys Ile Asp Thr Thr Pro Leu Val
            740                 745                 750

Gln Glu Met Val Lys Glu Thr Lys Gln Leu Leu Glu Ala Ser Ala Arg
        755                 760                 765

Leu Ala Ala Glu Asn Thr Ser Leu Val Ala Glu Ala Leu Val Gly Gln
    770                 775                 780

Thr Ser Glu Met Val Ala Ser Asn Ala Ile Val Ser Lys Ile Thr Ser
785                 790                 795                 800

Ser Ile Thr Gln Pro Ser Ser Lys Thr Ser Tyr Gly Ser Gly Ser Ser
                805                 810                 815

Thr Thr Ser Asn Leu Ile Ser Asp Val Asp Glu Ser Thr Gln Arg Ala
            820                 825                 830

Leu Lys Ala Gly Val Val Met Leu Ala Ala Val Gly Leu Thr Gly Phe
        835                 840                 845

Arg Phe Arg Lys Glu Ser Lys Ala Ala Ala Leu Glu His His His
    850                 855                 860

His His
865

<210> SEQ ID NO 21
<211> LENGTH: 2508
<212> TYPE: DNA
<213> ORGANISM: Streptococcus pyogenes

<400> SEQUENCE: 21
atgagtgtag gcgtatctca ccaagtcaaa gcagatgata gagcctcagg agaaacgaag     60
gcgagtaata ctcacgacga tagtttacca aaaccagaaa caattcaaga ggcaaaggca    120
```

```
actattgatg cagttgaaaa aactctcagt caacaaaaag cagaactgac agagcttgct    180
accgctctga caaaaactac tgctgaaatc aaccacttaa aagagcagca agataatgaa    240
caaaaagctt taacctctgc acaagaaatt tacactaata ctcttgcaag tagtgaggag    300
acgctattag cccaaggagc cgaacatcaa agagagttaa cagctactga aacagagctt    360
cataatgctc aagcagatca acattcaaaa gagactgcat tgtcagaaca aaaagctagc    420
atttcagcag aaactactcg agctcaagat ttagtggaac aagtcaaaac gtctgaacaa    480
aatattgcta agctcaatgc tatgattagc aatcctgatg ctatcactaa agcagctcaa    540
acggctaatg ataatacaaa agcattaagc tcagaattgg agaaggctaa agctgactta    600
gaaaatcaaa aagctaaagt taaaaagcaa ttgactgaag agttggcagc tcagaaagct    660
gctctagcag aaaaagaggc agaacttagt cgtcttaaat cctcagctcc gtctactcaa    720
gatagcattg tgggtaataa taccatgaaa gcaccgcaag gctatcctct tgaagaactt    780
aaaaaattag aagctagtgg ttatattgga tcagctagtt acaataatta ttacaaagag    840
catgcagatc aaattattgc caaagctagt ccaggtaatc aattaaatca ataccaagat    900
attccagcag atcgtaatcg ctttgttgat cccgataatt tgacaccaga agtgcaaaat    960
gagctagcgc agtttgcagc tcacatgatt aatagtgtaa aagacaatt aggtctacca   1020 ccagttactg ttacagcagg atcacaagaa tttgcaagat tacttagtac cagctataag   1080
aaaactcatg gtaatacaag accatcattt gtctacggac agccaggggt atcagggcat   1140
tatggtgttg ggcctcatga taaaactatt attgaagact ctgccggagc gtcagggctc   1200
attcgaaatg atgataacat gtacgagaat atcggtgctt ttaacgatgt gcatactgtg   1260
aatggtatta acgtggtat ttatgacagt atcaagtata tgctctttac agatcattta   1320
cacggaaata catacggcca tgctattaac ttttacgtg tagataaaca taaccctaat   1380
gcgcctgttt accttggatt ttcaaccagc aatgtaggat cttttgaatga acactttgta   1440 atgtttccag agtctaacat tgctaaccat caacgcttta ataagacccc tataaaagcc   1500
gttggaagta caaagattta tgcccaaaga gtaggcactg tatctgatac tattgcagcg   1560
atcaaaggaa aagtaagctc attagaaaat cgtttgtcgg ctattcatca agaagctgat   1620
attatggcag cccaagctaa agtaagtcaa cttcaaggta aattagcaag cacacttaag   1680
cagtcagaca gcttaaatct ccaagtgaga caattaaatg atactaaagg ttcttttgaga   1740 acagaattac tagcagctaa agcaaaacaa gcacaactcg aagctactcg tgatcaatca   1800
ttagctaagc tagcatcgtt gaaagccgca ctgcaccaga cagaagcctt agcagagcaa   1860
gccgcagcca gagtgacagc actggtggct aaaaaagctc atttgcaata tctaagggac   1920
tttaaattga atcctaaccg ccttcaagtg atacgtgagc gcattgataa tactaagcaa   1980
gatttggcta aaactacctc atctttgtta aatgcacaag aagctttagc agccttacaa   2040
gctaaacaaa gcagtctaga agctactatt gctaccacag aacaccagtt gactttgctt   2100
aaaaccttag ctaacgaaaa ggaatatcgc cacttagacg aagatatagc tactgtgcct   2160
gatttgcaag tagctccacc tcttacgggc gtaaaaccgc tatcatatag taagatagat   2220
actactccgc ttgttcaaga aatggttaaa gaaacgaaac aactattaga agcttcagca   2280
agattagctg ctgaaaatac aagtcttgta gcagaagcgc ttgttggcca aacctctgaa   2340
atggtagcaa gtaatgccat tgtgtctaaa atcacatctt cgattactca gccctcatct   2400
aagacatctt atggctcagg atcttctaca acgagcaatc tcatttctga tgttgatgaa   2460
agtactcaac gtgcggccgc actcgagcac caccaccacc accaccac             2508
```

<210> SEQ ID NO 22
<211> LENGTH: 836
<212> TYPE: PRT
<213> ORGANISM: Streptococcus pyogenes

<400> SEQUENCE: 22

```
Met Ser Val Gly Val Ser His Gln Val Lys Ala Asp Asp Arg Ala Ser
 1               5                  10                  15

Gly Glu Thr Lys Ala Ser Asn Thr His Asp Asp Ser Leu Pro Lys Pro
            20                  25                  30

Glu Thr Ile Gln Glu Ala Lys Ala Thr Ile Asp Ala Val Glu Lys Thr
        35                  40                  45

Leu Ser Gln Gln Lys Ala Glu Leu Thr Glu Leu Ala Thr Ala Leu Thr
    50                  55                  60

Lys Thr Thr Ala Glu Ile Asn His Leu Lys Glu Gln Gln Asp Asn Glu
65                  70                  75                  80

Gln Lys Ala Leu Thr Ser Ala Gln Glu Ile Tyr Thr Asn Thr Leu Ala
                85                  90                  95

Ser Ser Glu Glu Thr Leu Leu Ala Gln Gly Ala Glu His Gln Arg Glu
            100                 105                 110

Leu Thr Ala Thr Glu Thr Glu Leu His Asn Ala Gln Ala Asp Gln His
        115                 120                 125

Ser Lys Glu Thr Ala Leu Ser Glu Gln Lys Ala Ser Ile Ser Ala Glu
    130                 135                 140

Thr Thr Arg Ala Gln Asp Leu Val Glu Gln Val Lys Thr Ser Glu Gln
145                 150                 155                 160

Asn Ile Ala Lys Leu Asn Ala Met Ile Ser Asn Pro Asp Ala Ile Thr
                165                 170                 175

Lys Ala Ala Gln Thr Ala Asn Asp Asn Thr Lys Ala Leu Ser Ser Glu
            180                 185                 190

Leu Glu Lys Ala Lys Ala Asp Leu Glu Asn Gln Lys Ala Lys Val Lys
        195                 200                 205

Lys Gln Leu Thr Glu Glu Leu Ala Ala Gln Lys Ala Ala Leu Ala Glu
    210                 215                 220

Lys Glu Ala Glu Leu Ser Arg Leu Lys Ser Ser Ala Pro Ser Thr Gln
225                 230                 235                 240

Asp Ser Ile Val Gly Asn Asn Thr Met Lys Ala Pro Gln Gly Tyr Pro
                245                 250                 255

Leu Glu Glu Leu Lys Lys Leu Glu Ala Ser Gly Tyr Ile Gly Ser Ala
            260                 265                 270

Ser Tyr Asn Asn Tyr Tyr Lys Glu His Ala Asp Gln Ile Ile Ala Lys
        275                 280                 285

Ala Ser Pro Gly Asn Gln Leu Asn Gln Tyr Gln Asp Ile Pro Ala Asp
    290                 295                 300

Arg Asn Arg Phe Val Asp Pro Asp Asn Leu Thr Pro Glu Val Gln Asn
305                 310                 315                 320

Glu Leu Ala Gln Phe Ala Ala His Met Ile Asn Ser Val Arg Arg Gln
                325                 330                 335

Leu Gly Leu Pro Pro Val Thr Val Thr Ala Gly Ser Gln Glu Phe Ala
            340                 345                 350

Arg Leu Leu Ser Thr Ser Tyr Lys Lys Thr His Gly Asn Thr Arg Pro
        355                 360                 365

Ser Phe Val Tyr Gly Gln Pro Gly Val Ser Gly His Tyr Gly Val Gly
    370                 375                 380
```

```
Pro His Asp Lys Thr Ile Ile Glu Asp Ser Ala Gly Ala Ser Gly Leu
385                 390                 395                 400

Ile Arg Asn Asp Asn Met Tyr Glu Asn Ile Gly Ala Phe Asn Asp
        405                 410                 415

Val His Thr Val Asn Gly Ile Lys Arg Gly Ile Tyr Asp Ser Ile Lys
            420                 425                 430

Tyr Met Leu Phe Thr Asp His Leu His Gly Asn Thr Tyr Gly His Ala
        435                 440                 445

Ile Asn Phe Leu Arg Val Asp Lys His Asn Pro Asn Ala Pro Val Tyr
    450                 455                 460

Leu Gly Phe Ser Thr Ser Asn Val Gly Ser Leu Asn Glu His Phe Val
465                 470                 475                 480

Met Phe Pro Glu Ser Asn Ile Ala Asn His Gln Arg Phe Asn Lys Thr
                485                 490                 495

Pro Ile Lys Ala Val Gly Ser Thr Lys Asp Tyr Ala Gln Arg Val Gly
                500                 505                 510

Thr Val Ser Asp Thr Ile Ala Ala Ile Lys Gly Lys Val Ser Ser Leu
            515                 520                 525

Glu Asn Arg Leu Ser Ala Ile His Gln Glu Ala Asp Ile Met Ala Ala
        530                 535                 540

Gln Ala Lys Val Ser Gln Leu Gln Gly Lys Leu Ala Ser Thr Leu Lys
545                 550                 555                 560

Gln Ser Asp Ser Leu Asn Leu Gln Val Arg Gln Leu Asn Asp Thr Lys
                565                 570                 575

Gly Ser Leu Arg Thr Glu Leu Leu Ala Ala Lys Ala Lys Gln Ala Gln
                580                 585                 590

Leu Glu Ala Thr Arg Asp Gln Ser Leu Ala Lys Leu Ala Ser Leu Lys
            595                 600                 605

Ala Ala Leu His Gln Thr Glu Ala Leu Ala Glu Gln Ala Ala Ala Arg
        610                 615                 620

Val Thr Ala Leu Val Ala Lys Lys Ala His Leu Gln Tyr Leu Arg Asp
625                 630                 635                 640

Phe Lys Leu Asn Pro Asn Arg Leu Gln Val Ile Arg Glu Arg Ile Asp
                645                 650                 655

Asn Thr Lys Gln Asp Leu Ala Lys Thr Thr Ser Ser Leu Leu Asn Ala
                660                 665                 670

Gln Glu Ala Leu Ala Ala Leu Gln Ala Lys Gln Ser Ser Leu Glu Ala
            675                 680                 685

Thr Ile Ala Thr Thr Glu His Gln Leu Thr Leu Leu Lys Thr Leu Ala
        690                 695                 700

Asn Glu Lys Glu Tyr Arg His Leu Asp Glu Asp Ile Ala Thr Val Pro
705                 710                 715                 720

Asp Leu Gln Val Ala Pro Pro Leu Thr Gly Val Lys Pro Leu Ser Tyr
                725                 730                 735

Ser Lys Ile Asp Thr Thr Pro Leu Val Gln Glu Met Val Lys Glu Thr
                740                 745                 750

Lys Gln Leu Leu Glu Ala Ser Ala Arg Leu Ala Ala Glu Asn Thr Ser
            755                 760                 765

Leu Val Ala Glu Ala Leu Val Gly Gln Thr Ser Glu Met Val Ala Ser
        770                 775                 780

Asn Ala Ile Val Ser Lys Ile Thr Ser Ile Thr Gln Pro Ser Ser
785                 790                 795                 800

Lys Thr Ser Tyr Gly Ser Gly Ser Ser Thr Thr Ser Asn Leu Ile Ser
```

```
                      805                 810                 815
Asp Val Asp Glu Ser Thr Gln Arg Ala Ala Ala Leu Glu His His His
        820                 825                 830

His His His His
        835

<210> SEQ ID NO 23
<211> LENGTH: 2508
<212> TYPE: DNA
<213> ORGANISM: Streptococcus pyogenes

<400> SEQUENCE: 23
atgagtgtag cgtatctca ccaagtcaaa gcagatgata gagcctcagg agaaacgaag      60
gcgagtaata ctcacgacga tagtttacca aaaccagaaa caattcaaga ggcaaaggca     120
actattgatg cagttgaaaa actctcagt caacaaaaag cagaactgac agagcttgct     180
accgctctga caaaaactac tgctgaaatc aaccacttaa agagcagca agataatgaa      240 caaaaagctt taacctctgc acaagaaatt tacactaata ctcttgcaag tagtgaggag     300
acgctattag cccaaggagc cgaacatcaa agagagttaa cagctactga acagagctt      360 cataatgctc aagcagatca acattcaaaa gagactgcat tgtcagaaca aaaagctagc     420
atttcagcag aaactactcg agctcaagat ttagtggaac aagtcaaaac gtctgaacaa     480
aatattgcta agctcaatgc tatgattagc aatcctgatg ctatcactaa agcagctcaa     540
acggctaatg ataatacaaa agcattaagc tcagaattgg agaaggctaa agctgactta     600
gaaaatcaaa aagctaaagt taaaaagcaa ttgactgaag agttggcagc tcagaaagct     660
gctctagcag aaaagaggc agaacttagt cgtcttaaat cctcagctcc gtctactcaa     720
gatagcattg tgggtaataa taccatgaaa gcaccgcaag gctatcctct tgaagaactt     780
aaaaaattag aagctagtgg ttatattgga tcagctagtt acaataatta ttacaaagag     840
catgcagatc aaattattgc caaagctagt ccaggtaatc aattaaatca ataccaagat     900
attccagcag atcgtaatcg ctttgttgat cccgataatt tgacaccaga agtgcaaaat     960
gagctagcgc agtttgcagc tcacatgatt aatagtgtac gtcgtcaatt aggtctacca    1020
ccagttactg ttacagcagg atcacaagaa tttgcaagat tacttagtac cagctataag    1080
aaaactcatg gtaatacaag accatcattt gtctacggac agccaggggt atcagggcat    1140
tatggtgttg ggcctcatga taaaactatt attgaagact ctgccggagc gtcagggctc    1200
attcgaaatg atgataacat gtacgagaat atcggtgctt taacgatgt gcatactgtg    1260 aatggtatta acgtggtat ttatgacagt atcaagtata tgctctttac agatcattta    1320
cacgaaaata catacggcca tgctattaac tttttacgtg tagataaaca taaccctaat    1380
gcgcctgttt accttggatt ttcaaccagc aatgtaggat ctttgaatga acactttgta    1440
atgtttccag agtctaacat tgctaaccat caacgcttta ataagacccc tataaaagcc    1500
gttggaagta caaagattat tgcccaaaga gtaggcactg tatctgatac tattgcagcg    1560
atcaaaggaa aagtaagctc attagaaaat cgtttgtcgg ctattcatca agaagctgat    1620
attatggcag cccaagctaa agtaagtcaa cttcaaggta aattagcaag cacacttaag    1680
cagtcagaca gcttaaatct ccaagtgaga caattaaatg atactaaagg ttcttttgaga   1740 acagaattac tagcagctaa agcaaaacaa gcacaactcg aagctactcg tgatcaatca    1800
ttagctaagc tagcatcgtt gaaagccgca ctgcaccaga cagaagcctt agcagagcaa    1860
gccgcagcca gagtgacagc actggtggct aaaaagagct atttgcaata tctaagggac    1920
```

-continued

```
tttaaattga atcctaaccg ccttcaagtg atacgtgagc gcattgataa tactaagcaa    1980
gatttggcta aaactacctc atctttgtta aatgcacaag aagctttagc agccttacaa    2040
gctaaacaaa gcagtctaga agctactatt gctaccacag aacaccagtt gactttgctt    2100
aaaaccttag ctaacgaaaa ggaatatcgc cacttagacg aagatatagc tactgtgcct    2160
gatttgcaag tagctccacc tcttacgggc gtaaaaccgc tatcatatag taagatagat    2220
actactccgc ttgttcaaga aatggttaaa gaaacgaaac aactattaga agcttcagca    2280
agattagctg ctgaaaatac aagtcttgta gcagaagcgc ttgttggcca aacctctgaa    2340
atggtagcaa gtaatgccat tgtgtctaaa atcacatctt cgattactca gccctcatct    2400
aagacatctt atggctcagg atcttctaca acgagcaatc tcatttctga tgttgatgaa    2460
agtactcaac gtgcggccgc actcgagcac caccaccacc accaccac                2508
```

<210> SEQ ID NO 24
<211> LENGTH: 836
<212> TYPE: PRT
<213> ORGANISM: Streptococcus pyogenes

<400> SEQUENCE: 24

```
Met Ser Val Gly Val Ser His Gln Val Lys Ala Asp Asp Arg Ala Ser
 1               5                  10                  15

Gly Glu Thr Lys Ala Ser Asn Thr His Asp Asp Ser Leu Pro Lys Pro
            20                  25                  30

Glu Thr Ile Gln Glu Ala Lys Ala Thr Ile Asp Ala Val Glu Lys Thr
        35                  40                  45

Leu Ser Gln Gln Lys Ala Glu Leu Thr Glu Leu Ala Thr Ala Leu Thr
    50                  55                  60

Lys Thr Thr Ala Glu Ile Asn His Leu Lys Gln Gln Asp Asn Glu
65                  70                  75                  80

Gln Lys Ala Leu Thr Ser Ala Gln Glu Ile Tyr Thr Asn Thr Leu Ala
                85                  90                  95

Ser Ser Glu Glu Thr Leu Leu Ala Gln Gly Ala Glu His Gln Arg Glu
            100                 105                 110

Leu Thr Ala Thr Glu Thr Glu Leu His Asn Ala Gln Ala Asp Gln His
        115                 120                 125

Ser Lys Glu Thr Ala Leu Ser Glu Gln Lys Ala Ser Ile Ser Ala Glu
    130                 135                 140

Thr Thr Arg Ala Gln Asp Leu Val Glu Gln Val Lys Thr Ser Glu Gln
145                 150                 155                 160

Asn Ile Ala Lys Leu Asn Ala Met Ile Ser Asn Pro Asp Ala Ile Thr
                165                 170                 175

Lys Ala Ala Gln Thr Ala Asn Asp Asn Thr Lys Ala Leu Ser Ser Glu
            180                 185                 190

Leu Glu Lys Ala Lys Ala Asp Leu Glu Asn Gln Lys Ala Lys Val Lys
        195                 200                 205

Lys Gln Leu Thr Glu Glu Leu Ala Ala Gln Lys Ala Ala Leu Ala Glu
    210                 215                 220

Lys Glu Ala Glu Leu Ser Arg Leu Lys Ser Ser Ala Pro Ser Thr Gln
225                 230                 235                 240

Asp Ser Ile Val Gly Asn Asn Thr Met Lys Ala Pro Gln Gly Tyr Pro
                245                 250                 255

Leu Glu Glu Leu Lys Lys Leu Glu Ala Ser Gly Tyr Ile Gly Ser Ala
            260                 265                 270

Ser Tyr Asn Asn Tyr Tyr Lys Glu His Ala Asp Gln Ile Ile Ala Lys
```

```
                275                 280                 285
Ala Ser Pro Gly Asn Gln Leu Asn Gln Tyr Gln Asp Ile Pro Ala Asp
290                 295                 300
Arg Asn Arg Phe Val Asp Pro Asp Asn Leu Thr Pro Glu Val Gln Asn
305                 310                 315                 320
Glu Leu Ala Gln Phe Ala Ala His Met Ile Asn Ser Val Arg Arg Gln
            325                 330                 335
Leu Gly Leu Pro Pro Val Thr Val Thr Ala Gly Ser Gln Glu Phe Ala
        340                 345                 350
Arg Leu Leu Ser Thr Ser Tyr Lys Lys Thr His Gly Asn Thr Arg Pro
    355                 360                 365
Ser Phe Val Tyr Gly Gln Pro Gly Val Ser Gly His Tyr Gly Val Gly
370                 375                 380
Pro His Asp Lys Thr Ile Ile Glu Asp Ser Ala Gly Ala Ser Gly Leu
385                 390                 395                 400
Ile Arg Asn Asp Asp Asn Met Tyr Glu Asn Ile Gly Ala Phe Asn Asp
            405                 410                 415
Val His Thr Val Asn Gly Ile Lys Arg Gly Ile Tyr Asp Ser Ile Lys
        420                 425                 430
Tyr Met Leu Phe Thr Asp His Leu His Gly Asn Thr Tyr Gly His Ala
    435                 440                 445
Ile Asn Phe Leu Arg Val Asp Lys His Asn Pro Asn Ala Pro Val Tyr
450                 455                 460
Leu Gly Phe Ser Thr Ser Asn Val Gly Ser Leu Asn Glu His Phe Val
465                 470                 475                 480
Met Phe Pro Glu Ser Asn Ile Ala Asn His Gln Arg Phe Asn Lys Thr
            485                 490                 495
Pro Ile Lys Ala Val Gly Ser Thr Lys Asp Tyr Ala Gln Arg Val Gly
        500                 505                 510
Thr Val Ser Asp Thr Ile Ala Ala Ile Lys Gly Lys Val Ser Ser Leu
    515                 520                 525
Glu Asn Arg Leu Ser Ala Ile His Gln Glu Ala Asp Ile Met Ala Ala
530                 535                 540
Gln Ala Lys Val Ser Gln Leu Gln Gly Lys Leu Ala Ser Thr Leu Lys
545                 550                 555                 560
Gln Ser Asp Ser Leu Asn Leu Gln Val Arg Gln Leu Asn Asp Thr Lys
            565                 570                 575
Gly Ser Leu Arg Thr Glu Leu Leu Ala Ala Lys Ala Lys Gln Ala Gln
        580                 585                 590
Leu Glu Ala Thr Arg Asp Gln Ser Leu Ala Lys Leu Ala Ser Leu Lys
    595                 600                 605
Ala Ala Leu His Gln Thr Glu Ala Leu Ala Glu Gln Ala Ala Ala Arg
610                 615                 620
Val Thr Ala Leu Val Ala Lys Lys Ala His Leu Gln Tyr Leu Arg Asp
625                 630                 635                 640
Phe Lys Leu Asn Pro Asn Arg Leu Gln Val Ile Arg Glu Arg Ile Asp
            645                 650                 655
Asn Thr Lys Gln Asp Leu Ala Lys Thr Thr Ser Ser Leu Leu Asn Ala
        660                 665                 670
Gln Glu Ala Leu Ala Ala Leu Gln Ala Lys Gln Ser Ser Leu Glu Ala
    675                 680                 685
Thr Ile Ala Thr Thr Glu His Gln Leu Thr Leu Leu Lys Thr Leu Ala
690                 695                 700
```

```
Asn Glu Lys Glu Tyr Arg His Leu Asp Glu Asp Ile Ala Thr Val Pro
705                 710                 715                 720

Asp Leu Gln Val Ala Pro Pro Leu Thr Gly Val Lys Pro Leu Ser Tyr
            725                 730                 735

Ser Lys Ile Asp Thr Thr Pro Leu Val Gln Glu Met Val Lys Glu Thr
        740                 745                 750

Lys Gln Leu Leu Glu Ala Ser Ala Arg Leu Ala Ala Glu Asn Thr Ser
    755                 760                 765

Leu Val Ala Glu Ala Leu Val Gly Gln Thr Ser Glu Met Val Ala Ser
770                 775                 780

Asn Ala Ile Val Ser Lys Ile Thr Ser Ser Ile Thr Gln Pro Ser Ser
785                 790                 795                 800

Lys Thr Ser Tyr Gly Ser Gly Ser Ser Thr Thr Ser Asn Leu Ile Ser
                805                 810                 815

Asp Val Asp Glu Ser Thr Gln Arg Ala Ala Ala Leu Glu His His His
                820                 825                 830

His His His His
            835

<210> SEQ ID NO 25
<211> LENGTH: 2472
<212> TYPE: DNA
<213> ORGANISM: Streptococcus pyogenes

<400> SEQUENCE: 25
atgagtgtag cgtatctca ccaagtcaaa gcagatgata gagcctcagg agaaacgaag       60
gcgagtaata ctcacgacga tagtttacca aaaccagaaa caattcaaga ggcaaaggca      120
actattgatg cagttgaaaa aactctcagt caacaaaaag cagaactgac agagcttgct      180
accgctctga caaaaactac tgctgaaatc aaccacttaa aagagcagca agataatgaa      240
caaaaagctt taacctctgc acaagaaatt tacactaata ctcttgcaag tagtgaggag      300
acgctattag cccaaggagc cgaacatcaa agagagttaa cagctactga acagagctt       360 cataatgctc aagcagatca acattcaaaa gagactgcat tgtcagaaca aaaagctagc      420
atttcagcag aaactactcg agctcaagat ttagtggaac aagtcaaaac gtctgaacaa      480
aatattgcta agctcaatgc tatgattagc aatcctgatg ctatcactaa agcagctcaa      540
acggctaatg ataatacaaa agcattaagc tcagaattgg agaaggctaa agctgactta      600
gaaaatcaaa aagctaaagt taaaagcaa ttgactgaag agttggcagc tcagaaagct      660
gctctagcag aaaaagaggc agaacttagt cgtcttaaat cctcagctcc gtctactcaa      720
gatagcattg tgggtaataa taccatgaaa gcaccgcaag ctatcctct tgaagaactt      780 aaaaaattag aagctagtgg ttatattgga tcagctagtt acaataatta ttacaaagag      840
catgcagatc aaattattgc caaagctagt ccaggtaatc aattaaatca ataccaagat      900
attccagcag atcgtaatcg ctttgttgat cccgataatt tgacaccaga agtgcaaaat      960
gagctagcgc agtttgcagc tcacatgatt aatagtgtac gtcgtcaatt aggtctacca     1020
ccagttactg ttacagcagg atcacaagaa tttgcaagat tacttagtac cagctataag     1080
aaaactcatg gtaatacaag accatcattt gtctacggac agccaggggt atcagggcat     1140
tatggtgttg ggcctcatga taaaactatt attgaagact ctgccggagc gtcagggctc     1200
attcgaaatg atgataacat gtacgagaat atcggtgctt ttaacgatgt gcatactgtg     1260
aatggtatta acgtggtat ttatgacagt atcaagtata tgctctttac agatcattta     1320
cacggaaata catacggcca tgctattaac ttttacgtg tagataaaca taaccctaat     1380
```

-continued

```
gcgcctgttt accttggatt ttcaaccagc aatgtaggat ctttgaatga acactttgta    1440
atgtttccag agtctaacat tgctaaccat caacgcttta ataagacccc tataaaagcc    1500
gttggaagta caaagatta tgcccaaaga gtaggcactg tatctgatac tattgcagcg    1560
atcaaaggaa aagtaagctc attagaaaat cgtttgtcgg ctattcatca agaagctgat    1620
attatggcag cccaagctaa agtaagtcaa cttcaaggta aattagcaag cacacttaag    1680
cagtcagaca gcttaaatct ccaagtgaga caattaaatg atactaaagg ttctttgaga    1740
acagaattac tagcagctaa agcaaaacaa gcacaactcg aagctactcg tgatcaatca    1800
ttagctaagc tagcatcgtt gaaagccgca ctgcaccaga cagaagcctt agcagagcaa    1860
gccgcagcca gagtgacagc actggtggct aaaaaagctc atttgcaata tctaagggac    1920
tttaaattga atcctaaccg ccttcaagtg atacgtgagc gcattgataa tactaagcaa    1980
gatttggcta aaactacctc atctttgtta aatgcacaag aagctttagc agccttacaa    2040
gctaaacaaa gcagtctaga agctactatt gctaccacag aacaccagtt gactttgctt    2100
aaaaccttag ctaacgaaaa ggaatatcgc cacttagacg aagatatagc tactgtgcct    2160
gatttgcaag tagctccacc tcttacgggc gtaaaaccgc tatcatatag taagatagat    2220
actactccgc ttgttcaaga aatggttaaa gaaacgaaac aactattaga agcttcagca    2280
agattagctg ctgaaaatac aagtcttgta gcagaagcgc ttgttggcca aacctctgaa    2340
atggtagcaa gtaatgccat tgtgtctaaa atcacatctt cgattactca gccctcatct    2400
aagacatctt atggctcagg atcttctaca acgagcaatc tcatttctga tgttgatgaa    2460
agtactcaac gt                                                        2472
```

<210> SEQ ID NO 26
<211> LENGTH: 824
<212> TYPE: PRT
<213> ORGANISM: Streptococcus pyogenes

<400> SEQUENCE: 26

```
Met Ser Val Gly Val Ser His Gln Val Lys Ala Asp Asp Arg Ala Ser
 1               5                  10                  15

Gly Glu Thr Lys Ala Ser Asn Thr His Asp Asp Ser Leu Pro Lys Pro
            20                  25                  30

Glu Thr Ile Gln Glu Ala Lys Ala Thr Ile Asp Ala Val Glu Lys Thr
        35                  40                  45

Leu Ser Gln Gln Lys Ala Glu Leu Thr Glu Leu Ala Thr Ala Leu Thr
    50                  55                  60

Lys Thr Thr Ala Glu Ile Asn His Leu Lys Glu Gln Gln Asp Asn Glu
65                  70                  75                  80

Gln Lys Ala Leu Thr Ser Ala Gln Glu Ile Tyr Thr Asn Thr Leu Ala
                85                  90                  95

Ser Ser Glu Glu Thr Leu Leu Ala Gln Gly Ala Glu His Gln Arg Glu
            100                 105                 110

Leu Thr Ala Thr Glu Thr Glu Leu His Asn Ala Gln Ala Asp Gln His
        115                 120                 125

Ser Lys Glu Thr Ala Leu Ser Glu Gln Lys Ala Ser Ile Ser Ala Glu
    130                 135                 140

Thr Thr Arg Ala Gln Asp Leu Val Glu Gln Val Lys Thr Ser Glu Gln
145                 150                 155                 160

Asn Ile Ala Lys Leu Asn Ala Met Ile Ser Asn Pro Asp Ala Ile Thr
                165                 170                 175
```

```
Lys Ala Ala Gln Thr Ala Asn Asp Asn Thr Lys Ala Leu Ser Ser Glu
            180                 185                 190

Leu Glu Lys Ala Lys Ala Asp Leu Glu Asn Gln Lys Ala Lys Val Lys
        195                 200                 205

Lys Gln Leu Thr Glu Glu Leu Ala Ala Gln Lys Ala Ala Leu Ala Glu
210                 215                 220

Lys Glu Ala Glu Leu Ser Arg Leu Lys Ser Ser Ala Pro Ser Thr Gln
225                 230                 235                 240

Asp Ser Ile Val Gly Asn Asn Thr Met Lys Ala Pro Gln Gly Tyr Pro
                245                 250                 255

Leu Glu Glu Leu Lys Lys Leu Glu Ala Ser Gly Tyr Ile Gly Ser Ala
            260                 265                 270

Ser Tyr Asn Asn Tyr Tyr Lys Glu His Ala Asp Gln Ile Ile Ala Lys
        275                 280                 285

Ala Ser Pro Gly Asn Gln Leu Asn Gln Tyr Gln Asp Ile Pro Ala Asp
290                 295                 300

Arg Asn Arg Phe Val Asp Pro Asp Asn Leu Thr Pro Glu Val Gln Asn
305                 310                 315                 320

Glu Leu Ala Gln Phe Ala Ala His Met Ile Asn Ser Val Arg Arg Gln
                325                 330                 335

Leu Gly Leu Pro Pro Val Thr Val Thr Ala Gly Ser Gln Glu Phe Ala
            340                 345                 350

Arg Leu Leu Ser Thr Ser Tyr Lys Lys Thr His Gly Asn Thr Arg Pro
        355                 360                 365

Ser Phe Val Tyr Gly Gln Pro Gly Val Ser Gly His Tyr Gly Val Gly
370                 375                 380

Pro His Asp Lys Thr Ile Ile Glu Asp Ser Ala Gly Ala Ser Gly Leu
385                 390                 395                 400

Ile Arg Asn Asp Asp Asn Met Tyr Glu Asn Ile Gly Ala Phe Asn Asp
                405                 410                 415

Val His Thr Val Asn Gly Ile Lys Arg Gly Ile Tyr Asp Ser Ile Lys
            420                 425                 430

Tyr Met Leu Phe Thr Asp His Leu His Gly Asn Thr Tyr Gly His Ala
        435                 440                 445

Ile Asn Phe Leu Arg Val Asp Lys His Asn Pro Asn Ala Pro Val Tyr
450                 455                 460

Leu Gly Phe Ser Thr Ser Asn Val Gly Ser Leu Asn Glu His Phe Val
465                 470                 475                 480

Met Phe Pro Glu Ser Asn Ile Ala Asn His Gln Arg Phe Asn Lys Thr
                485                 490                 495

Pro Ile Lys Ala Val Gly Ser Thr Lys Asp Tyr Ala Gln Arg Val Gly
            500                 505                 510

Thr Val Ser Asp Thr Ile Ala Ala Ile Lys Gly Lys Val Ser Ser Leu
        515                 520                 525

Glu Asn Arg Leu Ser Ala Ile His Gln Glu Ala Asp Ile Met Ala Ala
530                 535                 540

Gln Ala Lys Val Ser Gln Leu Gln Gly Lys Leu Ala Ser Thr Leu Lys
545                 550                 555                 560

Gln Ser Asp Ser Leu Asn Leu Gln Val Arg Gln Leu Asn Asp Thr Lys
                565                 570                 575

Gly Ser Leu Arg Thr Glu Leu Leu Ala Ala Lys Ala Lys Gln Ala Gln
            580                 585                 590

Leu Glu Ala Thr Arg Asp Gln Ser Leu Ala Lys Leu Ala Ser Leu Lys
        595                 600                 605
```

```
Ala Ala Leu His Gln Thr Glu Ala Leu Ala Glu Gln Ala Ala Arg
        610                 615                 620

Val Thr Ala Leu Val Ala Lys Lys Ala His Leu Gln Tyr Leu Arg Asp
625                 630                 635                 640

Phe Lys Leu Asn Pro Asn Arg Leu Gln Val Ile Arg Glu Arg Ile Asp
                645                 650                 655

Asn Thr Lys Gln Asp Leu Ala Lys Thr Thr Ser Ser Leu Leu Asn Ala
            660                 665                 670

Gln Glu Ala Leu Ala Ala Leu Gln Ala Lys Gln Ser Ser Leu Glu Ala
        675                 680                 685

Thr Ile Ala Thr Thr Glu His Gln Leu Thr Leu Leu Lys Thr Leu Ala
        690                 695                 700

Asn Glu Lys Glu Tyr Arg His Leu Asp Glu Asp Ile Ala Thr Val Pro
705                 710                 715                 720

Asp Leu Gln Val Ala Pro Pro Leu Thr Gly Val Lys Pro Leu Ser Tyr
                725                 730                 735

Ser Lys Ile Asp Thr Thr Pro Leu Val Gln Glu Met Val Lys Glu Thr
            740                 745                 750

Lys Gln Leu Leu Glu Ala Ser Ala Arg Leu Ala Ala Glu Asn Thr Ser
        755                 760                 765

Leu Val Ala Glu Ala Leu Val Gly Gln Thr Ser Glu Met Val Ala Ser
770                 775                 780

Asn Ala Ile Val Ser Lys Ile Thr Ser Ser Ile Thr Gln Pro Ser Ser
785                 790                 795                 800

Lys Thr Ser Tyr Gly Ser Gly Ser Ser Thr Thr Ser Asn Leu Ile Ser
                805                 810                 815

Asp Val Asp Glu Ser Thr Gln Arg
            820

<210> SEQ ID NO 27
<211> LENGTH: 2502
<212> TYPE: DNA
<213> ORGANISM: Streptococcus pyogenes

<400> SEQUENCE: 27
atgggatcgc atcaccatca ccatcacgct agtagtgtag gcgtatctca ccaagtcaaa      60
gcagatgata gagcctcagg agaaacgaag gcgagtaata ctcacgacga tagtttacca     120
aaaccagaaa caattcaaga ggcaaaggca actattgatg cagttgaaaa aactctcagt     180
caacaaaaag cagaactgac agagcttgct accgctctga caaaaactac tgctgaaatc     240
aaccacttaa aagagcagca agataatgaa caaaaagctt taacctctgc acaagaaatt     300
tacactaata ctcttgcaag tagtgaggag acgctattag cccaaggagc cgaacaccaa     360
agagagttaa cagctactga acagagcttc ataatgctc aagcagatca acattcaaaa     420
gagactgcat tgtcagaaca aaaagctagc atttcagcag aaactactcg agctcaagat     480
ttagtggaac aagtcaaaac gtctgaacaa atattgcta agctcaatgc tatgattagc     540
aatcctgatg ctatcactaa agcagctcaa acggctaatg ataatacaaa agcattaagc     600
tcagaattgg agaaggctaa agctgactta gaaaatcaaa aagctaaagt taaaagcaa     660 ttgactgaag agttggcagc tcagaaagct gctctagcag aaaagaggc agaacttagt     720 cgtcttaaat cctcagctcc gtctactcaa gatagcattg tgggtaataa taccatgaaa     780
gcaccgcaag ctatcctct tgaagaactt aaaaattag aagctagtgg ttatattgga     840
tcagctagtt acaataatta ttacaaagag catgcagatc aaattattgc caaagctagt     900
```

```
ccaggtaatc aattaaatca ataccaagat attccagcag atcgtaatcg ctttgttgat    960
cccgataatt tgacaccaga agtgcaaaat gagctagcgc agtttgcagc tcacatgatt   1020
aatagtgtaa gaagacaatt aggtctacca ccagttactg ttacagcagg atcacaagaa   1080
tttgcaagat tacttagtac cagctataag aaaactcatg gtaatacaag accatcattt   1140
gtctacggac agccagggt atcagggcat tatggtgttg ggcctcatga taaaactatt   1200
attgaagact ctgccggagc gtcagggctc attcgaaatg atgataacat gtacgagaat   1260
atcggtgctt ttaacgatgt gcatactgtg aatggtatta acgtggtat ttatgacagt   1320
atcaagtata tgctctttac agatcattta cacggaaata catacggcca tgctattaac   1380
tttttacgtg tagataaaca taaccctaat gcgcctgttt accttggatt ttcaaccagc   1440
aatgtaggat ctttgaatga acactttgta atgtttccag agtctaacat tgctaaccat   1500
caacgcttta ataagacccc tataaaagcc gttggaagta caaaagacta tgcccaaaga   1560
gtaggcactg tatctgatac tattgcagcg atcaaaggaa agtaagctc attagaaaat   1620
cgtttgtcgg ctattcatca agaagctgat attatggcag cccaagctaa agtaagtcaa   1680
cttcaaggta aattagcaag cacacttaag cagtcagaca gcttaaatct ccaagtgaga   1740
caattaaatg atactaaagg ttctttgaga acagaattac tagcagctaa agcaaaacaa   1800
gcacaactcg aagctactcg tgatcaatca ttagctaagc tagcatcgtt gaaagccgca   1860
ctgcaccaga cagaagcctt agcagagcaa gccgcagcca gagtgacagc actggtggct   1920
aaaaaagctc atttgcaata tctaagggac tttaaattga atcctaaccg ccttcaagtg   1980
atacgtgagc gcattgataa tactaagcaa gatttggcta aaactacctc atctttgtta   2040
aatgcacaag aagctttagc agccttacaa gctaaacaaa gcagtctaga agctactatt   2100
gctaccacag aacaccagtt gactttgctt aaaaaccttag ctaacgaaaa ggaatatcgc   2160
cacttagacg aagatatagc tactgtgcct gatttgcaag tagctccacc tcttacgggc   2220
gtaaaaccgc tatcatatag taagatagat actactccgc ttgttcaaga aatggttaaa   2280
gaaacgaaac aactattaga agcttcagca agattagctg ctgaaaatac aagtcttgta   2340
gcagaagcgc ttgttggcca aacctctgaa atggtagcaa gtaatgccat tgtgtctaaa   2400
atcacatctt cgattactca gccctcatct aagacatctt atggctcagg atcttctaca   2460
acgagcaatc tcatttctga tgttgatgaa agtactcaac gt                      2502
```

<210> SEQ ID NO 28
<211> LENGTH: 834
<212> TYPE: PRT
<213> ORGANISM: Streptococcus pyogenes

<400> SEQUENCE: 28

```
Met Gly Ser His His His His His His Ala Ser Ser Val Gly Val Ser
  1               5                  10                  15

His Gln Val Lys Ala Asp Asp Arg Ala Ser Gly Glu Thr Lys Ala Ser
                 20                  25                  30

Asn Thr His Asp Asp Ser Leu Pro Lys Pro Glu Thr Ile Gln Glu Ala
             35                  40                  45

Lys Ala Thr Ile Asp Ala Val Glu Lys Thr Leu Ser Gln Gln Lys Ala
         50                  55                  60

Glu Leu Thr Glu Leu Ala Thr Ala Leu Thr Lys Thr Thr Ala Glu Ile
 65                  70                  75                  80

Asn His Leu Lys Glu Gln Gln Asp Asn Glu Gln Lys Ala Leu Thr Ser
                 85                  90                  95
```

```
Ala Gln Glu Ile Tyr Thr Asn Thr Leu Ala Ser Ser Glu Glu Thr Leu
            100                 105                 110

Leu Ala Gln Gly Ala Glu His Gln Arg Glu Leu Thr Ala Thr Glu Thr
            115                 120                 125

Glu Leu His Asn Ala Gln Ala Asp Gln His Ser Lys Glu Thr Ala Leu
            130                 135                 140

Ser Glu Gln Lys Ala Ser Ile Ser Ala Glu Thr Thr Arg Ala Gln Asp
145                 150                 155                 160

Leu Val Glu Gln Val Lys Thr Ser Gln Asn Ile Ala Lys Leu Asn
            165                 170                 175

Ala Met Ile Ser Asn Pro Asp Ala Ile Thr Lys Ala Ala Gln Thr Ala
            180                 185                 190

Asn Asp Asn Thr Lys Ala Leu Ser Ser Glu Leu Glu Lys Ala Lys Ala
            195                 200                 205

Asp Leu Glu Asn Gln Lys Ala Lys Val Lys Lys Gln Leu Thr Glu Glu
            210                 215                 220

Leu Ala Ala Gln Lys Ala Ala Leu Ala Glu Lys Glu Ala Glu Leu Ser
225                 230                 235                 240

Arg Leu Lys Ser Ser Ala Pro Ser Thr Gln Asp Ser Ile Val Gly Asn
                    245                 250                 255

Asn Thr Met Lys Ala Pro Gln Gly Tyr Pro Leu Glu Glu Leu Lys Lys
            260                 265                 270

Leu Glu Ala Ser Gly Tyr Ile Gly Ser Ala Ser Tyr Asn Asn Tyr Tyr
            275                 280                 285

Lys Glu His Ala Asp Gln Ile Ile Ala Lys Ala Ser Pro Gly Asn Gln
            290                 295                 300

Leu Asn Gln Tyr Gln Asp Ile Pro Ala Asp Arg Asn Arg Phe Val Asp
305                 310                 315                 320

Pro Asp Asn Leu Thr Pro Glu Val Gln Asn Glu Leu Ala Gln Phe Ala
                    325                 330                 335

Ala His Met Ile Asn Ser Val Arg Arg Gln Leu Gly Leu Pro Pro Val
            340                 345                 350

Thr Val Thr Ala Gly Ser Gln Glu Phe Ala Arg Leu Leu Ser Thr Ser
            355                 360                 365

Tyr Lys Lys Thr His Gly Asn Thr Arg Pro Ser Phe Val Tyr Gly Gln
            370                 375                 380

Pro Gly Val Ser Gly His Tyr Val Gly Pro His Asp Lys Thr Ile
385                 390                 395                 400

Ile Glu Asp Ser Ala Gly Ala Ser Gly Leu Ile Arg Asn Asp Asn
                    405                 410                 415

Met Tyr Glu Asn Ile Gly Ala Phe Asn Asp Val His Thr Val Asn Gly
            420                 425                 430

Ile Lys Arg Gly Ile Tyr Asp Ser Ile Lys Tyr Met Leu Phe Thr Asp
            435                 440                 445

His Leu His Gly Asn Thr Tyr Gly His Ala Ile Asn Phe Leu Arg Val
            450                 455                 460

Asp Lys His Asn Pro Asn Ala Pro Val Tyr Leu Gly Phe Ser Thr Ser
465                 470                 475                 480

Asn Val Gly Ser Leu Asn Glu His Phe Val Met Phe Pro Glu Ser Asn
                    485                 490                 495

Ile Ala Asn His Gln Arg Phe Asn Lys Thr Pro Ile Lys Ala Val Gly
            500                 505                 510

Ser Thr Lys Asp Tyr Ala Gln Arg Val Gly Thr Val Ser Asp Thr Ile
```

```
              515                 520                 525
Ala Ala Ile Lys Gly Lys Val Ser Ser Leu Glu Asn Arg Leu Ser Ala
530                 535                 540

Ile His Gln Glu Ala Asp Ile Met Ala Gln Ala Lys Val Ser Gln
545                 550                 555                 560

Leu Gln Gly Lys Leu Ala Ser Thr Leu Lys Gln Ser Asp Ser Leu Asn
                565                 570                 575

Leu Gln Val Arg Gln Leu Asn Asp Thr Lys Gly Ser Leu Arg Thr Glu
                580                 585                 590

Leu Leu Ala Ala Lys Ala Lys Gln Ala Gln Leu Glu Ala Thr Arg Asp
                595                 600                 605

Gln Ser Leu Ala Lys Leu Ala Ser Leu Lys Ala Ala Leu His Gln Thr
                610                 615                 620

Glu Ala Leu Ala Glu Gln Ala Ala Ala Arg Val Thr Ala Leu Val Ala
625                 630                 635                 640

Lys Lys Ala His Leu Gln Tyr Leu Arg Asp Phe Lys Leu Asn Pro Asn
                645                 650                 655

Arg Leu Gln Val Ile Arg Glu Arg Ile Asp Asn Thr Lys Gln Asp Leu
                660                 665                 670

Ala Lys Thr Thr Ser Ser Leu Leu Asn Ala Gln Glu Ala Leu Ala Ala
                675                 680                 685

Leu Gln Ala Lys Gln Ser Ser Leu Glu Ala Thr Ile Ala Thr Thr Glu
                690                 695                 700

His Gln Leu Thr Leu Lys Thr Leu Ala Asn Glu Lys Glu Tyr Arg
705                 710                 715                 720

His Leu Asp Glu Asp Ile Ala Thr Val Pro Asp Leu Gln Val Ala Pro
                725                 730                 735

Pro Leu Thr Gly Val Lys Pro Leu Ser Tyr Ser Lys Ile Asp Thr Thr
                740                 745                 750

Pro Leu Val Gln Glu Met Val Lys Glu Thr Lys Gln Leu Leu Glu Ala
                755                 760                 765

Ser Ala Arg Leu Ala Ala Glu Asn Thr Ser Leu Val Ala Glu Ala Leu
770                 775                 780

Val Gly Gln Thr Ser Glu Met Val Ala Ser Asn Ala Ile Val Ser Lys
785                 790                 795                 800

Ile Thr Ser Ser Ile Thr Gln Pro Ser Ser Lys Thr Ser Tyr Gly Ser
                805                 810                 815

Gly Ser Ser Thr Thr Ser Asn Leu Ile Ser Asp Val Asp Glu Ser Thr
                820                 825                 830

Gln Arg

<210> SEQ ID NO 29
<211> LENGTH: 2511
<212> TYPE: DNA
<213> ORGANISM: Streptococcus pyogenes

<400> SEQUENCE: 29
atggctagta gtgtaggcgt atctcaccaa gtcaaagcag atgatagagc ctcaggagaa      60
acgaaggcga gtaatactca cgacgatagt ttaccaaaac cagaaacaat tcaagaggca     120
aaggcaacta ttgatgcagt tgaaaaaact ctcagtcaac aaaaagcaga actgacagag     180
cttgctaccg ctctgacgaa aactactgct gaaatcaacc atttaaaaga gcagcaagat     240
aatgaacaaa aagcttttaa ctctgcacaa gaaatttaca ctaatactct tgcaagtagt     300
gaggagacgc tattagccca aggagccgaa catcaaagag agttaacagc tactgaaaca     360
```

```
gagcttcata atgctcaagc agatcaacat tcaaaagaga ctgcattgtc agaacaaaaa      420
gctagcattt cagcagaaac tactcgagct caagatttag tggaacaagt caaaacgtct      480
gaacaaaata ttgctaagct caatgctatg attagcaatc ctgatgctat cactaaagca      540
gctcaaacgg ctaatgataa tacaaaagca ttaagctcag aattggagaa ggctaaagct      600
gacttagaaa atcaaaaagc taagttaaaa aagcaattga ctgaagagtt ggcagctcag      660
aaagctgctc tagcagaaaa agaggcagaa cttagtcgtc ttaaatcctc agctccgtct      720
actcaagata gcattgtggg taataatacc atgaaagcac cgcaaggcta tcctcttgaa      780
gaacttaaaa aattagaagc tagtggttat attggatcag ctagttacaa taattattac      840
aaagagcatg cagatcaaat tattgccaaa gctagtccag gtaatcaatt aaatcaatac      900
caagatattc cagcagatcg taatcgcttt gttgatcccg ataatttgac accagaagtg      960
caaaatgagc tagcgcagtt tgcagctcac atgattaata gtgtaagaag acaattaggt     1020
ctaccaccag ttactgttac agcaggatca caagaatttg caagattact tagtaccagc     1080
tataagaaaa ctcatggtaa tacaagacca tcatctgtct acggacagcc aggggtatca     1140
gggcattatg gtgttgggcc tcatgataaa actattattg aagactctgc cggagcgtca     1200
gggctcattc gaaatgatga taacatgtac gagaatatcg gtgcttttaa cgatgtgcat     1260
actgtgaatg gtattaaacg tggtatttat gacagtatca agtatatgct ctttacagat     1320
catttacacg gaaatacata cggccatgct attaactttt acgtgtagga taaacataac     1380
cctaatgcgc ctgtttacct tggatttttca accagcaatg taggatcttt gaatgaacac     1440
tttgtaatgt ttccagagtc taacattgct aaccatcaac gctttaataa gaccccctata     1500 aaagccgttg gaagtacaaa agattatgcc caaagagtag gcactgtatc tgatactatt     1560
gcagcgatca aggaaaagt aagctcatta gaaaatcgtt tgtcggctat tcatcaagaa     1620
gctgatatta tggcagccca agctaaagta agtcaacttc aaggtaaatt agcaagcaca     1680
cttaagcagt cagacagctt aaatctccaa gtgagacaat taaatgatac taaaggttct     1740
ttgagaacag aattactagc agctaaagca aaacaagcac aactcgaagc tactcgtgat     1800
caatcattag ctaagctagc atcgttgaaa gccgcactgc accagacaga agccttagca     1860
gagcaagccg cagccagagt gacagcactg gtggctaaaa aagctcattt gcaatatcta     1920
agggacttta aattgaatcc taaccgcctt caagtgatac gtgagcgcat tgataatact     1980
aagcaagatt tggctaaaac tacctcatct ttgttaaatg cacaagaagc tttagcagcc     2040
ttacaagcta aacaaagcag tctagaagct actattgcta ccacagaaca ccagttgact     2100
ttgcttaaaa ccttagctaa cgaaaaggaa tatcgccact tagacgaaga tatagctact     2160
gtgcctgatt tgcaagtagc tccacctctt acgggcgtaa aaccgctatc atatagtaag     2220
atagatacta ctccgcttgt tcaagaaatg gttaaagaaa cgaaacaact attagaagct     2280
tcagcaagat tagctgctga aaatacaagt cttgtagcag aagcgcttgt tggccaaacc     2340
tctgaaatgg tagcaagtaa tgccattgtg tctaaaatca catcttcgat tactcagccc     2400
tcatctaaga catcttatgg ctcaggatct tctacaacga gcaatctcat ttctgatgtt     2460
gatgaaagta ctcaacgtgc ggccgcactc gagcaccacc accaccacca c              2511
```

<210> SEQ ID NO 30
<211> LENGTH: 837
<212> TYPE: PRT
<213> ORGANISM: Streptococcus pyogenes

<400> SEQUENCE: 30

```
Met Ala Ser Ser Val Gly Val Ser His Gln Val Lys Ala Asp Asp Arg
 1               5                  10                  15
Ala Ser Gly Glu Thr Lys Ala Ser Asn Thr His Asp Asp Ser Leu Pro
             20                  25                  30
Lys Pro Glu Thr Ile Gln Glu Ala Lys Ala Thr Ile Asp Ala Val Glu
         35                  40                  45
Lys Thr Leu Ser Gln Gln Lys Ala Glu Leu Thr Glu Leu Ala Thr Ala
     50                  55                  60
Leu Thr Lys Thr Thr Ala Glu Ile Asn His Leu Lys Glu Gln Gln Asp
 65                  70                  75                  80
Asn Glu Gln Lys Ala Leu Thr Ser Ala Gln Glu Ile Tyr Thr Asn Thr
                 85                  90                  95
Leu Ala Ser Ser Glu Glu Thr Leu Leu Ala Gln Gly Ala Glu His Gln
             100                 105                 110
Arg Glu Leu Thr Ala Thr Glu Thr Glu Leu His Asn Ala Gln Ala Asp
         115                 120                 125
Gln His Ser Lys Glu Thr Ala Leu Ser Glu Gln Lys Ala Ser Ile Ser
     130                 135                 140
Ala Glu Thr Thr Arg Ala Gln Asp Leu Val Glu Gln Val Lys Thr Ser
145                 150                 155                 160
Glu Gln Asn Ile Ala Lys Leu Asn Ala Met Ile Ser Asn Pro Asp Ala
                 165                 170                 175
Ile Thr Lys Ala Ala Gln Thr Ala Asn Asp Asn Thr Lys Ala Leu Ser
             180                 185                 190
Ser Glu Leu Glu Lys Ala Lys Ala Asp Leu Glu Asn Gln Lys Ala Lys
         195                 200                 205
Val Lys Lys Gln Leu Thr Glu Glu Leu Ala Ala Gln Lys Ala Ala Leu
     210                 215                 220
Ala Glu Lys Glu Ala Glu Leu Ser Arg Leu Lys Ser Ser Ala Pro Ser
225                 230                 235                 240
Thr Gln Asp Ser Ile Val Gly Asn Asn Thr Met Lys Ala Pro Gln Gly
                 245                 250                 255
Tyr Pro Leu Glu Glu Leu Lys Lys Leu Glu Ala Ser Gly Tyr Ile Gly
             260                 265                 270
Ser Ala Ser Tyr Asn Asn Tyr Tyr Lys Glu His Ala Asp Gln Ile Ile
         275                 280                 285
Ala Lys Ala Ser Pro Gly Asn Gln Leu Asn Gln Tyr Gln Asp Ile Pro
     290                 295                 300
Ala Asp Arg Asn Arg Phe Val Asp Pro Asp Asn Leu Thr Pro Glu Val
305                 310                 315                 320
Gln Asn Glu Leu Ala Gln Phe Ala Ala His Met Ile Asn Ser Val Arg
                 325                 330                 335
Arg Gln Leu Gly Leu Pro Pro Val Thr Val Thr Ala Gly Ser Gln Glu
             340                 345                 350
Phe Ala Arg Leu Leu Ser Thr Ser Tyr Lys Lys Thr His Gly Asn Thr
         355                 360                 365
Arg Pro Ser Ser Val Tyr Gly Gln Pro Gly Val Ser Gly His Tyr Gly
     370                 375                 380
Val Gly Pro His Asp Lys Thr Ile Ile Glu Asp Ser Ala Gly Ala Ser
385                 390                 395                 400
Gly Leu Ile Arg Asn Asp Asp Asn Met Tyr Glu Asn Ile Gly Ala Phe
                 405                 410                 415
Asn Asp Val His Thr Val Asn Gly Ile Lys Arg Gly Ile Tyr Asp Ser
```

```
                    420             425             430
Ile Lys Tyr Met Leu Phe Thr Asp His Leu His Gly Asn Thr Tyr Gly
        435                     440             445

His Ala Ile Asn Phe Leu Arg Val Asp Lys His Asn Pro Asn Ala Pro
    450                     455             460

Val Tyr Leu Gly Phe Ser Thr Ser Asn Val Gly Ser Leu Asn Glu His
465                 470              475             480

Phe Val Met Phe Pro Glu Ser Asn Ile Ala Asn His Gln Arg Phe Asn
                485             490              495

Lys Thr Pro Ile Lys Ala Val Gly Ser Thr Lys Asp Tyr Ala Gln Arg
            500             505             510

Val Gly Thr Val Ser Asp Thr Ile Ala Ala Ile Lys Gly Lys Val Ser
        515             520              525

Ser Leu Glu Asn Arg Leu Ser Ala Ile His Gln Glu Ala Asp Ile Met
        530             535             540

Ala Ala Gln Ala Lys Val Ser Gln Leu Gln Gly Lys Leu Ala Ser Thr
545             550             555             560

Leu Lys Gln Ser Asp Ser Leu Asn Leu Gln Val Arg Gln Leu Asn Asp
                565             570             575

Thr Lys Gly Ser Leu Arg Thr Glu Leu Leu Ala Ala Lys Ala Lys Gln
            580             585             590

Ala Gln Leu Glu Ala Thr Arg Asp Gln Ser Leu Ala Lys Leu Ala Ser
        595             600             605

Leu Lys Ala Ala Leu His Gln Thr Glu Ala Leu Ala Glu Gln Ala Ala
    610             615             620

Ala Arg Val Thr Ala Leu Val Ala Lys Lys Ala His Leu Gln Tyr Leu
625             630             635             640

Arg Asp Phe Lys Leu Asn Pro Asn Arg Leu Gln Val Ile Arg Glu Arg
                645             650             655

Ile Asp Asn Thr Lys Gln Asp Leu Ala Lys Thr Thr Ser Ser Leu Leu
            660             665             670

Asn Ala Gln Glu Ala Leu Ala Ala Leu Gln Ala Lys Gln Ser Ser Leu
        675             680             685

Glu Ala Thr Ile Ala Thr Thr Glu His Gln Leu Thr Leu Leu Lys Thr
    690             695             700

Leu Ala Asn Glu Lys Glu Tyr Arg His Leu Glu Asp Ile Ala Thr
705             710             715             720

Val Pro Asp Leu Gln Val Ala Pro Pro Leu Thr Gly Val Lys Pro Leu
                725             730             735

Ser Tyr Ser Lys Ile Asp Thr Thr Pro Leu Val Gln Glu Met Val Lys
            740             745             750

Glu Thr Lys Gln Leu Leu Glu Ala Ser Ala Arg Leu Ala Ala Glu Asn
        755             760             765

Thr Ser Leu Val Ala Glu Ala Leu Val Gly Gln Thr Ser Glu Met Val
    770             775             780

Ala Ser Asn Ala Ile Val Ser Lys Ile Thr Ser Ser Ile Thr Gln Pro
785             790             795             800

Ser Ser Lys Thr Ser Tyr Gly Ser Gly Ser Thr Thr Ser Asn Leu
                805             810             815

Ile Ser Asp Val Asp Glu Ser Thr Gln Arg Ala Ala Leu Glu His
            820             825             830

His His His His
        835
```

<210> SEQ ID NO 31
<211> LENGTH: 2502
<212> TYPE: DNA
<213> ORGANISM: Streptococcus pyogenes

<400> SEQUENCE: 31

| | | | | | |
|---|---|---|---|---|---|
| atgggatcgc | atcaccatca | ccatcacgct | agtagtgtag | gcgtatctca | ccaagtcaaa | 60 |
| gcagatgata | gagcctcagg | agaaacgaag | gcgagtaata | ctcacgacga | tagtttacca | 120 |
| aaaccagaaa | caattcaaga | ggcaaaggca | actattgatg | cagttgaaaa | aactctcagt | 180 |
| caacaaaaag | cagaactgac | agagcttgct | accgctctga | caaaaactac | tgctgaaatc | 240 |
| aaccacttaa | aagagcagca | agataatgaa | caaaaagctt | taacctctgc | acaagaaatt | 300 |
| tacactaata | ctcttgcaag | tagtgaggag | acgctattag | cccaaggagc | cgaacatcaa | 360 |
| agagagttaa | cagctactga | aacagagctt | cataatgctc | aagcagatca | acattcaaaa | 420 |
| gagactgcat | tgtcagaaca | aaaagctagc | atttcagcag | aaactactcg | agctcaagat | 480 |
| ttagtggaac | aagtcaaaac | gtctgaacaa | atatattgcta | agctcaatgc | tatgattagc | 540 |
| aatcctgatg | ctatcactaa | agcagctcaa | acggctaatg | ataatacaaa | agcattaagc | 600 |
| tcagaattgg | agaaggctaa | agctgactta | gaaaatcaaa | aagctaaagt | taaaaagcaa | 660 |
| ttgactgaag | agttggcagc | tcagaaagct | gctctagcag | aaaagaggc | agaacttagt | 720 |
| cgtcttaaat | cctcagctcc | gtctactcaa | gatagcattg | tgggtaataa | taccatgaaa | 780 |
| gcaccgcaag | gctatcctct | tgaagaactt | aaaaaattag | aagctagtgg | ttatattgga | 840 |
| tcagctagtt | acaataatta | ttacaaagag | catgcagatc | aaattattgc | caaagctagt | 900 |
| ccaggtaatc | aattaaatca | ataccaagat | attccagcag | atcgtaatcg | ctttgttgat | 960 |
| cccgataatt | tgacaccaga | agtgcaaaat | gagctagcgc | agtttgcagc | tcacatgatt | 1020 |
| aatagtgtac | gtcgtcaatt | aggtctacca | ccagttactg | ttacagcagg | atcacaagaa | 1080 |
| tttgcaagat | tacttagtac | cagctataag | aaaactcatg | gtaatacaag | accatcattt | 1140 |
| gtctacggac | agccagggt | atcagggcat | tatggtgttg | ggcctcatga | taaaactatt | 1200 |
| attgaagact | ctgccggagc | gtcagggctc | attcgaaatg | atgataacat | gtacgagaat | 1260 |
| atcggtgctt | ttaacgatgt | gcatactgtg | aatggtatta | aacgtggtat | ttatgacagt | 1320 |
| atcaagtata | tgctctcttac | agatcattta | cacggaaata | catacggcca | tgctattaac | 1380 |
| tttttacgtg | tagataaaca | taaccctaat | gcgcctgttt | accttggatt | ttcaaccagc | 1440 |
| aatgtaggat | ctttgaatga | acactttgta | atgtttccag | agtctaacat | tgctaaccat | 1500 |
| caacgcttta | ataagacccc | tataaaagcc | gttggaagta | caaaagatta | tgcccaaaga | 1560 |
| gtaggcactg | tatctgatac | tattgcagcg | atcaaaggaa | aagtaagctc | attagaaaat | 1620 |
| cgtttgtcgg | ctattcatca | agaagctgat | attatggcag | cccaagctaa | agtaagtcaa | 1680 |
| cttcaaggta | aattagcaag | cacacttaag | cagtcagaca | gcttaaatct | ccaagtgaga | 1740 |
| caattaaatg | atactaaagg | ttctttgaga | acagaattac | tagcagctaa | agcaaaacaa | 1800 |
| gcacaactcg | aagctactcg | tgatcaatca | ttagctaagc | tagcatcgtt | gaaagccgca | 1860 |
| ctgcaccaga | cagaagcctt | agcagagcaa | gccgcagcca | gagtgacagc | actggtggct | 1920 |
| aaaaaagctc | atttgcaata | tctaagggac | tttaaattga | atcctaaccg | ccttcaagtg | 1980 |
| atacgtgagc | gcattgataa | tactaagcaa | gatttggcta | aaactacctc | atctttgtta | 2040 |
| aatgcacaag | aagctttagc | agccttacaa | gctaaacaaa | gcagtctaga | agctactatt | 2100 |
| gctaccacag | aacaccagtt | gactttgctt | aaaaccttag | ctaacgaaaa | ggaatatcgc | 2160 |

-continued

```
cacttagacg aagatatagc tactgtgcct gatttgcaag tagctccacc tcttacgggc    2220
gtaaaaccgc tatcatatag taagatagat actactccgc ttgttcaaga aatggttaaa    2280
gaaacgaaac aactattaga agcttcagca agattagctg ctgaaaatac aagtcttgta    2340
gcagaagcgc ttgttggcca aacctctgaa atggtagcaa gtaatgccat tgtgtctaaa    2400
atcacatctt cgattactca gccctcatct aagacatctt atggctcagg atcttctaca    2460
acgagcaatc tcatttctga tgttgatgaa agtactcaac gt                      2502
```

<210> SEQ ID NO 32
<211> LENGTH: 834
<212> TYPE: PRT
<213> ORGANISM: Streptococcus pyogenes

<400> SEQUENCE: 32

```
Met Gly Ser His His His His His His Ala Ser Ser Val Gly Val Ser
  1               5                  10                  15

His Gln Val Lys Ala Asp Asp Arg Ala Ser Gly Glu Thr Lys Ala Ser
                 20                  25                  30

Asn Thr His Asp Asp Ser Leu Pro Lys Pro Glu Thr Ile Gln Glu Ala
             35                  40                  45

Lys Ala Thr Ile Asp Ala Val Glu Lys Thr Leu Ser Gln Gln Lys Ala
         50                  55                  60

Glu Leu Thr Glu Leu Ala Thr Ala Leu Thr Lys Thr Thr Ala Glu Ile
 65                  70                  75                  80

Asn His Leu Lys Glu Gln Gln Asp Asn Glu Gln Lys Ala Leu Thr Ser
                 85                  90                  95

Ala Gln Glu Ile Tyr Thr Asn Thr Leu Ala Ser Ser Glu Glu Thr Leu
            100                 105                 110

Leu Ala Gln Gly Ala Glu His Gln Arg Glu Leu Thr Ala Thr Glu Thr
        115                 120                 125

Glu Leu His Asn Ala Gln Ala Asp Gln His Ser Lys Glu Thr Ala Leu
    130                 135                 140

Ser Glu Gln Lys Ala Ser Ile Ser Ala Glu Thr Thr Arg Ala Gln Asp
145                 150                 155                 160

Leu Val Glu Gln Val Lys Thr Ser Glu Gln Asn Ile Ala Lys Leu Asn
                165                 170                 175

Ala Met Ile Ser Asn Pro Asp Ala Ile Thr Lys Ala Ala Gln Thr Ala
            180                 185                 190

Asn Asp Asn Thr Lys Ala Leu Ser Ser Glu Leu Glu Lys Ala Lys Ala
        195                 200                 205

Asp Leu Glu Asn Gln Lys Ala Lys Val Lys Lys Gln Leu Thr Glu Glu
    210                 215                 220

Leu Ala Ala Gln Lys Ala Ala Leu Ala Glu Lys Glu Ala Glu Leu Ser
225                 230                 235                 240

Arg Leu Lys Ser Ser Ala Pro Ser Thr Gln Asp Ser Ile Val Gly Asn
                245                 250                 255

Asn Thr Met Lys Ala Pro Gln Gly Tyr Pro Leu Glu Glu Leu Lys Lys
            260                 265                 270

Leu Glu Ala Ser Gly Tyr Ile Gly Ser Ala Ser Tyr Asn Asn Tyr Tyr
        275                 280                 285

Lys Glu His Ala Asp Gln Ile Ile Ala Lys Ala Ser Pro Gly Asn Gln
    290                 295                 300

Leu Asn Gln Tyr Gln Asp Ile Pro Ala Asp Arg Asn Arg Phe Val Asp
305                 310                 315                 320
```

-continued

Pro Asp Asn Leu Thr Pro Glu Val Gln Asn Glu Leu Ala Gln Phe Ala
            325                 330                 335

Ala His Met Ile Asn Ser Val Arg Arg Gln Leu Gly Leu Pro Pro Val
        340                 345                 350

Thr Val Thr Ala Gly Ser Gln Glu Phe Ala Arg Leu Leu Ser Thr Ser
            355                 360                 365

Tyr Lys Lys Thr His Gly Asn Thr Arg Pro Ser Phe Val Tyr Gly Gln
    370                 375                 380

Pro Gly Val Ser Gly His Tyr Gly Val Gly Pro His Asp Lys Thr Ile
385                 390                 395                 400

Ile Glu Asp Ser Ala Gly Ala Ser Gly Leu Ile Arg Asn Asp Asp Asn
            405                 410                 415

Met Tyr Glu Asn Ile Gly Ala Phe Asn Asp Val His Thr Val Asn Gly
        420                 425                 430

Ile Lys Arg Gly Ile Tyr Asp Ser Ile Lys Tyr Met Leu Phe Thr Asp
            435                 440                 445

His Leu His Gly Asn Thr Tyr Gly His Ala Ile Asn Phe Leu Arg Val
    450                 455                 460

Asp Lys His Asn Pro Asn Ala Pro Val Tyr Leu Gly Phe Ser Thr Ser
465                 470                 475                 480

Asn Val Gly Ser Leu Asn Glu His Phe Val Met Phe Pro Glu Ser Asn
            485                 490                 495

Ile Ala Asn His Gln Arg Phe Asn Lys Thr Pro Ile Lys Ala Val Gly
        500                 505                 510

Ser Thr Lys Asp Tyr Ala Gln Arg Val Gly Thr Val Ser Asp Thr Ile
    515                 520                 525

Ala Ala Ile Lys Gly Lys Val Ser Ser Leu Glu Asn Arg Leu Ser Ala
530                 535                 540

Ile His Gln Glu Ala Asp Ile Met Ala Ala Gln Ala Lys Val Ser Gln
545                 550                 555                 560

Leu Gln Gly Lys Leu Ala Ser Thr Leu Lys Gln Ser Asp Ser Leu Asn
            565                 570                 575

Leu Gln Val Arg Gln Leu Asn Asp Thr Lys Gly Ser Leu Arg Thr Glu
        580                 585                 590

Leu Leu Ala Ala Lys Ala Lys Gln Ala Gln Leu Glu Ala Thr Arg Asp
    595                 600                 605

Gln Ser Leu Ala Lys Leu Ala Ser Leu Lys Ala Ala Leu His Gln Thr
610                 615                 620

Glu Ala Leu Ala Glu Gln Ala Ala Arg Val Thr Ala Leu Val Ala
625                 630                 635                 640

Lys Lys Ala His Leu Gln Tyr Leu Arg Asp Phe Lys Leu Asn Pro Asn
            645                 650                 655

Arg Leu Gln Val Ile Arg Glu Arg Ile Asp Asn Thr Lys Gln Asp Leu
        660                 665                 670

Ala Lys Thr Thr Ser Ser Leu Leu Asn Ala Gln Glu Ala Leu Ala Ala
    675                 680                 685

Leu Gln Ala Lys Gln Ser Ser Leu Glu Ala Thr Ile Ala Thr Thr Glu
690                 695                 700

His Gln Leu Thr Leu Leu Lys Thr Leu Ala Asn Glu Lys Glu Tyr Arg
705                 710                 715                 720

His Leu Asp Glu Asp Ile Ala Thr Val Pro Asp Leu Gln Val Ala Pro
            725                 730                 735

Pro Leu Thr Gly Val Lys Pro Leu Ser Tyr Ser Lys Ile Asp Thr Thr
        740                 745                 750

Pro Leu Val Gln Glu Met Val Lys Glu Thr Lys Gln Leu Leu Glu Ala
            755                 760                 765

Ser Ala Arg Leu Ala Ala Glu Asn Thr Ser Leu Val Ala Glu Ala Leu
        770                 775                 780

Val Gly Gln Thr Ser Glu Met Val Ala Ser Asn Ala Ile Val Ser Lys
785                 790                 795                 800

Ile Thr Ser Ser Ile Thr Gln Pro Ser Ser Lys Thr Ser Tyr Gly Ser
            805                 810                 815

Gly Ser Ser Thr Thr Ser Asn Leu Ile Ser Asp Val Asp Glu Ser Thr
            820                 825                 830

Gln Arg

<210> SEQ ID NO 33
<211> LENGTH: 915
<212> TYPE: DNA
<213> ORGANISM: Streptococcus pyogenes

<400> SEQUENCE: 33
atgcaagtca aagcagatga tagagcctca ggagaaacga aggcgagtaa tactcacgac        60
gatagtttac caaaaccaga acaattcaa gaggcaaagg caactattga tgcagttgaa       120
aaaactctca gtcaacaaaa agcagaactg acagagcttg ctaccgctct gacaaaaact       180
actgctgaaa tcaaccactt aaaagagcag caagataatg aacaaaaagc tttaacctct       240
gcacaagaaa tttacactaa tactcttgca agtagtgagg acgctatt agcccaagga        300 gccgaacatc aaagagagtt aacagctact gaaacagagc ttcataatgc tcaagcagat       360
caacattcaa aagagactgc attgtcagaa caaaaagcta gcatttcagc agaaactact       420
cgagctcaag atttagtgga acaagtcaaa acgtctgaac aaaatattgc taagctcaat       480
gctatgatta gcaatcctga tgctatcact aaagcagctc aaacggctaa tgataataca       540
aaagcattaa gctcagaatt ggagaaggct aaagctgact tagaaaatca aaaagctaaa       600
gttaaaaagc aattgactga gagttggca gctcagaaag ctgctctagc agaaaaagag        660
gcagaactta gtcgtcttaa atcctcagct ccgtctactc aagatagcat tgtgggtaat       720 ataccatga agcaccgca aggctatcct cttgaagaac ttaaaaaatt agaagctagt        780
ggttatattg gatcagctag ttacaataat tattacaaag agcatgcaga tcaaattatt       840
gccaaagcta gtccaggtaa tcaattaaat caataccaag cggccgcact cgagcaccac       900
caccaccacc accac                                                        915

<210> SEQ ID NO 34
<211> LENGTH: 305
<212> TYPE: PRT
<213> ORGANISM: Streptococcus pyogenes

<400> SEQUENCE: 34

Met Gln Val Lys Ala Asp Asp Arg Ala Ser Gly Glu Thr Lys Ala Ser
1               5                   10                  15

Asn Thr His Asp Asp Ser Leu Pro Lys Pro Glu Thr Ile Gln Glu Ala
            20                  25                  30

Lys Ala Thr Ile Asp Ala Val Glu Lys Thr Leu Ser Gln Gln Lys Ala
        35                  40                  45

Glu Leu Thr Glu Leu Ala Thr Ala Leu Thr Lys Thr Thr Ala Glu Ile
    50                  55                  60

Asn His Leu Lys Glu Gln Gln Asp Asn Glu Gln Lys Ala Leu Thr Ser
65                  70                  75                  80

```
Ala Gln Glu Ile Tyr Thr Asn Thr Leu Ala Ser Ser Glu Glu Thr Leu
                85                  90                  95

Leu Ala Gln Gly Ala Glu His Gln Arg Glu Leu Thr Ala Thr Glu Thr
            100                 105                 110

Glu Leu His Asn Ala Gln Ala Asp Gln His Ser Lys Glu Thr Ala Leu
        115                 120                 125

Ser Glu Gln Lys Ala Ser Ile Ser Ala Glu Thr Thr Arg Ala Gln Asp
130                 135                 140

Leu Val Glu Gln Val Lys Thr Ser Glu Gln Asn Ile Ala Lys Leu Asn
145                 150                 155                 160

Ala Met Ile Ser Asn Pro Asp Ala Ile Thr Lys Ala Ala Gln Thr Ala
                165                 170                 175

Asn Asp Asn Thr Lys Ala Leu Ser Ser Glu Leu Glu Lys Ala Lys Ala
            180                 185                 190

Asp Leu Glu Asn Gln Lys Ala Lys Val Lys Lys Gln Leu Thr Glu Glu
        195                 200                 205

Leu Ala Ala Gln Lys Ala Ala Leu Ala Glu Lys Glu Ala Glu Leu Ser
210                 215                 220

Arg Leu Lys Ser Ser Ala Pro Ser Thr Gln Asp Ser Ile Val Gly Asn
225                 230                 235                 240

Asn Thr Met Lys Ala Pro Gln Gly Tyr Pro Leu Glu Glu Leu Lys Lys
                245                 250                 255

Leu Glu Ala Ser Gly Tyr Ile Gly Ser Ala Ser Tyr Asn Asn Tyr Tyr
            260                 265                 270

Lys Glu His Ala Asp Gln Ile Ile Ala Lys Ala Ser Pro Gly Asn Gln
        275                 280                 285

Leu Asn Gln Tyr Gln Ala Ala Leu Glu His His His His His His
290                 295                 300

His
305

<210> SEQ ID NO 35
<211> LENGTH: 113
<212> TYPE: PRT
<213> ORGANISM: Streptococcus pyogenes

<400> SEQUENCE: 35

Met Thr Leu Lys Lys His Tyr Tyr Leu Leu Ser Leu Ala Leu Val
1               5                   10                  15

Thr Val Gly Ala Ala Phe Asn Thr Ser Gln Ser Val Ser Ala Gln Val
            20                  25                  30

Tyr Ser Asn Glu Gly Tyr His Gln His Leu Thr Asp Glu Lys Ser His
        35                  40                  45

Leu Gln Tyr Ser Lys Asp Asn Ala Gln Leu Gln Leu Arg Asn Ile Leu
50                  55                  60

Asp Gly Tyr Gln Asn Asp Leu Gly Arg His Tyr Ser Ser Tyr Tyr Tyr
65                  70                  75                  80

Tyr Asn Leu Arg Thr Val Met Gly Leu Ser Ser Glu Gln Asp Ile Glu
                85                  90                  95

Lys His Tyr Glu Glu Leu Lys Asn Lys Leu His Asp Met Tyr Asn His
            100                 105                 110

Tyr

<210> SEQ ID NO 36
<211> LENGTH: 342
```

```
<212> TYPE: DNA
<213> ORGANISM: Streptococcus pyogenes

<400> SEQUENCE: 36
atgacactaa aaaaacacta ttatcttctc agcctgctag ctcttgtaac ggttggtgct      60
gcctttaaca caagccagag tgtcagtgca caagtttata gcaatgaagg gtatcaccag     120
catttgactg atgaaaaatc acacctgcaa tatagtaaag acaacgcaca acttcaattg     180
agaaatatcc ttgacggcta ccaaaatgac ctagggagac actactctag ctattattac     240
tacaacctaa gaaccgttat gggactatca agtgagcaag acattgaaaa acactatgaa     300
gagcttaaga acaagttaca tgatatgtac aatcattatt aa                        342

<210> SEQ ID NO 37
<211> LENGTH: 19
<212> TYPE: PRT
<213> ORGANISM: Streptococcus pyogenes

<400> SEQUENCE: 37

Thr Leu Lys Lys His Tyr Tyr Leu Leu Ser Leu Leu Ala Leu Val Thr
1               5                   10                  15

Val Gly Ala

<210> SEQ ID NO 38
<211> LENGTH: 93
<212> TYPE: PRT
<213> ORGANISM: Streptococcus pyogenes

<400> SEQUENCE: 38

Ala Phe Asn Thr Ser Gln Ser Val Ser Ala Gln Val Tyr Ser Asn Glu
1               5                   10                  15

Gly Tyr His Gln His Leu Thr Asp Glu Lys Ser His Leu Gln Tyr Ser
                20                  25                  30

Lys Asp Asn Ala Gln Leu Gln Leu Arg Asn Ile Leu Asp Gly Tyr Gln
            35                  40                  45

Asn Asp Leu Gly Arg His Tyr Ser Ser Tyr Tyr Tyr Asn Leu Arg
        50                  55                  60

Thr Val Met Gly Leu Ser Ser Glu Gln Asp Ile Glu Lys His Tyr Glu
65                  70                  75                  80

Glu Leu Lys Asn Lys Leu His Asp Met Tyr Asn His Tyr
                85                  90

<210> SEQ ID NO 39
<211> LENGTH: 428
<212> TYPE: PRT
<213> ORGANISM: Streptococcus pyogenes

<400> SEQUENCE: 39

Met Ser His Met Lys Lys Arg Pro Glu Val Leu Ser Pro Ala Gly Thr
1               5                   10                  15

Leu Glu Lys Leu Lys Val Ala Ile Asp Tyr Gly Ala Asp Ala Val Phe
                20                  25                  30

Val Gly Gly Gln Ala Tyr Gly Leu Arg Ser Arg Ala Gly Asn Phe Ser
            35                  40                  45

Met Glu Glu Leu Gln Gly Ile Asp Tyr Ala His Ala Arg Gly Ala
        50                  55                  60

Lys Val Tyr Val Ala Ala Asn Met Val Thr His Glu Gly Asn Glu Ile
65                  70                  75                  80

Gly Ala Gly Glu Trp Phe Arg Gln Leu Arg Asp Met Gly Leu Asp Ala
```

```
                    85                  90                  95
Val Ile Val Ser Asp Pro Ala Leu Ile Val Cys Ser Thr Glu Ala
                100                 105                 110
Pro Gly Leu Glu Ile His Leu Ser Thr Gln Ala Ser Ser Thr Asn Tyr
                115                 120                 125
Glu Thr Phe Glu Phe Trp Lys Ala Met Gly Leu Thr Arg Val Val Leu
130                 135                 140
Ala Arg Glu Val Asn Met Ala Glu Leu Ala Glu Ile Arg Lys Arg Thr
145                 150                 155                 160
Asp Val Glu Ile Glu Ala Phe Val His Gly Ala Met Cys Ile Ser Tyr
                165                 170                 175
Ser Gly Arg Cys Val Leu Ser Asn His Met Ser His Arg Asp Ala Asn
                180                 185                 190
Arg Gly Gly Cys Ser Gln Ser Cys Arg Trp Lys Tyr Asp Leu Tyr Asp
                195                 200                 205
Met Pro Phe Gly Gly Glu Arg Arg Ser Leu Lys Gly Glu Ile Pro Glu
                210                 215                 220
Asp Tyr Ser Met Ser Ser Val Asp Met Cys Met Ile Asp His Ile Pro
225                 230                 235                 240
Asp Leu Ile Glu Asn Gly Val Asp Ser Leu Lys Ile Glu Gly Arg Met
                245                 250                 255
Lys Ser Ile His Tyr Val Ser Thr Val Thr Asn Cys Tyr Lys Ala Ala
                260                 265                 270
Val Gly Ala Tyr Met Glu Ser Pro Glu Ala Phe Tyr Ala Ile Lys Glu
                275                 280                 285
Glu Leu Ile Asp Glu Leu Trp Lys Val Ala Gln Arg Glu Leu Ala Thr
                290                 295                 300
Gly Phe Tyr Tyr Gly Ile Pro Thr Glu Asn Glu Gln Leu Phe Gly Ala
305                 310                 315                 320
Arg Arg Lys Ile Pro Gln Tyr Lys Phe Val Gly Glu Val Val Ala Phe
                325                 330                 335
Asp Ser Ala Ser Met Thr Ala Thr Ile Arg Gln Arg Asn Val Ile Met
                340                 345                 350
Glu Gly Asp Arg Ile Glu Cys Tyr Gly Pro Gly Phe Arg His Phe Glu
                355                 360                 365
Thr Val Val Lys Asp Leu His Asp Ala Asp Gly Gln Lys Ile Asp Arg
                370                 375                 380
Ala Pro Asn Pro Met Glu Leu Leu Thr Ile Ser Leu Pro Arg Glu Val
385                 390                 395                 400
Lys Pro Gly Asp Met Ile Arg Ala Cys Lys Glu Gly Leu Val Asn Leu
                405                 410                 415
Tyr Gln Lys Asp Gly Thr Ser Lys Thr Val Arg Thr
                420                 425

<210> SEQ ID NO 40
<211> LENGTH: 1287
<212> TYPE: DNA
<213> ORGANISM: Streptococcus pyogenes

<400> SEQUENCE: 40
atgtcacata tgaaaaaacg tcccgaggtc ttatcacctg ctggaacact tgaaaaatta      60
aaagttgcga ttgactatgg cgcagatgct gttttgttg gagggcaggc ctatggccta     120
agaagccgcg ctggtaactt ctctatggaa gaattgcaag aaggcattga ttatgcacat     180
gcgcgtggag ctaaggtcta tgttgctgct aacatggtta cccacgaagg gaacgaaatt     240
```

-continued

```
ggtgcgggcg agtggtttcg tcaactgcgt gatatggggc ttgatgcggt cattgtttca    300
gatccagcct tgattgttat tgttcaaca gaagcccag gtttggaaat tcatttgtca    360
acgcaagctt catctaccaa ttacgagacc tttgaatttt ggaaagccat gggcttgacc    420
cgagttgttt tagctcgcga ggttaatatg gccgagttag cagaaatccg caagcggaca    480
gatgtggaaa ttgaagcctt tgtccatgga gccatgtgta tctcttattc aggccgctgt    540
gttttgtcaa accacatgag tcaccgtgat gccaacaggg gcggctgctc acagtcttgc    600
cgctggaagt atgatttgta tgacatgcca tttggaggag agcgccgctc cttaaaaggg    660
gaaattccag aagactattc tatgtcctct gttgacatgt gtatgattga ccatattcct    720
gacctgattg aaaatggggt tgatagctta aaaattgaag gccgaatgaa atctatccac    780
tacgtctcaa ccgtaaccaa ctgttacaag gcggctgtag gtgcttacat ggaaagccca    840
gaagcttttt atgctatcaa agaggaattg attgacgagt tgtggaaggt tgcccagcgc    900
gagttggcta caggttttta ctatggtatc ccaactgaaa atgaacaatt atttggtgct    960
cgccgcaaaa ttccacaata taaatttgtc ggagaagtag ttgcctttga ctcagctagc    1020
atgacagcga ccattcgtca gcgtaatgtc atcatggaag gcgatcggat tgaatgttat    1080
ggaccaggtt tccgtcattt tgaaacggtt gttaaggact acatgatgc ggatggccaa    1140 aagattgacc gtgccccaaa tccaatggaa ctcttaacca tctctttacc gagagaagtt    1200
aagccagggg atatgattag ggcttgcaag gaaggtctgg ttaacctcta tcaaaaagat    1260
ggcaccagta aaactgttag aacatag                                       1287
```

<210> SEQ ID NO 41
<211> LENGTH: 265
<212> TYPE: PRT
<213> ORGANISM: Streptococcus pyogenes

<400> SEQUENCE: 41

```
Met Thr Thr Met Gln Lys Thr Ile Ser Leu Leu Ser Leu Ala Leu Leu
 1               5                  10                  15

Ile Gly Leu Leu Gly Thr Ser Gly Lys Ala Ile Ser Val Tyr Ala Gln
            20                  25                  30

Asp Gln His Thr Asp Asn Val Ile Ala Glu Ser Thr Ile Ser Gln Val
        35                  40                  45

Ser Val Glu Ala Ser Met Arg Gly Thr Glu Pro Tyr Ile Asp Ala Thr
    50                  55                  60

Val Thr Thr Asp Gln Pro Val Arg Gln Pro Thr Gln Ala Thr Ile Thr
65                  70                  75                  80

Leu Lys Asp Ala Ser Asp Asn Thr Ile Asn Ser Trp Val Tyr Thr Met
                85                  90                  95

Ala Ala Gln Gln Arg Arg Phe Thr Ala Trp Phe Asp Leu Thr Gly Gln
            100                 105                 110

Lys Ser Gly Asp Tyr His Val Thr Val Thr Val His Thr Gln Glu Lys
        115                 120                 125

Ala Val Thr Gly Gln Ser Gly Thr Val His Phe Asp Gln Asn Lys Ala
    130                 135                 140

Arg Lys Thr Pro Thr Asn Met Gln Gln Lys Asp Thr Ser Lys Ala Met
145                 150                 155                 160

Thr Asn Ser Val Asp Val Asp Thr Lys Ala Gln Thr Asn Gln Ser Ala
                165                 170                 175

Asn Gln Glu Ile Asp Ser Thr Ser Asn Pro Phe Arg Ser Ala Thr Asn
            180                 185                 190
```

```
His Arg Ser Thr Ser Leu Lys Arg Ser Thr Lys Asn Glu Lys Leu Thr
        195                 200                 205

Pro Thr Ala Ser Asn Ser Gln Lys Asn Gly Ser Asn Lys Thr Lys Met
    210                 215                 220

Leu Val Asp Lys Glu Glu Val Lys Pro Thr Ser Lys Arg Gly Phe Pro
225                 230                 235                 240

Trp Val Leu Leu Gly Leu Val Val Ser Leu Ala Ala Gly Leu Phe Ile
                245                 250                 255

Ala Ile Gln Lys Val Ser Arg Arg Lys
                260             265
```

<210> SEQ ID NO 42
<211> LENGTH: 798
<212> TYPE: DNA
<213> ORGANISM: Streptococcus pyogenes

<400> SEQUENCE: 42

```
atgacaacta tgcaaaaaac aattagctta ttatcactag ctttacttat tggtttgctg      60
gggacttctg gcaaagccat atctgtgtat gcacaagatc agcacactga taatgttata     120
gctgaatcaa ctattagtca ggtcagtgtt gaagccagta tgcgtggaac agaaccttat     180
attgatgcta cagtcaccac agatcaacct gtcagacaac caactcaggc aacgataaca     240
cttaaagacg ctagtgataa tactattaat agttgggtat atactatggc agcgcaacag     300
cgtcgtttta cagcttggtt tgatttaact ggacaaaaga gtggtgacta tcatgtaact     360
gtcaccgttc atactcaaga aaaggcagta actggtcaat caggaactgt tcattttgat     420
caaaacaaag ctagaaaaac accaactaat atgcaacaaa aggatacttc taaagcaatg     480
acgaattcag tcgatgtaga cacaaaagct caaacaaatc aatcagctaa ccaagaaata     540
gattctactt caaatccttt cagatcagct actaatcatc gatcaacttc cttaaagcga     600
tctactaaaa atgagaaact tacaccaact gctagtaata gccaaaaaaa cggtagcaac     660
aagacaaaaa tgctagtgga caaagaggaa gtaaaaccta cttcaaaaag aggattccct     720
tgggtcttat taggtctagt agtcagttta gctgcaggtt tatttatagc tattcaaaaa     780
gtatctagac gaaaataa                                                   798
```

<210> SEQ ID NO 43
<211> LENGTH: 30
<212> TYPE: PRT
<213> ORGANISM: Streptococcus pyogenes

<400> SEQUENCE: 43

```
Thr Thr Met Gln Lys Thr Ile Ser Leu Leu Ser Leu Ala Leu Leu Ile
1               5                   10                  15

Gly Leu Leu Gly Thr Ser Gly Lys Ala Ile Ser Val Tyr Ala
            20                  25                  30
```

<210> SEQ ID NO 44
<211> LENGTH: 234
<212> TYPE: PRT
<213> ORGANISM: Streptococcus pyogenes

<400> SEQUENCE: 44

```
Gln Asp Gln His Thr Asp Asn Val Ile Ala Glu Ser Thr Ile Ser Gln
1               5                   10                  15

Val Ser Val Glu Ala Ser Met Arg Gly Thr Glu Pro Tyr Ile Asp Ala
            20                  25                  30
```

```
Thr Val Thr Thr Asp Gln Pro Val Arg Gln Pro Thr Gln Ala Thr Ile
            35                  40                  45

Thr Leu Lys Asp Ala Ser Asp Asn Thr Ile Asn Ser Trp Val Tyr Thr
 50                  55                  60

Met Ala Ala Gln Gln Arg Arg Phe Thr Ala Trp Phe Asp Leu Thr Gly
 65                  70                  75                  80

Gln Lys Ser Gly Asp Tyr His Val Thr Val Thr Val His Thr Gln Glu
                 85                  90                  95

Lys Ala Val Thr Gly Gln Ser Gly Thr Val His Phe Asp Gln Asn Lys
            100                 105                 110

Ala Arg Lys Thr Pro Thr Asn Met Gln Gln Lys Asp Thr Ser Lys Ala
            115                 120                 125

Met Thr Asn Ser Val Asp Val Asp Thr Lys Ala Gln Thr Asn Gln Ser
130                 135                 140

Ala Asn Gln Glu Ile Asp Ser Thr Ser Asn Pro Phe Arg Ser Ala Thr
145                 150                 155                 160

Asn His Arg Ser Thr Ser Leu Lys Arg Ser Thr Lys Asn Glu Lys Leu
                165                 170                 175

Thr Pro Thr Ala Ser Asn Ser Gln Lys Asn Gly Ser Asn Lys Thr Lys
            180                 185                 190

Met Leu Val Asp Lys Glu Glu Val Lys Pro Thr Ser Lys Arg Gly Phe
            195                 200                 205

Pro Trp Val Leu Leu Gly Leu Val Val Ser Leu Ala Ala Gly Leu Phe
210                 215                 220

Ile Ala Ile Gln Lys Val Ser Arg Arg Lys
225                 230

<210> SEQ ID NO 45
<211> LENGTH: 278
<212> TYPE: PRT
<213> ORGANISM: Streptococcus pyogenes

<400> SEQUENCE: 45

Met Thr Gln Met Asn Tyr Thr Gly Lys Val Lys Arg Val Ala Ile Ile
 1                   5                  10                  15

Ala Asn Gly Lys Tyr Gln Ser Lys Arg Val Ala Ser Lys Leu Phe Ser
                 20                  25                  30

Val Phe Lys Asp Asp Pro Asp Phe Tyr Leu Ser Lys Lys Asn Pro Asp
             35                  40                  45

Ile Val Ile Ser Ile Gly Gly Asp Gly Met Leu Leu Ser Ala Phe His
             50                  55                  60

Met Tyr Glu Lys Glu Leu Asp Lys Val Arg Phe Val Gly Ile His Thr
 65                  70                  75                  80

Gly His Leu Gly Phe Tyr Thr Asp Tyr Arg Asp Phe Glu Val Asp Lys
                 85                  90                  95

Leu Ile Asp Asn Leu Arg Lys Asp Lys Gly Glu Gln Ile Ser Tyr Pro
            100                 105                 110

Ile Leu Lys Val Ala Ile Thr Leu Asp Asp Gly Arg Val Val Lys Ala
            115                 120                 125

Arg Ala Leu Asn Glu Ala Thr Val Lys Arg Ile Glu Lys Thr Met Val
130                 135                 140

Ala Asp Val Ile Ile Asn His Val Lys Phe Glu Ser Phe Arg Gly Asp
145                 150                 155                 160

Gly Ile Ser Val Ser Thr Pro Thr Gly Ser Thr Ala Tyr Asn Lys Ser
                165                 170                 175
```

```
Leu Gly Gly Ala Val Leu His Pro Thr Ile Glu Ala Leu Gln Leu Thr
            180                 185                 190

Glu Ile Ser Ser Leu Asn Asn Arg Val Phe Arg Thr Leu Gly Ser Ser
        195                 200                 205

Ile Ile Ile Pro Lys Lys Asp Lys Ile Glu Leu Val Pro Lys Arg Leu
210                 215                 220

Gly Ile Tyr Thr Ile Ser Ile Asp Asn Lys Thr Tyr Gln Leu Lys Asn
225                 230                 235                 240

Val Thr Lys Val Glu Tyr Phe Ile Asp Asp Glu Lys Ile His Phe Val
                245                 250                 255

Ser Ser Pro Ser His Thr Ser Phe Trp Glu Arg Val Lys Asp Ala Phe
            260                 265                 270

Ile Gly Glu Ile Asp Ser
            275

<210> SEQ ID NO 46
<211> LENGTH: 837
<212> TYPE: DNA
<213> ORGANISM: Streptococcus pyogenes

<400> SEQUENCE: 46
atgacacaga tgaattatac aggtaaggta aaacgagttg ctattattgc aaatggtaag      60
taccaaagta aacgcgtcgc ctccaaactt ttctccgtat ttaaagatga tcctgatttc     120
tatctttcaa agaaaaatcc ggatattgtg atttctattg cggagatgg gatgctctta      180 tctgcctttc acatgtatga aaagaatta gataaggtac gttttgtagg aatccacacc      240
ggtcatcttg ctttttatac cgattatagg gattttgaag ttgataaatt aattgataat      300
ttaagaaaag acaagggaga acaaatctct tatccgattt taaagttgc tattacttta      360 gatgatggtc gtgtggttaa agcgcgtgct ttgaatgaag cgacggttaa gcgtattgaa      420
aaaacgatgg tagcagatgt tattattaac catgtcaaat ttgaaagctt ccgaggtgat      480
gggatttcag tatcgacccc gacagggagc acagcctaca ataaatcttt aggtggtgct      540
gtcttgcatc cgacgattga agcgctgcaa ttgacgaaa tttccagtct taataaccgt      600
gtctttagaa ccttgggctc atcaatcatt attcccaaaa aagataagat tgagttagtg      660
ccaaaacgat taggaattta taccatttcc attgataata aaacctatca gttaaaaaat      720
gtgacgaagg tggagtattt tatcgacgat gagaaaattc attttgtttc ctctccgagt      780
catacgagct tttgggaaag ggtcaaggat gcctttattg agagattga ctcatga       837

<210> SEQ ID NO 47
<211> LENGTH: 4
<212> TYPE: PRT
<213> ORGANISM: Streptococcus pyogenes

<400> SEQUENCE: 47

Met Thr Gln Met
  1

<210> SEQ ID NO 48
<211> LENGTH: 274
<212> TYPE: PRT
<213> ORGANISM: Streptococcus pyogenes

<400> SEQUENCE: 48

Asn Tyr Thr Gly Lys Val Lys Arg Val Ala Ile Ile Ala Asn Gly Lys
  1               5                  10                  15

Tyr Gln Ser Lys Arg Val Ala Ser Lys Leu Phe Ser Val Phe Lys Asp
```

```
            20                  25                  30
Asp Pro Asp Phe Tyr Leu Ser Lys Lys Asn Pro Asp Ile Val Ile Ser
            35                  40                  45

Ile Gly Gly Asp Gly Met Leu Leu Ser Ala Phe His Met Tyr Glu Lys
 50                  55                  60

Glu Leu Asp Lys Val Arg Phe Val Gly Ile His Thr Gly His Leu Gly
 65                  70                  75                  80

Phe Tyr Thr Asp Tyr Arg Asp Phe Glu Val Asp Lys Leu Ile Asp Asn
                    85                  90                  95

Leu Arg Lys Asp Lys Gly Glu Gln Ile Ser Tyr Pro Ile Leu Lys Val
                100                 105                 110

Ala Ile Thr Leu Asp Asp Gly Arg Val Val Lys Ala Arg Ala Leu Asn
                115                 120                 125

Glu Ala Thr Val Lys Arg Ile Glu Lys Thr Met Val Ala Asp Val Ile
            130                 135                 140

Ile Asn His Val Lys Phe Glu Ser Phe Arg Gly Asp Gly Ile Ser Val
145                 150                 155                 160

Ser Thr Pro Thr Gly Ser Thr Ala Tyr Asn Lys Ser Leu Gly Gly Ala
                165                 170                 175

Val Leu His Pro Thr Ile Glu Ala Leu Gln Leu Thr Glu Ile Ser Ser
                180                 185                 190

Leu Asn Asn Arg Val Phe Arg Thr Leu Gly Ser Ser Ile Ile Ile Pro
                195                 200                 205

Lys Lys Asp Lys Ile Glu Leu Val Pro Lys Arg Leu Gly Ile Tyr Thr
                210                 215                 220

Ile Ser Ile Asp Asn Lys Thr Tyr Gln Leu Lys Asn Val Thr Lys Val
225                 230                 235                 240

Glu Tyr Phe Ile Asp Asp Glu Lys Ile His Phe Val Ser Ser Pro Ser
                245                 250                 255

His Thr Ser Phe Trp Glu Arg Val Lys Asp Ala Phe Ile Gly Glu Ile
                260                 265                 270

Asp Ser

<210> SEQ ID NO 49
<211> LENGTH: 743
<212> TYPE: PRT
<213> ORGANISM: Streptococcus pyogenes

<400> SEQUENCE: 49

Met Arg Asn Glu Met Ala Lys Ile Met Asn Val Thr Gly Glu Glu Val
 1                   5                  10                  15

Ile Ala Leu Ala Ala Thr Tyr Met Thr Lys Ala Asp Val Ala Phe Val
                    20                  25                  30

Ala Lys Ala Leu Ala Tyr Ala Thr Ala Ala His Phe Tyr Gln Val Arg
            35                  40                  45

Lys Ser Gly Glu Pro Tyr Ile Val His Pro Ile Gln Val Ala Gly Ile
         50                  55                  60

Leu Ala Asp Leu His Leu Asp Ala Val Thr Val Ala Cys Gly Phe Leu
 65                  70                  75                  80

His Asp Val Val Glu Asp Thr Asp Ile Thr Leu Asp Glu Ile Glu Ala
                    85                  90                  95

Asp Phe Gly His Asp Ala Arg Asp Ile Val Asp Gly Val Thr Lys Leu
                100                 105                 110

Gly Glu Val Glu Tyr Lys Ser His Glu Glu Gln Leu Ala Glu Asn His
            115                 120                 125
```

-continued

Arg Lys Met Leu Met Ala Met Ser Lys Asp Ile Arg Val Ile Leu Val
    130                 135                 140

Lys Leu Ala Asp Arg Leu His Asn Met Arg Thr Leu Lys His Leu Arg
145                 150                 155                 160

Lys Asp Lys Gln Glu Arg Ile Ser Arg Glu Thr Met Glu Ile Tyr Ala
                165                 170                 175

Pro Leu Ala His Arg Leu Gly Ile Ser Arg Ile Lys Trp Glu Leu Glu
            180                 185                 190

Asp Leu Ala Phe Arg Tyr Leu Asn Glu Thr Glu Phe Tyr Lys Ile Ser
        195                 200                 205

His Met Met Lys Glu Lys Arg Arg Glu Arg Glu Ala Leu Val Glu Ala
    210                 215                 220

Ile Val Ser Lys Val Lys Thr Tyr Thr Thr Gln Gln Gly Leu Phe Gly
225                 230                 235                 240

Asp Val Tyr Gly Arg Pro Lys His Ile Tyr Ser Ile Tyr Arg Lys Met
                245                 250                 255

Arg Asp Lys Lys Lys Arg Phe Asp Gln Ile Phe Asp Leu Ile Ala Ile
            260                 265                 270

Arg Cys Val Met Glu Thr Gln Ser Asp Val Tyr Ala Met Val Gly Tyr
        275                 280                 285

Ile His Glu Leu Trp Arg Pro Met Pro Gly Arg Phe Lys Asp Tyr Ile
    290                 295                 300

Ala Ala Pro Lys Ala Asn Gly Tyr Gln Ser Ile His Thr Thr Val Tyr
305                 310                 315                 320

Gly Pro Lys Gly Pro Ile Glu Ile Gln Ile Arg Thr Lys Asp Met His
                325                 330                 335

Gln Val Ala Glu Tyr Gly Val Ala Ala His Trp Ala Tyr Lys Lys Gly
            340                 345                 350

Val Arg Gly Lys Val Asn Gln Ala Glu Gln Ala Val Gly Met Asn Trp
        355                 360                 365

Ile Lys Glu Leu Val Glu Leu Gln Asp Ala Ser Asn Gly Asp Ala Val
    370                 375                 380

Asp Phe Val Asp Ser Val Lys Glu Asp Ile Phe Ser Glu Arg Ile Tyr
385                 390                 395                 400

Val Phe Thr Pro Thr Gly Ala Val Gln Glu Leu Pro Lys Glu Ser Gly
                405                 410                 415

Pro Ile Asp Phe Ala Tyr Ala Ile His Thr Gln Ile Gly Glu Lys Ala
            420                 425                 430

Thr Gly Ala Lys Val Asn Gly Arg Met Val Pro Leu Thr Ala Lys Leu
        435                 440                 445

Lys Thr Gly Asp Val Val Glu Ile Ile Thr Asn Ala Asn Ser Phe Gly
    450                 455                 460

Pro Ser Arg Asp Trp Val Lys Leu Val Lys Thr Asn Lys Ala Arg Asn
465                 470                 475                 480

Lys Ile Arg Gln Phe Phe Lys Asn Gln Asp Lys Glu Leu Ser Val Asn
                485                 490                 495

Lys Gly Arg Asp Leu Leu Val Ser Tyr Phe Gln Glu Gln Gly Tyr Val
            500                 505                 510

Ala Asn Lys Tyr Leu Asp Lys Arg Ile Glu Ala Ile Leu Pro Lys
        515                 520                 525

Val Ser Val Lys Ser Glu Glu Ser Leu Tyr Ala Ala Val Gly Phe Gly
    530                 535                 540

Asp Ile Ser Pro Ile Ser Val Phe Asn Lys Leu Thr Glu Lys Glu Arg

```
            545                 550                 555                 560
Arg Glu Glu Arg Ala Lys Ala Lys Ala Glu Ala Glu Glu Leu Val
                565                 570                 575
Lys Gly Gly Glu Val Lys His Glu Asn Lys Asp Val Leu Lys Val Arg
            580                 585                 590
Ser Glu Asn Gly Val Ile Ile Gln Gly Ala Ser Gly Leu Leu Met Arg
        595                 600                 605
Ile Ala Lys Cys Cys Asn Pro Val Pro Gly Asp Pro Ile Asp Gly Tyr
        610                 615                 620
Ile Thr Lys Gly Arg Gly Ile Ala Ile His Arg Ser Asp Cys His Asn
625                 630                 635                 640
Ile Lys Ser Gln Asp Gly Tyr Gln Glu Arg Leu Ile Glu Val Glu Trp
                645                 650                 655
Asp Leu Asp Asn Ser Ser Lys Asp Tyr Gln Ala Glu Ile Asp Ile Tyr
                660                 665                 670
Gly Leu Asn Arg Ser Gly Leu Leu Asn Asp Val Leu Gln Ile Leu Ser
            675                 680                 685
Asn Ser Thr Lys Ser Ile Ser Thr Val Asn Ala Gln Pro Thr Lys Asp
        690                 695                 700
Met Lys Phe Ala Asn Ile His Val Ser Phe Gly Ile Pro Asn Leu Thr
705                 710                 715                 720
His Leu Thr Thr Val Val Glu Lys Ile Lys Ala Val Pro Asp Val Tyr
                725                 730                 735
Ser Val Lys Arg Thr Asn Gly
            740

<210> SEQ ID NO 50
<211> LENGTH: 2232
<212> TYPE: DNA
<213> ORGANISM: Streptococcus pyogenes

<400> SEQUENCE: 50
atgaggaacg aaatggcaaa aataatgaac gtaacaggag aagaagtcat tgccttagcg      60
gccacctata tgaccaaggc tgatgtggct tttgtggcaa aggctttagc atatgcaaca     120
gcggcccatt tctaccaagt gagaaagtca ggcgaaccct atatcgtcca tccgattcag     180
gtggcgggga ttctggctga tttgcatctg atgctgtga cagttgcttg tggcttttta      240
catgatgtcg tagaagatac ggatattacc ttagatgaga tcgaagcaga ctttggccat     300
gatgctcgtg atatcgttga tggtgtcacc aagttaggtg aagttgagta caaatctcat     360
gaggagcaac tcgccgaaaa ccatcgcaaa atgctgatgg ctatgtccaa agatattcgc     420
gtgattttgg tgaaattggc tgaccgcctg cataatatgc gcaccctcaa acatttgcgc     480
aaggacaaac aagagcgcat tcgcgcgaaa accatggaaa tctatgcccc cttggcgcat     540
cgtttgggga ttagtcgcat caaatgggaa ctagaagatt tggcttttcg ttacctcaat     600
gaaaccgaat tttacaaaat ttcccatatg atgaaagaaa acgtcgcga gcgtgaagct     660 ttggtagagg ctattgtcag taaggtcaaa acctatacga cacaacaagg ttgtttggaa     720
gatgtgtatg ccgaccaaaa acacatttat tcgatttatc ggaaaatgcg ggacaaaaag     780
aaacgattcg atcagatttt tgatctgatt gccattcgtt gtgtcatgga acgcaaagc     840 gatgtctatg ctatggttgg ctatattcat gagctttggc gtcccatgcc aggccgcttc     900
aaggattata ttgcagctcc taaagctaat ggctaccagt ctattcatac caccgtgtat     960
gggccaaaag gacctattga gattcaaatc agaactaagg acatgcatca gtggctgag   1020
```

```
tacggggttg ctgctcactg ggcttataaa aaaggcgtgc gtggtaaggt caatcaagct    1080
gagcaagccg ttggcatgaa ctggatcaaa gagctggtag aattgcaaga tgcctcaaat    1140
ggcgatgcag tggactttgt ggattcggtc aaagaagaca tttttctga acggatttat    1200
gtctttacac cgacaggggc cgttcaggag ttaccaaaag aatcaggtcc tattgatttt    1260
gcttatgcga tccatacgca aatcggtgaa aaagcaacag gtgccaaagt caatggacgt    1320
atggttcctc tcactgccaa gttaaaaaca ggagatgtgg ttgaaatcat caccaatgcc    1380
aattcctttg gccctagtcg agactgggta aaactggtca aaccaataa ggctcgcaac     1440
aaaattcgtc agttctttaa aaatcaagac aaggaattgt cagtgaataa aggccgtgat    1500
ttgttggtgt cttattttca gagcagggc tacgttgcca ataaatacct tgacaaaaaa     1560
cgcattgaag ccatccttcc aaaagtcagt gtgaagagcg aagaatcact ctatgcagcc    1620
gttgggtttg gtgacattag tcctatcagt gtctttaaca agttaaccga aaagagcgc     1680
cgtgaagaag aaagggccaa ggctaaagca gaagctgaag aattggttaa gggcggtgag    1740
gtcaaacacg aaaacaaaga tgtgctcaag gttcgcagtg aaaatggagt cattatccaa    1800
ggagcatcag gcctcttgat gcggattgcc aagtgttgta atcctgtacc tggtgatcct    1860
attgacggct acattaccaa agggcgtggc attgcgattc acagatcgga ctgtcataac    1920
attaagagtc aagatggcta ccaagaacgc ttgattgagg tcgagtggga tttggacaat    1980
tcgagtaaag attatcaggc tgaaattgat atctatgggc tcaatcgtag tggtctgctt    2040
aatgatgtgc tccaaatttt atcaaactca accaagagca tatcgacagt caatgctcag    2100
ccgaccaagg acatgaagtt tgctaatatt cacgtgagct ttggcattcc aaatctgacg    2160
catctgacca ctgttgtcga aaaaatcaag gcagttccag atgtttatag cgtgaagcgg    2220
accaatggct aa                                                       2232
```

<210> SEQ ID NO 51
<211> LENGTH: 323
<212> TYPE: PRT
<213> ORGANISM: Streptococcus pyogenes

<400> SEQUENCE: 51

```
Met Lys Thr Arg Ile Thr Glu Leu Leu Asn Ile Asp Tyr Pro Ile Phe
  1               5                  10                  15

Gln Gly Gly Met Ala Trp Val Ala Asp Gly Asp Leu Ala Gly Ala Val
             20                  25                  30

Ser Asn Ala Gly Gly Leu Gly Ile Ile Gly Gly Asn Ala Pro Lys
         35                  40                  45

Glu Val Val Lys Ala Asn Ile Asp Arg Val Lys Ala Ile Thr Asp Arg
     50                  55                  60

Pro Phe Gly Val Asn Ile Met Leu Leu Ser Pro Phe Ala Asp Asp Ile
 65                  70                  75                  80

Val Asp Leu Val Ile Glu Glu Gly Val Lys Val Thr Thr Gly Ala
                 85                  90                  95

Gly Asn Pro Gly Lys Tyr Met Glu Arg Leu His Gln Ala Gly Ile Ile
            100                 105                 110

Val Val Pro Val Val Pro Ser Val Ala Leu Ala Lys Arg Met Glu Lys
        115                 120                 125

Leu Gly Val Asp Ala Val Ile Ala Glu Gly Met Glu Ala Gly Gly His
    130                 135                 140

Ile Gly Lys Leu Thr Thr Met Ser Leu Val Arg Gln Val Val Glu Ala
145                 150                 155                 160
```

```
Val Ser Ile Pro Val Ile Ala Gly Gly Ile Ala Asp Gly His Gly
            165                 170                 175

Ala Ala Ala Ala Phe Met Leu Gly Ala Glu Ala Val Gln Ile Gly Thr
        180                 185                 190

Arg Phe Val Val Ala Lys Glu Ser Asn Ala His Gln Asn Phe Lys Asp
        195                 200                 205

Lys Ile Leu Ala Ala Lys Asp Ile Asp Thr Val Ile Ser Ala Gln Val
        210                 215                 220

Val Gly His Pro Val Arg Ser Ile Lys Asn Lys Leu Thr Ser Ala Tyr
225                 230                 235                 240

Ala Lys Ala Glu Lys Ala Phe Leu Ile Gly Gln Lys Thr Ala Thr Asp
                245                 250                 255

Ile Glu Glu Met Gly Ala Gly Ser Leu Arg His Ala Val Ile Glu Gly
            260                 265                 270

Asp Val Val Asn Gly Ser Val Met Ala Gly Gln Ile Ala Gly Leu Val
        275                 280                 285

Arg Lys Glu Glu Ser Cys Glu Thr Ile Leu Lys Asp Ile Tyr Tyr Gly
        290                 295                 300

Ala Ala Arg Val Ile Gln Asn Glu Ala Lys Arg Trp Gln Ser Val Ser
305                 310                 315                 320

Ile Glu Lys

<210> SEQ ID NO 52
<211> LENGTH: 972
<212> TYPE: DNA
<213> ORGANISM: Streptococcus pyogenes

<400> SEQUENCE: 52
atgaaaacac gtattacaga attacttaat attgattacc ccattttca aggaggaatg      60 gcttggttg ctgatggtga tttagcaggt gcagtttcta atgctggtgg tttaggcatt     120
ataggtggtg gcaatgctcc caagaagtc gttaaagcta atattgatcg tgtcaaagct     180
attactgata gacctttgg ggttaatatc atgcttttat ctccttttgc tgatgatatc     240
gttgatctgg tcattgaaga aggtgttaaa gtagtaacaa caggcgcagg aaatccagga     300
aagtatatgg aaagactgca ccaggcgggt ataatcgttg ttcctgttgt cccaagcgtt     360
gcgctagcca aacgtatgga aaagcttggg gtagatgctg ttattgctga gggtatggaa     420
gctggaggac atattggcaa gttaacgact atgtctttag taagacaagt tgttgaagcg     480
gtttcgattc ctgtcattgc ggcaggtggt atagctgatg gtcatggtgc agcagcagca     540
tttatgttag gagcagaggc tgttcaaatt ggaactcgct tgttgttgc taaagaatcc     600 aatgctcacc aaaattttaa agataaaatc ttagcagcaa aagatattga tacggtgatt     660
tctgcgcagg ttgtgggcca ccctgtccgt tctattaaaa ataaattgac ctcagcttac     720
gctaaagcag aaaaagcatt tttaattggt caaaaaacag ctactgatat tgaagaaatg     780
ggagcaggat cgcttcgaca cgctgttatt gaaggcgatg tagtcaatgg atctgttatg     840
gctggccaaa ttgcagggct tgtgagaaaa gaagaaagct gtgaaacgat tttaaaagat     900
atttattatg gtgcagctcg tgttattcaa aatgaagcta agcgctggca atctgtttca     960
atagaaaagt ag                                                        972

<210> SEQ ID NO 53
<211> LENGTH: 313
<212> TYPE: PRT
<213> ORGANISM: Streptococcus pyogenes
```

<400> SEQUENCE: 53

| | | | | | | | | | | | | | | |
|---|---|---|---|---|---|---|---|---|---|---|---|---|---|---|
| Met | Thr | Lys | Ile | Tyr | Lys | Thr | Ile | Thr | Glu | Leu | Val | Gly | Gln | Thr | Pro |
| 1 | | | | 5 | | | | | 10 | | | | | 15 | |
| Ile | Ile | Lys | Leu | Asn | Arg | Leu | Ile | Pro | Asn | Glu | Ala | Ala | Asp | Val | Tyr |
| | | | 20 | | | | | 25 | | | | | 30 | | |
| Val | Lys | Leu | Glu | Ala | Phe | Asn | Pro | Gly | Ser | Ser | Val | Lys | Asp | Arg | Ile |
| | | 35 | | | | | 40 | | | | | 45 | | | |
| Ala | Leu | Ser | Met | Ile | Glu | Ala | Glu | Ala | Glu | Gly | Leu | Ile | Ser | Pro |
| | 50 | | | | | 55 | | | | | 60 | | | | |
| Gly | Asp | Val | Ile | Ile | Glu | Pro | Thr | Ser | Gly | Asn | Thr | Gly | Ile | Gly | Leu |
| 65 | | | | | 70 | | | | | 75 | | | | | 80 |
| Ala | Trp | Val | Gly | Ala | Ala | Lys | Gly | Tyr | Arg | Val | Ile | Ile | Val | Met | Pro |
| | | | | 85 | | | | | 90 | | | | | 95 | |
| Glu | Thr | Met | Ser | Leu | Glu | Arg | Arg | Gln | Ile | Ile | Gln | Ala | Tyr | Gly | Ala |
| | | | 100 | | | | | 105 | | | | | 110 | | |
| Glu | Leu | Val | Leu | Thr | Pro | Gly | Ala | Glu | Gly | Met | Lys | Gly | Ala | Ile | Ala |
| | | 115 | | | | | 120 | | | | | 125 | | | |
| Lys | Ala | Glu | Thr | Leu | Ala | Ile | Glu | Leu | Gly | Ala | Trp | Met | Pro | Met | Gln |
| 130 | | | | | 135 | | | | | 140 | | | | | |
| Phe | Asn | Asn | Pro | Ala | Asn | Pro | Ser | Ile | His | Glu | Lys | Thr | Thr | Ala | Gln |
| 145 | | | | | 150 | | | | | 155 | | | | | 160 |
| Glu | Ile | Leu | Glu | Ala | Phe | Lys | Glu | Ile | Ser | Leu | Asp | Ala | Phe | Val | Ser |
| | | | | 165 | | | | | 170 | | | | | 175 | |
| Gly | Val | Gly | Thr | Gly | Gly | Thr | Leu | Ser | Gly | Val | Ser | His | Val | Leu | Lys |
| | | | 180 | | | | | 185 | | | | | 190 | | |
| Lys | Ala | Asn | Pro | Glu | Thr | Val | Ile | Tyr | Ala | Val | Glu | Ala | Glu | Ser |
| | | 195 | | | | | 200 | | | | | 205 | | | |
| Ala | Val | Leu | Ser | Gly | Gln | Glu | Pro | Gly | Pro | His | Lys | Ile | Gln | Gly | Ile |
| 210 | | | | | 215 | | | | | 220 | | | | | |
| Ser | Ala | Gly | Phe | Ile | Pro | Asn | Thr | Leu | Asp | Thr | Lys | Ala | Tyr | Asp | Gln |
| 225 | | | | | 230 | | | | | 235 | | | | | 240 |
| Ile | Ile | Arg | Val | Lys | Ser | Lys | Asp | Ala | Leu | Glu | Thr | Ala | Arg | Leu | Thr |
| | | | | 245 | | | | | 250 | | | | | 255 | |
| Gly | Ala | Lys | Glu | Gly | Phe | Leu | Val | Gly | Ile | Ser | Ser | Gly | Ala | Ala | Leu |
| | | | 260 | | | | | 265 | | | | | 270 | | |
| Tyr | Ala | Ala | Ile | Glu | Val | Ala | Lys | Gln | Leu | Gly | Lys | Gly | Lys | His | Val |
| | | 275 | | | | | 280 | | | | | 285 | | | |
| Leu | Thr | Ile | Leu | Pro | Asp | Asn | Gly | Glu | Arg | Tyr | Leu | Ser | Thr | Glu | Leu |
| 290 | | | | | 295 | | | | | 300 | | | | | |
| Tyr | Asp | Val | Pro | Val | Ile | Lys | Thr | Lys |
| 305 | | | | | 310 | | | |

<210> SEQ ID NO 54
<211> LENGTH: 942
<212> TYPE: DNA
<213> ORGANISM: Streptococcus pyogenes

<400> SEQUENCE: 54

| | |
|---|---|
| atgactaaaa tttacaaaac tataacagaa ttagtaggtc aaacacctat tatcaaactt | 60 |
| aaccgtttaa ttccaaacga agctgctgac gtttatgtaa aattagaagc ttttaaccca | 120 |
| ggatcttctg ttaaagatcg tattgcttta tcgatgattg aagctgctga agctgaaggt | 180 |
| ctgataagtc ctggtgacgt tattatcgaa ccaacaagtg gtaatacagg tattggtctt | 240 |
| gcatgggtag gtgctgctaa agggtatcga gtcattattg ttatgcccga aactatgagc | 300 |

-continued

```
ttggaaagac ggcaaatcat tcaggcttat ggtgcagagc ttgtcttaac acctggagca    360
gaaggtatga aagggctat tgcaaaagct gaaactttag caatagaact aggtgcttgg     420
atgcctatgc aatttaataa ccctgccaat ccaagcatcc atgaaaaaac aacagctcaa    480
gaaattttgg aagcttttaa ggagatttct ttagatgcat tcgtatctgg tgttggtact    540
ggaggaacac tttctggtgt tcacatgtc ttgaaaaaag ctaaccctga aactgttatc     600
tatgctgttg aagctgaaga atctgctgtc ttatctggtc aagagcctgg accacataaa    660
attcaaggta tatcagctgg atttatccca aacacgttag ataccaaagc ctatgaccaa    720
attatccgtg ttaaatcgaa agatgcttta gaaactgctc gactaacagg agctaaggaa    780
ggcttcctgg ttgggatttc ttctggagct gctctttacg ccgctattga agtcgctaaa    840
cagttaggaa aagcaaaca tgtgttaact attttaccag ataatggcga acgctattta    900
tcgactgaac tctatgatgt accagtaatt aagacgaaat aa                       942
```

<210> SEQ ID NO 55
<211> LENGTH: 52
<212> TYPE: PRT
<213> ORGANISM: Streptococcus pyogenes

<400> SEQUENCE: 55

```
Phe Leu Val Gly Ile Ser Ser Gly Ala Ala Leu Tyr Ala Ala Ile Glu
1               5                   10                  15

Val Ala Lys Gln Leu Gly Lys Gly Lys His Val Leu Thr Ile Leu Pro
            20                  25                  30

Asp Asn Gly Glu Arg Tyr Leu Ser Thr Glu Leu Tyr Asp Val Pro Val
        35                  40                  45

Ile Lys Thr Lys
    50
```

<210> SEQ ID NO 56
<211> LENGTH: 261
<212> TYPE: PRT
<213> ORGANISM: Streptococcus pyogenes

<400> SEQUENCE: 56

```
Met Thr Lys Ile Tyr Lys Thr Ile Thr Glu Leu Val Gly Gln Thr Pro
1               5                   10                  15

Ile Ile Lys Leu Asn Arg Leu Ile Pro Asn Glu Ala Ala Asp Val Tyr
            20                  25                  30

Val Lys Leu Glu Ala Phe Asn Pro Gly Ser Ser Val Lys Asp Arg Ile
        35                  40                  45

Ala Leu Ser Met Ile Glu Ala Ala Glu Ala Glu Gly Leu Ile Ser Pro
    50                  55                  60

Gly Asp Val Ile Ile Glu Pro Thr Ser Gly Asn Thr Gly Ile Gly Leu
65                  70                  75                  80

Ala Trp Val Gly Ala Ala Lys Gly Tyr Arg Val Ile Ile Val Met Pro
                85                  90                  95

Glu Thr Met Ser Leu Glu Arg Arg Gln Ile Ile Gln Ala Tyr Gly Ala
            100                 105                 110

Glu Leu Val Leu Thr Pro Gly Ala Glu Gly Met Lys Gly Ala Ile Ala
        115                 120                 125

Lys Ala Glu Thr Leu Ala Ile Glu Leu Gly Ala Trp Met Pro Met Gln
    130                 135                 140

Phe Asn Asn Pro Ala Asn Pro Ser Ile His Glu Lys Thr Thr Ala Gln
145                 150                 155                 160
```

-continued

```
Glu Ile Leu Glu Ala Phe Lys Glu Ile Ser Leu Asp Ala Phe Val Ser
            165                 170                 175

Gly Val Gly Thr Gly Thr Leu Ser Gly Val Ser His Val Leu Lys
        180                 185                 190

Lys Ala Asn Pro Glu Thr Val Ile Tyr Ala Val Glu Ala Glu Ser
        195                 200                 205

Ala Val Leu Ser Gly Gln Glu Pro Gly His Lys Ile Gln Gly Ile
    210                 215                 220

Ser Ala Gly Phe Ile Pro Asn Thr Leu Asp Thr Lys Ala Tyr Asp Gln
225                 230                 235                 240

Ile Ile Arg Val Lys Ser Lys Asp Ala Leu Glu Thr Ala Arg Leu Thr
                245                 250                 255

Gly Ala Lys Glu Gly
                260

<210> SEQ ID NO 57
<211> LENGTH: 452
<212> TYPE: PRT
<213> ORGANISM: Streptococcus pyogenes

<400> SEQUENCE: 57

Met Lys Val Ile Ser Asn Phe Gln Asn Lys Ile Leu Ile Leu Gly
1               5                   10                  15

Leu Ala Lys Ser Gly Glu Ala Ala Lys Leu Leu Thr Lys Leu Gly
            20                  25                  30

Ala Leu Val Thr Val Asn Asp Ser Lys Pro Phe Asp Gln Asn Pro Ala
            35                  40                  45

Ala Gln Ala Leu Leu Glu Glu Gly Ile Lys Val Ile Cys Gly Ser His
    50                  55                  60

Pro Val Glu Leu Leu Asp Glu Asn Phe Glu Tyr Met Val Lys Asn Pro
65                  70                  75                  80

Gly Ile Pro Tyr Asp Asn Pro Met Val Lys Arg Ala Leu Ala Lys Glu
                85                  90                  95

Ile Pro Ile Leu Thr Glu Val Glu Leu Ala Tyr Phe Val Ser Glu Ala
            100                 105                 110

Pro Ile Ile Gly Ile Thr Gly Ser Asn Gly Lys Thr Thr Thr Thr Thr
            115                 120                 125

Met Ile Ala Asp Val Leu Asn Ala Gly Gly Gln Ser Ala Leu Leu Ser
    130                 135                 140

Gly Asn Ile Gly Tyr Pro Ala Ser Lys Val Val Gln Lys Ala Ile Ala
145                 150                 155                 160

Gly Asp Thr Leu Val Met Glu Leu Ser Ser Phe Gln Leu Val Gly Val
                165                 170                 175

Asn Ala Phe Arg Pro His Ile Ala Val Ile Thr Asn Leu Met Pro Thr
            180                 185                 190

His Leu Asp Tyr His Gly Ser Phe Glu Asp Tyr Val Ala Ala Lys Trp
        195                 200                 205

Met Ile Gln Ala Gln Met Thr Glu Ser Asp Tyr Leu Ile Leu Asn Ala
    210                 215                 220

Asn Gln Glu Ile Ser Ala Thr Leu Ala Lys Thr Thr Lys Ala Thr Val
225                 230                 235                 240

Ile Pro Phe Ser Thr Gln Lys Val Val Asp Gly Ala Tyr Leu Lys Asp
                245                 250                 255

Gly Ile Leu Tyr Phe Lys Glu Gln Ala Ile Ile Ala Ala Thr Asp Leu
            260                 265                 270
```

-continued

```
Gly Val Pro Gly Ser His Asn Ile Glu Asn Ala Leu Ala Thr Ile Ala
        275                 280                 285

Val Ala Lys Leu Ser Gly Ile Ala Asp Asp Ile Ile Ala Gln Cys Leu
    290                 295                 300

Ser His Phe Gly Val Lys His Arg Leu Gln Arg Val Gly Gln Ile
305                 310                 315                 320

Lys Asp Ile Thr Phe Tyr Asn Asp Ser Lys Ser Thr Asn Ile Leu Ala
                325                 330                 335

Thr Gln Lys Ala Leu Ser Gly Phe Asp Asn Ser Arg Leu Ile Leu Ile
            340                 345                 350

Ala Gly Gly Leu Asp Arg Gly Asn Glu Phe Asp Asp Leu Val Pro Asp
        355                 360                 365

Leu Leu Gly Leu Lys Gln Met Ile Ile Leu Gly Glu Ser Ala Glu Arg
    370                 375                 380

Met Lys Arg Ala Ala Asn Lys Ala Glu Val Ser Tyr Leu Glu Ala Arg
385                 390                 395                 400

Asn Val Ala Glu Ala Thr Glu Leu Ala Phe Lys Leu Ala Gln Thr Gly
                405                 410                 415

Asp Thr Ile Leu Leu Ser Pro Ala Asn Ala Ser Trp Asp Met Tyr Pro
            420                 425                 430

Asn Phe Glu Val Arg Gly Asp Glu Phe Leu Ala Thr Phe Asp Cys Leu
        435                 440                 445

Arg Gly Asp Ala
    450
```

<210> SEQ ID NO 58
<211> LENGTH: 1359
<212> TYPE: DNA
<213> ORGANISM: Streptococcus pyogenes

<400> SEQUENCE: 58

```
atgaaagtga taagtaattt tcaaaacaaa aaaatattaa tattggggtt agccaaatcg      60
ggcgaagcag cagcaaaatt attgaccaaa cttggtgctt tagtgactgt taatgatagt     120
aaaccatttg accaaaatcc agcggcacaa gccttgttgg aagaggggat taaggtcatt     180
tgtggtagcc acccagtaga attattagat gagaactttg agtacatggt taaaaaccct     240
gggattcctt atgataatcc tatggttaaa cgcgcccttg caaggaaat tcccatcttg      300 actgaagtag aattggctta tttcgtatct gaagcgccta ttatcgggat tacaggatca     360
aacgggaaga caaccacaac gacaatgatt gccgatgttt tgaatgctgg cgggcaatct     420
gcactcttat ctggaaacat tggttatcct gcttcaaaag ttgttcaaaa agcaattgct     480
ggtgatactt tggtgatgga attgtcctct tttcaattag tgggagtgaa tgcttttcgc     540
cctcatattg ctgtcatcac taatttaatg ccgactcacc tggactatca tggcagtttt     600
gaggattatg ttgctgctaa atggatgatt caagctcaga tgacagaatc agactacctt     660 atttaaatg ctaatcaaga gatttcagca actctagcta agaccaccaa agcaacagtg     720
attccttttt caactcaaaa agtggttgat ggagcttatc tgaaggatgg aatactctat     780
tttaaagaac aggcgattat agctgcaact gacttaggtg tcccaggtag ccacaacatt     840
gaaaatgccc tagcaactat tgcagttgcc aagttatctg gtattgctga tgatattatt     900
gcccagtgcc tttcacattt tggaggcgtt aaacatcgtt tgcaacgggt tggtcaaatc     960
aaagatatta ccttctacaa tgacagtaag tcaaccaata ttttagccac tcaaaaagct    1020
ttatcaggtt ttgataacag tcgcttgatt ttgattgctg gcggtctaga tcgtggcaat    1080
```

```
gaatttgacg atttggtgcc agaccttta ggacttaagc agatgattat tttgggagaa    1140
tccgcagagc gtatgaagcg agctgctaac aaagcagagg tctcttatct tgaagctaga    1200
aatgtggcag aagcaacaga gcttgctttt aagctggccc aaacaggcga tactatcttg    1260
cttagcccag ccaatgctag ctgggatatg tatcctaatt ttgaggttcg tggggatgaa    1320
tttttggcaa cctttgattg tttaagagga gatgcctaa                          1359
```

<210> SEQ ID NO 59
<211> LENGTH: 25
<212> TYPE: PRT
<213> ORGANISM: Streptococcus pyogenes

<400> SEQUENCE: 59

Met Lys Val Ile Ser Asn Phe Gln Asn Lys Lys Ile Leu Ile Leu Gly
1               5                   10                  15

Leu Ala Lys Ser Gly Glu Ala Ala Ala
            20                  25

<210> SEQ ID NO 60
<211> LENGTH: 427
<212> TYPE: PRT
<213> ORGANISM: Streptococcus pyogenes

<400> SEQUENCE: 60

Lys Leu Leu Thr Lys Leu Gly Ala Leu Val Thr Val Asn Asp Ser Lys
1               5                   10                  15

Pro Phe Asp Gln Asn Pro Ala Ala Gln Ala Leu Leu Glu Glu Gly Ile
            20                  25                  30

Lys Val Ile Cys Gly Ser His Pro Val Glu Leu Leu Asp Glu Asn Phe
        35                  40                  45

Glu Tyr Met Val Lys Asn Pro Gly Ile Pro Tyr Asp Asn Pro Met Val
    50                  55                  60

Lys Arg Ala Leu Ala Lys Glu Ile Pro Ile Leu Thr Glu Val Glu Leu
65                  70                  75                  80

Ala Tyr Phe Val Ser Glu Ala Pro Ile Ile Gly Ile Thr Gly Ser Asn
                85                  90                  95

Gly Lys Thr Thr Thr Thr Thr Met Ile Ala Asp Val Leu Asn Ala Gly
            100                 105                 110

Gly Gln Ser Ala Leu Leu Ser Gly Asn Ile Gly Tyr Pro Ala Ser Lys
        115                 120                 125

Val Val Gln Lys Ala Ile Ala Gly Asp Thr Leu Val Met Glu Leu Ser
    130                 135                 140

Ser Phe Gln Leu Val Gly Val Asn Ala Phe Arg Pro His Ile Ala Val
145                 150                 155                 160

Ile Thr Asn Leu Met Pro Thr His Leu Asp Tyr His Gly Ser Phe Glu
                165                 170                 175

Asp Tyr Val Ala Ala Lys Trp Met Ile Gln Ala Gln Met Thr Glu Ser
            180                 185                 190

Asp Tyr Leu Ile Leu Asn Ala Asn Gln Glu Ile Ser Ala Thr Leu Ala
        195                 200                 205

Lys Thr Thr Lys Ala Thr Val Ile Pro Phe Ser Thr Gln Lys Val Val
    210                 215                 220

Asp Gly Ala Tyr Leu Lys Asp Gly Ile Leu Tyr Phe Lys Glu Gln Ala
225                 230                 235                 240

Ile Ile Ala Ala Thr Asp Leu Gly Val Pro Gly Ser His Asn Ile Glu
                245                 250                 255

-continued

```
Asn Ala Leu Ala Thr Ile Ala Val Ala Lys Leu Ser Gly Ile Ala Asp
                260                 265                 270
Asp Ile Ile Ala Gln Cys Leu Ser His Phe Gly Gly Val Lys His Arg
            275                 280                 285
Leu Gln Arg Val Gly Gln Ile Lys Asp Ile Thr Phe Tyr Asn Asp Ser
        290                 295                 300
Lys Ser Thr Asn Ile Leu Ala Thr Gln Lys Ala Leu Ser Gly Phe Asp
305                 310                 315                 320
Asn Ser Arg Leu Ile Leu Ile Ala Gly Gly Leu Asp Arg Gly Asn Glu
                325                 330                 335
Phe Asp Asp Leu Val Pro Asp Leu Leu Gly Leu Lys Gln Met Ile Ile
            340                 345                 350
Leu Gly Glu Ser Ala Glu Arg Met Lys Arg Ala Ala Asn Lys Ala Glu
        355                 360                 365
Val Ser Tyr Leu Glu Ala Arg Asn Val Ala Glu Ala Thr Glu Leu Ala
    370                 375                 380
Phe Lys Leu Ala Gln Thr Gly Asp Thr Ile Leu Leu Ser Pro Ala Asn
385                 390                 395                 400
Ala Ser Trp Asp Met Tyr Pro Asn Phe Glu Val Arg Gly Asp Glu Phe
                405                 410                 415
Leu Ala Thr Phe Asp Cys Leu Arg Gly Asp Ala
            420                 425

<210> SEQ ID NO 61
<211> LENGTH: 357
<212> TYPE: PRT
<213> ORGANISM: Streptococcus pyogenes

<400> SEQUENCE: 61

Met Arg Lys Leu Tyr Ser Phe Leu Ala Gly Val Leu Gly Val Ile Val
1               5                   10                  15
Ile Leu Thr Ser Leu Ser Phe Ile Leu Gln Lys Ser Gly Ser Gly
                20                  25                  30
Ser Gln Ser Asp Lys Leu Val Ile Tyr Asn Trp Gly Asp Tyr Ile Asp
            35                  40                  45
Pro Ala Leu Leu Lys Lys Phe Thr Lys Glu Thr Gly Ile Glu Val Gln
        50                  55                  60
Tyr Glu Thr Phe Asp Ser Asn Glu Ala Met Tyr Thr Lys Ile Lys Gln
65                  70                  75                  80
Gly Gly Thr Thr Tyr Asp Ile Ala Val Pro Ser Asp Tyr Thr Ile Asp
                85                  90                  95
Lys Met Ile Lys Glu Asn Leu Leu Asn Lys Leu Asp Lys Ser Lys Leu
            100                 105                 110
Val Gly Met Asp Asn Ile Gly Lys Glu Phe Leu Gly Lys Ser Phe Asp
        115                 120                 125
Pro Gln Asn Asp Tyr Ser Leu Pro Tyr Phe Trp Gly Thr Val Gly Ile
    130                 135                 140
Val Tyr Asn Asp Gln Leu Val Asp Lys Ala Pro Met His Trp Glu Asp
145                 150                 155                 160
Leu Trp Arg Pro Glu Tyr Lys Asn Ser Ile Met Leu Ile Asp Gly Ala
                165                 170                 175
Arg Glu Met Leu Gly Val Gly Leu Thr Thr Phe Gly Tyr Ser Val Asn
            180                 185                 190
Ser Lys Asn Leu Glu Gln Leu Gln Ala Ala Glu Arg Lys Leu Gln Gln
        195                 200                 205
```

| Leu | Thr | Pro | Asn | Val | Lys | Ala | Ile | Val | Ala | Asp | Glu | Met | Lys | Gly | Tyr |
|---|---|---|---|---|---|---|---|---|---|---|---|---|---|---|---|
| | 210 | | | | 215 | | | | 220 | | | | | | |

| Met | Ile | Gln | Gly | Asp | Ala | Ala | Ile | Gly | Ile | Thr | Phe | Ser | Gly | Glu | Ala |
|---|---|---|---|---|---|---|---|---|---|---|---|---|---|---|---|
| 225 | | | | | 230 | | | | 235 | | | | | 240 | |

| Ser | Glu | Met | Leu | Asp | Ser | Asn | Glu | His | Leu | His | Tyr | Ile | Val | Pro | Ser |
|---|---|---|---|---|---|---|---|---|---|---|---|---|---|---|---|
| | | | 245 | | | | | 250 | | | | | 255 | | |

| Glu | Gly | Ser | Asn | Leu | Trp | Phe | Asp | Asn | Leu | Val | Leu | Pro | Lys | Thr | Met |
|---|---|---|---|---|---|---|---|---|---|---|---|---|---|---|---|
| | | | 260 | | | | | 265 | | | | | 270 | | |

| Lys | His | Glu | Lys | Glu | Ala | Tyr | Ala | Phe | Leu | Asn | Phe | Ile | Asn | Arg | Pro |
|---|---|---|---|---|---|---|---|---|---|---|---|---|---|---|---|
| | | 275 | | | | | 280 | | | | | 285 | | | |

| Glu | Asn | Ala | Ala | Gln | Asn | Ala | Ala | Tyr | Ile | Gly | Tyr | Ala | Thr | Pro | Asn |
|---|---|---|---|---|---|---|---|---|---|---|---|---|---|---|---|
| | 290 | | | | | 295 | | | | | 300 | | | | |

| Lys | Lys | Ala | Lys | Ala | Leu | Leu | Pro | Asp | Glu | Ile | Lys | Asn | Asp | Pro | Ala |
|---|---|---|---|---|---|---|---|---|---|---|---|---|---|---|---|
| 305 | | | | | 310 | | | | | 315 | | | | | 320 |

| Phe | Tyr | Pro | Thr | Asp | Asp | Ile | Ile | Lys | Lys | Leu | Glu | Val | Tyr | Asp | Asn |
|---|---|---|---|---|---|---|---|---|---|---|---|---|---|---|---|
| | | | | 325 | | | | | 330 | | | | | 335 | |

| Leu | Gly | Ser | Arg | Trp | Leu | Gly | Ile | Tyr | Asn | Asp | Leu | Tyr | Leu | Gln | Phe |
|---|---|---|---|---|---|---|---|---|---|---|---|---|---|---|---|
| | | | 340 | | | | | 345 | | | | | 350 | | |

| Lys | Met | Tyr | Arg | Lys |
|---|---|---|---|---|
| | | | 355 | |

```
<210> SEQ ID NO 62
<211> LENGTH: 1074
<212> TYPE: DNA
<213> ORGANISM: Streptococcus pyogenes

<400> SEQUENCE: 62
atgcgtaaac tttattcctt tctagcagga gttttgggtg ttattgttat tttaacaagt      60
ctttctttca tcttgcagaa aaaatcgggt tctggtagtc aatcggataa attagttatt     120
tataactggg gagattacat tgatccagct ttgctcaaaa aattcaccaa agaaacgggc     180
attgaagtgc agtatgaaac tttcgattcc aatgaagcca tgtacactaa atcaagcag     240
ggcggaacca cttacgacat tgctgttcct agtgattaca ccattgataa aatgatcaaa     300
gaaacctac tcaataagct tgataagtca aaattagttg gcatggataa tatcgggaaa     360
gaattttag ggaaaagctt tgacccacaa aacgactatt cttttgcctta tttctgggga     420
accgttggga ttgtttataa tgatcaatta gttgataagg cgcctatgca ctgggaagat     480
ctgtggcgtc cagaatataa aaatagtatt atgctgattg atggagcgcg tgaaatgcta     540
ggggttggtt taacaacttt tggttatagt gtgaattcta aaaatctaga gcagttgcag     600
gcagccgaga gaaaactgca gcagttgacg ccgaatgtta aagccattgt agcagatgag     660
atgaaaggct acatgattca aggtgacgct gctattggaa ttacctttc tggtgaagcc     720
agtgagatgt tagatagtaa cgaacacctt cactacatcg tgccttcaga agggtctaac     780
ctttggtttg ataatttggt actaccaaaa accatgaaac acgaaaaaga agcttatgct     840
tttttgaact tatcaatcg tcctgaaaat gctgcgcaaa atgctgcata tattggttat     900
gcgacaccaa ataaaaaagc caaggcctta cttccagatg aataaaaaa tgatcctgct     960
ttttatccaa cagatgacat tatcaaaaaa ttggaagttt atgacaattt agggtcaaga    1020
tggttgggga tttataatga tttataccctc caattaaaa tgtatcgcaa ataa          1074

<210> SEQ ID NO 63
<211> LENGTH: 24
<212> TYPE: PRT
<213> ORGANISM: Streptococcus pyogenes
```

<400> SEQUENCE: 63

Met Arg Lys Leu Tyr Ser Phe Leu Ala Gly Val Leu Gly Val Ile Val
1               5                   10                  15

Ile Leu Thr Ser Leu Ser Phe Ile
            20

<210> SEQ ID NO 64
<211> LENGTH: 333
<212> TYPE: PRT
<213> ORGANISM: Streptococcus pyogenes

<400> SEQUENCE: 64

Leu Gln Lys Lys Ser Gly Ser Gly Ser Gln Ser Asp Lys Leu Val Ile
1               5                   10                  15

Tyr Asn Trp Gly Asp Tyr Ile Asp Pro Ala Leu Leu Lys Lys Phe Thr
            20                  25                  30

Lys Glu Thr Gly Ile Glu Val Gln Tyr Glu Thr Phe Asp Ser Asn Glu
        35                  40                  45

Ala Met Tyr Thr Lys Ile Lys Gln Gly Gly Thr Thr Tyr Asp Ile Ala
    50                  55                  60

Val Pro Ser Asp Tyr Thr Ile Asp Lys Met Ile Lys Glu Asn Leu Leu
65                  70                  75                  80

Asn Lys Leu Asp Lys Ser Lys Leu Val Gly Met Asp Asn Ile Gly Lys
                85                  90                  95

Glu Phe Leu Gly Lys Ser Phe Asp Pro Gln Asn Asp Tyr Ser Leu Pro
            100                 105                 110

Tyr Phe Trp Gly Thr Val Gly Ile Val Tyr Asn Asp Gln Leu Val Asp
        115                 120                 125

Lys Ala Pro Met His Trp Glu Asp Leu Trp Arg Pro Glu Tyr Lys Asn
    130                 135                 140

Ser Ile Met Leu Ile Asp Gly Ala Arg Glu Met Leu Gly Val Gly Leu
145                 150                 155                 160

Thr Thr Phe Gly Tyr Ser Val Asn Ser Lys Asn Leu Glu Gln Leu Gln
                165                 170                 175

Ala Ala Glu Arg Lys Leu Gln Gln Leu Thr Pro Asn Val Lys Ala Ile
            180                 185                 190

Val Ala Asp Glu Met Lys Gly Tyr Met Ile Gln Gly Asp Ala Ala Ile
        195                 200                 205

Gly Ile Thr Phe Ser Gly Glu Ala Ser Glu Met Leu Asp Ser Asn Glu
    210                 215                 220

His Leu His Tyr Ile Val Pro Ser Glu Gly Ser Asn Leu Trp Phe Asp
225                 230                 235                 240

Asn Leu Val Leu Pro Lys Thr Met Lys His Glu Lys Glu Ala Tyr Ala
                245                 250                 255

Phe Leu Asn Phe Ile Asn Arg Pro Glu Asn Ala Ala Gln Asn Ala Ala
            260                 265                 270

Tyr Ile Gly Tyr Ala Thr Pro Asn Lys Lys Ala Lys Ala Leu Leu Pro
        275                 280                 285

Asp Glu Ile Lys Asn Asp Pro Ala Phe Tyr Pro Thr Asp Ile Ile
    290                 295                 300

Lys Lys Leu Glu Val Tyr Asp Asn Leu Gly Ser Arg Trp Leu Gly Ile
305                 310                 315                 320

Tyr Asn Asp Leu Tyr Leu Gln Phe Lys Met Tyr Arg Lys
                325                 330

<210> SEQ ID NO 65
<211> LENGTH: 17
<212> TYPE: PRT
<213> ORGANISM: Streptococcus pyogenes

<400> SEQUENCE: 65

Trp Leu Gly Ile Tyr Asn Asp Leu Tyr Leu Gln Phe Lys Met Tyr Arg
1               5                   10                  15

Lys

<210> SEQ ID NO 66
<211> LENGTH: 340
<212> TYPE: PRT
<213> ORGANISM: Streptococcus pyogenes

<400> SEQUENCE: 66

Met Arg Lys Leu Tyr Ser Phe Leu Ala Gly Val Leu Gly Val Ile Val
1               5                   10                  15

Ile Leu Thr Ser Leu Ser Phe Ile Leu Gln Lys Ser Gly Ser Gly
            20                  25                  30

Ser Gln Ser Asp Lys Leu Val Ile Tyr Asn Trp Gly Asp Tyr Ile Asp
        35                  40                  45

Pro Ala Leu Leu Lys Lys Phe Thr Lys Glu Thr Gly Ile Glu Val Gln
    50                  55                  60

Tyr Glu Thr Phe Asp Ser Asn Glu Ala Met Tyr Thr Lys Ile Lys Gln
65                  70                  75                  80

Gly Gly Thr Thr Tyr Asp Ile Ala Val Pro Ser Asp Tyr Thr Ile Asp
                85                  90                  95

Lys Met Ile Lys Glu Asn Leu Leu Asn Lys Leu Asp Lys Ser Lys Leu
            100                 105                 110

Val Gly Met Asp Asn Ile Gly Lys Glu Phe Leu Gly Lys Ser Phe Asp
        115                 120                 125

Pro Gln Asn Asp Tyr Ser Leu Pro Tyr Phe Trp Gly Thr Val Gly Ile
    130                 135                 140

Val Tyr Asn Asp Gln Leu Val Asp Lys Ala Pro Met His Trp Glu Asp
145                 150                 155                 160

Leu Trp Arg Pro Glu Tyr Lys Asn Ser Ile Met Leu Ile Asp Gly Ala
                165                 170                 175

Arg Glu Met Leu Gly Val Gly Leu Thr Thr Phe Gly Tyr Ser Val Asn
            180                 185                 190

Ser Lys Asn Leu Glu Gln Leu Gln Ala Ala Glu Arg Lys Leu Gln Gln
        195                 200                 205

Leu Thr Pro Asn Val Lys Ala Ile Val Ala Asp Glu Met Lys Gly Tyr
    210                 215                 220

Met Ile Gln Gly Asp Ala Ala Ile Gly Ile Thr Phe Ser Gly Glu Ala
225                 230                 235                 240

Ser Glu Met Leu Asp Ser Asn Glu His Leu His Tyr Ile Val Pro Ser
                245                 250                 255

Glu Gly Ser Asn Leu Trp Phe Asp Asn Leu Val Leu Pro Lys Thr Met
            260                 265                 270

Lys His Glu Lys Glu Ala Tyr Ala Phe Leu Asn Phe Ile Asn Arg Pro
        275                 280                 285

Glu Asn Ala Ala Gln Asn Ala Ala Tyr Ile Gly Tyr Ala Thr Pro Asn
    290                 295                 300

Lys Lys Ala Lys Ala Leu Leu Pro Asp Glu Ile Lys Asn Asp Pro Ala
305                 310                 315                 320

```
Phe Tyr Pro Thr Asp Asp Ile Ile Lys Lys Leu Glu Val Tyr Asp Asn
                325                 330                 335

Leu Gly Ser Arg
            340

<210> SEQ ID NO 67
<211> LENGTH: 316
<212> TYPE: PRT
<213> ORGANISM: Streptococcus pyogenes

<400> SEQUENCE: 67

Leu Gln Lys Lys Ser Gly Ser Gly Ser Gln Ser Asp Lys Leu Val Ile
  1               5                  10                  15

Tyr Asn Trp Gly Asp Tyr Ile Asp Pro Ala Leu Leu Lys Lys Phe Thr
                 20                  25                  30

Lys Glu Thr Gly Ile Glu Val Gln Tyr Glu Thr Phe Asp Ser Asn Glu
             35                  40                  45

Ala Met Tyr Thr Lys Ile Lys Gln Gly Gly Thr Thr Tyr Asp Ile Ala
         50                  55                  60

Val Pro Ser Asp Tyr Thr Ile Asp Lys Met Ile Lys Glu Asn Leu Leu
 65                  70                  75                  80

Asn Lys Leu Asp Lys Ser Lys Leu Val Gly Met Asp Asn Ile Gly Lys
                 85                  90                  95

Glu Phe Leu Gly Lys Ser Phe Asp Pro Gln Asn Asp Tyr Ser Leu Pro
            100                 105                 110

Tyr Phe Trp Gly Thr Val Gly Ile Val Tyr Asn Asp Gln Leu Val Asp
        115                 120                 125

Lys Ala Pro Met His Trp Glu Asp Leu Trp Arg Pro Glu Tyr Lys Asn
130                 135                 140

Ser Ile Met Leu Ile Asp Gly Ala Arg Glu Met Leu Gly Val Gly Leu
145                 150                 155                 160

Thr Thr Phe Gly Tyr Ser Val Asn Ser Lys Asn Leu Glu Gln Leu Gln
                165                 170                 175

Ala Ala Glu Arg Lys Leu Gln Gln Leu Thr Pro Asn Val Lys Ala Ile
            180                 185                 190

Val Ala Asp Glu Met Lys Gly Tyr Met Ile Gln Gly Asp Ala Ala Ile
        195                 200                 205

Gly Ile Thr Phe Ser Gly Glu Ala Ser Glu Met Leu Asp Ser Asn Glu
210                 215                 220

His Leu His Tyr Ile Val Pro Ser Glu Gly Ser Asn Leu Trp Phe Asp
225                 230                 235                 240

Asn Leu Val Leu Pro Lys Thr Met Lys His Glu Lys Glu Ala Tyr Ala
                245                 250                 255

Phe Leu Asn Phe Ile Asn Arg Pro Glu Asn Ala Ala Gln Asn Ala Ala
            260                 265                 270

Tyr Ile Gly Tyr Ala Thr Pro Asn Lys Lys Ala Lys Ala Leu Leu Pro
        275                 280                 285

Asp Glu Ile Lys Asn Asp Pro Ala Phe Tyr Pro Thr Asp Asp Ile Ile
        290                 295                 300

Lys Lys Leu Glu Val Tyr Asp Asn Leu Gly Ser Arg
305                 310                 315

<210> SEQ ID NO 68
<211> LENGTH: 254
<212> TYPE: PRT
<213> ORGANISM: Streptococcus pyogenes
```

<400> SEQUENCE: 68

| Met | Ala | Gln | Arg | Ile | Ile | Val | Ile | Thr | Gly | Ala | Ser | Gly | Gly | Leu | Ala |
| 1 | | | | 5 | | | | | 10 | | | | | 15 | |

| Gln | Ala | Ile | Val | Lys | Gln | Leu | Pro | Lys | Glu | Asp | Ser | Leu | Ile | Leu | Leu |
| | | | 20 | | | | | 25 | | | | | 30 | | |

| Gly | Arg | Asn | Lys | Glu | Arg | Leu | Glu | His | Cys | Tyr | Gln | His | Ile | Asp | Asn |
| | | | 35 | | | | | 40 | | | | | 45 | | |

| Lys | Glu | Cys | Leu | Glu | Leu | Asp | Ile | Thr | Asn | Pro | Val | Ala | Ile | Glu | Lys |
| | 50 | | | | | 55 | | | | | 60 | | | | |

| Met | Val | Ala | Gln | Ile | Tyr | Gln | Arg | Tyr | Gly | Arg | Ile | Asp | Val | Leu | Ile |
| 65 | | | | | 70 | | | | | 75 | | | | | 80 |

| Asn | Asn | Ala | Gly | Tyr | Gly | Ala | Phe | Lys | Gly | Phe | Glu | Glu | Phe | Ser | Ala |
| | | | | 85 | | | | | 90 | | | | | 95 | |

| Gln | Glu | Ile | Ala | Asp | Met | Phe | Gln | Val | Asn | Thr | Leu | Ala | Ser | Ile | His |
| | | | 100 | | | | | 105 | | | | | 110 | | |

| Phe | Ala | Cys | Leu | Ile | Gly | Gln | Lys | Met | Ala | Glu | Gln | Gly | Gln | Gly | His |
| | | | 115 | | | | | 120 | | | | | 125 | | |

| Leu | Ile | Asn | Ile | Val | Ser | Met | Ala | Gly | Leu | Ile | Ala | Ser | Ala | Lys | Ser |
| | 130 | | | | | 135 | | | | | 140 | | | | |

| Ser | Ile | Tyr | Ser | Ala | Thr | Lys | Phe | Ala | Leu | Ile | Gly | Phe | Ser | Asn | Ala |
| 145 | | | | | 150 | | | | | 155 | | | | | 160 |

| Leu | Arg | Leu | Glu | Leu | Ala | Asp | Lys | Gly | Val | Tyr | Val | Thr | Thr | Val | Asn |
| | | | | 165 | | | | | 170 | | | | | 175 | |

| Pro | Gly | Pro | Ile | Ala | Thr | Lys | Phe | Phe | Asp | Gln | Ala | Asp | Pro | Ser | Gly |
| | | | 180 | | | | | 185 | | | | | 190 | | |

| His | Tyr | Leu | Glu | Ser | Val | Gly | Lys | Phe | Thr | Leu | Gln | Pro | Asn | Gln | Val |
| | | | 195 | | | | | 200 | | | | | 205 | | |

| Ala | Lys | Arg | Leu | Val | Ser | Ile | Ile | Gly | Lys | Asn | Lys | Arg | Glu | Leu | Asn |
| | 210 | | | | | 215 | | | | | 220 | | | | |

| Leu | Pro | Phe | Ser | Leu | Ala | Val | Thr | His | Gln | Phe | Tyr | Thr | Leu | Phe | Pro |
| 225 | | | | | 230 | | | | | 235 | | | | | 240 |

| Lys | Leu | Ser | Asp | Tyr | Leu | Ala | Arg | Lys | Val | Phe | Asn | Tyr | Lys |
| | | | | 245 | | | | | 250 | | | | |

<210> SEQ ID NO 69
<211> LENGTH: 765
<212> TYPE: DNA
<213> ORGANISM: Streptococcus pyogenes

<400> SEQUENCE: 69

```
atggcacaaa gaatcattgt tatcacggga gcttctggag gactggctca ggcaattgtt      60
aagcagttac ccaaggaaga cagcttgatt ttattaggac gtaacaaaga acgcctagaa     120
cactgttatc agcatattga acaaaagaa tgcctcgagt tggatattac caatccagta     180
gccattgaga aatggtcgc ccagatttac cagcgctatg gccgtattga tgtcttgatt     240
aataatgctg gctacggagc tttcaaaggc tttgaagagt tttctgccca gaaatagct      300 gatatgtttc aggttaacac cctagcgagc attcactttg cttgcttgat tggtcagaaa     360
atggcagagc aggggcaagg tcaccttatt aatattgtgt ccatggcagg cttgattgcg     420
tcagccaaat cgagcattta ttcagccacc aagtttgccc ttatcggatt tccaatgcc      480 cttcgcttag aattagcgga taagggggtt tacgtgacca ccgtgaatcc aggtcccatt     540
gccaccaagt ttttgacca agctgacccg tctggacatt atttggaaag cgttggtaaa      600
tttactctcc aaccaaatca agtggctaag cgtttggttt ctattatcgg gaaaaataaa     660
```

```
cgagaattga atttgccctt tagtttagcg gtgacccatc aattttacac ccttttccct    720
aaattatctg attatcttgc aagaaggta  tttaattata aatga                    765
```

<210> SEQ ID NO 70
<211> LENGTH: 497
<212> TYPE: PRT
<213> ORGANISM: Streptococcus pyogenes

<400> SEQUENCE: 70

| Met | Ile | Glu | Lys | Tyr | Leu | Glu | Ser | Ser | Ile | Glu | Ser | Lys | Cys | Gln | Leu |
|---|---|---|---|---|---|---|---|---|---|---|---|---|---|---|---|
| 1 | | | | 5 | | | | | 10 | | | | | 15 | |

| Ile | Val | Leu | Phe | Phe | Lys | Thr | Ser | Tyr | Leu | Pro | Ile | Thr | Glu | Val | Ala |
| | | | 20 | | | | | 25 | | | | | 30 | | |

| Glu | Lys | Thr | Gly | Leu | Thr | Phe | Leu | Gln | Leu | Asn | His | Tyr | Cys | Glu | Glu |
| | | 35 | | | | | 40 | | | | | 45 | | | |

| Leu | Asn | Ala | Phe | Phe | Pro | Gly | Ser | Leu | Ser | Met | Thr | Ile | Gln | Lys | Arg |
| | 50 | | | | | 55 | | | | | 60 | | | | |

| Met | Ile | Ser | Cys | Gln | Phe | Thr | His | Pro | Phe | Lys | Glu | Thr | Tyr | Leu | Tyr |
| 65 | | | | | 70 | | | | | 75 | | | | | 80 |

| Gln | Leu | Tyr | Ala | Ser | Ser | Asn | Val | Leu | Gln | Leu | Leu | Ala | Phe | Leu | Ile |
| | | | | 85 | | | | | 90 | | | | | 95 | |

| Lys | Asn | Gly | Ser | His | Ser | Arg | Pro | Leu | Thr | Asp | Phe | Ala | Arg | Ser | His |
| | | | 100 | | | | | 105 | | | | | 110 | | |

| Phe | Leu | Ser | Asn | Ser | Ser | Ala | Tyr | Arg | Met | Arg | Glu | Ala | Leu | Ile | Pro |
| | | 115 | | | | | 120 | | | | | 125 | | | |

| Leu | Leu | Arg | Asn | Phe | Glu | Leu | Lys | Leu | Ser | Lys | Asn | Lys | Ile | Val | Gly |
| | 130 | | | | | 135 | | | | | 140 | | | | |

| Glu | Glu | Tyr | Arg | Ile | Arg | Tyr | Leu | Ile | Ala | Leu | Leu | Tyr | Ser | Lys | Phe |
| 145 | | | | | 150 | | | | | 155 | | | | | 160 |

| Gly | Ile | Lys | Val | Tyr | Asp | Leu | Thr | Gln | Gln | Asp | Lys | Asn | Thr | Ile | His |
| | | | | 165 | | | | | 170 | | | | | 175 | |

| Ser | Phe | Leu | Ser | His | Ser | Ser | Thr | His | Leu | Lys | Thr | Ser | Pro | Trp | Leu |
| | | | 180 | | | | | 185 | | | | | 190 | | |

| Ser | Glu | Ser | Phe | Ser | Phe | Tyr | Asp | Ile | Leu | Leu | Ala | Leu | Ser | Trp | Lys |
| | | 195 | | | | | 200 | | | | | 205 | | | |

| Arg | His | Gln | Phe | Ser | Val | Thr | Ile | Pro | Gln | Thr | Arg | Ile | Phe | Gln | Gln |
| | 210 | | | | | 215 | | | | | 220 | | | | |

| Leu | Lys | Lys | Leu | Phe | Val | Tyr | Asp | Ser | Leu | Lys | Lys | Ser | Ser | His | Asp |
| 225 | | | | | 230 | | | | | 235 | | | | | 240 |

| Ile | Ile | Glu | Thr | Tyr | Cys | Gln | Leu | Asn | Phe | Ser | Ala | Gly | Asp | Leu | Asp |
| | | | | 245 | | | | | 250 | | | | | 255 | |

| Tyr | Leu | Tyr | Leu | Ile | Tyr | Ile | Thr | Ala | Asn | Asn | Ser | Phe | Ala | Ser | Leu |
| | | | 260 | | | | | 265 | | | | | 270 | | |

| Gln | Trp | Thr | Pro | Glu | His | Ile | Arg | Gln | Tyr | Cys | Gln | Leu | Phe | Glu | Glu |
| | | 275 | | | | | 280 | | | | | 285 | | | |

| Asn | Asp | Thr | Phe | Arg | Leu | Leu | Leu | Asn | Pro | Ile | Ile | Thr | Leu | Leu | Pro |
| | 290 | | | | | 295 | | | | | 300 | | | | |

| Asn | Leu | Lys | Glu | Gln | Lys | Ala | Ser | Leu | Val | Lys | Ala | Leu | Met | Phe | Phe |
| 305 | | | | | 310 | | | | | 315 | | | | | 320 |

| Ser | Lys | Ser | Phe | Leu | Phe | Asn | Leu | Gln | His | Phe | Ile | Pro | Glu | Thr | Asn |
| | | | | 325 | | | | | 330 | | | | | 335 | |

| Leu | Phe | Val | Ser | Pro | Tyr | Tyr | Lys | Gly | Asn | Gln | Lys | Leu | Tyr | Thr | Ser |
| | | | 340 | | | | | 345 | | | | | 350 | | |

| Leu | Lys | Leu | Ile | Val | Glu | Glu | Trp | Met | Ala | Lys | Leu | Pro | Gly | Lys | Arg |
| | | 355 | | | | | 360 | | | | | 365 | | | |

```
Asp Leu Asn His Lys His Phe His Leu Phe Cys His Tyr Val Glu Gln
        370                 375                 380

Ser Leu Arg Asn Ile Gln Pro Pro Leu Val Val Phe Val Ala Ser
385                 390                 395                 400

Asn Phe Ile Asn Ala His Leu Leu Thr Asp Ser Phe Pro Arg Tyr Phe
                405                 410                 415

Ser Asp Lys Ser Ile Asp Phe His Ser Tyr Tyr Leu Leu Gln Asp Asn
                420                 425                 430

Val Tyr Gln Ile Pro Asp Leu Lys Pro Asp Leu Val Ile Thr His Ser
            435                 440                 445

Gln Leu Ile Pro Phe Val His His Glu Leu Thr Lys Gly Ile Ala Val
        450                 455                 460

Ala Glu Ile Ser Phe Asp Glu Ser Ile Leu Ser Ile Gln Glu Leu Met
465                 470                 475                 480

Tyr Gln Val Lys Glu Glu Lys Phe Gln Ala Asp Leu Thr Lys Gln Leu
                485                 490                 495

Thr
```

<210> SEQ ID NO 71
<211> LENGTH: 1494
<212> TYPE: DNA
<213> ORGANISM: Streptococcus pyogenes

<400> SEQUENCE: 71

```
ttgatagaaa aatacttgga atcatcaatc gaatcaaaat gtcagttaat tgtcttgttt      60
tttaagacat cttatttgcc aataactgag gtagcagaaa aaactggctt aacctttta     120
caactaaacc attattgtga ggaactgaat gccttttccc ctggtagtct gtctatgacc     180
atccaaaaaa ggatgatatc ttgccaattt acacatcctt taaagaaac ttatctttac      240
caactctatg catcatctaa tgtcttacaa ttactagcct ttttaataaa aaatggttcc     300
cactctcgtc cccttacgga ttttgcaaga agtcattttt tatcaaactc ctcagcttat     360
cggatgcgcg aagcattgat tcctttatta agaaactttg aattaaaact ctctaagaac     420
aagattgtcg gtgaggaata tcgcatccgt tacctcatcg ctctgctata tagtaagttt     480
ggcattaaag tttatgactt gacgcagcaa gacaaaaaca ctattcatag cttttttatcc    540
catagttcca cccaccttaa aacctctcct tggttatcgg aatcgttttc tttctatgac     600
attttattag ctttatcgtg gaagcggcat caatttttcgg taactattcc ccaaaccaga    660
atttttcaac aattaaaaaa acttttttgtc tacgattctt tgaaaaaaag tagccatgat    720
attatcgaaa cttactgcca actaaacttt tcagcaggag atttggacta cctctatta     780
atttatatca ccgctaataa ttcttttgcg agcttacaat ggacacctga gcatatcaga    840
caatattgtc aacttttttga agaaaatgat acttttcgcc tgcttttaaa tcctatcatc    900
actcttttac ctaacctaaa agagcaaaag gctagtttag taaaagctct tatgttttt    960
tcaaaatcat tcttgttaa tctgcaacat tttattcctg agaccaactt attcgttttct   1020
ccgtactata aaggaaacca aaaactctat acgtccttaa agttaattgt cgaagagtgg   1080
atggccaaac ttcctggtaa gcgtgacttg aaccataagc atttttcatct tttttgccac   1140
tatgtcgagc aaagtctaag aaatatccaa cctccttag ttgttgtttt cgtagccagt    1200
aatttttatca atgctcatct cctaacggat tctttttccaa ggtatttctc ggataaaagc   1260
attgattttc attcctatta tctattgcaa gataatgttt atcaaattcc tgatttaaag    1320
ccagatttgg tcatcactca cagtcaactg attcctttg ttcaccatga acttacaaaa      1380
```

```
ggaattgctg ttgctgaaat atcttttgat gaatcgattc tgtctatcca agaattgatg    1440
tatcaagtta aagaggaaaa attccaagct gatttaacca agcaattaac ataa          1494
```

<210> SEQ ID NO 72
<211> LENGTH: 632
<212> TYPE: PRT
<213> ORGANISM: Streptococcus pyogenes

<400> SEQUENCE: 72

```
Met Ile Gln Ile Gly Lys Leu Phe Ala Gly Arg Tyr Arg Ile Leu Lys
  1               5                  10                  15

Ser Ile Gly Arg Gly Gly Met Ala Asp Val Tyr Leu Ala Asn Asp Leu
             20                  25                  30

Ile Leu Asp Asn Glu Asp Val Ala Ile Lys Val Leu Arg Thr Asn Tyr
         35                  40                  45

Gln Thr Asp Gln Val Ala Val Ala Arg Phe Gln Arg Glu Ala Arg Ala
     50                  55                  60

Met Ala Glu Leu Asn His Pro Asn Ile Val Ala Ile Arg Asp Ile Gly
 65                  70                  75                  80

Glu Glu Asp Gly Gln Gln Phe Leu Val Met Glu Tyr Val Asp Gly Ala
                 85                  90                  95

Asp Leu Lys Arg Tyr Ile Gln Asn His Ala Pro Leu Ser Asn Asn Glu
            100                 105                 110

Val Val Arg Ile Met Glu Glu Val Leu Ser Ala Met Thr Leu Ala His
        115                 120                 125

Gln Lys Gly Ile Val His Arg Asp Leu Lys Pro Gln Asn Ile Leu Leu
    130                 135                 140

Thr Lys Glu Gly Val Val Lys Val Thr Asp Phe Gly Ile Ala Val Ala
145                 150                 155                 160

Phe Ala Glu Thr Ser Leu Thr Gln Thr Asn Ser Met Leu Gly Ser Val
                165                 170                 175

His Tyr Leu Ser Pro Glu Gln Ala Arg Gly Ser Lys Ala Thr Ile Gln
            180                 185                 190

Ser Asp Ile Tyr Ala Met Gly Ile Met Leu Phe Glu Met Leu Thr Gly
        195                 200                 205

His Ile Pro Tyr Asp Gly Asp Ser Ala Val Thr Ile Ala Leu Gln His
    210                 215                 220

Phe Gln Lys Pro Leu Pro Ser Ile Ile Glu Glu Asn His Asn Val Pro
225                 230                 235                 240

Gln Ala Leu Glu Asn Val Val Ile Arg Ala Thr Ala Lys Lys Leu Ser
                245                 250                 255

Asp Arg Tyr Gly Ser Thr Phe Glu Met Ser Arg Asp Leu Met Thr Ala
            260                 265                 270

Leu Ser Tyr Asn Arg Ser Arg Glu Arg Lys Ile Ile Phe Glu Asn Val
        275                 280                 285

Glu Ser Thr Lys Pro Leu Pro Lys Val Ala Ser Gly Pro Thr Ala Ser
    290                 295                 300

Val Lys Leu Ser Pro Pro Thr Pro Thr Val Leu Thr Gln Glu Ser Arg
305                 310                 315                 320

Leu Asp Gln Thr Asn Gln Thr Asp Ala Leu Gln Pro Pro Thr Lys Lys
                325                 330                 335

Lys Lys Ser Gly Arg Phe Leu Gly Thr Leu Phe Lys Ile Leu Phe Ser
            340                 345                 350

Phe Phe Ile Val Gly Val Ala Leu Phe Thr Tyr Leu Ile Leu Thr Lys
```

```
            355                 360                 365
Pro Thr Ser Val Lys Val Pro Asn Val Ala Gly Thr Ser Leu Lys Val
    370                 375                 380

Ala Lys Gln Glu Leu Tyr Asp Val Gly Leu Lys Val Gly Lys Ile Arg
385                 390                 395                 400

Gln Ile Glu Ser Asp Thr Val Ala Glu Gly Asn Val Val Arg Thr Asp
                405                 410                 415

Pro Lys Ala Gly Thr Ala Lys Arg Gln Gly Ser Ser Ile Thr Leu Tyr
            420                 425                 430

Val Ser Ile Gly Asn Lys Gly Phe Asp Met Glu Asn Tyr Lys Gly Leu
        435                 440                 445

Asp Tyr Gln Glu Ala Met Asn Ser Leu Ile Glu Thr Tyr Gly Val Pro
    450                 455                 460

Lys Ser Lys Ile Lys Ile Glu Arg Ile Val Thr Asn Glu Tyr Pro Glu
465                 470                 475                 480

Asn Thr Val Ile Ser Gln Ser Pro Ser Ala Gly Asp Lys Phe Asn Pro
                485                 490                 495

Asn Gly Lys Ser Lys Ile Thr Leu Ser Val Ala Val Ser Asp Thr Ile
            500                 505                 510

Thr Met Pro Met Val Thr Glu Tyr Ser Tyr Ala Asp Ala Val Asn Thr
        515                 520                 525

Leu Thr Ala Leu Gly Ile Asp Ala Ser Arg Ile Lys Ala Tyr Val Pro
    530                 535                 540

Ser Ser Ser Ser Ala Thr Gly Phe Val Pro Ile His Ser Pro Ser Ser
545                 550                 555                 560

Lys Ala Ile Val Ser Gly Gln Ser Pro Tyr Tyr Gly Thr Ser Leu Ser
                565                 570                 575

Leu Ser Asp Lys Gly Glu Ile Ser Leu Tyr Leu Tyr Pro Glu Glu Thr
            580                 585                 590

His Ser Ser Ser Ser Ser Ser Ser Thr Ser Ser Ser Asn Ser Ser
        595                 600                 605

Ser Ile Asn Asp Ser Thr Ala Pro Gly Ser Asn Thr Glu Leu Ser Pro
    610                 615                 620

Ser Glu Thr Thr Ser Gln Thr Pro
625                 630

<210> SEQ ID NO 73
<211> LENGTH: 1899
<212> TYPE: DNA
<213> ORGANISM: Streptococcus pyogenes

<400> SEQUENCE: 73
atgattcaga ttggcaaatt atttgctggt cgttatcgca ttctgaaatc tattggccgc      60
ggtggtatgg cggatgttta tttagcaaat gacttgatct tggataatga agacgttgca     120
atcaaggtct tgcgtaccaa ttatcaaaca gatcaggtag cagttgcgcg tttccaacga     180
gaagcgcggg ccatggctga attgaaccat cccaatattg ttgccatccg ggatataggt     240
gaagaagacg gacagcaatt tttagtaatg gaatatgtgg atggtgctga cctaaagaga     300
tacattcaaa atcatgctcc attatctaat aatgaagtgg ttagaattat ggaagaagtc     360
ctttctgcta tgactttagc ccaccaaaaa ggaattgtac acagagattt aaaacctcaa     420
aatatcctac taactaagga gggtgttgtc aaagtaactg atttcggcat cgcagtagcc     480
tttgcagaaa aagcttgac acaaactaat tcgatgttag cagtgttca ttacttgtct     540 ccagaacagg ctcgcggctc caaagcgacg attcaaagtg atatttatgc gatggggatt     600
```

-continued

```
atgctctttg agatgttgac aggccatatc ccttatgacg gcgatagtgc tgttacgatt    660
gccttgcaac attttcaaaa gcctcttcca tctattatcg aggagaacca caatgtgcca    720
caagctttgg agaatgttgt tattcgagca acagccaaga aattaagtga tcgttacggg    780
tcaacctttg aaatgagtcg tgacttaatg acggcgctta gttataatcg tagtcgggag    840
cgtaagatta tctttgagaa tgttgaaagt accaaacccc tccccaaagt ggcctcaggt    900
cccaccgctt ctgtaaaatt gtctccccct accccaacag tgttaacaca ggaaagtcga    960
ttagatcaaa ctaatcaaac agatgcttta cagccccccca ccaaaaagaa aaaagtggt   1020 cgttttttag gtactttatt caaaattctt ttttctttct ttattgtagg tgtagcactc   1080
tttacttatc ttatactaac taaaccaact tctgtgaaag ttcctaatgt agcaggcact   1140
agtcttaaag ttgccaaaca agaactgtat gatgttgggc taaaagtggg taaaatcagg   1200
caaattgaga gtgatacggt tgctgaggga aatgtagtta acagatcc taaagcagga    1260 acagctaaga ggcaaggctc aagcattacg ctttatgtgt caattggaaa caaaggtttt   1320
gacatggaaa actacaaagg actagattat caagaagcta tgaatagttt gatagaaact   1380
tatggtgttc caaatcaaa aatcaaaatt gagcgcattg taactaatga atatcctgaa   1440
aatacagtca tcagtcaatc gccaagtgcg ggtgataaat ttaatccaaa cggaaagtct   1500 aaaattcgc tcagtgttgc tgttagtgat acgatcacta tgcctatggt aacagaatat   1560
agttatgcag atgcagtcaa taccttaaca gctttaggta tagatgcatc tagaataaaa   1620
gcttatgtgc caagctctag ctcagcaacg ggctttgtgc caattcattc tcctagttct   1680
aaagctattg tcagtggtca atctccttac tatggaacgt ctttgagtct gtctgataaa   1740
ggagagatta gtctttacct ttatccagaa gaaacacact cttctagtag ctcatcgagt   1800
tcaacgtcaa gttcaaacag ttcttcaata aatgatagta ctgcaccagg tagcaacact   1860
gaattaagcc catcagaaac tacttctcaa acaccttaa                           1899
```

<210> SEQ ID NO 74
<211> LENGTH: 423
<212> TYPE: PRT
<213> ORGANISM: Streptococcus pyogenes

<400> SEQUENCE: 74

```
Met Asp Leu Ile Leu Phe Leu Leu Val Leu Val Leu Leu Gly Leu Gly
 1               5                  10                  15

Ala Tyr Leu Leu Phe Lys Val Asn Gly Leu Gln His Gln Leu Ala Gln
            20                  25                  30

Thr Leu Glu Gly Asn Ala Asp Asn Leu Ser Asp Gln Met Thr Tyr Gln
        35                  40                  45

Leu Asp Thr Ala Asn Lys Gln Gln Leu Leu Glu Leu Thr Gln Leu Met
    50                  55                  60

Asn Arg Gln Gln Ala Gly Leu Tyr Gln Gln Leu Thr Asp Ile Arg Asp
65                  70                  75                  80

Val Leu His Arg Ser Leu Ser Asp Ser Arg Asp Arg Ser Asp Lys Arg
                85                  90                  95

Leu Glu Lys Ile Asn Gln Gln Val Asn Gln Ser Leu Lys Asn Met Gln
            100                 105                 110

Glu Ser Asn Glu Lys Arg Leu Glu Lys Met Arg Gln Ile Val Glu Glu
        115                 120                 125

Lys Leu Glu Glu Thr Leu Lys Asn Arg Leu His Ala Ser Phe Asp Ser
    130                 135                 140
```

```
Val Ser Lys Gln Leu Glu Ser Val Asn Lys Gly Leu Gly Glu Met Arg
145                 150                 155                 160

Ser Val Ala Gln Asp Val Gly Thr Leu Asn Lys Val Leu Ser Asn Thr
                165                 170                 175

Lys Thr Arg Gly Ile Leu Gly Glu Leu Gln Leu Gly Gln Ile Ile Glu
            180                 185                 190

Asp Ile Met Thr Ser Ser Gln Tyr Glu Arg Glu Phe Val Thr Val Ser
            195                 200                 205

Gly Ser Ser Glu Arg Val Glu Tyr Ala Ile Lys Leu Pro Gly Asn Gly
210                 215                 220

Gln Gly Gly Tyr Ile Tyr Leu Pro Ile Asp Ser Lys Phe Pro Leu Glu
225                 230                 235                 240

Asp Tyr Tyr Arg Leu Glu Asp Ala Tyr Glu Val Gly Asp Lys Leu Ala
                245                 250                 255

Ile Glu Ala Ser Arg Lys Ala Leu Leu Ala Ala Ile Lys Arg Phe Ala
                260                 265                 270

Lys Asp Ile His Lys Lys Tyr Leu Asn Pro Pro Glu Thr Thr Asn Phe
            275                 280                 285

Gly Val Met Phe Leu Pro Thr Glu Gly Leu Tyr Ser Glu Val Val Arg
            290                 295                 300

Asn Ala Ser Phe Phe Asp Ser Leu Arg Arg Glu Glu Asn Ile Val Val
305                 310                 315                 320

Ala Gly Pro Ser Thr Leu Ser Ala Leu Leu Asn Ser Leu Ser Val Gly
                325                 330                 335

Phe Lys Thr Leu Asn Ile Gln Lys Asn Ala Asp Asp Ile Ser Lys Ile
                340                 345                 350

Leu Gly Asn Val Lys Leu Glu Phe Asp Lys Phe Gly Gly Leu Leu Ala
            355                 360                 365

Lys Ala Gln Lys Gln Met Asn Thr Ala Asn Thr Leu Asp Gln Leu
            370                 375                 380

Ile Ser Thr Arg Thr Asn Ala Ile Val Arg Ala Leu Asn Thr Val Glu
385                 390                 395                 400

Thr Tyr Gln Asp Gln Ala Thr Lys Ser Leu Leu Asn Met Pro Leu Leu
                405                 410                 415

Glu Glu Glu Asn Asn Glu Asn
            420

<210> SEQ ID NO 75
<211> LENGTH: 1272
<212> TYPE: DNA
<213> ORGANISM: Streptococcus pyogenes

<400> SEQUENCE: 75 atggaccta tcttgttcct tttggtcttg gttctcttag gtttaggggc ttatctgttg      60
ttcaaagtca acggccttca acatcagctt gcccaaaccc tagaaggcaa cgcggataat    120
ttgtctgacc aaatgaccta ccagttggat acagctaaca acaacaatt gttagagcta    180 acacagctga tgaaccgaca caagcaggc ctttaccaac aattaacaga tattcgtgac    240
gtcttgcacc gtagtttgtc tgatagtagg gaccggtctg acaaacgctt agaaaaaatt    300
aaccagcagg tcaaccaatc gctcaaaaat atgcaagaat ctaacgaaaa acgtttggag    360
aaaatgcgcc agatcgttga agaaaaattg gaagaaacct taaaaaatcg tctgcacgcc    420
tctttcgatt ctgtatccaa gcaactagaa agtgtcaata aaggcttggg agaaatgcgt    480
agcgtggctc aagatgtggg tactttaaat aaggttttgt ccaataccaa acacgaggc     540
```

-continued

```
attttaggcg aacttcaact aggccaaatc attgaggata tcatgacatc aagccagtac    600
gaaagagaat ttgtaacggt tagtggttct agtgaacgcg tagaatatgc gattaagctc    660
ccaggaaatg gtcaaggcgg ttatatttac ctaccgattg actcaaaatt ccctcttgaa    720
gattattacc gattagaaga tgcttacgaa gttggtgata aactggccat cgaggctagc    780
cgaaaagcac ttctggcagc tatcaaacgc tttgccaaag acattcataa aaagtacttg    840
aaccccccag agacgaccaa tttcggagtt atgttcttac caacagaagg tctttattca    900
gaagtggtca gaaatgcgtc tttctttgat agccttcgtc gggaagaaaa tattgtggtt    960
gcaggccctt cgaccctgtc tgctttgctg aattccttat ctgttggttt caagaccctt   1020
aatatccaaa aaatgctga tgacatcagt aaaattttag gcaatgtcaa gttagaattc   1080
gataaatttg gcggcctgct tgccaaggct caaaaacaaa tgaatacagc taataatacg   1140
ctggatcagc tcatttcaac aaggacaaat gccattgttc gagccttgaa taccgttgaa   1200
acttatcaag accaagcaac aaaatctctc ttgaacatgc ccttattaga agaggaaaat   1260
aatgaaaatt aa                                                       1272
```

<210> SEQ ID NO 76
<211> LENGTH: 420
<212> TYPE: PRT
<213> ORGANISM: Streptococcus pyogenes

<400> SEQUENCE: 76

```
Met Thr Lys Glu Lys Leu Val Ala Phe Ser Gln Ala His Ala Glu Pro
  1               5                  10                  15

Ala Trp Leu Gln Glu Arg Arg Leu Ala Ala Leu Glu Ala Ile Pro Asn
             20                  25                  30

Leu Glu Leu Pro Thr Ile Glu Arg Val Lys Phe His Arg Trp Asn Leu
         35                  40                  45

Gly Asp Gly Thr Leu Thr Glu Asn Glu Ser Leu Ala Ser Val Pro Asp
     50                  55                  60

Phe Ile Ala Ile Gly Asp Asn Pro Lys Leu Val Gln Val Gly Thr Gln
 65                  70                  75                  80

Thr Val Leu Glu Gln Leu Pro Met Ala Leu Ile Asp Lys Gly Val Val
                 85                  90                  95

Phe Ser Asp Phe Tyr Thr Ala Leu Glu Glu Ile Pro Glu Val Ile Glu
            100                 105                 110

Ala His Phe Gly Gln Ala Leu Ala Phe Asp Glu Asp Lys Leu Ala Ala
        115                 120                 125

Tyr His Thr Ala Tyr Phe Asn Ser Ala Ala Val Leu Tyr Val Pro Asp
    130                 135                 140

His Leu Glu Ile Thr Thr Pro Ile Glu Ala Ile Phe Leu Gln Asp Ser
145                 150                 155                 160

Asp Ser Asp Val Pro Phe Asn Lys His Val Leu Val Ile Ala Gly Lys
                165                 170                 175

Glu Ser Lys Phe Thr Tyr Leu Glu Arg Phe Glu Ser Ile Gly Asn Ala
            180                 185                 190

Thr Gln Lys Ile Ser Ala Asn Ile Ser Val Glu Val Ile Ala Gln Ala
        195                 200                 205

Gly Ser Gln Ile Lys Phe Ser Ala Ile Asp Arg Leu Gly Pro Ser Val
    210                 215                 220

Thr Thr Tyr Ile Ser Arg Arg Gly Arg Leu Glu Lys Asp Ala Asn Ile
225                 230                 235                 240

Asp Trp Ala Leu Ala Val Met Asn Glu Gly Asn Val Ile Ala Asp Phe
```

```
                245                 250                 255
Asp Ser Asp Leu Ile Gly Gln Gly Ser Gln Ala Asp Leu Lys Val Val
            260                 265                 270

Ala Ala Ser Ser Gly Arg Gln Val Gln Gly Ile Asp Thr Arg Val Thr
            275                 280                 285

Asn Tyr Gly Gln Arg Thr Val Gly His Ile Leu Gln His Gly Val Ile
        290                 295                 300

Leu Glu Arg Gly Thr Leu Thr Phe Asn Gly Ile Gly His Ile Leu Lys
305                 310                 315                 320

Asp Ala Lys Gly Ala Asp Ala Gln Gln Glu Ser Arg Val Leu Met Leu
                325                 330                 335

Ser Asp Gln Ala Arg Ala Asp Ala Asn Pro Ile Leu Leu Ile Asp Glu
            340                 345                 350

Asn Glu Val Thr Ala Gly His Ala Ala Ser Ile Gly Gln Val Asp Pro
            355                 360                 365

Glu Asp Met Tyr Tyr Leu Met Ser Arg Gly Leu Asp Gln Glu Thr Ala
        370                 375                 380

Glu Arg Leu Val Ile Arg Gly Phe Leu Gly Ala Val Ile Ala Glu Ile
385                 390                 395                 400

Pro Ile Pro Ser Val Arg Gln Glu Ile Ile Lys Val Leu Asp Glu Lys
                405                 410                 415

Leu Leu Asn Arg
            420

<210> SEQ ID NO 77
<211> LENGTH: 1263
<212> TYPE: DNA
<213> ORGANISM: Streptococcus pyogenes

<400> SEQUENCE: 77
atgacaaaag aaaaactagt ggcttttteg caagcccacg ctgagcctgc ttggctgcaa      60
gaacggcgtt tagcggcatt agaagccatt ccaaatttgg aattaccaac catcgaaagg     120
gttaaatttc accgttggaa tctaggagat ggtaccttaa cagaaaatga agtctagct      180 agtgttccag attttatagc tattggagat aacccaaagc ttgttcaggt aggcacgcaa     240
acagtcttag aacagttacc aatggcgtta attgacaagg gagttgtttt cagtgatttt     300
tatacggcgc ttgaggaaat cccagaagta attgaagctc attttggtca ggcattagct     360
tttgatgaag acaaactagc tgcctaccac actgcttatt ttaatagcgc agccgtgctc     420
tacgttcctg atcacttgga atcacaact cctattgaag ctattttctt acaagatagt     480
gacagtgacg ttcctttaa caagcatgtt ctagtgattg caggaaaaga agtaagttc      540 acctatttag agcgttttga atctattggc aatgccactc aaaagatcag cgctaatatc     600
agtgtagaag tgattgctca agcaggcagc cagattaaat tctcggctat cgaccgctta     660
ggtccttcag tgacaaccta tattagccgt cgaggacgtt tagagaagga tgccaacatt     720
gattgggcct tagctgtgat gaatgaaggc aatgtcattg ctgattttga cagtgatttg     780
attggtcagg gctcacaagc tgatttgaaa gttgttgcag cctcaagtgg tcgtcaggta     840
caaggtattg acacgcgcgt gaccaactat ggtcaacgta cggtcggtca tattttacag     900
catggtgtga ttttggaacg tggcacctta acgtttaacg ggattggtca tattctaaaa     960
gacgctaagg gagctgatgc tcaacaagaa agccgtgttt tgatgctttc tgaccaagca    1020
agagccgatg ccaatccaat cctcttaatt gatgaaaatg aagtaacagc aggtcatgca    1080
gcttctatcg gtcaggttga ccctgaagat atgtattact tgatgagtcg aggactggat    1140
```

-continued caagaaacag cagaacgatt ggttattaga ggattcctag gagcggttat cgctgaaatt    1200
cctattccat cagtccgcca agagattatt aaggttttag atgagaaatt gcttaatcgt    1260
taa                                                                   1263

<210> SEQ ID NO 78
<211> LENGTH: 184
<212> TYPE: PRT
<213> ORGANISM: Streptococcus pyogenes

<400> SEQUENCE: 78

Met Lys Trp Ser Gly Phe Met Lys Thr Lys Ser Lys Arg Phe Leu Asn
1               5                   10                  15

Leu Ala Thr Leu Cys Leu Ala Leu Leu Gly Thr Thr Leu Leu Met Ala
            20                  25                  30

His Pro Val Gln Ala Glu Val Ile Ser Lys Arg Asp Tyr Met Thr Arg
        35                  40                  45

Phe Gly Leu Gly Asp Leu Glu Asp Asp Ser Ala Asn Tyr Pro Ser Asn
    50                  55                  60

Leu Glu Ala Arg Tyr Lys Gly Tyr Leu Glu Gly Tyr Glu Lys Gly Leu
65                  70                  75                  80

Lys Gly Asp Asp Ile Pro Glu Arg Pro Lys Ile Gln Val Pro Glu Asp
                85                  90                  95

Val Gln Pro Ser Asp His Gly Asp Tyr Arg Asp Gly Tyr Glu Glu Gly
            100                 105                 110

Phe Gly Glu Gly Gln His Lys Arg Asp Pro Leu Glu Thr Glu Ala Glu
        115                 120                 125

Asp Asp Ser Gln Gly Gly Arg Gln Glu Gly Arg Gln Gly His Gln Glu
    130                 135                 140

Gly Ala Asp Ser Ser Asp Leu Asn Val Glu Glu Ser Asp Gly Leu Ser
145                 150                 155                 160

Val Ile Asp Glu Val Val Gly Val Ile Tyr Gln Ala Phe Ser Thr Ile
                165                 170                 175

Trp Thr Tyr Leu Ser Gly Leu Phe
            180

<210> SEQ ID NO 79
<211> LENGTH: 555
<212> TYPE: DNA
<213> ORGANISM: Streptococcus pyogenes

<400> SEQUENCE: 79
atgaaatgga gtggttttat gaaaacaaaa tcaaaacgct ttttaaaccct agcaacccctt     60 tgcttggccc tactaggaac aactttgcta atggcacatc ccgtacaggc ggaggtgata    120
tcaaaaagag actatatgac tcgcttcggg ttaggcgatt tagaagatga ttcagctaac    180
tatccttcaa atttagaagc tagatataaa ggatatttag gggatatga aaaaggctta    240 aaaggagatg atataccccga acggcccaag attcaggttc ctgaggatgt tcagccatct    300
gaccatggcg actatagaga tggttatgag aaggatttg gagaaggaca acataaacgt    360
gatccattag aaacagaagc agaagatgat tctcaaggag acgtcaaga aggacgtcaa    420 ggacatcaag aaggagcaga ttctagtgat ttgaacgttg aagaaagcga cggtttgtct    480
gttattgatg aagtagttgg agtaatttat caagcattta gtactatttg gacatactta    540
agcggtttgt tctaa                                                      555

```
<210> SEQ ID NO 80
<211> LENGTH: 32
<212> TYPE: PRT
<213> ORGANISM: Streptococcus pyogenes

<400> SEQUENCE: 80

Met Lys Trp Ser Gly Phe Met Lys Thr Lys Ser Lys Arg Phe Leu Asn
 1               5                  10                  15

Leu Ala Thr Leu Cys Leu Ala Leu Leu Gly Thr Thr Leu Leu Met Ala
             20                  25                  30

<210> SEQ ID NO 81
<211> LENGTH: 152
<212> TYPE: PRT
<213> ORGANISM: Streptococcus pyogenes

<400> SEQUENCE: 81

His Pro Val Gln Ala Glu Val Ile Ser Lys Arg Asp Tyr Met Thr Arg
 1               5                  10                  15

Phe Gly Leu Gly Asp Leu Glu Asp Ser Ala Asn Tyr Pro Ser Asn
             20                  25                  30

Leu Glu Ala Arg Tyr Lys Gly Tyr Leu Glu Gly Tyr Glu Lys Gly Leu
             35                  40                  45

Lys Gly Asp Asp Ile Pro Glu Arg Pro Lys Ile Gln Val Pro Glu Asp
 50                  55                  60

Val Gln Pro Ser Asp His Gly Asp Tyr Arg Asp Gly Tyr Glu Glu Gly
 65                  70                  75                  80

Phe Gly Glu Gly Gln His Lys Arg Asp Pro Leu Glu Thr Glu Ala Glu
             85                  90                  95

Asp Asp Ser Gln Gly Gly Arg Gln Gly Arg Gln Gly His Gln Glu
            100                 105                 110

Gly Ala Asp Ser Ser Asp Leu Asn Val Glu Glu Ser Asp Gly Leu Ser
            115                 120                 125

Val Ile Asp Glu Val Val Gly Val Ile Tyr Gln Ala Phe Ser Thr Ile
            130                 135                 140

Trp Thr Tyr Leu Ser Gly Leu Phe
145                 150

<210> SEQ ID NO 82
<211> LENGTH: 180
<212> TYPE: PRT
<213> ORGANISM: Streptococcus pyogenes

<400> SEQUENCE: 82

Met Lys His Ile Leu Phe Ile Val Gly Ser Leu Arg Glu Gly Ser Phe
 1               5                  10                  15

Asn His Gln Leu Ala Ala Gln Ala Gln Lys Ala Leu Glu His Gln Ala
             20                  25                  30

Val Val Ser Tyr Leu Asn Trp Lys Asp Val Pro Val Leu Asn Gln Asp
             35                  40                  45

Ile Glu Ala Asn Ala Pro Leu Pro Val Val Asp Ala Arg Gln Ala Val
 50                  55                  60

Gln Ser Ala Asp Ala Ile Trp Ile Phe Thr Pro Val Tyr Asn Phe Ser
 65                  70                  75                  80

Ile Pro Gly Ser Val Lys Asn Leu Leu Asp Trp Leu Ser Arg Ala Leu
             85                  90                  95

Asp Leu Ser Asp Pro Thr Gly Pro Ser Ala Ile Gly Gly Lys Val Val
            100                 105                 110
```

```
Thr Val Ser Ser Val Ala Asn Gly Gly His Asp Gln Val Phe Asp Gln
        115                 120                 125

Phe Lys Ala Leu Leu Pro Phe Ile Arg Thr Ser Val Ala Gly Glu Phe
130                 135                 140

Thr Lys Ala Thr Val Asn Pro Asp Ala Trp Gly Thr Gly Arg Leu Glu
145                 150                 155                 160

Ile Ser Lys Glu Thr Lys Ala Asn Leu Leu Ser Gln Ala Glu Ala Leu
                165                 170                 175

Leu Ala Ala Ile
        180

<210> SEQ ID NO 83
<211> LENGTH: 543
<212> TYPE: DNA
<213> ORGANISM: Streptococcus pyogenes

<400> SEQUENCE: 83
atgaaacata ttttatttat tgttggctcg cttcgtgaag ggtcttttaa ccatcaatta      60
gcggctcaag cacaaaaagc tctggaacat caagcagttg tatcttactt aaattggaaa     120
gacgttcctg ttttgaatca agatatcgaa gctaatgcac ctttaccagt tgttgacgct     180
cgtcaagctg ttcagtcagc ggatgctatc tggattttta caccagttta caacttctct     240
attccaggtt ctgttaaaaa cctgctagac tggttgtctc gtgctcttga tttgtctgat     300
ccgacgggcc catctgctat tggcggtaag gtggttacgg tctcttcagt tgcaaatggc     360
gggcatgatc aagtatttga tcagtttaaa gcactattgc cgtttatccg aacttcagta     420
gcaggagagt ttacaaaagc aactgtgaat cctgatgcct ggggaacagg aaggcttgag     480
atttcaaaag agacaaaagc aaacttgcta tctcaggcag aggctctttt agcggctatt     540
tag                                                                   543

<210> SEQ ID NO 84
<211> LENGTH: 256
<212> TYPE: PRT
<213> ORGANISM: Streptococcus pyogenes

<400> SEQUENCE: 84

Met Thr Asp Val Ser Arg Ile Leu Lys Glu Ala Arg Asp Gln Gly Arg
1               5                   10                  15

Leu Thr Thr Leu Asp Tyr Ala Asn Leu Ile Phe Asp Asp Phe Met Glu
            20                  25                  30

Leu His Gly Asp Arg His Phe Ser Asp Asp Gly Ala Ile Val Gly Gly
        35                  40                  45

Leu Ala Tyr Leu Ala Gly Gln Pro Val Thr Val Ile Gly Ile Gln Lys
    50                  55                  60

Gly Lys Asn Leu Gln Asp Asn Leu Ala Arg Asn Phe Gly Gln Pro Asn
65                  70                  75                  80

Pro Glu Gly Tyr Arg Lys Ala Leu Arg Leu Met Lys Gln Ala Glu Lys
                85                  90                  95

Phe Gly Arg Pro Val Val Thr Phe Ile Asn Thr Ala Gly Ala Tyr Pro
            100                 105                 110

Gly Val Gly Ala Glu Glu Arg Gly Gln Gly Glu Ala Ile Ala Lys Asn
        115                 120                 125

Leu Met Glu Met Ser Asp Leu Lys Val Pro Ile Ile Ala Ile Ile Ile
    130                 135                 140

Gly Glu Gly Gly Ser Gly Gly Ala Leu Ala Leu Ala Val Ala Asp Gln
145                 150                 155                 160
```

```
Val Trp Met Leu Glu Asn Thr Met Tyr Ala Val Leu Ser Pro Glu Gly
            165                 170                 175

Phe Ala Ser Ile Leu Trp Lys Asp Gly Ser Arg Ala Thr Glu Ala Ala
        180                 185                 190

Glu Leu Met Lys Ile Thr Ala Gly Glu Leu Tyr Lys Met Gly Ile Val
        195                 200                 205

Asp Arg Ile Ile Pro Glu His Gly Tyr Phe Ser Ser Glu Ile Val Asp
    210                 215                 220

Ile Ile Lys Ala Asn Leu Ile Glu Gln Ile Thr Ser Leu Gln Ala Lys
225                 230                 235                 240

Pro Leu Asp Gln Leu Leu Asp Glu Arg Tyr Gln Arg Phe Arg Lys Tyr
                245                 250                 255

<210> SEQ ID NO 85
<211> LENGTH: 771
<212> TYPE: DNA
<213> ORGANISM: Streptococcus pyogenes

<400> SEQUENCE: 85
atgacagatg tatcaagaat tttaaaagaa gcgcgtgatc aagggcgttt aacaactttg      60
gattacgcca accttatttt cgatgacttt atggaactgc atggcgatcg ccattttca     120 gatgatggtg ccattgtagg tggcctagct tatttggcgg acaacctgt tacggtcatt     180 ggtattcaaa aggtaagaa tttacaggat aatttggcaa ggaattttgg ccagcccaat     240
ccagaaggtt atcgtaaagc tttgcgcctt atgaaacagg cagaaaaatt ggacgacca     300 gttgttacgt ttatcaatac tgcaggagcc tatccaggtg tcggtgcgga agaacgagga     360
cagggtgagg ccattgctaa aaatttgatg gaaatgagtg atctcaaggt tcccattatc     420
gccatcatta ttggtgaagg aggctctggt ggtgcattag ccttagcggt tgccgatcag     480
gtctggatgc ttgaaaatac tatgtatgcg gttcttagcc cagaaggctt tgcttctatt     540
ttatggaagg atggttcaag ggcgaccgag gccgctgaat tgatgaaaat cacagcgggt     600
gaactctaca aaatgggaat agtagaccgt attattccag aacatggtta tttttcaagt     660
gaaatcgttg acatcatcaa agctaacctc atcgaacaaa taaccagttt gcaagctaag     720
ccattagacc aattattaga tgagcgctac caacgctttc gtaaatatta a             771

<210> SEQ ID NO 86
<211> LENGTH: 448
<212> TYPE: PRT
<213> ORGANISM: Streptococcus pyogenes

<400> SEQUENCE: 86

Met Ala Ile Thr Val Ala Asp Ile Arg Arg Glu Val Lys Glu Lys Asn
  1               5                  10                  15

Val Thr Phe Leu Arg Leu Met Phe Thr Asp Ile Met Gly Val Met Lys
            20                  25                  30

Asn Val Glu Ile Pro Ala Thr Lys Glu Gln Leu Asp Lys Val Leu Ser
        35                  40                  45

Asn Lys Val Met Phe Asp Gly Ser Ser Ile Glu Gly Phe Val Arg Ile
    50                  55                  60

Asn Glu Ser Asp Met Tyr Leu Tyr Pro Asp Leu Asp Thr Trp Ile Val
65                  70                  75                  80

Phe Pro Trp Gly Asp Glu Asn Gly Ala Val Ala Gly Leu Ile Cys Asp
                85                  90                  95

Ile Tyr Thr Ala Glu Gly Lys Pro Phe Ala Gly Asp Pro Arg Gly Asn
```

```
                 100                 105                 110
Leu Lys Arg Ala Leu Lys His Met Asn Glu Ile Gly Tyr Lys Ser Phe
            115                 120                 125
Asn Leu Gly Pro Glu Pro Glu Phe Phe Leu Phe Lys Met Asp Asp Lys
            130                 135                 140
Gly Asn Pro Thr Leu Glu Val Asn Asp Asn Gly Tyr Phe Asp Leu
145                 150                 155                 160
Ala Pro Ile Asp Leu Ala Asp Asn Thr Arg Arg Glu Ile Val Asn Ile
            165                 170                 175
Leu Thr Lys Met Gly Phe Glu Val Glu Ala Ser His His Glu Val Ala
            180                 185                 190
Val Gly Gln His Glu Ile Asp Phe Lys Tyr Ala Asp Val Leu Lys Ala
            195                 200                 205
Cys Asp Asn Ile Gln Ile Phe Lys Leu Val Val Lys Thr Ile Ala Arg
            210                 215                 220
Glu His Gly Leu Tyr Ala Thr Phe Met Ala Lys Pro Lys Phe Gly Ile
225                 230                 235                 240
Ala Gly Ser Gly Met His Cys Asn Met Ser Leu Phe Asp Asn Gln Gly
            245                 250                 255
Asn Asn Ala Phe Tyr Asp Glu Ala Asp Lys Arg Gly Met Gln Leu Ser
            260                 265                 270
Glu Asp Ala Tyr Tyr Phe Leu Gly Gly Leu Met Lys His Ala Tyr Asn
            275                 280                 285
Tyr Thr Ala Ile Thr Asn Pro Thr Val Asn Ser Tyr Lys Arg Leu Val
            290                 295                 300
Pro Gly Tyr Glu Ala Pro Val Tyr Val Ala Trp Ala Gly Ser Asn Arg
305                 310                 315                 320
Ser Pro Leu Ile Arg Val Pro Ala Ser Arg Gly Met Gly Thr Arg Leu
            325                 330                 335
Glu Leu Arg Ser Val Asp Pro Thr Ala Asn Pro Tyr Leu Ala Leu Ala
            340                 345                 350
Val Leu Leu Glu Ala Gly Leu Asp Gly Ile Ile Asn Lys Ile Glu Ala
            355                 360                 365
Pro Glu Pro Val Glu Ala Asn Ile Tyr Thr Met Thr Met Glu Glu Arg
370                 375                 380
Asn Glu Ala Gly Ile Ile Asp Leu Pro Ser Thr Leu His Asn Ala Leu
385                 390                 395                 400
Lys Ala Leu Gln Lys Asp Asp Val Val Gln Lys Ala Leu Gly Tyr His
            405                 410                 415
Ile Tyr Thr Asn Phe Leu Glu Ala Lys Arg Ile Glu Trp Ser Ser Tyr
            420                 425                 430
Ala Thr Phe Val Ser Gln Trp Glu Ile Asp His Tyr Ile His Asn Tyr
            435                 440                 445

<210> SEQ ID NO 87
<211> LENGTH: 1347
<212> TYPE: DNA
<213> ORGANISM: Streptococcus pyogenes

<400> SEQUENCE: 87
atggcaataa cagtagctga cattcgtcgt gaagtcaaag aaaaaaatgt aacgtttctt       60
cgcttgatgt tcactgatat catgggcgtt atgaaaaatg tggagattcc tgcaactaaa      120
gaacagttag acaaagtatt gtctaacaag gttatgtttg atggttcatc tatcgaaggt      180
tttgtacgga tcaatgagtc agatatgtac ctttaccccg atttagacac ttggattgtt      240
```

```
tttccctggg gagatgaaaa tggagcagtt gcaggtttaa tttgtgatat ttatacagca    300
gaaggaaagc cttttgcagg agatcctaga ggaaatttaa aaagagccct gaaacacatg    360
aacgagatcg gctacaaatc atttaatctt ggaccagaac cagaattttt ccttttttaag   420 atggatgata aaggtaatcc gacacttgaa gttaacgata atggtggtta ttttgattta    480
gcgccaattg acttagcaga caacacgcgc cgtgaaattg tgaatatttt aacgaaaatg    540
ggttttgaag tggaagctag tcatcatgaa gtggctgttg gtcaacatga gattgatttt    600
aaatatgcag atgttttgaa agcttgtgat aatattcaaa ttttttaagct agttgtaaaa    660 acgattgccc gtgaacatgg actttatgct actttcatgg ctaaaccaaa atttggaata    720
gctggatcag ggatgcactg taacatgtct ttgtttgata accaaggtaa taatgctttt    780
tatgatgaag ctgataagcg agggatgcag ttatcagaag atgcttatta tttcttggga    840
ggactaatga agcatgctta taactacact gctatcacta accctacagt gaattcttat    900
aaacgattag ttccaggtta tgaggcacct gtttatgtcg cttgggctgg aagtaatcgt    960
tcaccgctta tccgtgttcc agcatcacgt ggtatgggaa cgcgtttgga gttacgttcg   1020
gttgatccga cagctaatcc ttatttagcc ttggctgttc tcttggaagc tggattagat   1080
ggtatcatta acaaaattga agctccagaa cccgttgaag ctaacattta taccatgaca   1140
atggaagaac gaaatgaagc aggcattatt gatttgccat caacgcttca taatgcctta   1200
aaagctcttc aaaaagatga tgtggtacaa aaggcactag gttaccatat ctacactaat   1260
ttcttagaag caaaacgaat tgaatggtct tcctatgcaa cttttgtttc tcaatgggaa   1320
attgaccatt atattcataa ttattag                                      1347
```

<210> SEQ ID NO 88
<211> LENGTH: 520
<212> TYPE: PRT
<213> ORGANISM: Streptococcus pyogenes

<400> SEQUENCE: 88

```
Met Thr Glu Ile Ser Ile Leu Asn Asp Val Gln Lys Ile Ile Val Leu
  1               5                  10                  15

Asp Tyr Gly Ser Gln Tyr Asn Gln Leu Ile Ala Arg Arg Ile Arg Glu
                 20                  25                  30

Phe Gly Val Phe Ser Glu Leu Lys Ser His Lys Ile Thr Ala Gln Glu
             35                  40                  45

Leu Arg Glu Ile Asn Pro Ile Gly Ile Val Leu Ser Gly Gly Pro Asn
         50                  55                  60

Ser Val Tyr Ala Asp Asn Ala Phe Gly Ile Asp Pro Glu Ile Phe Glu
 65                  70                  75                  80

Leu Gly Ile Pro Ile Leu Gly Ile Cys Tyr Gly Met Gln Leu Ile Thr
                 85                  90                  95

His Lys Leu Gly Gly Lys Val Val Pro Ala Gly Gln Ala Gly Asn Arg
            100                 105                 110

Glu Tyr Gly Gln Ser Thr Leu His Leu Arg Glu Thr Ser Lys Leu Phe
        115                 120                 125

Ser Gly Thr Pro Gln Glu Gln Leu Val Leu Met Ser His Gly Asp Ala
    130                 135                 140

Val Thr Glu Ile Pro Glu Gly Phe His Leu Val Gly Asp Ser Asn Asp
145                 150                 155                 160

Cys Pro Tyr Ala Ala Ile Glu Asn Thr Glu Lys Asn Leu Tyr Gly Ile
                165                 170                 175
```

```
Gln Phe His Pro Glu Val Arg His Ser Val Tyr Gly Asn Asp Ile Leu
            180                 185                 190
Lys Asn Phe Ala Ile Ser Ile Cys Gly Ala Arg Gly Asp Trp Ser Met
        195                 200                 205
Asp Asn Phe Ile Asp Met Glu Ile Ala Lys Ile Arg Glu Thr Val Gly
    210                 215                 220
Asp Arg Lys Val Leu Leu Gly Leu Ser Gly Val Asp Ser Ser Val
225                 230                 235                 240
Val Gly Val Leu Leu Gln Lys Ala Ile Gly Asp Gln Leu Thr Cys Ile
            245                 250                 255
Phe Val Asp His Gly Leu Leu Arg Lys Asp Glu Gly Asp Gln Val Met
        260                 265                 270
Gly Met Leu Gly Gly Lys Phe Gly Leu Asn Ile Ile Arg Val Asp Ala
    275                 280                 285
Ser Lys Arg Phe Leu Asp Leu Leu Ala Asp Val Glu Asp Pro Glu Lys
    290                 295                 300
Lys Arg Lys Ile Ile Gly Asn Glu Phe Val Tyr Val Phe Asp Asp Glu
305                 310                 315                 320
Ala Ser Lys Leu Lys Gly Val Asp Phe Leu Ala Gln Gly Thr Leu Tyr
            325                 330                 335
Thr Asp Ile Ile Glu Ser Gly Thr Glu Thr Ala Gln Thr Ile Lys Ser
        340                 345                 350
His His Asn Val Gly Gly Leu Pro Glu Asp Met Gln Phe Glu Leu Ile
    355                 360                 365
Glu Pro Leu Asn Thr Leu Phe Lys Asp Glu Val Arg Ala Leu Gly Ile
    370                 375                 380
Ala Leu Gly Met Pro Glu Glu Ile Val Trp Arg Gln Pro Phe Pro Gly
385                 390                 395                 400
Pro Gly Leu Ala Ile Arg Val Met Gly Ala Ile Thr Glu Glu Lys Leu
            405                 410                 415
Glu Thr Val Arg Glu Ser Asp Ala Ile Leu Arg Glu Ile Ala Lys
        420                 425                 430
Ala Gly Leu Asp Arg Asp Val Trp Gln Tyr Phe Thr Val Asn Thr Gly
    435                 440                 445
Val Arg Ser Val Gly Val Met Gly Asp Gly Arg Thr Tyr Asp Tyr Thr
450                 455                 460
Ile Ala Ile Arg Ala Ile Thr Ser Ile Asp Gly Met Thr Ala Asp Phe
465                 470                 475                 480
Ala Gln Leu Pro Trp Asp Val Leu Lys Lys Ile Ser Thr Arg Ile Val
            485                 490                 495
Asn Glu Val Asp His Val Asn Arg Ile Val Tyr Asp Ile Thr Ser Lys
        500                 505                 510
Pro Pro Ala Thr Val Glu Trp Glu
        515                 520

<210> SEQ ID NO 89
<211> LENGTH: 1563
<212> TYPE: DNA
<213> ORGANISM: Streptococcus pyogenes

<400> SEQUENCE: 89
atgactgaaa tttcaatttt gaatgatgtt caaaaaatta tcgttcttga ttatggtagc      60
cagtacaatc agcttattgc tagacgtatt cgagagtttg gtgttttctc cgaactaaaa     120
agccataaaa tcaccgctca agaacttcgt gagatcaatc ccataggtat cgttttatca     180
```

-continued

```
ggagggccta actctgttta cgctgataac gcctttggca ttgaccctga aatctttgaa    240
ctagggattc cgattcttgg tatctgttac ggtatgcaat taatcaccca taaattaggt    300
ggtaaagttg ttcctgctgg acaagctggt aatcgtgaat acggtcagtc aacccttcat    360
cttcgtgaaa cgtcaaaatt attttcaggc acacctcaag aacaactcgt tttgatgagc    420
catggtgatg ctgttactga aattccagaa ggtttccacc ttgttggaga ctcaaatgac    480
tgtccctatg cagctattga aaatactgag aaaaaccttt acggtattca gttccaccca    540
gaagtgagac actctgttta tggaaatgac attcttaaaa actttgctat atcaatttgt    600
ggcgcgcgtg gtgattggtc aatggataat tttattgaca tggaaattgc taaaattcgt    660
gaaactgtag gcgatcgtaa agttcttcta ggtctttctg gtggagttga ttcttcagtt    720
gttggtgttc tacttcaaaa agctatcggt gaccaattaa cttgtatttt cgttgatcac    780
ggtcttcttc gtaaagacga gggcgatcaa gttatgggaa tgcttggggg caaatttggc    840
ctaaatatta tccgtgtgga tgcttcaaaa cgtttcttag accttcttgc agacgttgaa    900
gatcctgaga aaaacgtaa aattattggt aatgaatttg tctatgtttt tgatgatgaa    960
gccagcaaat taaaggtgt tgacttcctt gcccaaggaa cactttatac tgatatcatt   1020
gagtcaggaa cagaaactgc tcaaaccatc aaatcacatc acaatgtggg tggtctcccc   1080
gaagacatgc agtttgaatt gattgagccc ttaaacactc ttttcaaaga tgaagttcga   1140
gcgcttggaa tcgctcttgg aatgcctgaa gaaattgttt ggcgccaacc atttccaggt   1200
cctggacttg ctatccgtgt catgggagca attactgaag aaaaacttga accgttcgc   1260
gaatcagacg ctatccttcg tgaagaaatt gctaaggctg gacttgatcg tgacgtgtgg   1320
caatacttta cagttaacac aggtgtccgt tctgtaggcg tcatgggaga tggtcgtact   1380
tatgattata ccatcgccat tcgtgctatt acgtctattg atggtatgac agctgacttt   1440
gctcaacttc cttgggatgt cttgaaaaaa atctcaacac gtatcgtaaa tgaagttgac   1500
cacgttaacc gtatcgtcta cgacatcaca agtaaaccac ccgcaacagt tgaatgggaa   1560
taa                                                                1563
```

<210> SEQ ID NO 90
<211> LENGTH: 448
<212> TYPE: PRT
<213> ORGANISM: Streptococcus pyogenes

<400> SEQUENCE: 90

```
Met Ser Gln Ser Thr Ala Thr Tyr Ile Asn Val Ile Gly Ala Gly Leu
  1               5                  10                  15

Ala Gly Ser Glu Ala Ala Tyr Gln Ile Ala Lys Arg Gly Ile Pro Val
                 20                  25                  30

Lys Leu Tyr Glu Met Arg Gly Val Lys Ala Thr Pro Gln His Lys Thr
             35                  40                  45

Thr Asn Phe Ala Glu Leu Val Cys Ser Asn Ser Phe Arg Gly Asp Ser
         50                  55                  60

Leu Thr Asn Ala Val Gly Leu Leu Lys Glu Glu Met Arg Arg Leu Asp
 65                  70                  75                  80

Ser Ile Ile Met Arg Asn Gly Glu Ala Asn Arg Val Pro Ala Gly Gly
                 85                  90                  95

Ala Met Ala Val Asp Arg Glu Gly Tyr Ala Glu Ser Val Thr Ala Glu
                100                 105                 110

Leu Glu Asn His Pro Leu Ile Glu Val Ile Arg Gly Glu Ile Thr Glu
            115                 120                 125
```

Ile Pro Asp Asp Ala Ile Thr Val Ile Ala Thr Gly Pro Leu Thr Ser
        130                 135                 140

Asp Ala Leu Ala Glu Lys Ile His Ala Leu Asn Gly Gly Asp Gly Phe
145                 150                 155                 160

Tyr Phe Tyr Asp Ala Ala Pro Ile Ile Asp Lys Ser Thr Ile Asp
                165                 170                 175

Met Ser Lys Val Tyr Leu Lys Ser Arg Tyr Asp Lys Gly Glu Ala Ala
                180                 185                 190

Tyr Leu Asn Cys Pro Met Thr Lys Glu Glu Phe Met Ala Phe His Glu
                195                 200                 205

Ala Leu Thr Thr Ala Glu Glu Ala Pro Leu Asn Ala Phe Glu Lys Glu
        210                 215                 220

Lys Tyr Phe Glu Gly Cys Met Pro Ile Glu Val Met Ala Lys Arg Gly
225                 230                 235                 240

Ile Lys Thr Met Leu Tyr Gly Pro Met Lys Pro Val Gly Leu Glu Tyr
                245                 250                 255

Pro Asp Asp Tyr Thr Gly Pro Arg Asp Gly Glu Phe Lys Thr Pro Tyr
                260                 265                 270

Ala Val Val Gln Leu Arg Gln Asp Asn Ala Ala Gly Ser Leu Tyr Asn
        275                 280                 285

Ile Val Gly Phe Gln Thr His Leu Lys Trp Gly Glu Gln Lys Arg Val
290                 295                 300

Phe Gln Met Ile Pro Gly Leu Glu Asn Ala Glu Phe Val Arg Tyr Gly
305                 310                 315                 320

Val Met His Arg Asn Ser Tyr Met Asp Ser Pro Asn Leu Leu Thr Glu
                325                 330                 335

Thr Phe Gln Ser Arg Ser Asn Pro Asn Leu Phe Phe Ala Gly Gln Met
                340                 345                 350

Thr Gly Val Glu Gly Tyr Val Glu Ser Ala Ala Ser Gly Leu Val Ala
        355                 360                 365

Gly Ile Asn Ala Ala Arg Leu Phe Lys Arg Glu Glu Ala Leu Ile Phe
        370                 375                 380

Pro Gln Thr Thr Ala Ile Gly Ser Leu Pro His Tyr Val Thr His Ala
385                 390                 395                 400

Asp Ser Lys His Phe Gln Pro Met Asn Val Asn Phe Gly Ile Ile Lys
                405                 410                 415

Glu Leu Glu Gly Pro Arg Ile Arg Asp Lys Lys Glu Arg Tyr Glu Ala
                420                 425                 430

Ile Ala Ser Arg Ala Leu Ala Asp Leu Asp Thr Cys Leu Ala Ser Leu
        435                 440                 445

<210> SEQ ID NO 91
<211> LENGTH: 1347
<212> TYPE: DNA
<213> ORGANISM: Streptococcus pyogenes

<400> SEQUENCE: 91
ttgtctcaat caactgcaac ttatattaat gttattggag ctgggctagc tggttctgaa     60
gctgcctatc agattgctaa gcgcggtatc cccgttaaat tgtatgaaat gcgtggtgtc    120
aaagcaacac cgcaacataa aaccactaat tttgccgaat tggtctgttc caactcattt    180
cgtggtgata gcttaaccaa tgcagtcggt cttctcaaag aagaaatgcg gcgattagac    240
tccattatta tgcgtaatgg tgaagctaac cgcgtacctg ctgggggagc aatggctgtt    300
gaccgtgagg ggtatgcaga gagtgtcact gcagagttgg aaaatcatcc tctcattgag    360

-continued

```
gtcattcgtg gtgaaattac agaaatccct gacgatgcta tcacggttat cgcgacggga    420
ccgctgactt cggatgccct ggcagaaaaa attcacgcgc taaatggtgg cgacggattc    480
tattttacg atgcagcagc gcctatcatt gataaatcta ccattgatat gagcaaggtt    540
taccttaaat ctcgctacga taaaggcgaa gctgcttacc tcaactgccc tatgaccaaa    600
gaagaattca tggctttcca tgaagctctg acaaccgcag aagaagcccc gctgaatgcc    660
tttgaaaaag aaaagtattt tgaaggctgt atgccgattg aagttatggc taaacgtggc    720
attaaaacca tgctttatgg acctatgaaa cccgttggat tggaatatcc agatgactat    780
acaggtcctc gcgatggaga atttaaaacg ccatatgccg tcgtgcaatt gcgtcaagat    840
aatgcagctg aagcctttta taatatcgtt ggtttccaaa cccatctcaa atgggtgag   900
caaaaacgcg ttttccaaat gattccaggg cttgaaaatg ctgagtttgt ccgctacggc    960
gtcatgcatc gcaattccta tatggattca ccaaatcttt taaccgaaac cttccaatct   1020
cggagcaatc caaaccttt ctttgcaggt cagatgactg gagttgaagg ttatgtcgaa   1080
tcagctgctt caggtttagt agcaggaatc aatgctgctc gtttgttcaa aagagaagaa   1140
gcacttattt ttcctcagac aacagctatt gggagtttgc ctcattatgt gactcatgcc   1200
gacagtaagc atttccaacc aatgaacgtc aactttggca tcatcaaaga gttagaaggc   1260
ccacgcattc gtgacaaaaa agaacgttat gaagctattg ctagtcgtgc tttggcagat   1320
ttagacacct gcttagcgtc gctttaa                                      1347
```

<210> SEQ ID NO 92
<211> LENGTH: 360
<212> TYPE: PRT
<213> ORGANISM: Streptococcus pyogenes

<400> SEQUENCE: 92

```
Met Pro Lys Lys Ile Leu Phe Thr Gly Gly Thr Val Gly His Val
 1               5                  10                  15

Thr Leu Asn Leu Ile Leu Ile Pro Lys Phe Ile Lys Asp Gly Trp Glu
            20                  25                  30

Val His Tyr Ile Gly Asp Lys Asn Gly Ile Glu His Thr Glu Ile Glu
        35                  40                  45

Lys Ser Gly Leu Asp Val Thr Phe His Ala Ile Ala Thr Gly Lys Leu
    50                  55                  60

Arg Arg Tyr Phe Ser Trp Gln Asn Leu Ala Asp Val Phe Lys Val Ala
65                  70                  75                  80

Leu Gly Leu Leu Gln Ser Leu Phe Ile Val Ala Lys Leu Arg Pro Gln
                85                  90                  95

Ala Leu Phe Ser Lys Gly Gly Pro Val Ser Val Pro Pro Val Val Ala
            100                 105                 110

Ala Lys Leu Leu Gly Lys Pro Val Phe Ile His Glu Ser Asp Arg Ser
        115                 120                 125

Met Gly Leu Ala Asn Lys Ile Ala Tyr Lys Phe Ala Thr Thr Met Tyr
    130                 135                 140

Thr Thr Phe Glu Gln Glu Asp Gln Leu Ser Lys Val Lys His Leu Gly
145                 150                 155                 160

Ala Val Thr Lys Val Phe Lys Asp Ala Asn Gln Met Pro Glu Ser Thr
                165                 170                 175

Gln Leu Glu Ala Val Lys Glu Tyr Phe Ser Arg Asp Leu Lys Thr Leu
            180                 185                 190

Leu Phe Ile Gly Gly Ser Ala Gly Ala His Val Phe Asn Gln Phe Ile
        195                 200                 205
```

```
Ser Asp His Pro Glu Leu Lys Gln Arg Tyr Asn Ile Ile Asn Ile Thr
    210                 215                 220

Gly Asp Pro His Leu Asn Glu Leu Ser Ser His Leu Tyr Arg Val Asp
225                 230                 235                 240

Tyr Val Thr Asp Leu Tyr Gln Pro Leu Met Ala Met Ala Asp Leu Val
                245                 250                 255

Val Thr Arg Gly Gly Ser Asn Thr Leu Phe Glu Leu Leu Ala Met Ala
            260                 265                 270

Lys Leu His Leu Ile Val Pro Leu Gly Lys Glu Ala Ser Arg Gly Asp
        275                 280                 285

Gln Leu Glu Asn Ala Thr Tyr Phe Glu Lys Arg Gly Tyr Ala Lys Gln
    290                 295                 300

Leu Gln Glu Pro Asp Leu Thr Leu His Asn Phe Asp Gln Ala Met Ala
305                 310                 315                 320

Asp Leu Phe Glu His Gln Ala Asp Tyr Glu Ala Thr Met Leu Ala Thr
                325                 330                 335

Lys Glu Ile Gln Ser Pro Asp Phe Phe Tyr Asp Leu Leu Arg Ala Asp
            340                 345                 350

Ile Ser Ser Ala Ile Lys Glu Lys
        355                 360

<210> SEQ ID NO 93
<211> LENGTH: 1083
<212> TYPE: DNA
<213> ORGANISM: Streptococcus pyogenes

<400> SEQUENCE: 93
atgcctaaga agatttttatt tacaggtggt ggaactgtag gtcatgtcac cttgaacctc      60
attctcatac caaaatttat caaggacggt tgggaagtac attatattgg tgataaaaat     120
ggcattgaac atacagaaat tgaaaagtca ggccttgacg tgacctttca tgctatcgcg     180
acaggcaagc ttagacgcta ttttttcatgg caaaatctag ctgatgtttt taaggttgca     240
cttggcctcc tacagtctct ctttattgtt gccaagcttc gccctcaagc cctttttttcc    300 aaaggtggtt ttgtctcagt accgccagtt gtggctgcta aattgcttgg taaaccagtc     360
tttattcatg aatcagatcg gtcaatggga ctagcaaaca agattgccta caaatttgca     420
actaccatgt ataccacttt tgagcaggaa gaccagttgt ctaaagttaa acaccttgga     480
gcggtgacaa aggttttcaa agatgccaac caaatgcctg aatcaactca gttagaggcg     540
gtgaaagagt attttagtag agacctaaaa accctcttgt ttattggtgg ttcggcaggg     600
gcgcatgtgt ttaatcagtt tattagtgat catccagaat tgaagcaacg ttataatatc     660
atcaatatta caggagaccc tcaccttaat gaattgagtt ctcatctgta tcgagtagat     720
tatgttaccg atctctacca acctttgatg gcgatggctg accttgtagt gacaagaggg     780
ggctctaata cacttttttga gctactggca atggctaagc tacacctcat cgttcctctt     840
ggtaaagaag ctagccgtgg cgatcagtta gaaaatgcca cttatttttga aagaggggc     900 tacgctaaac aattacagga acctgattta actttgcata attttgatca ggcaatggct     960
gatttgtttg aacatcaggc tgattatgag gctactatgt tggcaactaa ggagattcag    1020
tcaccggact ctttttatga cctttgaga gctgatatta gctccgcgat taaggagaag    1080
taa                                                                   1083

<210> SEQ ID NO 94
<211> LENGTH: 604
```

<212> TYPE: PRT
<213> ORGANISM: Streptococcus pyogenes

<400> SEQUENCE: 94

```
Met Cys Gly Ile Val Gly Val Val Gly Asn Arg Asn Ala Thr Asp Ile
 1               5                  10                  15

Leu Met Gln Gly Leu Glu Lys Leu Glu Tyr Arg Gly Tyr Asp Ser Ala
            20                  25                  30

Gly Ile Phe Val Ala Asn Ala Asn Gln Thr Asn Leu Ile Lys Ser Val
        35                  40                  45

Gly Arg Ile Ala Asp Leu Arg Ala Lys Ile Gly Ile Asp Val Ala Gly
    50                  55                  60

Ser Thr Gly Ile Gly His Thr Arg Trp Ala Thr His Gly Gln Ser Thr
65                  70                  75                  80

Glu Asp Asn Ala His Pro His Thr Ser Gln Thr Gly Arg Phe Val Leu
                85                  90                  95

Val His Asn Gly Val Ile Glu Asn Tyr Leu His Ile Lys Thr Glu Phe
            100                 105                 110

Leu Ala Gly His Asp Phe Lys Gly Gln Thr Asp Thr Glu Ile Ala Val
        115                 120                 125

His Leu Ile Gly Lys Phe Val Glu Glu Asp Lys Leu Ser Val Leu Glu
    130                 135                 140

Ala Phe Lys Lys Ser Leu Ser Ile Ile Glu Gly Ser Tyr Ala Phe Ala
145                 150                 155                 160

Leu Met Asp Ser Gln Ala Thr Asp Thr Ile Tyr Val Ala Lys Asn Lys
                165                 170                 175

Ser Pro Leu Leu Ile Gly Leu Gly Glu Gly Tyr Asn Met Val Cys Ser
            180                 185                 190

Asp Ala Met Ala Met Ile Arg Glu Thr Ser Glu Phe Met Glu Ile His
        195                 200                 205

Asp Lys Glu Leu Val Ile Leu Thr Lys Asp Lys Val Thr Val Thr Asp
    210                 215                 220

Tyr Asp Gly Lys Glu Leu Ile Arg Asp Ser Tyr Thr Ala Glu Leu Asp
225                 230                 235                 240

Leu Ser Asp Ile Gly Lys Gly Thr Tyr Pro Phe Tyr Met Leu Lys Glu
                245                 250                 255

Ile Asp Glu Gln Pro Thr Val Met Arg Gln Leu Ile Ser Thr Tyr Ala
            260                 265                 270

Asp Glu Thr Gly Asn Val Gln Val Asp Pro Ala Ile Ile Thr Ser Ile
        275                 280                 285

Gln Glu Ala Asp Arg Leu Tyr Ile Leu Ala Ala Gly Thr Ser Tyr His
    290                 295                 300

Ala Gly Phe Ala Thr Lys Asn Met Leu Glu Gln Leu Thr Asp Thr Pro
305                 310                 315                 320

Val Glu Leu Gly Val Ala Ser Glu Trp Gly Tyr His Met Pro Leu Leu
                325                 330                 335

Ser Lys Lys Pro Met Phe Ile Leu Leu Ser Gln Ser Gly Glu Thr Ala
            340                 345                 350

Asp Ser Arg Gln Val Leu Val Lys Ala Asn Ala Met Gly Ile Pro Ser
        355                 360                 365

Leu Thr Val Thr Asn Val Pro Gly Ser Thr Leu Ser Arg Glu Ala Thr
    370                 375                 380

Tyr Thr Met Leu Ile His Ala Gly Pro Glu Ile Ala Val Ala Ser Thr
385                 390                 395                 400
```

```
Lys Ala Tyr Thr Ala Gln Ile Ala Ala Leu Ala Phe Leu Ala Lys Ala
                405                 410                 415

Val Gly Glu Ala Asn Gly Lys Gln Glu Ala Leu Asp Phe Asn Leu Val
            420                 425                 430

His Glu Leu Ser Leu Val Ala Gln Ser Ile Glu Ala Thr Leu Ser Glu
        435                 440                 445

Lys Asp Leu Val Ala Glu Lys Val Gln Ala Leu Leu Ala Thr Thr Arg
    450                 455                 460

Asn Ala Phe Tyr Ile Gly Arg Gly Asn Asp Tyr Tyr Val Ala Met Glu
465                 470                 475                 480

Ala Ala Leu Lys Leu Lys Glu Ile Ser Tyr Ile Gln Cys Glu Gly Phe
                485                 490                 495

Ala Ala Gly Glu Leu Lys His Gly Thr Ile Ser Leu Ile Glu Glu Asp
            500                 505                 510

Thr Pro Val Ile Ala Leu Ile Ser Ser Gln Leu Val Ala Ser His
        515                 520                 525

Thr Arg Gly Asn Ile Gln Glu Val Ala Ala Arg Gly Ala His Val Leu
    530                 535                 540

Thr Val Val Glu Glu Gly Leu Asp Arg Glu Gly Asp Asp Ile Ile Val
545                 550                 555                 560

Asn Lys Val His Pro Phe Leu Ala Pro Ile Ala Met Val Ile Pro Thr
                565                 570                 575

Gln Leu Ile Ala Tyr Tyr Ala Ser Leu Gln Arg Gly Leu Asp Val Asp
            580                 585                 590

Lys Pro Arg Asn Leu Ala Lys Ala Val Thr Val Glu
        595                 600

<210> SEQ ID NO 95
<211> LENGTH: 1815
<212> TYPE: DNA
<213> ORGANISM: Streptococcus pyogenes

<400> SEQUENCE: 95
atgtgtggaa ttgttggagt tgttggaaat cgcaatgcaa cggatatttt aatgcaaggc      60
cttgaaaagc ttgaataccg gggttatgat tcagcaggaa ttttgtggc taatgccaat     120 caaacaaact tgattaaatc agtggggcgg attgctgatt tgcgtgccaa gattggcatt     180
gatgttgctg gttcaacagg gattggtcac acccgttggg caacgcatgg ccaatcaaca     240
gaggataatg cccatcctca cacgtcacaa actggacgtt ttgtacttgt tcataatggt     300
gtgattgaaa attaccttca cattaaaaca gagttcctag ctggacatga ttttaagggg     360
cagacagata ctgagattgc agtacacttg attggaaaat tgtggaaga agacaagttg     420 tcagtactgg aagcttttaa aaaatcttta agcattattg aaggttccta cgcctttgca     480
ttaatggata gccaagcaac tgatactatt tatgtggcta aaaacaagtc tccattgttg     540
attggacttg gtgaaggtta caacatggtt tgttcagatg ccatggccat gattcgtgaa     600
accagtgaat ttatggaaat tcatgataag gagctagtta ttttaaccaa agataaggta     660
actgttacag actacgatgg taaagagctg atacgagatt cctacactgc tgaattagac     720
ttatctgata ttggcaaagg gacttatcct ttctatatgc tgaaagaaat tgatgagcaa     780
ccaaccgtaa tgcgtcaatt aatttcaact tatgcagatg aaactggtaa cgtacaggtt     840
gatccggcta tcattacctc tatccaagag gctgaccgtc tttatatttt agcggcaggg     900
acttcctacc atgctggttt tgcaacaaaa aatatgcttg agcaattgac agatacacca     960
gttgagttgg gcgtggcttc tgagtggggt taccacatgc ctctgcttag caagaaacca    1020
```

```
atgtttattc tactaagcca atcaggagaa accgcagata gtcgtcaagt tttagtaaag    1080
gcaaatgcta tgggcattcc gagtttgaca gtaactaacg ttccaggatc aaccttatca    1140
cgtgaagcaa catacaccat gttgattcat gctggacctg aaattgctgt tgcgtctaca    1200
aaagcttaca ctgcacaaat tgctgcccett gccttttttgg ctaaggcagt tggtgaggca    1260
aatggtaagc aagaagctct tgactttaac ttggtacatg agttgtcatt ggttgcccaa    1320
tctattgagg cgactttgtc tgaaaaagat ctcgtggcag aaaaggttca agctttgcta    1380
gctactactc gtaatgcttt ttacatcggg cgtggcaatg attattacgt tgcgatggaa    1440
gctgctttga aattaaaaga gatttcttat attcaatgcg aaggctttgc ggctggtgaa    1500
ttgaaacatg gaaccatttc attaattgag gaggacacgc cagtaatcgc tttaatatcg    1560
tctagtcagt tggttgcctc tcatacgcgt ggtaatattc aagaagttgc tgcccgtggg    1620
gctcatgttt taacagttgt ggaagaaggg cttgaccgtg agggagatga cattattgtc    1680
aataaggttc atcctttcct agccccgatt gctatggtca ttccaactca actgattgct    1740
tactacgctt cattacaacg tggacttgat gttgataagc cacgtaattt ggctaaagct    1800
gtaacagtag aataa                                                    1815
```

<210> SEQ ID NO 96
<211> LENGTH: 659
<212> TYPE: PRT
<213> ORGANISM: Streptococcus pyogenes

<400> SEQUENCE: 96

```
Val Thr Phe Met Lys Lys Ser Lys Trp Leu Ala Ala Val Ser Val Ala
  1               5                  10                  15

Ile Leu Ser Val Ser Ala Leu Ala Ala Cys Gly Asn Lys Asn Ala Ser
             20                  25                  30

Gly Gly Ser Glu Ala Thr Lys Thr Tyr Lys Tyr Val Phe Val Asn Asp
         35                  40                  45

Pro Lys Ser Leu Asp Tyr Ile Leu Thr Asn Gly Gly Thr Thr Asp
     50                  55                  60

Val Ile Thr Gln Met Val Asp Gly Leu Leu Glu Asn Asp Glu Tyr Gly
 65                  70                  75                  80

Asn Leu Val Pro Ser Leu Ala Lys Asp Trp Lys Val Ser Lys Asp Gly
                 85                  90                  95

Leu Thr Tyr Thr Tyr Thr Leu Arg Asp Gly Val Ser Trp Tyr Thr Ala
            100                 105                 110

Asp Gly Glu Glu Tyr Ala Pro Val Thr Ala Glu Asp Phe Val Thr Gly
        115                 120                 125

Leu Lys His Ala Val Asp Asp Lys Ser Asp Ala Leu Tyr Val Val Glu
    130                 135                 140

Asp Ser Ile Lys Asn Leu Lys Ala Tyr Gln Asn Gly Glu Val Asp Phe
145                 150                 155                 160

Lys Glu Val Gly Val Lys Ala Leu Asp Asp Lys Thr Val Gln Tyr Thr
                165                 170                 175

Leu Asn Lys Pro Glu Ser Tyr Trp Asn Ser Lys Thr Thr Tyr Ser Val
            180                 185                 190

Leu Phe Pro Val Asn Ala Lys Phe Leu Lys Ser Lys Gly Lys Asp Phe
        195                 200                 205

Gly Thr Thr Asp Pro Ser Ser Ile Leu Val Asn Gly Ala Tyr Phe Leu
    210                 215                 220

Ser Ala Phe Thr Ser Lys Ser Ser Met Glu Phe His Lys Asn Glu Asn
```

```
            225                 230                 235                 240
Tyr Trp Asp Ala Lys Asn Val Gly Ile Glu Ser Val Lys Leu Thr Tyr
                245                 250                 255

Ser Asp Gly Ser Asp Pro Gly Ser Phe Tyr Lys Asn Phe Asp Lys Gly
                260                 265                 270

Glu Phe Ser Val Ala Arg Leu Tyr Pro Asn Asp Pro Thr Tyr Lys Ser
                275                 280                 285

Ala Lys Lys Asn Tyr Ala Asp Asn Ile Thr Tyr Gly Met Leu Thr Gly
                290                 295                 300

Asp Ile Arg His Leu Thr Trp Asn Leu Asn Arg Thr Ser Phe Lys Asn
305                 310                 315                 320

Thr Lys Lys Asp Pro Ala Gln Gln Asp Ala Gly Lys Lys Ala Leu Asn
                325                 330                 335

Asn Lys Asp Phe Arg Gln Ala Ile Gln Phe Ala Phe Asp Arg Ala Ser
                340                 345                 350

Phe Gln Ala Gln Thr Ala Gly Gln Asp Ala Lys Thr Lys Ala Leu Arg
                355                 360                 365

Asn Met Leu Val Pro Pro Thr Phe Val Thr Ile Gly Glu Ser Asp Phe
370                 375                 380

Gly Ser Glu Val Glu Lys Glu Met Ala Lys Leu Gly Asp Glu Trp Lys
385                 390                 395                 400

Asp Val Asn Leu Ala Asp Ala Gln Asp Gly Phe Tyr Asn Pro Glu Lys
                405                 410                 415

Ala Lys Ala Glu Phe Ala Lys Ala Lys Glu Ala Leu Thr Ala Glu Gly
                420                 425                 430

Val Thr Phe Pro Val Gln Leu Asp Tyr Pro Val Asp Gln Ala Asn Ala
                435                 440                 445

Ala Thr Val Gln Glu Ala Gln Ser Phe Lys Gln Ser Val Glu Ala Ser
                450                 455                 460

Leu Gly Lys Glu Asn Val Ile Val Asn Val Leu Glu Thr Glu Thr Ser
465                 470                 475                 480

Thr His Glu Ala Gln Gly Phe Tyr Ala Glu Thr Pro Glu Gln Gln Asp
                485                 490                 495

Tyr Asp Ile Ile Ser Ser Trp Trp Gly Pro Asp Tyr Gln Asp Pro Arg
                500                 505                 510

Thr Tyr Leu Asp Ile Met Ser Pro Val Gly Gly Ser Val Ile Gln
                515                 520                 525

Lys Leu Gly Ile Lys Ala Gly Gln Asn Lys Asp Val Val Ala Ala Ala
530                 535                 540

Gly Leu Asp Thr Tyr Gln Thr Leu Leu Asp Glu Ala Ala Ile Thr
545                 550                 555                 560

Asp Asp Asn Asp Ala Arg Tyr Lys Ala Tyr Lys Ala Gln Ala Tyr
                565                 570                 575

Leu Thr Asp Asn Ala Val Asp Ile Pro Val Val Ala Leu Gly Gly Thr
                580                 585                 590

Pro Arg Val Thr Lys Ala Val Pro Phe Ser Gly Gly Phe Ser Trp Ala
                595                 600                 605

Gly Ser Lys Gly Pro Leu Ala Tyr Lys Gly Met Lys Leu Gln Asp Lys
                610                 615                 620

Pro Val Thr Val Lys Gln Tyr Glu Lys Ala Lys Glu Lys Trp Met Lys
625                 630                 635                 640

Ala Lys Ala Lys Ser Asn Ala Lys Tyr Ala Glu Lys Leu Ala Asp His
                645                 650                 655
```

Val Glu Lys

<210> SEQ ID NO 97
<211> LENGTH: 1977
<212> TYPE: DNA
<213> ORGANISM: Streptococcus pyogenes

<400> SEQUENCE: 97

| | | | | | |
|---|---|---|---|---|---|
| gtgactttta | tgaagaaaag | taaatggttg | gcagctgtaa | gtgttgcgat | cttgtcagta | 60 |
| tccgctttgg | cagcttgtgg | taataaaaat | gcttcaggtg | gctcagaagc | tacaaaaacc | 120 |
| tacaagtacg | tttttgttaa | cgatccaaaa | tcattggatt | atattttgac | taatggcggt | 180 |
| ggaacgactg | atgtgataac | acaaatggtt | gatggtcttt | tggaaaacga | tgagtatggt | 240 |
| aatttagtac | catcacttgc | taaagattgg | aaggtttcaa | aagacggtct | gacttatact | 300 |
| tatactcttc | gcgatggtgt | ctcttggtat | acggctgatg | gtgaagaata | tgccccagta | 360 |
| acagcagaag | attttgtgac | tggttttgaag | cacgcggttg | acgataaatc | agatgctctt | 420 |
| tacgttgttg | aagattcaat | aaaaaactta | aaggcttacc | aaaatggtga | agtagatttt | 480 |
| aaagaagttg | gtgtcaaagc | ccttgacgat | aaaactgttc | agtatacttt | gaacaagcct | 540 |
| gaaagctact | ggaattcaaa | aacaacttat | agtgtgcttt | tcccagttaa | tgcgaaattt | 600 |
| ttgaagtcaa | aagtaaaga | ttttggtaca | accgatccat | catcaatcct | tgttaatggt | 660 |
| gcttacttct | tgagcgcctt | cacctcaaaa | tcatctatgg | aattccataa | aaatgaaaac | 720 |
| tactgggatg | ctaagaatgt | tgggatagaa | tctgttaaat | tgacttactc | agatggttca | 780 |
| gacccaggtt | cgttctacaa | gaactttgac | aagggtgagt | tcagcgttgc | acgactttac | 840 |
| ccaaatgacc | ctacctacaa | atcagctaag | aaaaactatg | ctgataacat | tacttacgga | 900 |
| atgttgactg | gagatatccg | tcatttaaca | tggaatttga | accgtacttc | tttcaaaaac | 960 |
| actaagaaag | accctgcaca | caagatgcc | ggtaagaaag | ctcttaacaa | caaggatttt | 1020 |
| cgtcaagcta | ttcagtttgc | ttttgaccga | gcgtcattcc | aagcacaaac | tgcaggtcaa | 1080 |
| gatgccaaaa | caaagccctt | acgtaacatg | cttgtcccac | caacatttgt | gaccattgga | 1140 |
| gaaagtgatt | ttggttcaga | agttgaaaag | gaaatggcaa | aacttggtga | tgaatggaaa | 1200 |
| gacgttaact | tagctgatgc | tcaagatggt | ttctataatc | ctgaaaaagc | aaaagctgag | 1260 |
| tttgcaaaag | ccaaagaagc | tttaacagct | gaaggtaa | ccttcccagt | tcaattagat | 1320 |
| taccctgttg | accaagcaaa | cgcagcaact | gttcaggaag | cccagtctt | caaacaatct | 1380 |
| gttgaagcat | ctcttggtaa | agagaatgtc | attgtcaatg | ttcttgaaac | agaaacatca | 1440 |
| actcacgaag | cccaaggctt | ctatgctgag | accccagaac | aacaagacta | cgatatcatt | 1500 |
| tcatcatggt | ggggaccaga | ctatcaagat | ccacggacct | accttgacat | catgagtcca | 1560 |
| gtaggtggtg | gatctgttat | ccaaaaactt | ggaatcaaag | caggtcaaaa | taaggatgtt | 1620 |
| gtggcagctg | caggccttga | tacctaccaa | actcttcttg | atgaagcagc | agcaattaca | 1680 |
| gacgacaacg | atgcgcgcta | taaagcttac | gcaaaagcac | aagcctacct | tacagataat | 1740 |
| gccgtagata | ttccagttgt | ggcattgggt | ggcactccac | gagttactaa | agccgttcca | 1800 |
| tttagcgggg | gcttctcttg | ggcagggtct | aaaggtcctc | tagcatataa | aggaatgaaa | 1860 |
| cttcaagaca | aacctgtcac | agtaaaacaa | tacgaaaaag | caaagaaaa | atggatgaaa | 1920 |
| gcaaaggcta | agtcaaatgc | aaaatatgct | gagaagttag | ctgatcacgt | tgaaaaa | 1977 |

<210> SEQ ID NO 98
<211> LENGTH: 25
<212> TYPE: PRT

<213> ORGANISM: Streptococcus pyogenes

<400> SEQUENCE: 98

Val Thr Phe Met Lys Lys Ser Lys Trp Leu Ala Ala Val Ser Val Ala
 1               5                  10                  15

Ile Leu Ser Val Ser Ala Leu Ala Ala
         20                  25

<210> SEQ ID NO 99
<211> LENGTH: 634
<212> TYPE: PRT
<213> ORGANISM: Streptococcus pyogenes

<400> SEQUENCE: 99

Cys Gly Asn Lys Asn Ala Ser Gly Ser Glu Ala Thr Lys Thr Tyr
 1               5                  10                  15

Lys Tyr Val Phe Val Asn Asp Pro Lys Ser Leu Asp Tyr Ile Leu Thr
             20                  25                  30

Asn Gly Gly Gly Thr Thr Asp Val Ile Thr Gln Met Val Asp Gly Leu
         35                  40                  45

Leu Glu Asn Asp Glu Tyr Gly Asn Leu Val Pro Ser Leu Ala Lys Asp
     50                  55                  60

Trp Lys Val Ser Lys Asp Gly Leu Thr Tyr Thr Tyr Thr Leu Arg Asp
 65                  70                  75                  80

Gly Val Ser Trp Tyr Thr Ala Asp Gly Glu Glu Tyr Ala Pro Val Thr
                 85                  90                  95

Ala Glu Asp Phe Val Thr Gly Leu Lys His Ala Val Asp Asp Lys Ser
            100                 105                 110

Asp Ala Leu Tyr Val Val Glu Asp Ser Ile Lys Asn Leu Lys Ala Tyr
        115                 120                 125

Gln Asn Gly Glu Val Asp Phe Lys Glu Val Gly Val Lys Ala Leu Asp
    130                 135                 140

Asp Lys Thr Val Gln Tyr Thr Leu Asn Lys Pro Glu Ser Tyr Trp Asn
145                 150                 155                 160

Ser Lys Thr Thr Tyr Ser Val Leu Phe Pro Val Asn Ala Lys Phe Leu
                165                 170                 175

Lys Ser Lys Gly Lys Asp Phe Gly Thr Thr Asp Pro Ser Ser Ile Leu
            180                 185                 190

Val Asn Gly Ala Tyr Phe Leu Ser Ala Phe Thr Ser Lys Ser Ser Met
        195                 200                 205

Glu Phe His Lys Asn Glu Asn Tyr Trp Asp Ala Lys Asn Val Gly Ile
    210                 215                 220

Glu Ser Val Lys Leu Thr Tyr Ser Asp Gly Ser Asp Pro Gly Ser Phe
225                 230                 235                 240

Tyr Lys Asn Phe Asp Lys Gly Glu Phe Ser Val Ala Arg Leu Tyr Pro
                245                 250                 255

Asn Asp Pro Thr Tyr Lys Ser Ala Lys Lys Asn Tyr Ala Asp Asn Ile
            260                 265                 270

Thr Tyr Gly Met Leu Thr Gly Asp Ile Arg His Leu Thr Trp Asn Leu
        275                 280                 285

Asn Arg Thr Ser Phe Lys Asn Thr Lys Asp Pro Ala Gln Gln Asp
    290                 295                 300

Ala Gly Lys Lys Ala Leu Asn Asn Lys Asp Phe Arg Gln Ala Ile Gln
305                 310                 315                 320

Phe Ala Phe Asp Arg Ala Ser Phe Gln Ala Gln Thr Ala Gly Gln Asp
                325                 330                 335

```
Ala Lys Thr Lys Ala Leu Arg Asn Met Leu Val Pro Pro Thr Phe Val
            340                 345                 350

Thr Ile Gly Glu Ser Asp Phe Gly Ser Glu Val Glu Lys Glu Met Ala
            355                 360                 365

Lys Leu Gly Asp Glu Trp Lys Asp Val Asn Leu Ala Asp Ala Gln Asp
            370                 375                 380

Gly Phe Tyr Asn Pro Glu Lys Ala Lys Ala Glu Phe Ala Lys Ala Lys
385                 390                 395                 400

Glu Ala Leu Thr Ala Glu Gly Val Thr Phe Pro Val Gln Leu Asp Tyr
                405                 410                 415

Pro Val Asp Gln Ala Asn Ala Ala Thr Val Gln Glu Ala Gln Ser Phe
            420                 425                 430

Lys Gln Ser Val Glu Ala Ser Leu Gly Lys Glu Asn Val Ile Val Asn
            435                 440                 445

Val Leu Glu Thr Glu Thr Ser Thr His Glu Ala Gln Gly Phe Tyr Ala
450                 455                 460

Glu Thr Pro Glu Gln Gln Asp Tyr Asp Ile Ile Ser Ser Trp Trp Gly
465                 470                 475                 480

Pro Asp Tyr Gln Asp Pro Arg Thr Tyr Leu Asp Ile Met Ser Pro Val
                485                 490                 495

Gly Gly Gly Ser Val Ile Gln Lys Leu Gly Ile Lys Ala Gly Gln Asn
            500                 505                 510

Lys Asp Val Val Ala Ala Gly Leu Asp Thr Tyr Gln Thr Leu Leu
            515                 520                 525

Asp Glu Ala Ala Ala Ile Thr Asp Asp Asn Asp Ala Arg Tyr Lys Ala
530                 535                 540

Tyr Ala Lys Ala Gln Ala Tyr Leu Thr Asp Asn Ala Val Asp Ile Pro
545                 550                 555                 560

Val Val Ala Leu Gly Gly Thr Pro Arg Val Thr Lys Ala Val Pro Phe
                565                 570                 575

Ser Gly Gly Phe Ser Trp Ala Gly Ser Lys Gly Pro Leu Ala Tyr Lys
            580                 585                 590

Gly Met Lys Leu Gln Asp Lys Pro Val Thr Val Lys Gln Tyr Glu Lys
            595                 600                 605

Ala Lys Glu Lys Trp Met Lys Ala Lys Ala Lys Ser Asn Ala Lys Tyr
            610                 615                 620

Ala Glu Lys Leu Ala Asp His Val Glu Lys
625                 630

<210> SEQ ID NO 100
<211> LENGTH: 424
<212> TYPE: PRT
<213> ORGANISM: Streptococcus pyogenes

<400> SEQUENCE: 100

Met Lys Ile Gly Lys Lys Ile Val Leu Met Phe Thr Ala Ile Val Leu
1               5                   10                  15

Thr Thr Val Leu Ala Leu Gly Val Tyr Leu Thr Ser Ala Tyr Thr Phe
            20                  25                  30

Ser Thr Gly Glu Leu Ser Lys Thr Phe Lys Asp Phe Ser Thr Ser Ser
            35                  40                  45

Asn Lys Ser Asp Ala Ile Lys Gln Thr Arg Ala Phe Ser Ile Leu Leu
            50                  55                  60

Met Gly Val Asp Thr Gly Ser Ser Glu Arg Ala Ser Lys Trp Glu Gly
65                  70                  75                  80
```

| | | | | | | | | | | | | |
|---|---|---|---|---|---|---|---|---|---|---|---|---|
|Asn|Ser|Asp|Ser|Met|Ile|Leu|Val|Thr|Val|Asn|Pro|Lys|Thr|Lys|Lys|
| | | | |85| | | |90| | | |95| | | |

Asn Ser Asp Ser Met Ile Leu Val Thr Val Asn Pro Lys Thr Lys Lys
                85              90              95

Thr Thr Met Thr Ser Leu Glu Arg Asp Thr Leu Thr Thr Leu Ser Gly
        100              105              110

Pro Lys Asn Asn Glu Met Asn Gly Val Glu Ala Lys Leu Asn Ala Ala
        115              120              125

Tyr Ala Ala Gly Gly Ala Gln Met Ala Ile Met Thr Val Gln Asp Leu
    130              135              140

Leu Asn Ile Thr Ile Asp Asn Tyr Val Gln Ile Asn Met Gln Gly Leu
145              150              155            160

Ile Asp Leu Val Asn Ala Val Gly Gly Ile Thr Val Thr Asn Glu Phe
            165            170              175

Asp Phe Pro Ile Ser Ile Ala Glu Asn Glu Pro Glu Tyr Gln Ala Thr
        180              185              190

Val Ala Pro Gly Thr His Lys Ile Asn Gly Glu Gln Ala Leu Val Tyr
            195            200              205

Ala Arg Met Arg Tyr Asp Asp Pro Glu Gly Asp Tyr Gly Arg Gln Lys
    210              215              220

Arg Gln Arg Glu Val Ile Gln Lys Val Leu Lys Ile Leu Ala Leu
225              230              235            240

Asp Ser Ile Ser Ser Tyr Arg Lys Ile Leu Ser Ala Val Ser Ser Asn
        245              250              255

Met Gln Thr Asn Ile Glu Ile Ser Ser Arg Thr Ile Pro Ser Leu Leu
        260              265              270

Gly Tyr Arg Asp Ala Leu Arg Thr Ile Lys Thr Tyr Gln Leu Lys Gly
    275              280              285

Glu Asp Ala Thr Leu Ser Asp Gly Gly Ser Tyr Gln Ile Val Thr Ser
        290              295              300

Asn His Leu Leu Glu Ile Gln Asn Arg Ile Arg Thr Glu Leu Gly Leu
305              310              315            320

His Lys Val Asn Gln Leu Lys Thr Asn Ala Thr Val Tyr Glu Asn Leu
            325            330              335

Tyr Gly Ser Thr Lys Ser Gln Thr Val Asn Asn Asn Tyr Asp Ser Ser
        340              345              350

Gly Gln Ala Pro Ser Tyr Ser Asp Ser His Ser Ser Tyr Ala Asn Tyr
    355              360              365

Ser Ser Gly Val Asp Thr Gly Gln Ser Ala Ser Thr Asp Gln Asp Ser
370              375              380

Thr Ala Ser Ser His Arg Pro Ala Thr Pro Ser Ser Ser Ser Asp Ala
385              390              395            400

Leu Ala Ala Asp Glu Ser Ser Ser Ser Gly Ser Gly Ser Leu Val Pro
            405            410              415

Pro Ala Asn Ile Asn Pro Gln Thr
        420

<210> SEQ ID NO 101
<211> LENGTH: 1275
<212> TYPE: DNA
<213> ORGANISM: Streptococcus pyogenes

<400> SEQUENCE: 101
atgaaaattg aaaaaaaat agttttaatg ttcacagcta ttgtgttaac aactgtcttg    60
gcattaggtg tctatctaac tagtgcttat accttctcaa caggagaatt atcaaagacc   120
tttaaagatt tttcgacatc ttcaaacaaa agtgatgcca ttaaacaaac aagagctttt   180

```
tctatcttgt tgatgggtgt tgatacaggc tcttcagagc gtgcctccaa gtgggaagga      240
aacagtgatt cgatgatttt ggttacggtt aatccaagaa ccaagaaaac aactatgact      300
agtttagaac gagataccet aaccacgtta tctggaccca aaaataatga aatgaatggt      360
gttgaagcta agcttaacgc tgcttatgca gcaggtggcg ctcagatggc tattatgacc      420
gtgcaagatc ttttgaatat caccattgat aactatgttc aaattaatat gcaaggcctt      480
attgatcttg tgaatgcagt tggagggatt acagttacaa atgagtttga ttttcctatc      540
tcgattgctg aaaacgaacc tgaatatcaa gctactgttg cgcctggaac acacaaaatt      600
aacggtgaac aagctttggt ttatgctcgt atgcgttatg atgatcctga gggagattat      660
ggtcgacaaa agcgtcaacg tgaagtcatt caaaaggtat tgaaaaaaat ccttgctctt      720
gatagcatta gctcttatcg aagattttta ctgctgtaa gtagtaatat gcaaacgaat      780
atcgaaatct cttctcgcac tatccctagt ctattaggtt atcgtgacgc acttagaact      840
attaagactt atcaactaaa aggagaagat gccactttat cagatggtgg atcataccaa      900
attgttacct ctaatcattt gttagaaatc caaaatcgta tccgaacaga attaggactt      960
cataaggtta atcaattaaa aacaaatgct actgtttatg aaaatttgta tgggtcaact     1020
aagtctcaga cagtaaacaa caactatgac tcttcaggcc aggctccatc ttattctgat     1080
agtcatagct cttacgctaa ttattcaagt ggagtagata ccggccagag tgctagtaca     1140
gaccaggact ctactgcttc aagccatagg ccagctacgc cgtcttcttc atcagatgct     1200
ttagcagctg atgagtctag ctcatcaggg tctggatcat tagttcctcc tgctaatatc     1260
aaccctcaga cctaa                                                      1275
```

<210> SEQ ID NO 102
<211> LENGTH: 33
<212> TYPE: PRT
<213> ORGANISM: Streptococcus pyogenes

<400> SEQUENCE: 102

Met Lys Ile Gly Lys Lys Ile Val Leu Met Phe Thr Ala Ile Val Leu
1               5                   10                  15

Thr Thr Val Leu Ala Leu Gly Val Tyr Leu Thr Ser Ala Tyr Thr Phe
            20                  25                  30

Ser

<210> SEQ ID NO 103
<211> LENGTH: 391
<212> TYPE: PRT
<213> ORGANISM: Streptococcus pyogenes

<400> SEQUENCE: 103

Thr Gly Glu Leu Ser Lys Thr Phe Lys Asp Phe Ser Thr Ser Ser Asn
1               5                   10                  15

Lys Ser Asp Ala Ile Lys Gln Thr Arg Ala Phe Ser Ile Leu Leu Met
            20                  25                  30

Gly Val Asp Thr Gly Ser Ser Glu Arg Ala Ser Lys Trp Glu Gly Asn
        35                  40                  45

Ser Asp Ser Met Ile Leu Val Thr Val Asn Pro Lys Thr Lys Lys Thr
    50                  55                  60

Thr Met Thr Ser Leu Glu Arg Asp Thr Leu Thr Leu Ser Gly Pro
65                  70                  75                  80

Lys Asn Asn Glu Met Asn Gly Val Glu Ala Lys Leu Asn Ala Ala Tyr
                85                  90                  95

```
Ala Ala Gly Gly Ala Gln Met Ala Ile Met Thr Val Gln Asp Leu Leu
            100                 105                 110

Asn Ile Thr Ile Asp Asn Tyr Val Gln Ile Asn Met Gln Gly Leu Ile
        115                 120                 125

Asp Leu Val Asn Ala Val Gly Gly Ile Thr Val Thr Asn Glu Phe Asp
    130                 135                 140

Phe Pro Ile Ser Ile Ala Glu Asn Pro Glu Tyr Gln Ala Thr Val
145                 150                 155                 160

Ala Pro Gly Thr His Lys Ile Asn Gly Glu Gln Ala Leu Val Tyr Ala
                165                 170                 175

Arg Met Arg Tyr Asp Asp Pro Glu Gly Asp Tyr Gly Arg Gln Lys Arg
            180                 185                 190

Gln Arg Glu Val Ile Gln Lys Val Leu Lys Ile Leu Ala Leu Asp
        195                 200                 205

Ser Ile Ser Ser Tyr Arg Lys Ile Leu Ser Ala Val Ser Ser Asn Met
    210                 215                 220

Gln Thr Asn Ile Glu Ile Ser Ser Arg Thr Ile Pro Ser Leu Leu Gly
225                 230                 235                 240

Tyr Arg Asp Ala Leu Arg Thr Ile Lys Thr Tyr Gln Leu Lys Gly Glu
                245                 250                 255

Asp Ala Thr Leu Ser Asp Gly Gly Ser Tyr Gln Ile Val Thr Ser Asn
            260                 265                 270

His Leu Leu Glu Ile Gln Asn Arg Ile Arg Thr Glu Leu Gly Leu His
        275                 280                 285

Lys Val Asn Gln Leu Lys Thr Asn Ala Thr Val Tyr Glu Asn Leu Tyr
    290                 295                 300

Gly Ser Thr Lys Ser Gln Thr Val Asn Asn Asn Tyr Asp Ser Ser Gly
305                 310                 315                 320

Gln Ala Pro Ser Tyr Ser Asp Ser His Ser Ser Tyr Ala Asn Tyr Ser
                325                 330                 335

Ser Gly Val Asp Thr Gly Gln Ser Ala Ser Thr Asp Gln Asp Ser Thr
            340                 345                 350

Ala Ser Ser His Arg Pro Ala Thr Pro Ser Ser Ser Ser Asp Ala Leu
        355                 360                 365

Ala Ala Asp Glu Ser Ser Ser Gly Ser Gly Ser Leu Val Pro Pro
    370                 375                 380

Ala Asn Ile Asn Pro Gln Thr
385                 390

<210> SEQ ID NO 104
<211> LENGTH: 541
<212> TYPE: PRT
<213> ORGANISM: Streptococcus pyogenes

<400> SEQUENCE: 104

Met Lys Lys Arg Lys Leu Leu Ala Val Thr Leu Leu Ser Thr Ile Leu
1               5                   10                  15

Leu Asn Ser Ala Val Pro Leu Val Val Ala Asp Thr Ser Leu Arg Asn
            20                  25                  30

Ser Thr Ser Ser Thr Asp Gln Pro Thr Thr Ala Asp Thr Asp Thr Asp
        35                  40                  45

Asp Glu Ser Glu Thr Pro Lys Lys Asp Lys Lys Ser Lys Glu Thr Ala
    50                  55                  60

Ser Gln His Asp Thr Gln Lys Asp His Lys Pro Ser Thr His Pro
65                  70                  75                  80
```

```
Thr Pro Pro Ser Asn Asp Thr Lys Gln Thr Asp Gln Ala Ser Ser Glu
                85                  90                  95

Ala Thr Asp Lys Pro Asn Lys Asp Lys Asn Asp Thr Lys Gln Pro Asp
                100                 105                 110

Ser Ser Asp Gln Ser Thr Pro Ser Pro Lys Asp Gln Ser Ser Gln Lys
            115                 120                 125

Glu Ser Gln Asn Lys Asp Gly Arg Pro Thr Pro Ser Pro Asp Gln Gln
    130                 135                 140

Lys Asp Gln Thr Pro Asp Lys Thr Pro Glu Lys Ser Ala Asp Lys Thr
145                 150                 155                 160

Pro Glu Lys Gly Pro Glu Lys Ala Thr Asp Lys Thr Pro Glu Pro Asn
                165                 170                 175

Arg Asp Ala Pro Lys Pro Ile Gln Pro Leu Ala Ala Ala Pro Val
                180                 185                 190

Phe Ile Pro Trp Arg Glu Ser Asp Lys Asp Leu Ser Lys Leu Lys Pro
        195                 200                 205

Ser Ser Arg Ser Ser Ala Ala Tyr Val Arg His Trp Thr Gly Asp Ser
    210                 215                 220

Ala Tyr Thr His Asn Leu Leu Ser Arg Arg Tyr Gly Ile Thr Ala Glu
225                 230                 235                 240

Gln Leu Asp Gly Phe Leu Asn Ser Leu Gly Ile His Tyr Asp Lys Glu
                245                 250                 255

Arg Leu Asn Gly Lys Arg Leu Leu Glu Trp Glu Lys Leu Thr Gly Leu
                260                 265                 270

Asp Val Arg Ala Ile Val Ala Ile Ala Met Ala Glu Ser Ser Leu Gly
            275                 280                 285

Thr Gln Gly Val Ala Lys Glu Lys Gly Ala Asn Met Phe Gly Tyr Gly
    290                 295                 300

Ala Phe Asp Phe Asn Pro Asn Asn Ala Lys Lys Tyr Ser Asp Glu Val
305                 310                 315                 320

Ala Ile Arg His Met Val Glu Asp Thr Ile Ile Ala Asn Lys Asn Gln
                325                 330                 335

Thr Phe Glu Arg Gln Asp Leu Lys Ala Lys Lys Trp Ser Leu Gly Gln
                340                 345                 350

Leu Asp Thr Leu Ile Asp Gly Gly Val Tyr Phe Thr Asp Thr Ser Gly
            355                 360                 365

Ser Gly Gln Arg Arg Ala Asp Ile Met Thr Lys Leu Asp Gln Trp Ile
    370                 375                 380

Asp Asp His Gly Ser Thr Pro Glu Ile Pro Glu His Leu Lys Ile Thr
385                 390                 395                 400

Ser Gly Thr Gln Phe Ser Glu Val Pro Val Gly Tyr Lys Arg Ser Gln
                405                 410                 415

Pro Gln Asn Val Leu Thr Tyr Lys Ser Glu Thr Tyr Ser Phe Gly Gln
                420                 425                 430

Cys Thr Trp Tyr Ala Tyr Asn Arg Val Lys Glu Leu Gly Tyr Gln Val
            435                 440                 445

Asp Arg Tyr Met Gly Asn Gly Gly Asp Trp Gln Arg Lys Pro Gly Phe
    450                 455                 460

Val Thr Thr His Lys Pro Lys Val Gly Tyr Val Val Ser Phe Ala Pro
465                 470                 475                 480

Gly Gln Ala Gly Ala Asp Ala Thr Tyr Gly His Val Ala Val Val Glu
                485                 490                 495

Gln Ile Lys Glu Asp Gly Ser Ile Leu Ile Ser Glu Ser Asn Val Met
```

Gly Leu Gly Thr Ile Ser Tyr Arg Thr Phe Thr Ala Glu Gln Ala Ser
        500                 505                 510
                515                 520                 525

Leu Leu Thr Tyr Val Val Gly Asp Lys Leu Pro Arg Pro
    530                 535                 540

<210> SEQ ID NO 105
<211> LENGTH: 1626
<212> TYPE: DNA
<213> ORGANISM: Streptococcus pyogenes

<400> SEQUENCE: 105

| | | | | | |
|---|---|---|---|---|---|
| atgaagaaaa | ggaaattgtt | agcagtaaca | ctattaagta | ccatactctt | aaacagtgca | 60 |
| gtgccattag | ttgttgctga | tacctccttg | cgtaatagca | catcatccac | tgatcagcct | 120 |
| actacagcag | atactgatac | ggatgacgag | agtgaaacac | caaaaaaaga | caaaaaaagc | 180 |
| aaggaaacag | cgtcgcagca | cgacacccaa | aaagaccata | agccatcaca | cactcaccca | 240 |
| accccccctt | caaatgatac | taagcagacc | gatcaggcat | catctgaagc | tactgacaaa | 300 |
| ccaaataaag | acaaaaacga | caccaagcaa | ccagacagca | gtgatcaatc | caccccatct | 360 |
| cccaaagacc | agtcgtctca | aaaagagtca | caaacaaag | acggccgacc | taccccatca | 420 |
| cctgatcagc | aaaagatca | gacacctgat | aaaacaccag | aaaatcagc | tgataaaacc | 480 |
| cctgaaaaag | gaccagaaaa | agcaactgat | aaaacaccag | agccaaatcg | tgacgctcca | 540 |
| aaacccatcc | aacctccttt | agcagctgct | cctgtcttta | taccttggag | agaaagtgac | 600 |
| aaagacctga | gcaagctaaa | accaagcagt | cgctcatcag | cggcttacgt | gagacactgg | 660 |
| acaggtgact | ctgcctacac | tcacaacctg | ttgtcacgcc | gttatgggat | tactgctgaa | 720 |
| cagctagatg | gttttttgaa | cagtctaggt | attcactatg | ataaagaacg | cttaaacgga | 780 |
| aagcgtttat | tagaatggga | aaaactaaca | ggactagacg | ttcgagctat | cgtagctatt | 840 |
| gcaatggcag | aaagctcact | aggtactcag | ggagttgcta | agaaaaagg | agccaatatg | 900 |
| tttggttatg | cgcctttga | cttcaaccca | aacaatgcca | aaaatacag | cgatgaggtt | 960 |
| gctattcgtc | acatggtaga | agacaccatc | attgccaaca | aaaccaaac | ctttgaaaga | 1020 |
| caagacctca | agcaaaaaa | atggtcacta | ggccagttgg | ataccttgat | tgatggtggg | 1080 |
| gtttacttta | cagatacaag | tggcagtggg | caaagacgag | cagatatcat | gaccaaacta | 1140 |
| gaccaatgga | tagatgatca | tggaagcaca | cctgagattc | cagaacatct | caagataact | 1200 |
| tccgggacac | aatttagcga | agtgcccgta | ggttataaaa | gaagtcagcc | acaaaacgtt | 1260 |
| ttgacctaca | agtcagagac | ctacagcttt | ggccaatgca | cttggtacgc | ctataatcgt | 1320 |
| gtcaaagagc | taggttatca | agtcgacagg | tacatgggta | acgtggcga | ctggcagcgc | 1380 |
| aagccaggtt | ttgtgaccac | ccataaacct | aaagtgggct | atgtcgtctc | atttgcacca | 1440 |
| ggccaagcag | gagcagatgc | aacctatggt | cacgttgctg | ttgtagagca | aatcaaagaa | 1500 |
| gatggttcta | tcttaatttc | agagtcaaat | gttatgggac | taggcaccat | ttcctatcgg | 1560 |
| acgttcacag | ctgagcaggc | tagtttgttg | acctatgtcg | tagggacaa | actcccaaga | 1620 |
| ccataa | | | | | | 1626 |

<210> SEQ ID NO 106
<211> LENGTH: 296
<212> TYPE: PRT
<213> ORGANISM: Streptococcus pyogenes

<400> SEQUENCE: 106

```
Met Ser Asp Lys His Ile Asn Leu Val Ile Val Thr Gly Met Ser Gly
  1               5                  10                  15

Ala Gly Lys Thr Val Ala Ile Gln Ser Phe Glu Asp Leu Gly Tyr Phe
             20                  25                  30

Thr Ile Asp Asn Met Pro Pro Ala Leu Val Pro Lys Phe Leu Glu Leu
         35                  40                  45

Ile Glu Gln Thr Asn Glu Asn Arg Arg Val Ala Leu Val Val Asp Met
 50                  55                  60

Arg Ser Arg Leu Phe Phe Lys Glu Ile Asn Ser Thr Leu Asp Ser Ile
 65                  70                  75                  80

Glu Ser Asn Pro Ser Ile Asp Phe Arg Ile Leu Phe Leu Asp Ala Thr
                 85                  90                  95

Asp Gly Glu Leu Val Ser Arg Tyr Lys Glu Thr Arg Arg Ser His Pro
                100                 105                 110

Leu Ala Ala Asp Gly Arg Val Leu Asp Gly Ile Arg Leu Glu Arg Glu
            115                 120                 125

Leu Leu Ser Pro Leu Lys Ser Met Ser Gln His Val Val Asp Thr Thr
        130                 135                 140

Lys Leu Thr Pro Arg Gln Leu Arg Lys Thr Ile Ser Asp Gln Phe Ser
145                 150                 155                 160

Glu Gly Ser Asn Gln Ala Ser Phe Arg Ile Glu Val Met Ser Phe Gly
                165                 170                 175

Phe Lys Tyr Gly Leu Pro Leu Asp Ala Asp Leu Val Phe Asp Val Arg
            180                 185                 190

Phe Leu Pro Asn Pro Tyr Tyr Gln Val Glu Leu Arg Glu Lys Thr Gly
        195                 200                 205

Leu Asp Glu Asp Val Phe Asn Tyr Val Met Ser His Pro Glu Ser Glu
210                 215                 220

Val Phe Tyr Lys His Leu Leu Asn Leu Ile Val Pro Ile Leu Pro Ala
225                 230                 235                 240

Tyr Gln Lys Glu Gly Lys Ser Val Leu Thr Val Ala Ile Gly Cys Thr
                245                 250                 255

Gly Gly Gln His Arg Ser Val Ala Phe Ala His Cys Leu Ala Glu Ser
            260                 265                 270

Leu Ala Thr Asp Trp Ser Val Asn Glu Ser His Arg Asp Gln Asn Arg
        275                 280                 285

Arg Lys Glu Thr Val Asn Arg Ser
290                 295

<210> SEQ ID NO 107
<211> LENGTH: 891
<212> TYPE: DNA
<213> ORGANISM: Streptococcus pyogenes

<400> SEQUENCE: 107
atgtcagaca aacacattaa tttagttatt gtgacaggaa tgagcggcgc tggaaaaaca      60
gttgccattc agtcttttga ggatctaggc tactttacca ttgataatat gcccccagcc    120
ttggttccaa aatttttaga attaattgaa caaaccaatg aaaatcgtag ggtggctttg    180
gttgtcgata tgagaagtcg tttgtttttc aaggaaatta attctacctt agatagtatt    240
gaaagcaatc ctagcattga ttttcggatt ctttttttgg atgcaacgga tggagaattg    300
gtgtcacgct ataaagaaac cagacggagc caccctttgg ctgcggacgg tcgtgtgctt    360
gatggtattc gattggaaag agaactccta tctcctttga aaagcatgag ccaacatgtg    420
gtggatacaa caaaattgac ccctagacaa ttgcgtaaaa ccatttcaga ccagtttttct    480
```

```
gaagggtcta atcaagcctc tttccgtatt gaagtgatga gctttgggtt caaatatggt    540
cttcctttgg atgcggattt ggttttttgat gtgcgttttc tacccaatcc ttattatcag   600
gtagagcttc gtgaaaaaac aggactagat gaggacgttt ttaattatgt gatgtctcac    660
ccagaatcag aggtgtttta caagcatttg ttaaacctta ttgtccctat cttaccggct    720
taccaaaaag aagggaagtc tgtcttgacg gtggctattg gctgcacagg aggccaacac    780
cgcagcgttg cctttgccca ttgcttggca gaaagtctgg caacagattg gtcggttaat    840
gaaagccatc gtgatcaaaa tcgtcgtaag gaaacggtga atcgttcatg a             891
```

<210> SEQ ID NO 108
<211> LENGTH: 278
<212> TYPE: PRT
<213> ORGANISM: Streptococcus pyogenes

<400> SEQUENCE: 108

```
Met Ile Ile Lys Lys Arg Thr Val Ala Ile Leu Ala Ile Ala Ser Ser
  1               5                  10                  15

Phe Phe Leu Val Ala Cys Gln Ala Thr Lys Ser Leu Lys Ser Gly Asp
                 20                  25                  30

Ala Trp Gly Val Tyr Gln Lys Gln Lys Ser Ile Thr Val Gly Phe Asp
             35                  40                  45

Asn Thr Phe Val Pro Met Gly Tyr Lys Asp Glu Ser Gly Arg Cys Lys
         50                  55                  60

Gly Phe Asp Ile Asp Leu Ala Lys Glu Val Phe His Gln Tyr Gly Leu
 65                  70                  75                  80

Lys Val Asn Phe Gln Ala Ile Asn Trp Asp Met Lys Glu Ala Glu Leu
                 85                  90                  95

Asn Asn Gly Lys Ile Asp Val Ile Trp Asn Gly Tyr Ser Ile Thr Lys
            100                 105                 110

Glu Arg Gln Asp Lys Val Ala Phe Thr Asp Ser Tyr Met Arg Asn Glu
        115                 120                 125

Gln Ile Ile Val Lys Lys Arg Ser Asp Ile Lys Thr Ile Ser Asp
    130                 135                 140

Met Lys His Lys Val Leu Gly Ala Gln Ser Ala Ser Ser Gly Tyr Asp
145                 150                 155                 160

Ser Leu Leu Arg Thr Pro Lys Leu Leu Lys Asp Phe Ile Lys Asn Lys
                165                 170                 175

Asp Ala Asn Gln Tyr Glu Thr Phe Thr Gln Ala Phe Ile Asp Leu Lys
            180                 185                 190

Ser Asp Arg Ile Asp Gly Ile Leu Ile Asp Lys Val Tyr Ala Asn Tyr
        195                 200                 205

Tyr Leu Ala Lys Glu Gly Gln Leu Glu Asn Tyr Arg Met Ile Pro Thr
    210                 215                 220

Thr Phe Glu Asn Glu Ala Phe Ser Val Gly Leu Arg Lys Glu Asp Lys
225                 230                 235                 240

Thr Leu Gln Ala Lys Ile Asn Arg Ala Phe Arg Val Leu Tyr Gln Asn
                245                 250                 255

Gly Lys Phe Gln Ala Ile Ser Glu Lys Trp Phe Gly Asp Asp Val Ala
            260                 265                 270

Thr Ala Asn Ile Lys Ser
        275
```

<210> SEQ ID NO 109
<211> LENGTH: 837

```
<212> TYPE: DNA
<213> ORGANISM: Streptococcus pyogenes

<400> SEQUENCE: 109
atgattataa aaaaaagaac cgtagcaatt ttagccatag ctagtagctt tttcttggta    60
gcttgtcaag ctactaaaag tcttaaatca ggagatgctt ggggagttta ccaaaagcaa   120
aaaagtatta cagttggttt tgacaatacg tttgttccta tgggctataa ggatgaaagc   180
ggcagatgca aaggttttga tattgatttg ctaaagaag ttttcacca atatggactc    240
aaggttaact ttcaagctat taattgggac atgaaagaag cagaactaaa caatggtaaa   300
attgatgtaa tctggaatgg ttattcaata actaaggagc gtcaggataa ggttgccttt   360
actgattctt acatgagaaa tgaacaaatt attgttgtca aaaaaagatc tgatattaaa   420
acaatatcag atatgaaaca taagtgttta ggagcacaat cagcttcatc aggttatgac   480
tccttgttaa gaactcctaa actgctgaaa gattttatta aaataaaga cgctaatcaa   540
tatgaaacct ttacacaagc ttttattgat ttaaaatcag atcgtatcga tggaatattg   600
attgacaaag tatatgccaa ttactattta gcaaaagaag ggcaattaga gaattatcgg   660
atgatcccaa cgacctttga aaatgaagca ttttcggttg acttagaaa agaagacaaa   720
acgttgcaag caaaaattaa tcgtgctttc agggtgcttt atcaaaatgg caaatttcaa   780
gctatttctg agaaatggtt tggagatgat gttgccactg ccaatattaa atcttaa     837

<210> SEQ ID NO 110
<211> LENGTH: 21
<212> TYPE: PRT
<213> ORGANISM: Streptococcus pyogenes

<400> SEQUENCE: 110

Met Ile Ile Lys Lys Arg Thr Val Ala Ile Leu Ala Ile Ala Ser Ser
 1               5                  10                  15
Phe Phe Leu Val Ala
            20

<210> SEQ ID NO 111
<211> LENGTH: 257
<212> TYPE: PRT
<213> ORGANISM: Streptococcus pyogenes

<400> SEQUENCE: 111

Cys Gln Ala Thr Lys Ser Leu Lys Ser Gly Asp Ala Trp Gly Val Tyr
 1               5                  10                  15
Gln Lys Gln Lys Ser Ile Thr Val Gly Phe Asp Asn Thr Phe Val Pro
            20                  25                  30
Met Gly Tyr Lys Asp Glu Ser Gly Arg Cys Lys Gly Phe Asp Ile Asp
            35                  40                  45
Leu Ala Lys Glu Val Phe His Gln Tyr Gly Leu Lys Val Asn Phe Gln
     50                  55                  60
Ala Ile Asn Trp Asp Met Lys Glu Ala Glu Leu Asn Asn Gly Lys Ile
 65                  70                  75                  80
Asp Val Ile Trp Asn Gly Tyr Ser Ile Thr Lys Glu Arg Gln Asp Lys
                 85                  90                  95
Val Ala Phe Thr Asp Ser Tyr Met Arg Asn Glu Gln Ile Ile Val Val
            100                 105                 110
Lys Lys Arg Ser Asp Ile Lys Thr Ile Ser Asp Met Lys His Lys Val
            115                 120                 125
Leu Gly Ala Gln Ser Ala Ser Ser Gly Tyr Asp Ser Leu Leu Arg Thr
```

```
                130                 135                 140
Pro Lys Leu Leu Lys Asp Phe Ile Lys Asn Lys Asp Ala Asn Gln Tyr
145                 150                 155                 160

Glu Thr Phe Thr Gln Ala Phe Ile Asp Leu Lys Ser Asp Arg Ile Asp
                165                 170                 175

Gly Ile Leu Ile Asp Lys Val Tyr Ala Asn Tyr Tyr Leu Ala Lys Glu
                180                 185                 190

Gly Gln Leu Glu Asn Tyr Arg Met Ile Pro Thr Thr Phe Glu Asn Glu
                195                 200                 205

Ala Phe Ser Val Gly Leu Arg Lys Glu Asp Lys Thr Leu Gln Ala Lys
210                 215                 220

Ile Asn Arg Ala Phe Arg Val Leu Tyr Gln Asn Gly Lys Phe Gln Ala
225                 230                 235                 240

Ile Ser Glu Lys Trp Phe Gly Asp Asp Val Ala Thr Ala Asn Ile Lys
                245                 250                 255

Ser

<210> SEQ ID NO 112
<211> LENGTH: 232
<212> TYPE: PRT
<213> ORGANISM: Streptococcus pyogenes

<400> SEQUENCE: 112

Met Lys Thr Leu Ala Phe Asp Thr Ser Asn Lys Thr Leu Ser Leu Ala
1               5                   10                  15

Ile Leu Asp Asp Glu Thr Leu Leu Ala Asp Met Thr Leu Asn Ile Gln
                20                  25                  30

Lys Lys His Ser Val Ser Leu Met Pro Ala Ile Asp Phe Leu Met Thr
                35                  40                  45

Cys Thr Asp Leu Lys Pro Gln Asp Leu Glu Arg Ile Val Val Ala Lys
                50                  55                  60

Gly Pro Gly Ser Tyr Thr Gly Leu Arg Val Ala Val Ala Thr Ala Lys
65                  70                  75                  80

Thr Leu Ala Tyr Ser Leu Asn Ile Ala Leu Val Gly Ile Ser Ser Leu
                85                  90                  95

Tyr Ala Leu Ala Ala Ser Thr Cys Lys Gln Tyr Pro Asn Thr Leu Val
                100                 105                 110

Val Pro Leu Ile Asp Ala Arg Arg Gln Asn Ala Tyr Val Gly Tyr Tyr
                115                 120                 125

Arg Gln Gly Lys Ser Val Met Pro Gln Ala His Ala Ser Leu Glu Val
130                 135                 140

Ile Ile Glu Gln Leu Val Glu Glu Gly Gln Leu Ile Phe Val Gly Glu
145                 150                 155                 160

Thr Ala Pro Phe Ala Glu Lys Ile Gln Lys Lys Leu Pro Gln Ala Ile
                165                 170                 175

Leu Leu Pro Thr Leu Pro Ser Ala Tyr Glu Cys Gly Leu Leu Gly Gln
                180                 185                 190

Ser Leu Ala Pro Glu Asn Val Asp Ala Phe Val Pro Gln Tyr Leu Lys
                195                 200                 205

Arg Val Glu Ala Glu Glu Asn Trp Leu Lys Asp Asn Glu Ile Lys Asp
210                 215                 220

Asp Ser His Tyr Val Lys Arg Ile
225                 230

<210> SEQ ID NO 113
```

```
<211> LENGTH: 699
<212> TYPE: DNA
<213> ORGANISM: Streptococcus pyogenes

<400> SEQUENCE: 113
atgaagacac ttgcatttga tacctcaaat aaaaccttgt cccttgctat acttgatgat    60
gagacacttc tagcagatat gacccttaac attcagaaaa acatagtgt tagccttatg    120 cctgctattg attttttgat gacttgtact gatcttaaac ctcaagattt agaaagaata   180
gtggttgcaa aaggccctgg atcttacaca ggtttacgag tggcagttgc tactgcaaaa   240
acgttagcgt acagtttaaa tattgcattg gtcgggattt cgagtctata tgctttggct   300
gcgtctactt gtaaacagta tccaaatact ttggtggtgc cattgattga tgctagaagg   360
caaaatgcgt atgtaggtta ttatcggcaa ggaaaatcag tgatgccaca agcccatgct   420
tcactagaag ttattataga acaattagta gaagaaggac agctgatttt tgttggggag   480
actgctcctt tgctgagaa aattcaaaag aaactacctc aggcgatact acttccaacc   540
cttccttctg cttacgaatg tggtcttttg gggcaaagtt tggcaccaga aaatgtagac   600
gcctttgtcc ctcaatatct caagagagtg gaagctgaag aaaactggct caaagataat   660
gagataaaag atgatagtca ctacgttaag cgaatctaa                          699

<210> SEQ ID NO 114
<211> LENGTH: 416
<212> TYPE: PRT
<213> ORGANISM: Streptococcus pyogenes

<400> SEQUENCE: 114

Met Leu Lys Arg Leu Trp Leu Ile Leu Gly Pro Leu Leu Ile Ala Phe
 1               5                  10                  15

Val Leu Val Val Ile Thr Ile Phe Ser Phe Pro Thr Gln Leu Asp His
                20                  25                  30

Ser Ile Ala Gln Glu Lys Ala Asn Ala Val Ala Ile Thr Asp Ser Ser
            35                  40                  45

Phe Lys Asn Gly Leu Ile Lys Arg Gln Ala Leu Ser Asp Glu Thr Cys
        50                  55                  60

Arg Phe Val Pro Phe Phe Gly Ser Ser Glu Trp Ser Arg Met Asp Ser
65                  70                  75                  80

Met His Pro Ser Val Leu Ala Glu Arg Tyr Lys Arg Ser Tyr Arg Pro
                85                  90                  95

Phe Leu Ile Gly Lys Arg Gly Ser Ala Ser Leu Ser His Tyr Tyr Gly
               100                 105                 110

Ile Gln Gln Ile Thr Asn Glu Met Gln Lys Lys Ala Ile Phe Val
           115                 120                 125

Val Ser Pro Gln Trp Phe Thr Ala Gln Gly Ile Asn Pro Ser Ala Val
       130                 135                 140

Gln Met Tyr Leu Ser Asn Thr Gln Val Ile Glu Phe Leu Leu Lys Ala
145                 150                 155                 160

Arg Thr Asp Lys Glu Ser Gln Phe Ala Ala Lys Arg Leu Leu Glu Leu
                165                 170                 175

Asn Pro Gly Val Ser Lys Ser Asn Leu Leu Lys Val Ser Lys Gly
            180                 185                 190

Lys Ser Leu Ser Arg Leu Asp Arg Ala Ile Leu Lys Cys Gln His Gln
        195                 200                 205

Val Ala Leu Arg Glu Glu Ser Leu Phe Ser Phe Leu Gly Lys Ser Thr
    210                 215                 220
```

```
Asn Tyr Glu Lys Arg Ile Leu Pro Arg Val Lys Gly Leu Pro Lys Val
225                 230                 235                 240

Phe Ser Tyr Lys Gln Leu Asn Ala Leu Ala Thr Lys Arg Gly Gln Leu
            245                 250                 255

Ala Thr Thr Asn Asn Arg Phe Gly Ile Lys Asn Thr Phe Tyr Arg Lys
        260                 265                 270

Arg Ile Ala Pro Lys Tyr Asn Leu Tyr Lys Asn Phe Gln Val Asn Tyr
    275                 280                 285

Ser Tyr Leu Ala Ser Pro Glu Tyr Asn Asp Phe Gln Leu Leu Leu Ser
290                 295                 300

Glu Phe Ala Lys Arg Lys Thr Asp Val Leu Phe Val Ile Thr Pro Val
305                 310                 315                 320

Asn Lys Ala Trp Ala Asp Tyr Thr Gly Leu Asn Gln Asp Lys Tyr Gln
                325                 330                 335

Ala Ala Val Arg Lys Ile Lys Phe Gln Leu Lys Ser Gln Gly Phe His
            340                 345                 350

Arg Ile Ala Asp Phe Ser Lys Asp Gly Glu Ser Tyr Phe Met Gln
        355                 360                 365

Asp Thr Ile His Leu Gly Trp Asn Gly Trp Leu Ala Phe Asp Lys Lys
    370                 375                 380

Val Gln Pro Phe Leu Glu Thr Lys Gln Pro Val Pro Asn Tyr Lys Met
385                 390                 395                 400

Asn Pro Tyr Phe Tyr Ser Lys Ile Trp Ala Asn Arg Lys Asp Leu Gln
                405                 410                 415
```

<210> SEQ ID NO 115
<211> LENGTH: 1251
<212> TYPE: DNA
<213> ORGANISM: Streptococcus pyogenes

<400> SEQUENCE: 115

```
atgcttaaga gactctggtt aattctaggt cctcttctta ttgcctttgt tttagtagtg      60
attactattt ttagttttcc tacacaactt gatcattcca tagctcagga aaaagcaaat     120
gccgttgcga tcacagatag ttcttttaaa atggtttga ttaaaagaca agctttatca      180
gatgagactt gtcgttttgt gccttttttt ggttctagcg aatggagtcg aatggatagt     240
atgcacccct cggtgcttgc agagcgctac aagcggagct atagaccatt tttaattggt     300
aagagaggat cagcatcttt gtcgcattat atggtatac aacaaattac caatgaaatg      360
caaaagaaaa aagccatctt tgtagtatct cctcaatggt ttactgctca agggattaat     420
cctagtgcgg ttcagatgta cttgtctaac actcaagtga ttgaattttt actaaaagct     480
agaactgata agaatcaca gtttgcagca aagcgtttgc ttgagcttaa ccctggtgtg      540
tctaaatcaa acttattgaa aaaagtaagt aagggtaagt ctcttagtcg ttagacaga      600
gctattttga atgtcaaca tcaagtagca ttgagagaag agtcccctttt tagttttta     660
ggcaaatcta ctaactatga aaaagaatt ttgcctcgcg ttaagggatt acctaaagta      720
ttttcgtata acaattgaa tgcattagca actaagagag gccaattagc aacaaccaac      780
aaccgttttg ggattaaaaa tacatttat cgtaaacgaa tagcacctaa atacaatctt      840
tataagaatt ccaagttaa ttatagttac ctggcgtcac cagaatacaa tgattttcag      900
cttttattat cagaatttgc taaacgaaaa acagatgtac tctttgttat aactcctgtt     960
aataaagctt gggcggatta taccggctta aatcaagata gtatcaagc ggcagttcgt     1020
aaaataaat tccagttaaa gtcacaagga tttcatcgca ttgctgactt ctcaaaagat     1080
```

```
ggtggtgagt cctactttat gcaagatacc atccatctcg gttggaatgg ctggttagct      1140
tttgataaga aagtgcaacc atttctagaa acgaagcagc cagtgcccaa ctataaaatg      1200
aacccttatt tttatagtaa aatttgggca aataggaaag acttgcaata g               1251
```

```
<210> SEQ ID NO 116
<211> LENGTH: 1647
<212> TYPE: PRT
<213> ORGANISM: Streptococcus pyogenes

<400> SEQUENCE: 116
```

```
Met Glu Lys Lys Gln Arg Phe Ser Leu Arg Lys Tyr Lys Ser Gly Thr
  1               5                  10                  15

Phe Ser Val Leu Ile Gly Ser Val Phe Leu Val Met Thr Thr Thr Val
             20                  25                  30

Ala Ala Asp Glu Leu Ser Thr Met Ser Glu Pro Thr Ile Thr Asn His
         35                  40                  45

Ala Gln Gln Ala Gln His Leu Thr Asn Thr Glu Leu Ser Ser Ala
     50                  55                  60

Glu Ser Lys Ser Gln Asp Thr Ser Gln Ile Thr Leu Lys Thr Asn Arg
 65                  70                  75                  80

Glu Lys Glu Gln Ser Gln Asp Leu Val Ser Glu Pro Thr Thr Glu
                 85                  90                  95

Leu Ala Asp Thr Asp Ala Ala Ser Met Ala Asn Thr Gly Ser Asp Ala
            100                 105                 110

Thr Gln Lys Ser Ala Ser Leu Pro Pro Val Asn Thr Asp Val His Asp
        115                 120                 125

Trp Val Lys Thr Lys Gly Ala Trp Asp Lys Gly Tyr Lys Gly Gln Gly
    130                 135                 140

Lys Val Val Ala Val Ile Asp Thr Gly Ile Asp Pro Ala His Gln Ser
145                 150                 155                 160

Met Arg Ile Ser Asp Val Ser Thr Ala Lys Val Lys Ser Lys Glu Asp
                165                 170                 175

Met Leu Ala Arg Gln Lys Ala Ala Gly Ile Asn Tyr Gly Ser Trp Ile
            180                 185                 190

Asn Asp Lys Val Val Phe Ala His Asn Tyr Val Glu Asn Ser Asp Asn
        195                 200                 205

Ile Lys Glu Asn Gln Phe Glu Asp Phe Asp Glu Trp Glu Asn Phe
    210                 215                 220

Glu Phe Asp Ala Glu Ala Glu Pro Lys Ala Ile Lys Lys His Lys Ile
225                 230                 235                 240

Tyr Arg Pro Gln Ser Thr Gln Ala Pro Lys Glu Thr Val Ile Lys Thr
                245                 250                 255

Glu Glu Thr Asp Gly Ser His Asp Ile Asp Trp Thr Gln Thr Asp Asp
            260                 265                 270

Asp Thr Lys Tyr Glu Ser His Gly Met His Val Thr Gly Ile Val Ala
        275                 280                 285

Gly Asn Ser Lys Glu Ala Ala Ala Thr Gly Glu Arg Phe Leu Gly Ile
    290                 295                 300

Ala Pro Glu Ala Gln Val Met Phe Met Arg Val Phe Ala Asn Asp Ile
305                 310                 315                 320

Met Gly Ser Ala Glu Ser Leu Phe Ile Lys Ala Ile Glu Asp Ala Val
                325                 330                 335

Ala Leu Gly Ala Asp Val Ile Asn Leu Ser Leu Gly Thr Ala Asn Gly
            340                 345                 350
```

```
Ala Gln Leu Ser Gly Ser Lys Pro Leu Met Glu Ala Ile Glu Lys Ala
            355                 360                 365

Lys Lys Ala Gly Val Ser Val Val Ala Ala Gly Asn Glu Arg Val
370                 375                 380

Tyr Gly Ser Asp His Asp Pro Leu Ala Thr Asn Pro Asp Tyr Gly
385                 390                 395                 400

Leu Val Gly Ser Pro Ser Thr Gly Arg Thr Pro Thr Ser Val Ala Ala
                405                 410                 415

Ile Asn Ser Lys Trp Val Ile Gln Arg Leu Met Thr Val Lys Glu Leu
            420                 425                 430

Glu Asn Arg Ala Asp Leu Asn His Gly Lys Ala Ile Tyr Ser Glu Ser
            435                 440                 445

Val Asp Phe Lys Asp Ile Lys Asp Ser Leu Gly Tyr Asp Lys Ser His
450                 455                 460

Gln Phe Ala Tyr Val Lys Glu Ser Thr Asp Ala Gly Tyr Asn Ala Gln
465                 470                 475                 480

Asp Val Lys Gly Lys Ile Ala Leu Ile Glu Arg Asp Pro Asn Lys Thr
                485                 490                 495

Tyr Asp Glu Met Ile Ala Leu Ala Lys Lys His Gly Ala Leu Gly Val
                500                 505                 510

Leu Ile Phe Asn Asn Lys Pro Gly Gln Ser Asn Arg Ser Met Arg Leu
            515                 520                 525

Thr Ala Asn Gly Met Gly Ile Pro Ser Ala Phe Ile Ser His Glu Phe
530                 535                 540

Gly Lys Ala Met Ser Gln Leu Asn Gly Asn Thr Gly Ser Leu Glu
545                 550                 555                 560

Phe Asp Ser Val Val Ser Lys Ala Pro Ser Gln Lys Gly Asn Glu Met
                565                 570                 575

Asn His Phe Ser Asn Trp Gly Leu Thr Ser Asp Gly Tyr Leu Lys Pro
            580                 585                 590

Asp Ile Thr Ala Pro Gly Gly Asp Ile Tyr Ser Thr Tyr Asn Asp Asn
            595                 600                 605

His Tyr Gly Ser Gln Thr Gly Thr Ser Met Ala Ser Pro Gln Ile Ala
610                 615                 620

Gly Ala Ser Leu Leu Val Lys Gln Tyr Leu Glu Lys Thr Gln Pro Asn
625                 630                 635                 640

Leu Pro Lys Glu Lys Ile Ala Asp Ile Val Lys Asn Leu Leu Met Ser
                645                 650                 655

Asn Ala Gln Ile His Val Asn Pro Glu Thr Lys Thr Thr Thr Ser Pro
            660                 665                 670

Arg Gln Gln Gly Ala Gly Leu Leu Asn Ile Asp Gly Ala Val Thr Ser
            675                 680                 685

Gly Leu Tyr Val Thr Gly Lys Asp Asn Tyr Gly Ser Ile Ser Leu Gly
690                 695                 700

Asn Ile Thr Asp Thr Met Thr Phe Asp Val Thr Val His Asn Leu Ser
705                 710                 715                 720

Asn Lys Asp Lys Thr Leu Arg Tyr Asp Thr Glu Leu Leu Thr Asp His
                725                 730                 735

Val Asp Pro Gln Lys Gly Arg Phe Thr Leu Thr Ser His Ser Leu Lys
                740                 745                 750

Thr Tyr Gln Gly Gly Glu Val Thr Val Pro Ala Asn Gly Lys Val Thr
            755                 760                 765

Val Arg Val Thr Met Asp Val Ser Gln Phe Thr Lys Glu Leu Thr Lys
770                 775                 780
```

-continued

```
Gln Met Pro Asn Gly Tyr Tyr Leu Glu Gly Phe Val Arg Phe Arg Asp
785                 790                 795                 800

Ser Gln Asp Asp Gln Leu Asn Arg Val Asn Ile Pro Phe Val Gly Phe
                805                 810                 815

Lys Gly Gln Phe Glu Asn Leu Ala Val Ala Glu Glu Ser Ile Tyr Arg
            820                 825                 830

Leu Lys Ser Gln Gly Lys Thr Gly Phe Tyr Phe Asp Glu Ser Gly Pro
        835                 840                 845

Lys Asp Asp Ile Tyr Val Gly Lys His Phe Thr Gly Leu Val Thr Leu
    850                 855                 860

Gly Ser Glu Thr Asn Val Ser Thr Lys Thr Ile Ser Asp Asn Gly Leu
865                 870                 875                 880

His Thr Leu Gly Thr Phe Lys Asn Ala Asp Gly Lys Phe Ile Leu Glu
                885                 890                 895

Lys Asn Ala Gln Gly Asn Pro Val Leu Ala Ile Ser Pro Asn Gly Asp
            900                 905                 910

Asn Asn Gln Asp Phe Ala Ala Phe Lys Gly Val Phe Leu Arg Lys Tyr
        915                 920                 925

Gln Gly Leu Lys Ala Ser Val Tyr His Ala Ser Asp Lys Glu His Lys
    930                 935                 940

Asn Pro Leu Trp Val Ser Pro Glu Ser Phe Lys Gly Asp Lys Asn Phe
945                 950                 955                 960

Asn Ser Asp Ile Arg Phe Ala Lys Ser Thr Thr Leu Leu Gly Thr Ala
                965                 970                 975

Phe Ser Gly Lys Ser Leu Thr Gly Ala Glu Leu Pro Asp Gly His Tyr
            980                 985                 990

His Tyr Val Val Ser Tyr Pro Asp Val Val Gly Ala Lys Arg Gln
        995                 1000                1005

Glu Met Thr Phe Asp Met Ile Leu Asp Arg Gln Lys Pro Val Leu Ser
    1010                1015                1020

Gln Ala Thr Phe Asp Pro Glu Thr Asn Arg Phe Lys Pro Glu Pro Leu
1025                1030                1035                1040

Lys Asp Arg Gly Leu Ala Gly Val Arg Lys Asp Ser Val Phe Tyr Leu
                1045                1050                1055

Glu Arg Lys Asp Asn Lys Pro Tyr Thr Val Thr Ile Asn Asp Ser Tyr
            1060                1065                1070

Lys Tyr Val Ser Val Glu Asp Asn Lys Thr Phe Val Glu Arg Gln Ala
        1075                1080                1085

Asp Gly Ser Phe Ile Leu Pro Leu Asp Lys Ala Lys Leu Gly Asp Phe
    1090                1095                1100

Tyr Tyr Met Val Glu Asp Phe Ala Gly Asn Val Ala Ile Ala Lys Leu
1105                1110                1115                1120

Gly Asp His Leu Pro Gln Thr Leu Gly Lys Thr Pro Ile Lys Leu Lys
                1125                1130                1135

Leu Thr Asp Gly Asn Tyr Gln Thr Lys Glu Thr Leu Lys Asp Asn Leu
            1140                1145                1150

Glu Met Thr Gln Ser Asp Thr Gly Leu Val Thr Asn Gln Ala Gln Leu
        1155                1160                1165

Ala Val Val His Arg Asn Gln Pro Gln Ser Leu Thr Lys Met Asn
    1170                1175                1180

Gln Asp Phe Phe Ile Ser Pro Asn Glu Asp Gly Asn Lys Asp Phe Val
1185                1190                1195                1200

Ala Phe Lys Gly Leu Lys Asn Asn Val Tyr Asn Asp Leu Thr Val Asn
```

-continued

```
                1205                1210                1215
Val Tyr Ala Lys Asp Asp His Gln Lys Gln Thr Pro Ile Trp Ser Ser
        1220                1225                1230

Gln Ala Gly Ala Ser Val Ser Ala Ile Glu Ser Thr Ala Trp Tyr Gly
        1235                1240                1245

Ile Thr Ala Arg Gly Ser Lys Val Met Pro Gly Asp Tyr Gln Tyr Val
        1250                1255                1260

Val Thr Tyr Arg Asp Glu His Gly Lys Glu His Gln Lys Gln Tyr Thr
1265                1270                1275                1280

Ile Ser Val Asn Asp Lys Lys Pro Met Ile Thr Gln Gly Arg Phe Asp
            1285                1290                1295

Thr Ile Asn Gly Val Asp His Phe Thr Pro Asp Lys Thr Lys Ala Leu
        1300                1305                1310

Asp Ser Ser Gly Ile Val Arg Glu Glu Val Phe Tyr Leu Ala Lys Lys
        1315                1320                1325

Asn Gly Arg Lys Phe Asp Val Thr Glu Gly Lys Asp Gly Ile Thr Val
        1330                1335                1340

Ser Asp Asn Lys Val Tyr Ile Pro Lys Asn Pro Asp Gly Ser Tyr Thr
1345                1350                1355                1360

Ile Ser Lys Arg Asp Gly Val Thr Leu Ser Asp Tyr Tyr Tyr Leu Val
            1365                1370                1375

Glu Asp Arg Ala Gly Asn Val Ser Phe Ala Thr Leu Arg Asp Leu Lys
        1380                1385                1390

Ala Val Gly Lys Asp Lys Ala Val Val Asn Phe Gly Leu Asp Leu Pro
        1395                1400                1405

Val Pro Glu Asp Lys Gln Ile Val Asn Phe Thr Tyr Leu Val Arg Asp
        1410                1415                1420

Ala Asp Gly Lys Pro Ile Glu Asn Leu Glu Tyr Tyr Asn Asn Ser Gly
1425                1430                1435                1440

Asn Ser Leu Ile Leu Pro Tyr Gly Lys Tyr Thr Val Glu Leu Leu Thr
            1445                1450                1455

Tyr Asp Thr Asn Ala Ala Lys Leu Glu Ser Asp Lys Ile Val Ser Phe
        1460                1465                1470

Thr Leu Ser Ala Asp Asn Asn Phe Gln Gln Val Thr Phe Lys Ile Thr
        1475                1480                1485

Met Leu Ala Thr Ser Gln Ile Thr Ala His Phe Asp His Leu Leu Pro
        1490                1495                1500

Glu Gly Ser Arg Val Ser Leu Lys Thr Ala Gln Asp Gln Leu Ile Pro
1505                1510                1515                1520

Leu Glu Gln Ser Leu Tyr Val Pro Lys Ala Tyr Gly Lys Thr Val Gln
            1525                1530                1535

Glu Gly Thr Tyr Glu Val Val Ser Leu Pro Lys Gly Tyr Arg Ile
        1540                1545                1550

Glu Gly Asn Thr Lys Val Asn Thr Leu Pro Asn Glu Val His Glu Leu
        1555                1560                1565

Ser Leu Arg Leu Val Lys Val Gly Asp Ala Ser Asp Ser Thr Gly Asp
        1570                1575                1580

His Lys Val Met Ser Lys Asn Asn Ser Gln Ala Leu Thr Ala Ser Ala
1585                1590                1595                1600

Thr Pro Thr Lys Ser Thr Thr Ser Ala Thr Ala Lys Ala Leu Pro Ser
            1605                1610                1615

Thr Gly Glu Lys Met Gly Leu Lys Leu Arg Ile Val Gly Leu Val Leu
        1620                1625                1630
```

Leu Gly Leu Thr Cys Val Phe Ser Arg Lys Lys Ser Thr Lys Asp
    1635                1640                1645

<210> SEQ ID NO 117
<211> LENGTH: 4944
<212> TYPE: DNA
<213> ORGANISM: Streptococcus pyogenes

<400> SEQUENCE: 117

| | | | | |
|---|---|---|---|---|
| gtggagaaaa | agcaacgttt | ttcccttaga | aaatacaaat | caggaacgtt | ttcggtctta | 60 |
| ataggaagcg | ttttcttggt | gatgacaaca | acagtagcag | cagatgagct | aagcacaatg | 120 |
| agcgaaccaa | caatcacgaa | tcacgctcaa | caacaagcgc | aacatctcac | caatacagag | 180 |
| ttgagctcag | ctgaatcaaa | atctcaagac | acatcacaaa | tcactctcaa | gacaaatcgt | 240 |
| gaaaaagagc | aatcacaaga | tctagtctct | gagccaacca | caactgagct | agctgacaca | 300 |
| gatgcagcat | caatggctaa | tacaggttct | gatgcgactc | aaaaaagcgc | ttctttaccg | 360 |
| ccagtcaata | cagatgttca | cgattgggta | aaaaccaaag | gagcttggga | caagggatac | 420 |
| aaaggacaag | gcaaggttgt | cgcagttatt | gacacaggga | tcgatccggc | ccatcaaagc | 480 |
| atgcgcatca | gtgatgtatc | aactgctaaa | gtaaaatcaa | aagaagacat | gctagcacgc | 540 |
| caaaaagccg | ccggtattaa | ttatgggagt | tggataaatg | ataaagttgt | ttttgcacat | 600 |
| aattatgtgg | aaaatagcga | taatatcaaa | gaaaatcaat | tcgaggattt | tgatgaggac | 660 |
| tgggaaaact | ttgagtttga | tgcagaggca | gagccaaaag | ccatcaaaaa | acacaagatc | 720 |
| tatcgtcccc | aatcaaccca | ggcaccgaaa | gaaactgtta | tcaaaacaga | agaaacagat | 780 |
| ggttcacatg | atattgactg | gacacaaaca | gacgatgaca | ccaaatacga | gtcacacggt | 840 |
| atgcatgtga | caggtattgt | agccggtaat | agcaaagaag | ccgctgctac | tggagaacgc | 900 |
| tttttaggaa | ttgcaccaga | ggcccaagtc | atgttcatgc | gtgttttttgc | caacgacatc | 960 |
| atgggatcag | ctgaatcact | ctttatcaaa | gctatcgaag | atgccgtggc | tttaggagca | 1020 |
| gatgtgatca | acctgagtct | tggaaccgct | aatgggggcac | agcttagtgg | cagcaagcct | 1080 |
| ctaatggaag | caattgaaaa | agctaaaaaa | gccggtgtat | cagttgttgt | agcagcagga | 1140 |
| aatgagcgcg | tctatggatc | tgaccatgat | gatccattgg | cgacaaatcc | agactatggt | 1200 |
| ttggtcggtt | ctcccctcaac | aggtcgaaca | ccaacatcag | tggcagctat | aaacagtaag | 1260 |
| tgggtgattc | aacgtctaat | gacggtcaaa | gaattagaaa | accgtgccga | tttaaaccat | 1320 |
| ggtaaagcca | tctattcaga | gtctgtcgac | tttaaagaca | taaagatag | cctaggttat | 1380 |
| gataaatcgc | atcaatttgc | ttatgtcaaa | gagtcaactg | atgcgggtta | taacgcacaa | 1440 |
| gacgttaaag | gtaaaattgc | tttaattgaa | cgtgatccca | ataaaaccta | tgacgaaatg | 1500 |
| attgctttgg | ctaagaaaca | tggagctctg | ggagtactta | ttttttaataa | caagcctggt | 1560 |
| caatcaaacc | gctcaatgcg | tctaacagct | aatgggatgg | gataccatc | tgctttcata | 1620 |
| tcgcacgaat | ttggtaaggc | catgtcccaa | ttaaatggca | atggtacagg | aagtttagag | 1680 |
| tttgacagtg | tggtctcaaa | agcaccgagt | caaaaaggca | atgaaatgaa | tcattttca | 1740 |
| aattggggcc | taacttctga | tggctatttta | aaacctgaca | ttactgcacc | aggtggcgat | 1800 |
| atctattcta | cctataacga | taaccactat | ggtagccaaa | caggaacaag | tatggcctct | 1860 |
| cctcagattg | ctggcgccag | ccttttggtc | aaacaatacc | tagaaaagac | tcagccaaac | 1920 |
| ttgccaaaag | aaaaaattgc | tgatatcgtt | aagaacctat | tgatgagcaa | tgctcaaatt | 1980 |
| catgttaatc | cagagacaaa | aacgaccacc | tcaccgcgtc | agcaagggc | aggattactt | 2040 |
| aatattgacg | gagctgtcac | tagcggcctt | tatgtgacag | gaaaagacaa | ctatggcagt | 2100 |

```
atatcattag gcaacatcac agatacgatg acgtttgatg tgactgttca caacctaagc    2160
aataaagaca aaacattacg ttatgacaca gaattgctaa cagatcatgt agacccacaa    2220
aagggccgct tcactttgac ttctcactcc ttaaaaacgt accaaggagg agaagttaca    2280
gtcccagcca atggaaaagt gactgtaagg gttaccatgg atgtctcaca gttcacaaaa    2340
gagctaacaa aacagatgcc aaatggttac tatctagaag gttttgtccg ctttagagat    2400
agtcaagatg accaactaaa tagagtaaac attccttttg ttggttttaa agggcaattt    2460
gaaaacttag cagttgcaga agagtccatt tacagattaa aatctcaagg caaaactggt    2520
ttttactttg atgaatcagg tccaaaagac gatatctatg tcggtaaaca ctttacagga    2580
cttgtcactc ttggttcaga gaccaatgtg tcaaccaaaa cgatttctga caatggtcta    2640
cacacacttg gcacctttaa aaatgcagat ggcaaattta tcttagaaaa aaatgcccaa    2700
ggaaaccctg tcttagccat ttctccaaat ggtgacaaca accaagattt tgcagccttc    2760
aaaggtgttt tcttgagaaa atatcaaggc ttaaaagcaa gtgtctacca tgctagtgac    2820
aaggaacaca aaaatccact gtgggtcagc ccagaaagct ttaaaggaga taaaaacttt    2880
aatagtgaca ttagatttgc aaaatcaacg accctgttag gcacagcatt ttctggaaaa    2940
tcgttaacag gagctgaatt accagatggg cattatcatt atgtggtgtc ttattaccca    3000
gatgtggtcg gtgccaaacg tcaagaaatg acatttgaca tgattttaga ccgacaaaaa    3060
ccggtactat cacaagcaac atttgatcct gaaacaaacc gattcaaacc agaaccccta    3120
aaagaccgtg gattagctgg tgttcgcaaa gacagtgtct tttatctaga aagaaaagac    3180
aacaagcctt atacagttac gataaacgat agctacaaat atgtctcagt agaagacaat    3240
aaaacatttg tggagcgaca agctgatggc agctttatct tgccgcttga taaagcaaaa    3300
ttaggggatt tctattacat ggtcgaggat tttgcaggga acgtggccat cgctaagtta    3360
ggagatcact taccacaaac attaggtaaa acaccaatta aacttaagct tacagacggt    3420
aattatcaga ccaaagaaac gcttaaagat aatcttgaaa tgacacagtc tgacacaggt    3480
ctagtcacaa atcaagccca gctagcagtg gtgcaccgca atcagccgca aagccagcta    3540
acaaagatga atcaggattt ctttatctca ccaaacgaag atgggaataa agactttgtg    3600
gcctttaaag gcttgaaaaa taacgtgtat aatgacttaa cggttaacgt atacgctaaa    3660
gatgaccacc aaaaacaaac ccctatctgg tctagtcaag caggcgctag tgtatccgct    3720
attgaaagta cagcctggta tggcataaca gcccgaggaa gcaaggtgat gccaggtgat    3780
tatcagtatg ttgtgaccta tcgtgacgaa catggtaaag aacatcaaaa gcagtacacc    3840
atatctgtga atgacaaaaa accaatgatc actcagggac gttttgatac cattaatggc    3900
gttgaccact ttactcctga caagacaaaa gcccttgact catcaggcat tgtccgcgaa    3960
gaagtctttt acttggccaa gaaaaatggc cgtaaatttg atgtgacaga aggtaaagat    4020
ggtatcacag ttagtgacaa taaggtgtat atccctaaaa atccagatgg ttcttacacc    4080
atttcaaaaa gagatggtgt cacactgtca gattattact accttgtcga agatagagct    4140
ggtaatgtgt cttttgctac cttgcgtgac ctaaaagcgg tcggaaaaga caaagcagta    4200
gtcaattttg gattagactt accggtccct gaagacaaac aaatagtgaa ctttacctac    4260
cttgtgcggg atgcagatgg taaaccgatt gaaacctcag agtattataa taactcaggt    4320
aacagtctta tcttgccata cggcaaatac acggtcgaat tgttgaccta tgacaccaat    4380
gcagccaaac tagagtcaga taaatcgtt tcctttacct tgtcagctga taacaacttc    4440
caacaagtta cctttaagat aacgatgtta gcaacttctc aaataactgc ccactttgat    4500
```

-continued

```
catcttttgc cagaaggcag tcgcgttagc cttaaaacag ctcaagatca gctaatcccg    4560
cttgaacagt ccttgtatgt gcctaaagct tatggcaaaa ccgttcaaga aggcacttac    4620
gaagttgttg tcagcctgcc taaaggctac cgtatcgaag caacacaaa ggtgaatacc     4680 ctaccaaatg aagtgcacga actatcatta cgccttgtca agtaggaga tgcctcagat     4740 tcaactggtg atcataaggt tatgtcaaaa ataattcac aggctttgac agcctctgcc     4800
acaccaacca agtcaacgac ctcagcaaca gcaaaagccc taccatcaac gggtgaaaaa    4860
atgggtctca agttgcgcat agtaggtctt gtgttactcg gacttacttg cgtctttagc    4920
cgaaaaaaat caaccaaaga ttga                                           4944
```

<210> SEQ ID NO 118
<211> LENGTH: 33
<212> TYPE: PRT
<213> ORGANISM: Streptococcus pyogenes

<400> SEQUENCE: 118

```
Met Glu Lys Lys Gln Arg Phe Ser Leu Arg Lys Tyr Lys Ser Gly Thr
  1               5                  10                  15

Phe Ser Val Leu Ile Gly Ser Val Phe Leu Val Met Thr Thr Thr Val
             20                  25                  30

Ala
```

<210> SEQ ID NO 119
<211> LENGTH: 1614
<212> TYPE: PRT
<213> ORGANISM: Streptococcus pyogenes

<400> SEQUENCE: 119

```
Ala Asp Glu Leu Ser Thr Met Ser Glu Pro Thr Ile Thr Asn His Ala
  1               5                  10                  15

Gln Gln Gln Ala Gln His Leu Thr Asn Thr Glu Leu Ser Ser Ala Glu
             20                  25                  30

Ser Lys Ser Gln Asp Thr Ser Gln Ile Thr Leu Lys Thr Asn Arg Glu
         35                  40                  45

Lys Glu Gln Ser Gln Asp Leu Val Ser Glu Pro Thr Thr Thr Glu Leu
     50                  55                  60

Ala Asp Thr Asp Ala Ala Ser Met Ala Asn Thr Gly Ser Asp Ala Thr
 65                  70                  75                  80

Gln Lys Ser Ala Ser Leu Pro Pro Val Asn Thr Asp Val His Asp Trp
                 85                  90                  95

Val Lys Thr Lys Gly Ala Trp Asp Lys Gly Tyr Lys Gly Gln Gly Lys
            100                 105                 110

Val Val Ala Val Ile Asp Thr Gly Ile Asp Pro Ala His Gln Ser Met
         115                 120                 125

Arg Ile Ser Asp Val Ser Thr Ala Lys Val Lys Ser Lys Glu Asp Met
     130                 135                 140

Leu Ala Arg Gln Lys Ala Ala Gly Ile Asn Tyr Gly Ser Trp Ile Asn
145                 150                 155                 160

Asp Lys Val Val Phe Ala His Asn Tyr Val Glu Asn Ser Asp Asn Ile
                165                 170                 175

Lys Glu Asn Gln Phe Glu Asp Phe Asp Glu Asp Trp Glu Asn Phe Glu
            180                 185                 190

Phe Asp Ala Glu Ala Glu Pro Lys Ala Ile Lys Lys His Lys Ile Tyr
        195                 200                 205
```

```
Arg Pro Gln Ser Thr Gln Ala Pro Lys Glu Thr Val Ile Lys Thr Glu
    210                 215                 220

Glu Thr Asp Gly Ser His Asp Ile Asp Trp Thr Gln Thr Asp Asp Asp
225                 230                 235                 240

Thr Lys Tyr Glu Ser His Gly Met His Val Thr Gly Ile Val Ala Gly
                245                 250                 255

Asn Ser Lys Glu Ala Ala Thr Gly Glu Arg Phe Leu Gly Ile Ala
            260                 265                 270

Pro Glu Ala Gln Val Met Phe Met Arg Val Phe Ala Asn Asp Ile Met
        275                 280                 285

Gly Ser Ala Glu Ser Leu Phe Ile Lys Ala Ile Glu Asp Ala Val Ala
    290                 295                 300

Leu Gly Ala Asp Val Ile Asn Leu Ser Leu Gly Thr Ala Asn Gly Ala
305                 310                 315                 320

Gln Leu Ser Gly Ser Lys Pro Leu Met Glu Ala Ile Glu Lys Ala Lys
                325                 330                 335

Lys Ala Gly Val Ser Val Val Ala Ala Gly Asn Glu Arg Val Tyr
            340                 345                 350

Gly Ser Asp His Asp Asp Pro Leu Ala Thr Asn Pro Asp Tyr Gly Leu
        355                 360                 365

Val Gly Ser Pro Ser Thr Gly Arg Thr Pro Thr Ser Val Ala Ala Ile
    370                 375                 380

Asn Ser Lys Trp Val Ile Gln Arg Leu Met Thr Val Lys Glu Leu Glu
385                 390                 395                 400

Asn Arg Ala Asp Leu Asn His Gly Lys Ala Ile Tyr Ser Glu Ser Val
                405                 410                 415

Asp Phe Lys Asp Ile Lys Asp Ser Leu Gly Tyr Asp Lys Ser His Gln
            420                 425                 430

Phe Ala Tyr Val Lys Glu Ser Thr Asp Ala Gly Tyr Asn Ala Gln Asp
        435                 440                 445

Val Lys Gly Lys Ile Ala Leu Ile Glu Arg Asp Pro Asn Lys Thr Tyr
    450                 455                 460

Asp Glu Met Ile Ala Leu Ala Lys Lys His Gly Ala Leu Gly Val Leu
465                 470                 475                 480

Ile Phe Asn Asn Lys Pro Gly Gln Ser Asn Arg Ser Met Arg Leu Thr
                485                 490                 495

Ala Asn Gly Met Gly Ile Pro Ser Ala Phe Ile Ser His Glu Phe Gly
            500                 505                 510

Lys Ala Met Ser Gln Leu Asn Gly Asn Gly Thr Gly Ser Leu Glu Phe
        515                 520                 525

Asp Ser Val Val Ser Lys Ala Pro Ser Gln Lys Gly Asn Glu Met Asn
    530                 535                 540

His Phe Ser Asn Trp Gly Leu Thr Ser Asp Gly Tyr Leu Lys Pro Asp
545                 550                 555                 560

Ile Thr Ala Pro Gly Gly Asp Ile Tyr Ser Thr Tyr Asn Asp Asn His
                565                 570                 575

Tyr Gly Ser Gln Thr Gly Thr Ser Met Ala Ser Pro Gln Ile Ala Gly
            580                 585                 590

Ala Ser Leu Leu Val Lys Gln Tyr Leu Glu Lys Thr Gln Pro Asn Leu
        595                 600                 605

Pro Lys Glu Lys Ile Ala Asp Ile Val Lys Asn Leu Leu Met Ser Asn
    610                 615                 620

Ala Gln Ile His Val Asn Pro Glu Thr Lys Thr Thr Ser Pro Arg
625                 630                 635                 640
```

-continued

Gln Gln Gly Ala Gly Leu Leu Asn Ile Asp Gly Ala Val Thr Ser Gly
              645                 650                 655
Leu Tyr Val Thr Gly Lys Asp Asn Tyr Gly Ser Ile Ser Leu Gly Asn
              660                 665                 670
Ile Thr Asp Thr Met Thr Phe Asp Val Thr Val His Asn Leu Ser Asn
              675                 680                 685
Lys Asp Lys Thr Leu Arg Tyr Asp Thr Glu Leu Leu Thr Asp His Val
              690                 695                 700
Asp Pro Gln Lys Gly Arg Phe Thr Leu Thr Ser His Ser Leu Lys Thr
705                 710                 715                 720
Tyr Gln Gly Gly Glu Val Thr Val Pro Ala Asn Gly Lys Val Thr Val
              725                 730                 735
Arg Val Thr Met Asp Val Ser Gln Phe Thr Lys Glu Leu Thr Lys Gln
              740                 745                 750
Met Pro Asn Gly Tyr Tyr Leu Glu Gly Phe Val Arg Phe Arg Asp Ser
              755                 760                 765
Gln Asp Asp Gln Leu Asn Arg Val Asn Ile Pro Phe Val Gly Phe Lys
              770                 775                 780
Gly Gln Phe Glu Asn Leu Ala Val Ala Glu Glu Ser Ile Tyr Arg Leu
785                 790                 795                 800
Lys Ser Gln Gly Lys Thr Gly Phe Tyr Phe Asp Glu Ser Gly Pro Lys
              805                 810                 815
Asp Asp Ile Tyr Val Gly Lys His Phe Thr Gly Leu Val Thr Leu Gly
              820                 825                 830
Ser Glu Thr Asn Val Ser Thr Lys Thr Ile Ser Asp Asn Gly Leu His
              835                 840                 845
Thr Leu Gly Thr Phe Lys Asn Ala Asp Gly Lys Phe Ile Leu Glu Lys
              850                 855                 860
Asn Ala Gln Gly Asn Pro Val Leu Ala Ile Ser Pro Asn Gly Asp Asn
865                 870                 875                 880
Asn Gln Asp Phe Ala Ala Phe Lys Gly Val Phe Leu Arg Lys Tyr Gln
              885                 890                 895
Gly Leu Lys Ala Ser Val Tyr His Ala Ser Asp Lys Glu His Lys Asn
              900                 905                 910
Pro Leu Trp Val Ser Pro Glu Ser Phe Lys Gly Asp Lys Asn Phe Asn
              915                 920                 925
Ser Asp Ile Arg Phe Ala Lys Ser Thr Thr Leu Leu Gly Thr Ala Phe
930                 935                 940
Ser Gly Lys Ser Leu Thr Gly Ala Glu Leu Pro Asp Gly His Tyr His
945                 950                 955                 960
Tyr Val Val Ser Tyr Tyr Pro Asp Val Val Gly Ala Lys Arg Gln Glu
              965                 970                 975
Met Thr Phe Asp Met Ile Leu Asp Arg Gln Lys Pro Val Leu Ser Gln
              980                 985                 990
Ala Thr Phe Asp Pro Glu Thr Asn Arg Phe Lys Pro Glu Pro Leu Lys
              995                 1000                1005
Asp Arg Gly Leu Ala Gly Val Arg Lys Asp Ser Val Phe Tyr Leu Glu
              1010                1015                1020
Arg Lys Asp Asn Lys Pro Tyr Thr Val Thr Ile Asn Asp Ser Tyr Lys
1025                1030                1035                1040
Tyr Val Ser Val Glu Asp Asn Lys Thr Phe Val Glu Arg Gln Ala Asp
              1045                1050                1055
Gly Ser Phe Ile Leu Pro Leu Asp Lys Ala Lys Leu Gly Asp Phe Tyr

```
                    1060              1065             1070
Tyr Met Val Glu Asp Phe Ala Gly Asn Val Ala Ile Ala Lys Leu Gly
            1075             1080             1085

Asp His Leu Pro Gln Thr Leu Gly Lys Thr Pro Ile Lys Leu Lys Leu
            1090             1095             1100

Thr Asp Gly Asn Tyr Gln Thr Lys Glu Thr Leu Lys Asp Asn Leu Glu
1105             1110             1115             1120

Met Thr Gln Ser Asp Thr Gly Leu Val Thr Asn Gln Ala Gln Leu Ala
            1125             1130             1135

Val Val His Arg Asn Gln Pro Gln Ser Gln Leu Thr Lys Met Asn Gln
            1140             1145             1150

Asp Phe Phe Ile Ser Pro Asn Glu Asp Gly Asn Lys Asp Phe Val Ala
            1155             1160             1165

Phe Lys Gly Leu Lys Asn Asn Val Tyr Asn Asp Leu Thr Val Asn Val
            1170             1175             1180

Tyr Ala Lys Asp Asp His Gln Lys Gln Thr Pro Ile Trp Ser Ser Gln
1185             1190             1195             1200

Ala Gly Ala Ser Val Ser Ala Ile Glu Ser Thr Ala Trp Tyr Gly Ile
            1205             1210             1215

Thr Ala Arg Gly Ser Lys Val Met Pro Gly Asp Tyr Gln Tyr Val Val
            1220             1225             1230

Thr Tyr Arg Asp Glu His Gly Lys Glu His Lys Gln Tyr Thr Ile
            1235             1240             1245

Ser Val Asn Asp Lys Lys Pro Met Ile Thr Gln Gly Arg Phe Asp Thr
            1250             1255             1260

Ile Asn Gly Val Asp His Phe Thr Pro Asp Lys Thr Lys Ala Leu Asp
1265             1270             1275             1280

Ser Ser Gly Ile Val Arg Glu Glu Val Phe Tyr Leu Ala Lys Lys Asn
            1285             1290             1295

Gly Arg Lys Phe Asp Val Thr Glu Gly Lys Asp Gly Ile Thr Val Ser
            1300             1305             1310

Asp Asn Lys Val Tyr Ile Pro Lys Asn Pro Asp Gly Ser Tyr Thr Ile
            1315             1320             1325

Ser Lys Arg Asp Gly Val Thr Leu Ser Asp Tyr Tyr Tyr Leu Val Glu
            1330             1335             1340

Asp Arg Ala Gly Asn Val Ser Phe Ala Thr Leu Arg Asp Leu Lys Ala
1345             1350             1355             1360

Val Gly Lys Asp Lys Ala Val Val Asn Phe Gly Leu Asp Leu Pro Val
            1365             1370             1375

Pro Glu Asp Lys Gln Ile Val Asn Phe Thr Tyr Leu Val Arg Asp Ala
            1380             1385             1390

Asp Gly Lys Pro Ile Glu Asn Leu Glu Tyr Tyr Asn Asn Ser Gly Asn
            1395             1400             1405

Ser Leu Ile Leu Pro Tyr Gly Lys Tyr Thr Val Glu Leu Leu Thr Tyr
            1410             1415             1420

Asp Thr Asn Ala Ala Lys Leu Glu Ser Asp Lys Ile Val Ser Phe Thr
1425             1430             1435             1440

Leu Ser Ala Asp Asn Asn Phe Gln Gln Val Thr Phe Lys Ile Thr Met
            1445             1450             1455

Leu Ala Thr Ser Gln Ile Thr Ala His Phe Asp His Leu Leu Pro Glu
            1460             1465             1470

Gly Ser Arg Val Ser Leu Lys Thr Ala Gln Asp Gln Leu Ile Pro Leu
            1475             1480             1485
```

```
Glu Gln Ser Leu Tyr Val Pro Lys Ala Tyr Gly Lys Thr Val Gln Glu
        1490                1495                1500

Gly Thr Tyr Glu Val Val Ser Leu Pro Lys Gly Tyr Arg Ile Glu
1505                1510                1515                1520

Gly Asn Thr Lys Val Asn Thr Leu Pro Asn Glu Val His Glu Leu Ser
                1525                1530                1535

Leu Arg Leu Val Lys Val Gly Asp Ala Ser Asp Ser Thr Gly Asp His
                1540                1545                1550

Lys Val Met Ser Lys Asn Asn Ser Gln Ala Leu Thr Ala Ser Ala Thr
                1555                1560                1565

Pro Thr Lys Ser Thr Thr Ser Ala Thr Ala Lys Ala Leu Pro Ser Thr
                1570                1575                1580

Gly Glu Lys Met Gly Leu Lys Leu Arg Ile Val Gly Leu Val Leu Leu
1585                1590                1595                1600

Gly Leu Thr Cys Val Phe Ser Arg Lys Lys Ser Thr Lys Asp
                1605                1610

<210> SEQ ID NO 120
<211> LENGTH: 34
<212> TYPE: PRT
<213> ORGANISM: Streptococcus pyogenes

<400> SEQUENCE: 120

Leu Pro Ser Thr Gly Glu Lys Met Gly Leu Lys Leu Arg Ile Val Gly
1               5                   10                  15

Leu Val Leu Leu Gly Leu Thr Cys Val Phe Ser Arg Lys Lys Ser Thr
                20                  25                  30

Lys Asp

<210> SEQ ID NO 121
<211> LENGTH: 1613
<212> TYPE: PRT
<213> ORGANISM: Streptococcus pyogenes

<400> SEQUENCE: 121

Met Glu Lys Lys Gln Arg Phe Ser Leu Arg Lys Tyr Lys Ser Gly Thr
1               5                   10                  15

Phe Ser Val Leu Ile Gly Ser Val Phe Leu Val Met Thr Thr Thr Val
                20                  25                  30

Ala Ala Asp Glu Leu Ser Thr Met Ser Glu Pro Thr Ile Thr Asn His
                35                  40                  45

Ala Gln Gln Ala Gln His Leu Thr Asn Thr Glu Leu Ser Ser Ala
    50                  55                  60

Glu Ser Lys Ser Gln Asp Thr Ser Gln Ile Thr Leu Lys Thr Asn Arg
65                  70                  75                  80

Glu Lys Glu Gln Ser Gln Asp Leu Val Ser Glu Pro Thr Thr Glu
                85                  90                  95

Leu Ala Asp Thr Asp Ala Ala Ser Met Ala Asn Thr Gly Ser Asp Ala
                100                 105                 110

Thr Gln Lys Ser Ala Ser Leu Pro Pro Val Asn Thr Asp Val His Asp
                115                 120                 125

Trp Val Lys Thr Lys Gly Ala Trp Asp Lys Gly Tyr Lys Gly Gln Gly
                130                 135                 140

Lys Val Val Ala Val Ile Asp Thr Gly Ile Asp Pro Ala His Gln Ser
145                 150                 155                 160

Met Arg Ile Ser Asp Val Ser Thr Ala Lys Val Lys Ser Lys Glu Asp
                165                 170                 175
```

Met Leu Ala Arg Gln Lys Ala Ala Gly Ile Asn Tyr Gly Ser Trp Ile
                180                 185                 190

Asn Asp Lys Val Val Phe Ala His Asn Tyr Val Glu Asn Ser Asp Asn
            195                 200                 205

Ile Lys Glu Asn Gln Phe Glu Asp Phe Asp Glu Asp Trp Glu Asn Phe
210                 215                 220

Glu Phe Asp Ala Glu Ala Glu Pro Lys Ala Ile Lys Lys His Lys Ile
225                 230                 235                 240

Tyr Arg Pro Gln Ser Thr Gln Ala Pro Lys Glu Thr Val Ile Lys Thr
                245                 250                 255

Glu Glu Thr Asp Gly Ser His Asp Ile Asp Trp Thr Gln Thr Asp Asp
                260                 265                 270

Asp Thr Lys Tyr Glu Ser His Gly Met His Val Thr Gly Ile Val Ala
                275                 280                 285

Gly Asn Ser Lys Glu Ala Ala Thr Gly Glu Arg Phe Leu Gly Ile
                290                 295                 300

Ala Pro Glu Ala Gln Val Met Phe Met Arg Val Phe Ala Asn Asp Ile
305                 310                 315                 320

Met Gly Ser Ala Glu Ser Leu Phe Ile Lys Ala Ile Glu Asp Ala Val
                325                 330                 335

Ala Leu Gly Ala Asp Val Ile Asn Leu Ser Leu Gly Thr Ala Asn Gly
                340                 345                 350

Ala Gln Leu Ser Gly Ser Lys Pro Leu Met Glu Ala Ile Glu Lys Ala
                355                 360                 365

Lys Lys Ala Gly Val Ser Val Val Ala Ala Gly Asn Glu Arg Val
370                 375                 380

Tyr Gly Ser Asp His Asp Pro Leu Ala Thr Asn Pro Asp Tyr Gly
385                 390                 395                 400

Leu Val Gly Ser Pro Ser Thr Gly Arg Thr Pro Thr Ser Val Ala Ala
                405                 410                 415

Ile Asn Ser Lys Trp Val Ile Gln Arg Leu Met Thr Val Lys Glu Leu
                420                 425                 430

Glu Asn Arg Ala Asp Leu Asn His Gly Lys Ala Ile Tyr Ser Glu Ser
                435                 440                 445

Val Asp Phe Lys Asp Ile Lys Asp Ser Leu Gly Tyr Asp Lys Ser His
450                 455                 460

Gln Phe Ala Tyr Val Lys Glu Ser Thr Asp Ala Gly Tyr Asn Ala Gln
465                 470                 475                 480

Asp Val Lys Gly Lys Ile Ala Leu Ile Glu Arg Asp Pro Asn Lys Thr
                485                 490                 495

Tyr Asp Glu Met Ile Ala Leu Ala Lys Lys His Gly Ala Leu Gly Val
                500                 505                 510

Leu Ile Phe Asn Asn Lys Pro Gly Gln Ser Asn Arg Ser Met Arg Leu
                515                 520                 525

Thr Ala Asn Gly Met Gly Ile Pro Ser Ala Phe Ile Ser His Glu Phe
530                 535                 540

Gly Lys Ala Met Ser Gln Leu Asn Gly Asn Gly Thr Gly Ser Leu Glu
545                 550                 555                 560

Phe Asp Ser Val Val Ser Lys Ala Pro Ser Gln Lys Gly Asn Glu Met
                565                 570                 575

Asn His Phe Ser Asn Trp Gly Leu Thr Ser Asp Gly Tyr Leu Lys Pro
                580                 585                 590

Asp Ile Thr Ala Pro Gly Gly Asp Ile Tyr Ser Thr Tyr Asn Asp Asn

```
            595                 600                 605
His Tyr Gly Ser Gln Thr Gly Thr Ser Met Ala Ser Pro Gln Ile Ala
610                 615                 620

Gly Ala Ser Leu Leu Val Lys Gln Tyr Leu Glu Lys Thr Gln Pro Asn
625                 630                 635                 640

Leu Pro Lys Glu Lys Ile Ala Asp Ile Val Lys Asn Leu Leu Met Ser
                645                 650                 655

Asn Ala Gln Ile His Val Asn Pro Glu Thr Lys Thr Thr Thr Ser Pro
                660                 665                 670

Arg Gln Gln Gly Ala Gly Leu Leu Asn Ile Asp Gly Ala Val Thr Ser
                675                 680                 685

Gly Leu Tyr Val Thr Gly Lys Asp Asn Tyr Gly Ser Ile Ser Leu Gly
690                 695                 700

Asn Ile Thr Asp Thr Met Thr Phe Asp Val Thr Val His Asn Leu Ser
705                 710                 715                 720

Asn Lys Asp Lys Thr Leu Arg Tyr Asp Thr Glu Leu Leu Thr Asp His
                725                 730                 735

Val Asp Pro Gln Lys Gly Arg Phe Thr Leu Thr Ser His Ser Leu Lys
                740                 745                 750

Thr Tyr Gln Gly Gly Glu Val Thr Val Pro Ala Asn Gly Lys Val Thr
                755                 760                 765

Val Arg Val Thr Met Asp Val Ser Gln Phe Thr Lys Glu Leu Thr Lys
770                 775                 780

Gln Met Pro Asn Gly Tyr Tyr Leu Glu Gly Phe Val Arg Phe Arg Asp
785                 790                 795                 800

Ser Gln Asp Asp Gln Leu Asn Arg Val Asn Ile Pro Phe Val Gly Phe
                805                 810                 815

Lys Gly Gln Phe Glu Asn Leu Ala Val Ala Glu Ser Ile Tyr Arg
                820                 825                 830

Leu Lys Ser Gln Gly Lys Thr Gly Phe Tyr Phe Asp Glu Ser Gly Pro
                835                 840                 845

Lys Asp Asp Ile Tyr Val Gly Lys His Phe Thr Gly Leu Val Thr Leu
850                 855                 860

Gly Ser Glu Thr Asn Val Ser Thr Lys Thr Ile Ser Asp Asn Gly Leu
865                 870                 875                 880

His Thr Leu Gly Thr Phe Lys Asn Ala Asp Gly Lys Phe Ile Leu Glu
                885                 890                 895

Lys Asn Ala Gln Gly Asn Pro Val Leu Ala Ile Ser Pro Asn Gly Asp
                900                 905                 910

Asn Asn Gln Asp Phe Ala Ala Phe Lys Gly Val Phe Leu Arg Lys Tyr
                915                 920                 925

Gln Gly Leu Lys Ala Ser Val Tyr His Ala Ser Asp Lys Glu His Lys
                930                 935                 940

Asn Pro Leu Trp Val Ser Pro Glu Ser Phe Lys Gly Asp Lys Asn Phe
945                 950                 955                 960

Asn Ser Asp Ile Arg Phe Ala Lys Ser Thr Thr Leu Leu Gly Thr Ala
                965                 970                 975

Phe Ser Gly Lys Ser Leu Thr Gly Ala Glu Leu Pro Asp Gly His Tyr
                980                 985                 990

His Tyr Val Val Ser Tyr Tyr Pro Asp Val Val Gly Ala Lys Arg Gln
                995                 1000                1005

Glu Met Thr Phe Asp Met Ile Leu Asp Arg Gln Lys Pro Val Leu Ser
                1010                1015                1020
```

-continued

```
Gln Ala Thr Phe Asp Pro Glu Thr Asn Arg Phe Lys Pro Glu Pro Leu
1025                1030                1035                1040

Lys Asp Arg Gly Leu Ala Gly Val Arg Lys Asp Ser Val Phe Tyr Leu
            1045                1050                1055

Glu Arg Lys Asp Asn Lys Pro Tyr Thr Val Thr Ile Asn Asp Ser Tyr
            1060                1065                1070

Lys Tyr Val Ser Val Glu Asp Asn Lys Thr Phe Val Glu Arg Gln Ala
            1075                1080                1085

Asp Gly Ser Phe Ile Leu Pro Leu Asp Lys Ala Lys Leu Gly Asp Phe
            1090                1095                1100

Tyr Tyr Met Val Glu Asp Phe Ala Gly Asn Val Ala Ile Ala Lys Leu
1105                1110                1115                1120

Gly Asp His Leu Pro Gln Thr Leu Gly Lys Thr Pro Ile Lys Leu Lys
            1125                1130                1135

Leu Thr Asp Gly Asn Tyr Gln Thr Lys Glu Thr Leu Lys Asp Asn Leu
            1140                1145                1150

Glu Met Thr Gln Ser Asp Thr Gly Leu Val Thr Asn Gln Ala Gln Leu
            1155                1160                1165

Ala Val Val His Arg Asn Gln Pro Gln Ser Gln Leu Thr Lys Met Asn
            1170                1175                1180

Gln Asp Phe Phe Ile Ser Pro Asn Glu Asp Gly Asn Lys Asp Phe Val
1185                1190                1195                1200

Ala Phe Lys Gly Leu Lys Asn Asn Val Tyr Asn Asp Leu Thr Val Asn
            1205                1210                1215

Val Tyr Ala Lys Asp Asp His Gln Lys Gln Thr Pro Ile Trp Ser Ser
            1220                1225                1230

Gln Ala Gly Ala Ser Val Ser Ala Ile Glu Ser Thr Ala Trp Tyr Gly
            1235                1240                1245

Ile Thr Ala Arg Gly Ser Lys Val Met Pro Gly Asp Tyr Gln Tyr Val
            1250                1255                1260

Val Thr Tyr Arg Asp Glu His Gly Lys Glu His Gln Lys Gln Tyr Thr
1265                1270                1275                1280

Ile Ser Val Asn Asp Lys Lys Pro Met Ile Thr Gln Gly Arg Phe Asp
            1285                1290                1295

Thr Ile Asn Gly Val Asp His Phe Thr Pro Asp Lys Thr Lys Ala Leu
            1300                1305                1310

Asp Ser Ser Gly Ile Val Arg Glu Glu Val Phe Tyr Leu Ala Lys Lys
            1315                1320                1325

Asn Gly Arg Lys Phe Asp Val Thr Glu Gly Lys Asp Gly Ile Thr Val
            1330                1335                1340

Ser Asp Asn Lys Val Tyr Ile Pro Lys Asn Pro Asp Gly Ser Tyr Thr
1345                1350                1355                1360

Ile Ser Lys Arg Asp Gly Val Thr Leu Ser Asp Tyr Tyr Leu Val
            1365                1370                1375

Glu Asp Arg Ala Gly Asn Val Ser Phe Ala Thr Leu Arg Asp Leu Lys
            1380                1385                1390

Ala Val Gly Lys Asp Lys Ala Val Val Asn Phe Gly Leu Asp Leu Pro
            1395                1400                1405

Val Pro Glu Asp Lys Gln Ile Val Asn Phe Thr Leu Val Arg Asp
            1410                1415                1420

Ala Asp Gly Lys Pro Ile Glu Asn Leu Glu Tyr Tyr Asn Asn Ser Gly
1425                1430                1435                1440

Asn Ser Leu Ile Leu Pro Tyr Gly Lys Tyr Thr Val Glu Leu Leu Thr
            1445                1450                1455
```

-continued

```
Tyr Asp Thr Asn Ala Ala Lys Leu Glu Ser Asp Lys Ile Val Ser Phe
              1460                1465                1470

Thr Leu Ser Ala Asp Asn Asn Phe Gln Gln Val Thr Phe Lys Ile Thr
          1475                1480                1485

Met Leu Ala Thr Ser Gln Ile Thr Ala His Phe Asp His Leu Leu Pro
      1490                1495                1500

Glu Gly Ser Arg Val Ser Leu Lys Thr Ala Gln Asp Gln Leu Ile Pro
1505                1510                1515                1520

Leu Glu Gln Ser Leu Tyr Val Pro Lys Ala Tyr Gly Lys Thr Val Gln
                1525                1530                1535

Glu Gly Thr Tyr Glu Val Val Ser Leu Pro Lys Gly Tyr Arg Ile
            1540                1545                1550

Glu Gly Asn Thr Lys Val Asn Thr Leu Pro Asn Glu Val His Glu Leu
        1555                1560                1565

Ser Leu Arg Leu Val Lys Val Gly Asp Ala Ser Asp Ser Thr Gly Asp
    1570                1575                1580

His Lys Val Met Ser Lys Asn Asn Ser Gln Ala Leu Thr Ala Ser Ala
1585                1590                1595                1600

Thr Pro Thr Lys Ser Thr Thr Ser Ala Thr Ala Lys Ala
                1605                1610

<210> SEQ ID NO 122
<211> LENGTH: 1580
<212> TYPE: PRT
<213> ORGANISM: Streptococcus pyogenes

<400> SEQUENCE: 122

Ala Asp Glu Leu Ser Thr Met Ser Glu Pro Thr Ile Thr Asn His Ala
 1               5                  10                  15

Gln Gln Gln Ala Gln His Leu Thr Asn Thr Glu Leu Ser Ser Ala Glu
             20                  25                  30

Ser Lys Ser Gln Asp Thr Ser Gln Ile Thr Leu Lys Thr Asn Arg Glu
         35                  40                  45

Lys Glu Gln Ser Gln Asp Leu Val Ser Glu Pro Thr Thr Thr Glu Leu
     50                  55                  60

Ala Asp Thr Asp Ala Ala Ser Met Ala Asn Thr Gly Ser Asp Ala Thr
65                  70                  75                  80

Gln Lys Ser Ala Ser Leu Pro Pro Val Asn Thr Asp Val His Asp Trp
                 85                  90                  95

Val Lys Thr Lys Gly Ala Trp Asp Lys Gly Tyr Lys Gly Gln Gly Lys
            100                 105                 110

Val Val Ala Val Ile Asp Thr Gly Ile Asp Pro Ala His Gln Ser Met
        115                 120                 125

Arg Ile Ser Asp Val Ser Thr Ala Lys Val Lys Ser Lys Glu Asp Met
    130                 135                 140

Leu Ala Arg Gln Lys Ala Ala Gly Ile Asn Tyr Gly Ser Trp Ile Asn
145                 150                 155                 160

Asp Lys Val Val Phe Ala His Asn Tyr Val Glu Asn Ser Asp Asn Ile
                165                 170                 175

Lys Glu Asn Gln Phe Glu Asp Phe Asp Glu Asp Trp Glu Asn Phe Glu
            180                 185                 190

Phe Asp Ala Glu Ala Glu Pro Lys Ala Ile Lys Lys His Lys Ile Tyr
        195                 200                 205

Arg Pro Gln Ser Thr Gln Ala Pro Lys Glu Thr Val Ile Lys Thr Glu
    210                 215                 220
```

-continued

```
Glu Thr Asp Gly Ser His Asp Ile Asp Trp Thr Gln Thr Asp Asp
225                 230                 235                 240

Thr Lys Tyr Glu Ser His Gly Met His Val Thr Gly Ile Val Ala Gly
            245                 250                 255

Asn Ser Lys Glu Ala Ala Ala Thr Gly Glu Arg Phe Leu Gly Ile Ala
            260                 265                 270

Pro Glu Ala Gln Val Met Phe Met Arg Val Phe Ala Asn Asp Ile Met
            275                 280                 285

Gly Ser Ala Glu Ser Leu Phe Ile Lys Ala Ile Glu Asp Ala Val Ala
        290                 295                 300

Leu Gly Ala Asp Val Ile Asn Leu Ser Leu Gly Thr Ala Asn Gly Ala
305                 310                 315                 320

Gln Leu Ser Gly Ser Lys Pro Leu Met Glu Ala Ile Glu Lys Ala Lys
                325                 330                 335

Lys Ala Gly Val Ser Val Val Ala Ala Gly Asn Glu Arg Val Tyr
            340                 345                 350

Gly Ser Asp His Asp Asp Pro Leu Ala Thr Asn Pro Asp Tyr Gly Leu
        355                 360                 365

Val Gly Ser Pro Ser Thr Gly Arg Thr Pro Thr Ser Val Ala Ala Ile
    370                 375                 380

Asn Ser Lys Trp Val Ile Gln Arg Leu Met Thr Val Lys Glu Leu Glu
385                 390                 395                 400

Asn Arg Ala Asp Leu Asn His Gly Lys Ala Ile Tyr Ser Glu Ser Val
                405                 410                 415

Asp Phe Lys Asp Ile Lys Asp Ser Leu Gly Tyr Asp Lys Ser His Gln
                420                 425                 430

Phe Ala Tyr Val Lys Glu Ser Thr Asp Ala Gly Tyr Asn Ala Gln Asp
            435                 440                 445

Val Lys Gly Lys Ile Ala Leu Ile Glu Arg Asp Pro Asn Lys Thr Tyr
    450                 455                 460

Asp Glu Met Ile Ala Leu Ala Lys Lys His Gly Ala Leu Gly Val Leu
465                 470                 475                 480

Ile Phe Asn Asn Lys Pro Gly Gln Ser Asn Arg Ser Met Arg Leu Thr
                485                 490                 495

Ala Asn Gly Met Gly Ile Pro Ser Ala Phe Ile Ser His Glu Phe Gly
            500                 505                 510

Lys Ala Met Ser Gln Leu Asn Gly Asn Gly Thr Gly Ser Leu Glu Phe
            515                 520                 525

Asp Ser Val Val Ser Lys Ala Pro Ser Gln Lys Gly Asn Glu Met Asn
530                 535                 540

His Phe Ser Asn Trp Gly Leu Thr Ser Asp Gly Tyr Leu Lys Pro Asp
545                 550                 555                 560

Ile Thr Ala Pro Gly Gly Asp Ile Tyr Ser Thr Tyr Asn Asp Asn His
                565                 570                 575

Tyr Gly Ser Gln Thr Gly Thr Ser Met Ala Ser Pro Gln Ile Ala Gly
            580                 585                 590

Ala Ser Leu Leu Val Lys Gln Tyr Leu Glu Lys Thr Gln Pro Asn Leu
        595                 600                 605

Pro Lys Glu Lys Ile Ala Asp Ile Val Lys Asn Leu Leu Met Ser Asn
        610                 615                 620

Ala Gln Ile His Val Asn Pro Glu Thr Lys Thr Thr Ser Pro Arg
625                 630                 635                 640

Gln Gln Gly Ala Gly Leu Leu Asn Ile Asp Gly Ala Val Thr Ser Gly
```

```
                    645                 650                 655
Leu Tyr Val Thr Gly Lys Asp Asn Tyr Gly Ser Ile Ser Leu Gly Asn
                660                 665                 670
Ile Thr Asp Thr Met Thr Phe Asp Val Thr Val His Asn Leu Ser Asn
                675                 680                 685
Lys Asp Lys Thr Leu Arg Tyr Asp Thr Glu Leu Leu Thr Asp His Val
                690                 695                 700
Asp Pro Gln Lys Gly Arg Phe Thr Leu Thr His Ser Leu Lys Thr
705                 710                 715                 720
Tyr Gln Gly Gly Glu Val Thr Val Pro Ala Asn Gly Lys Val Thr Val
                725                 730                 735
Arg Val Thr Met Asp Val Ser Gln Phe Thr Lys Glu Leu Thr Lys Gln
                740                 745                 750
Met Pro Asn Gly Tyr Tyr Leu Glu Gly Phe Val Arg Phe Arg Asp Ser
                755                 760                 765
Gln Asp Asp Gln Leu Asn Arg Val Asn Ile Pro Phe Val Gly Phe Lys
                770                 775                 780
Gly Gln Phe Glu Asn Leu Ala Val Ala Glu Glu Ser Ile Tyr Arg Leu
785                 790                 795                 800
Lys Ser Gln Gly Lys Thr Gly Phe Tyr Phe Asp Glu Ser Gly Pro Lys
                805                 810                 815
Asp Asp Ile Tyr Val Gly Lys His Phe Thr Gly Leu Val Thr Leu Gly
                820                 825                 830
Ser Glu Thr Asn Val Ser Thr Lys Thr Ile Ser Asp Asn Gly Leu His
                835                 840                 845
Thr Leu Gly Thr Phe Lys Asn Ala Asp Gly Lys Phe Ile Leu Glu Lys
                850                 855                 860
Asn Ala Gln Gly Asn Pro Val Leu Ala Ile Ser Pro Asn Gly Asp Asn
865                 870                 875                 880
Asn Gln Asp Phe Ala Ala Phe Lys Gly Val Phe Leu Arg Lys Tyr Gln
                885                 890                 895
Gly Leu Lys Ala Ser Val Tyr His Ala Ser Asp Lys Glu His Lys Asn
                900                 905                 910
Pro Leu Trp Val Ser Pro Glu Ser Phe Lys Gly Asp Lys Asn Phe Asn
                915                 920                 925
Ser Asp Ile Arg Phe Ala Lys Ser Thr Thr Leu Leu Gly Thr Ala Phe
                930                 935                 940
Ser Gly Lys Ser Leu Thr Gly Ala Glu Leu Pro Asp Gly His Tyr His
945                 950                 955                 960
Tyr Val Val Ser Tyr Tyr Pro Asp Val Val Gly Ala Lys Arg Gln Glu
                965                 970                 975
Met Thr Phe Asp Met Ile Leu Asp Arg Gln Lys Pro Val Leu Ser Gln
                980                 985                 990
Ala Thr Phe Asp Pro Glu Thr Asn Arg Phe Lys Pro Glu Pro Leu Lys
                995                 1000                1005
Asp Arg Gly Leu Ala Gly Val Arg Lys Asp Ser Val Phe Tyr Leu Glu
        1010                1015                1020
Arg Lys Asp Asn Lys Pro Tyr Thr Val Thr Ile Asn Asp Ser Tyr Lys
1025                1030                1035                1040
Tyr Val Ser Val Glu Asp Asn Lys Thr Phe Val Glu Arg Gln Ala Asp
                1045                1050                1055
Gly Ser Phe Ile Leu Pro Leu Asp Lys Ala Lys Leu Gly Asp Phe Tyr
                1060                1065                1070
```

```
Tyr Met Val Glu Asp Phe Ala Gly Asn Val Ala Ile Ala Lys Leu Gly
        1075                1080                1085

Asp His Leu Pro Gln Thr Leu Gly Lys Thr Pro Ile Lys Leu Lys Leu
    1090                1095                1100

Thr Asp Gly Asn Tyr Gln Thr Lys Glu Thr Leu Lys Asp Asn Leu Glu
1105                1110                1115                1120

Met Thr Gln Ser Asp Thr Gly Leu Val Thr Asn Gln Ala Gln Leu Ala
        1125                1130                1135

Val Val His Arg Asn Gln Pro Gln Ser Gln Leu Thr Lys Met Asn Gln
            1140                1145                1150

Asp Phe Phe Ile Ser Pro Asn Glu Asp Gly Asn Lys Asp Phe Val Ala
    1155                1160                1165

Phe Lys Gly Leu Lys Asn Asn Val Tyr Asn Asp Leu Thr Val Asn Val
    1170                1175                1180

Tyr Ala Lys Asp Asp His Gln Lys Gln Thr Pro Ile Trp Ser Ser Gln
1185                1190                1195                1200

Ala Gly Ala Ser Val Ser Ala Ile Glu Ser Thr Ala Trp Tyr Gly Ile
        1205                1210                1215

Thr Ala Arg Gly Ser Lys Val Met Pro Gly Asp Tyr Gln Tyr Val Val
        1220                1225                1230

Thr Tyr Arg Asp Glu His Gly Lys Glu His Gln Lys Gln Tyr Thr Ile
        1235                1240                1245

Ser Val Asn Asp Lys Lys Pro Met Ile Thr Gln Gly Arg Phe Asp Thr
    1250                1255                1260

Ile Asn Gly Val Asp His Phe Thr Pro Asp Lys Thr Lys Ala Leu Asp
1265                1270                1275                1280

Ser Ser Gly Ile Val Arg Glu Glu Val Phe Tyr Leu Ala Lys Lys Asn
        1285                1290                1295

Gly Arg Lys Phe Asp Val Thr Glu Gly Lys Asp Gly Ile Thr Val Ser
            1300                1305                1310

Asp Asn Lys Val Tyr Ile Pro Lys Asn Pro Asp Gly Ser Tyr Thr Ile
    1315                1320                1325

Ser Lys Arg Asp Gly Val Thr Leu Ser Asp Tyr Tyr Tyr Leu Val Glu
    1330                1335                1340

Asp Arg Ala Gly Asn Val Ser Phe Ala Thr Leu Arg Asp Leu Lys Ala
1345                1350                1355                1360

Val Gly Lys Asp Lys Ala Val Val Asn Phe Gly Leu Asp Leu Pro Val
        1365                1370                1375

Pro Glu Asp Lys Gln Ile Val Asn Phe Thr Tyr Leu Val Arg Asp Ala
        1380                1385                1390

Asp Gly Lys Pro Ile Glu Asn Leu Glu Tyr Tyr Asn Asn Ser Gly Asn
        1395                1400                1405

Ser Leu Ile Leu Pro Tyr Gly Lys Tyr Thr Val Glu Leu Leu Thr Tyr
    1410                1415                1420

Asp Thr Asn Ala Ala Lys Leu Glu Ser Asp Lys Ile Val Ser Phe Thr
1425                1430                1435                1440

Leu Ser Ala Asp Asn Asn Phe Gln Gln Val Thr Phe Lys Ile Thr Met
        1445                1450                1455

Leu Ala Thr Ser Gln Ile Thr Ala His Phe Asp His Leu Leu Pro Glu
        1460                1465                1470

Gly Ser Arg Val Ser Leu Lys Thr Ala Gln Asp Gln Leu Ile Pro Leu
        1475                1480                1485

Glu Gln Ser Leu Tyr Val Pro Lys Ala Tyr Gly Lys Thr Val Gln Glu
    1490                1495                1500
```

```
Gly Thr Tyr Glu Val Val Ser Leu Pro Lys Gly Tyr Arg Ile Glu
1505                1510                1515                1520

Gly Asn Thr Lys Val Asn Thr Leu Pro Asn Glu Val His Glu Leu Ser
            1525                1530                1535

Leu Arg Leu Val Lys Val Gly Asp Ala Ser Asp Ser Thr Gly Asp His
        1540                1545                1550

Lys Val Met Ser Lys Asn Asn Ser Gln Ala Leu Thr Ala Ser Ala Thr
    1555                1560                1565

Pro Thr Lys Ser Thr Thr Ser Ala Thr Ala Lys Ala
    1570                1575                1580

<210> SEQ ID NO 123
<211> LENGTH: 484
<212> TYPE: PRT
<213> ORGANISM: Streptococcus pyogenes

<400> SEQUENCE: 123

Met Ala Lys Asn Asn Thr Asn Arg His Tyr Ser Leu Arg Lys Leu Lys
1               5                   10                  15

Thr Gly Thr Ala Ser Val Ala Val Ala Leu Thr Val Leu Gly Ala Gly
            20                  25                  30

Phe Ala Asn Gln Thr Glu Val Lys Ala Asn Gly Asp Gly Asn Pro Arg
        35                  40                  45

Glu Val Ile Glu Asp Leu Ala Ala Asn Asn Pro Ala Ile Gln Asn Ile
    50                  55                  60

Arg Leu Arg Tyr Glu Asn Lys Asp Leu Lys Ala Arg Leu Glu Asn Ala
65                  70                  75                  80

Met Glu Val Ala Gly Arg Asp Phe Lys Arg Ala Glu Glu Leu Glu Lys
                85                  90                  95

Ala Lys Gln Ala Leu Glu Asp Gln Arg Lys Asp Leu Glu Thr Lys Leu
            100                 105                 110

Lys Glu Leu Gln Gln Asp Tyr Asp Leu Ala Lys Glu Ser Thr Ser Trp
        115                 120                 125

Asp Arg Gln Arg Leu Glu Lys Glu Leu Glu Glu Lys Lys Glu Ala Leu
    130                 135                 140

Glu Leu Ala Ile Asp Gln Ala Ser Arg Asp Tyr His Arg Ala Thr Ala
145                 150                 155                 160

Leu Glu Lys Glu Leu Glu Glu Lys Lys Lys Ala Leu Glu Leu Ala Ile
                165                 170                 175

Asp Gln Ala Ser Gln Asp Tyr Asn Arg Ala Asn Val Leu Glu Lys Glu
            180                 185                 190

Leu Glu Thr Ile Thr Arg Glu Gln Glu Ile Asn Arg Asn Leu Leu Gly
        195                 200                 205

Asn Ala Lys Leu Glu Leu Asp Gln Leu Ser Ser Glu Lys Glu Gln Leu
    210                 215                 220

Thr Ile Glu Lys Ala Lys Leu Glu Glu Glu Lys Gln Ile Ser Asp Ala
225                 230                 235                 240

Ser Arg Gln Ser Leu Arg Arg Asp Leu Asp Ala Ser Arg Glu Ala Lys
                245                 250                 255

Lys Gln Val Glu Lys Asp Leu Ala Asn Leu Thr Ala Glu Leu Asp Lys
            260                 265                 270

Val Lys Glu Asp Lys Gln Ile Ser Asp Ala Ser Arg Gln Gly Leu Arg
        275                 280                 285

Arg Asp Leu Asp Ala Ser Arg Glu Ala Lys Lys Gln Val Glu Lys Asp
    290                 295                 300
```

```
Leu Ala Asn Leu Thr Ala Glu Leu Asp Lys Val Lys Glu Glu Lys Gln
305                 310                 315                 320

Ile Ser Asp Ala Ser Arg Gln Gly Leu Arg Arg Asp Leu Asp Ala Ser
                325                 330                 335

Arg Glu Ala Lys Lys Gln Val Glu Lys Ala Leu Glu Glu Ala Asn Ser
            340                 345                 350

Lys Leu Ala Ala Leu Glu Lys Leu Asn Lys Glu Leu Glu Glu Ser Lys
        355                 360                 365

Lys Leu Thr Glu Lys Glu Lys Ala Glu Leu Gln Ala Lys Leu Glu Ala
    370                 375                 380

Glu Ala Lys Ala Leu Lys Glu Gln Leu Ala Lys Gln Ala Glu Glu Leu
385                 390                 395                 400

Ala Lys Leu Arg Ala Gly Lys Ala Ser Asp Ser Gln Thr Pro Asp Thr
                405                 410                 415

Lys Pro Gly Asn Lys Ala Val Pro Gly Lys Gly Gln Ala Pro Gln Ala
            420                 425                 430

Gly Thr Lys Pro Asn Gln Asn Lys Ala Pro Met Lys Glu Thr Lys Arg
        435                 440                 445

Gln Leu Pro Ser Thr Gly Glu Thr Ala Asn Pro Phe Phe Thr Ala Ala
    450                 455                 460

Ala Leu Thr Val Met Ala Thr Ala Gly Val Ala Ala Val Val Lys Arg
465                 470                 475                 480

Lys Glu Glu Asn

<210> SEQ ID NO 124
<211> LENGTH: 550
<212> TYPE: PRT
<213> ORGANISM: Streptococcus pyogenes

<400> SEQUENCE: 124

Met Ser Phe Asp Gly Phe Phe Leu His His Leu Thr Asn Glu Leu Lys
1               5                   10                  15

Glu Asn Leu Leu Tyr Gly Arg Ile Gln Lys Val Asn Gln Pro Phe Glu
            20                  25                  30

Arg Glu Leu Val Leu Thr Ile Arg Asn His Arg Lys Asn Tyr Lys Leu
        35                  40                  45

Leu Leu Ser Ala His Pro Val Phe Gly Arg Val Gln Ile Thr Gln Ala
    50                  55                  60

Asp Phe Gln Asn Pro Gln Val Pro Asn Thr Phe Thr Met Ile Met Arg
65                  70                  75                  80

Lys Tyr Leu Gln Gly Ala Val Ile Glu Gln Leu Glu Gln Ile Asp Asn
                85                  90                  95

Asp Arg Ile Ile Glu Ile Lys Val Ser Asn Lys Asn Glu Ile Gly Asp
            100                 105                 110

Ala Ile Gln Ala Thr Leu Ile Ile Glu Ile Met Gly Lys His Ser Asn
        115                 120                 125

Ile Ile Leu Val Asp Arg Ala Glu Asn Lys Ile Ile Glu Ser Ile Lys
    130                 135                 140

His Val Gly Phe Ser Gln Asn Ser Tyr Arg Thr Ile Leu Pro Gly Ser
145                 150                 155                 160

Thr Tyr Ile Glu Pro Pro Lys Thr Ala Ala Val Asn Pro Phe Thr Ile
                165                 170                 175

Thr Asp Val Pro Leu Phe Glu Ile Leu Gln Thr Gln Glu Leu Thr Val
            180                 185                 190
```

```
Lys Ser Leu Gln Gln His Phe Gln Gly Leu Gly Arg Asp Thr Ala Lys
            195                 200                 205

Glu Leu Ala Glu Leu Leu Thr Thr Asp Lys Leu Lys Arg Phe Arg Glu
        210                 215                 220

Phe Phe Ala Arg Pro Thr Gln Ala Asn Leu Thr Thr Ala Ser Phe Ala
225                 230                 235                 240

Pro Val Leu Phe Ser Asp Ser His Ala Thr Phe Glu Thr Leu Ser Asp
                245                 250                 255

Met Leu Asp His Phe Tyr Gln Asp Lys Ala Glu Arg Asp Arg Ile Asn
            260                 265                 270

Gln Gln Ala Ser Asp Leu Ile His Arg Val Gln Thr Glu Leu Asp Lys
        275                 280                 285

Asn Arg Asn Lys Leu Ser Lys Gln Glu Ala Glu Leu Leu Ala Thr Glu
290                 295                 300

Asn Ala Glu Leu Phe Arg Gln Lys Gly Glu Leu Leu Thr Thr Tyr Leu
305                 310                 315                 320

Ser Leu Val Pro Asn Asn Gln Asp Ser Val Ile Leu Asp Asn Tyr Tyr
                325                 330                 335

Thr Gly Glu Lys Ile Glu Ile Ala Leu Asp Lys Ala Leu Thr Pro Asn
            340                 345                 350

Gln Asn Ala Gln Arg Tyr Phe Lys Lys Tyr Gln Lys Leu Lys Glu Ala
        355                 360                 365

Val Lys His Leu Ser Gly Leu Ile Ala Asp Thr Lys Gln Ser Ile Thr
370                 375                 380

Tyr Phe Glu Ser Val Asp Tyr Asn Leu Ser Gln Ala Ser Ile Asp Asp
385                 390                 395                 400

Ile Glu Asp Ile Arg Glu Glu Leu Tyr Gln Ala Gly Phe Leu Lys Ser
                405                 410                 415

Arg Gln Arg Asp Lys Arg His Lys Arg Lys Pro Glu Gln Tyr Leu
            420                 425                 430

Ala Ser Asp Gly Thr Thr Ile Leu Met Val Gly Arg Asn Asn Leu Gln
        435                 440                 445

Asn Glu Glu Leu Thr Phe Lys Met Ala Lys Lys Gly Glu Leu Trp Phe
450                 455                 460

His Ala Lys Asp Ile Pro Gly Ser His Val Ile Ile Lys Asp Asn Leu
465                 470                 475                 480

Asp Pro Ser Asp Glu Val Lys Thr Asp Ala Ala Glu Leu Ala Ala Tyr
                485                 490                 495

Tyr Ser Lys Ala Arg Leu Ser Asn Leu Val Gln Val Asp Met Ile Glu
            500                 505                 510

Ala Lys Lys Leu His Lys Pro Ser Gly Ala Lys Pro Gly Phe Val Thr
        515                 520                 525

Tyr Thr Gly Gln Lys Thr Leu Arg Val Thr Pro Asp Gln Ala Lys Ile
530                 535                 540

Leu Ser Met Lys Leu Ser
545                 550

<210> SEQ ID NO 125
<211> LENGTH: 291
<212> TYPE: PRT
<213> ORGANISM: Streptococcus pyogenes

<400> SEQUENCE: 125

Met Thr Lys Val Val Ile Lys Gln Leu Leu Gln Val Ile Val Val Phe
1               5                   10                  15
```

```
Met Ile Ser Leu Ser Thr Met Thr Asn Leu Val Tyr Ala Asp Lys Gly
         20                  25                  30

Gln Ile Tyr Gly Cys Ile Ile Gln Arg Asn Tyr Arg His Pro Ile Ser
     35                  40                  45

Gly Gln Ile Glu Asp Ser Gly Gly Glu His Ser Phe Asp Ile Gly Gln
 50                  55                  60

Gly Met Val Glu Gly Thr Val Tyr Ser Asp Ala Met Leu Glu Val Ser
 65                  70                  75                  80

Asp Ala Gly Lys Ile Val Leu Thr Phe Arg Met Ser Leu Ala Asp Tyr
                 85                  90                  95

Ser Gly Asn Tyr Gln Phe Trp Ile Gln Pro Gly Gly Thr Gly Ser Phe
            100                 105                 110

Gln Ala Val Asp Tyr Asn Ile Thr Gln Lys Gly Thr Asp Thr Asn Gly
        115                 120                 125

Thr Thr Leu Asp Ile Ala Ile Ser Leu Pro Thr Val Asn Ser Ile Ile
130                 135                 140

Arg Gly Ser Met Phe Val Glu Pro Met Gly Arg Glu Val Val Phe Tyr
145                 150                 155                 160

Leu Ser Ala Ser Glu Leu Ile Gln Lys Tyr Ser Gly Asn Met Leu Ala
                165                 170                 175

Gln Leu Val Thr Glu Thr Asp Asn Ser Gln Asn Gln Glu Val Lys Asp
            180                 185                 190

Ser Gln Lys Pro Val Asp Thr Lys Leu Gly Glu Ser Gln Asp Glu Ser
        195                 200                 205

His Thr Gly Ala Met Ile Thr Gln Asn Lys Pro Lys Ala Asn Ser Ser
    210                 215                 220

Asn Asn Lys Ser Leu Ser Asp Lys Lys Ile Leu Pro Ser Lys Met Gly
225                 230                 235                 240

Leu Thr Thr Ser Leu Glu Leu Lys Lys Glu Asp Lys Phe Arg Ser Lys
                245                 250                 255

Lys Asp Leu Ser Ile Met Ile Tyr Tyr Phe Pro Thr Phe Phe Leu Met
            260                 265                 270

Leu Gly Gly Phe Ala Val Trp Val Trp Lys Lys Arg Lys Lys Asn Asp
        275                 280                 285

Lys Thr Met
    290

<210> SEQ ID NO 126
<211> LENGTH: 22
<212> TYPE: PRT
<213> ORGANISM: Streptococcus pyogenes

<400> SEQUENCE: 126

Phe Ser Ile Ala Thr Gly Ser Gly Asn Ser Gln Gly Gly Ser Gly Ser
 1               5                  10                  15

Tyr Thr Pro Gly Lys Cys
             20

<210> SEQ ID NO 127
<211> LENGTH: 2805
<212> TYPE: DNA
<213> ORGANISM: Streptococcus pyogenes

<400> SEQUENCE: 127
atggccttta acacaagcca gagtgtcagt gcacaagttt atagcaatga agggtatcac      60
cagcatttga ctgatgaaaa atcacacctg caatatagta aagacaacgc acaacttcaa     120
```

```
ttgagaaata tccttgacgg ctaccaaaat gacctaggga gacactactc tagctattat    180
tactacaacc taagaaccgt tatgggacta tcaagtgagc aagacattga aaaacactat    240
gaagagctta agaacaagtt acatgatatg tacaatcatt atgctagcgg tggcggatcc    300
atgagtgtag gcgtatctca ccaagtcaaa gcagatgata gagcctcagg agaaacgaag    360
gcgagtaata ctcacgacga tagtttacca aaaccagaaa caattcaaga ggcaaaggca    420
actattgatg cagttgaaaa aactctcagt caacaaaaag cagaactgac agagcttgct    480
accgctctga caaaaactac tgctgaaatc aaccacttaa aagagcagca agataatgaa    540
caaaaagctt taacctctgc acaagaaatt tacactaata ctcttgcaag tagtgaggag    600
acgctattag cccaaggagc cgaacatcaa agagagttaa cagctactga aacagagctt    660
cataatgctc aagcagatca acattcaaaa gagactgcat tgtcagaaca aaaagctagc    720
atttcagcag aaactactcg agctcaagat ttagtggaac aagtcaaaac gtctgaacaa    780
aatattgcta agctcaatgc tatgattagc aatcctgatg ctatcactaa agcagctcaa    840
acggctaatg ataatacaaa agcattaagc tcagaattgg agaaggctaa agctgactta    900
gaaaatcaaa aagctaaagt taaaagcaa ttgactgaag agttggcagc tcagaaagct    960
gctctagcag aaaagaggc agaacttagt cgtcttaaat cctcagctcc gtctactcaa    1020
gatagcattg tgggtaataa taccatgaaa gcaccgcaag gctatcctct tgaagaactt    1080
aaaaaattag aagctagtgg ttatattgga tcagctagtt acaataatta ttacaaagag    1140
catgcagatc aaattattgc caaagctagt ccaggtaatc aattaaatca ataccaagat    1200
attccagcag atcgtaatcg cttttgttgat cccgataatt tgacaccaga agtgcaaaat    1260
gagctagcgc agtttgcagc tcacatgatt aatagtgtac gtcgtcaatt aggtctacca    1320
ccagttactg ttacagcagg atcacaagaa tttgcaagat tacttagtac cagctataag    1380
aaaactcatg gtaatacaag accatcattt gtctacggac agccagggt atcagggcat    1440 tatggtgttg ggcctcatga taaaactatt attgaagact ctgccggagc gtcagggctc    1500
attcgaaatg atgataacat gtacgagaat atcggtgctt ttaacgatgt gcatactgtg    1560
aatggtatta acgtggtat ttatgacagt atcaagtata tgctctttac agatcattta    1620
cacggaaata catacggcca tgctattaac tttttacgtg tagataaaca taaccctaat    1680
gcgcctgttt accttggatt ttcaaccagc aatgtaggat ctttgaatga acactttgta    1740
atgtttccag agtctaacat tgctaaccat caacgcttta ataagacccc tataaaagcc    1800 gttgaagta caaagatta tgcccaaaga gtaggcactg tatctgatac tattgcagcg    1860
atcaaaggaa aagtaagctc attagaaaat cgtttgtcgg ctattcatca agaagctgat    1920
attatggcag cccaagctaa agtaagtcaa cttcaaggta aattagcaag cacacttaag    1980
cagtcagaca gcttaaatct ccaagtgaga caattaaatg atactaaagg ttctttgaga    2040
acagaattac tagcagctaa agcaaaacaa gcacaactcg aagctactcg tgatcaatca    2100
ttagctaagc tagcatcgtt gaaagccgca ctgcaccaga cagaagcctt agcagagcaa    2160
gccgcagcca gagtgacagc actggtggct aaaaaagctc atttgcaata tctaagggac    2220
tttaaattga atcctaaccg ccttcaagtg atacgtgagc gcattgataa tactaagcaa    2280
gatttggcta aaaactacctc atcttttgtta aatgcacaag aagctttagc agccttacaa    2340
gctaaacaaa gcagtctaga agctactatt gctaccacag aacaccagtt gactttgctt    2400
aaaaccttag ctaacgaaaa ggaatatcgc cacttagacg aagatatagc tactgtgcct    2460
gatttgcaag tagctccacc tcttacgggc gtaaaaccgc tatcatatag taagatagat    2520
```

-continued

```
actactccgc ttgttcaaga aatggttaaa gaaacgaaac aactattaga agcttcagca    2580
agattagctg ctgaaaatac aagtcttgta gcagaagcgc ttgttggcca aacctctgaa    2640
atggtagcaa gtaatgccat tgtgtctaaa atcacatctt cgattactca gccctcatct    2700
aagacatctt atggctcagg atcttctaca acgagcaatc tcatttctga tgttgatgaa    2760
agtactcaac gtgcggccgc actcgagcac caccaccacc accac                    2805
```

<210> SEQ ID NO 128
<211> LENGTH: 935
<212> TYPE: PRT
<213> ORGANISM: Streptococcus pyogenes

<400> SEQUENCE: 128

```
Met Ala Phe Asn Thr Ser Gln Ser Val Ser Ala Gln Val Tyr Ser Asn
 1               5                  10                  15

Glu Gly Tyr His Gln His Leu Thr Asp Glu Lys Ser His Leu Gln Tyr
                20                  25                  30

Ser Lys Asp Asn Ala Gln Leu Gln Leu Arg Asn Ile Leu Asp Gly Tyr
            35                  40                  45

Gln Asn Asp Leu Gly Arg His Tyr Ser Ser Tyr Tyr Tyr Tyr Asn Leu
        50                  55                  60

Arg Thr Val Met Gly Leu Ser Ser Glu Gln Asp Ile Glu Lys His Tyr
65                  70                  75                  80

Glu Glu Leu Lys Asn Lys Leu His Asp Met Tyr Asn His Tyr Ala Ser
                85                  90                  95

Gly Gly Gly Ser Met Ser Val Gly Val Ser His Gln Val Lys Ala Asp
            100                 105                 110

Asp Arg Ala Ser Gly Glu Thr Lys Ala Ser Asn Thr His Asp Asp Ser
        115                 120                 125

Leu Pro Lys Pro Glu Thr Ile Gln Glu Ala Lys Ala Thr Ile Asp Ala
    130                 135                 140

Val Glu Lys Thr Leu Ser Gln Gln Lys Ala Glu Leu Thr Glu Leu Ala
145                 150                 155                 160

Thr Ala Leu Thr Lys Thr Thr Ala Glu Ile Asn His Leu Lys Glu Gln
                165                 170                 175

Gln Asp Asn Glu Gln Lys Ala Leu Thr Ser Ala Gln Glu Ile Tyr Thr
            180                 185                 190

Asn Thr Leu Ala Ser Ser Glu Glu Thr Leu Leu Ala Gln Gly Ala Glu
        195                 200                 205

His Gln Arg Glu Leu Thr Ala Thr Glu Thr Glu Leu His Asn Ala Gln
    210                 215                 220

Ala Asp Gln His Ser Lys Glu Thr Ala Leu Ser Glu Gln Lys Ala Ser
225                 230                 235                 240

Ile Ser Ala Glu Thr Thr Arg Ala Gln Asp Leu Val Glu Gln Val Lys
                245                 250                 255

Thr Ser Glu Gln Asn Ile Ala Lys Leu Asn Ala Met Ile Ser Asn Pro
            260                 265                 270

Asp Ala Ile Thr Lys Ala Ala Gln Thr Ala Asn Asp Asn Thr Lys Ala
        275                 280                 285

Leu Ser Ser Glu Leu Glu Lys Ala Lys Ala Asp Leu Glu Asn Gln Lys
    290                 295                 300

Ala Lys Val Lys Lys Gln Leu Thr Glu Glu Leu Ala Ala Gln Lys Ala
305                 310                 315                 320

Ala Leu Ala Glu Lys Glu Ala Glu Leu Ser Arg Leu Lys Ser Ser Ala
                325                 330                 335
```

```
Pro Ser Thr Gln Asp Ser Ile Val Gly Asn Asn Thr Met Lys Ala Pro
            340                 345                 350

Gln Gly Tyr Pro Leu Glu Glu Leu Lys Lys Leu Glu Ala Ser Gly Tyr
        355                 360                 365

Ile Gly Ser Ala Ser Tyr Asn Tyr Tyr Lys Glu His Ala Asp Gln
    370                 375                 380

Ile Ile Ala Lys Ala Ser Pro Gly Asn Gln Leu Asn Gln Tyr Gln Asp
385                 390                 395                 400

Ile Pro Ala Asp Arg Asn Arg Phe Val Asp Pro Asp Asn Leu Thr Pro
            405                 410                 415

Glu Val Gln Asn Glu Leu Ala Gln Phe Ala Ala His Met Ile Asn Ser
            420                 425                 430

Val Arg Arg Gln Leu Gly Leu Pro Pro Val Thr Val Thr Ala Gly Ser
            435                 440                 445

Gln Glu Phe Ala Arg Leu Leu Ser Thr Ser Tyr Lys Lys Thr His Gly
        450                 455                 460

Asn Thr Arg Pro Ser Phe Val Tyr Gly Gln Pro Gly Val Ser Gly His
465                 470                 475                 480

Tyr Gly Val Gly Pro His Asp Lys Thr Ile Ile Glu Asp Ser Ala Gly
                485                 490                 495

Ala Ser Gly Leu Ile Arg Asn Asp Asn Met Tyr Glu Asn Ile Gly
            500                 505                 510

Ala Phe Asn Asp Val His Thr Val Asn Gly Ile Lys Arg Gly Ile Tyr
            515                 520                 525

Asp Ser Ile Lys Tyr Met Leu Phe Thr Asp His Leu His Gly Asn Thr
    530                 535                 540

Tyr Gly His Ala Ile Asn Phe Leu Arg Val Asp Lys His Asn Pro Asn
545                 550                 555                 560

Ala Pro Val Tyr Leu Gly Phe Ser Thr Ser Asn Val Gly Ser Leu Asn
                565                 570                 575

Glu His Phe Val Met Phe Pro Glu Ser Asn Ile Ala Asn His Gln Arg
            580                 585                 590

Phe Asn Lys Thr Pro Ile Lys Ala Val Gly Ser Thr Lys Asp Tyr Ala
        595                 600                 605

Gln Arg Val Gly Thr Val Ser Asp Thr Ile Ala Ala Ile Lys Gly Lys
        610                 615                 620

Val Ser Ser Leu Glu Asn Arg Leu Ser Ala Ile His Gln Glu Ala Asp
625                 630                 635                 640

Ile Met Ala Ala Gln Ala Lys Val Ser Gln Leu Gln Gly Lys Leu Ala
                645                 650                 655

Ser Thr Leu Lys Gln Ser Asp Ser Leu Asn Leu Gln Val Arg Gln Leu
            660                 665                 670

Asn Asp Thr Lys Gly Ser Leu Arg Thr Glu Leu Leu Ala Ala Lys Ala
            675                 680                 685

Lys Gln Ala Gln Leu Glu Ala Thr Arg Asp Gln Ser Leu Ala Lys Leu
690                 695                 700

Ala Ser Leu Lys Ala Ala Leu His Gln Thr Glu Ala Leu Ala Glu Gln
705                 710                 715                 720

Ala Ala Ala Arg Val Thr Ala Leu Val Ala Lys Lys Ala His Leu Gln
                725                 730                 735

Tyr Leu Arg Asp Phe Lys Leu Asn Pro Asn Arg Leu Gln Val Ile Arg
            740                 745                 750

Glu Arg Ile Asp Asn Thr Lys Gln Asp Leu Ala Lys Thr Thr Ser Ser
```

```
                755                 760                 765
Leu Leu Asn Ala Gln Glu Ala Leu Ala Ala Leu Gln Ala Lys Gln Ser
    770                 775                 780

Ser Leu Glu Ala Thr Ile Ala Thr Thr Glu His Gln Leu Thr Leu Leu
785                 790                 795                 800

Lys Thr Leu Ala Asn Glu Lys Glu Tyr Arg His Leu Asp Glu Asp Ile
                805                 810                 815

Ala Thr Val Pro Asp Leu Gln Val Ala Pro Pro Leu Thr Gly Val Lys
                820                 825                 830

Pro Leu Ser Tyr Ser Lys Ile Asp Thr Thr Pro Leu Val Gln Glu Met
                835                 840                 845

Val Lys Glu Thr Lys Gln Leu Leu Glu Ala Ser Ala Arg Leu Ala Ala
    850                 855                 860

Glu Asn Thr Ser Leu Val Ala Glu Ala Leu Val Gly Gln Thr Ser Glu
865                 870                 875                 880

Met Val Ala Ser Asn Ala Ile Val Ser Lys Ile Thr Ser Ser Ile Thr
                885                 890                 895

Gln Pro Ser Ser Lys Thr Ser Tyr Gly Ser Gly Ser Ser Thr Thr Ser
                900                 905                 910

Asn Leu Ile Ser Asp Val Asp Glu Ser Thr Gln Arg Ala Ala Ala Leu
                915                 920                 925

Glu His His His His His His
    930                 935

<210> SEQ ID NO 129
<211> LENGTH: 7
<212> TYPE: PRT
<213> ORGANISM: Streptococcus pyogenes

<400> SEQUENCE: 129

Tyr Ala Ser Gly Gly Gly Ser
  1               5

<210> SEQ ID NO 130
<211> LENGTH: 2805
<212> TYPE: DNA
<213> ORGANISM: Streptococcus pyogenes

<400> SEQUENCE: 130
atgagtgtag gcgtatctca ccaagtcaaa gcagatgata gagcctcagg agaaacgaag      60
gcgagtaata ctcacgacga tagtttacca aaaccagaaa caattcaaga ggcaaaggca     120
actattgatg cagttgaaaa aactctcagt caacaaaaag cagaactgac agagcttgct     180
accgctctga caaaaactac tgctgaaatc aaccacttaa aagagcagca agataatgaa     240
caaaaagctt taacctctgc acaagaaatt tacactaata ctcttgcaag tagtgaggag     300
acgctattag cccaaggagc cgaacatcaa agagagttaa cagctactga acagagcttt     360
cataatgctc aagcagatca acattcaaaa gagactgcat tgtcagaaca aaaagctagc     420
atttcagcag aaactactcg agctcaagat ttagtggaac aagtcaaaac gtctgaacaa     480
aatattgcta agctcaatgc tatgattagc aatcctgatg ctatcactaa agcagctcaa     540
acggctaatg ataatacaaa agcattaagc tcagaattgg agaaggctaa agctgactta     600
gaaaatcaaa aagctaaagt taaaaagcaa ttgactgaag agttggcagc tcagaaagct     660
gctctagcag aaaagaggc agaacttagt cgtcttaaat cctcagctcc gtctactcaa     720
gatagcattg tgggtaataa taccatgaaa gcaccgcaag gctatcctct tgaagaactt     780
```

```
aaaaaattag aagctagtgg ttatattgga tcagctagtt acaataatta ttacaaagag      840
catgcagatc aaattattgc caaagctagt ccaggtaatc aattaaatca ataccaagat      900
attccagcag atcgtaatcg ctttgttgat cccgataatt tgacaccaga agtgcaaaat      960
gagctagcgc agtttgcagc tcacatgatt aatagtgtac gtcgtcaatt aggtctacca     1020
ccagttactg ttacagcagg atcacaagaa tttgcaagat tacttagtac cagctataag     1080
aaaactcatg gtaatacaag accatcattt gtctacggac agccaggggt atcagggcat     1140
tatggtgttg ggcctcatga taaaactatt attgaagact ctgccggagc gtcagggctc     1200
attcgaaatg atgataacat gtacgagaat atcggtgctt ttaacgatgt gcatactgtg     1260
aatggtatta aacgtggtat ttatgacagt atcaagtata tgctctttac agatcattta     1320
cacggaaata catacggcca tgctattaac tttttacgtg tagataaaca taaccctaat     1380
gcgcctgttt accttggatt ttcaaccagc aatgtaggat ctttgaatga cactttgta      1440 atgtttccag agtctaacat tgctaaccat caacgcttta ataagacccc tataaaagcc     1500
gttggaagta caaaagatta tgcccaaaga gtaggcactg tatctgatac tattgcagcg     1560
atcaaaggaa aagtaagctc attagaaaat cgtttgtcgg ctattcatca agaagctgat     1620
attatggcag cccaagctaa agtaagtcaa cttcaaggta aattagcaag cacacttaag     1680
cagtcagaca gcttaaatct ccaagtgaga caattaaatg atactaaagg ttctttgaga     1740
acagaattac tagcagctaa agcaaaacaa gcacaactcg aagctactcg tgatcaatca     1800
ttagctaagc tagcatcgtt gaaagccgca ctgcaccaga cagaagcctt agcagagcaa     1860
gccgcagcca gagtgacagc actggtggct aaaaaagctc atttgcaata tctaagggac     1920
tttaaattga atcctaaccg ccttcaagtg atacgtgagc gcattgataa tactaagcaa     1980
gatttggcta aaactacctc atctttgtta aatgcacaag aagctttagc agccttacaa     2040
gctaaacaaa gcagtctaga agctactatt gctaccacag aacaccagtt gactttgctt     2100
aaaaccttag ctaacgaaaa ggaatatcgc cacttagacg aagatatagc tactgtgcct     2160
gatttgcaag tagctccacc tcttacgggc gtaaaaccgc tatcatatag taagatagat     2220
actactccgc ttgttcaaga aatggttaaa gaaacgaaac aactattaga agcttcagca     2280
agattagctg ctgaaaatac aagtcttgta gcagaagcgc ttgttggcca aacctctgaa     2340
atggtagcaa gtaatgccat tgtgtctaaa atcacatctt cgattactca gccctcatct     2400
aagacatctt atggctcagg atcttctaca acgagcaatc tcatttctga tgttgatgaa     2460
agtactcaac gtgctagcgg tggcggatcc atggccttta acacaagcca gagtgtcagt     2520
gcacaagttt atagcaatga agggtatcac cagcatttga ctgatgaaaa atcacacctg     2580
caatatagta aagacaacgc acaacttcaa ttgagaaata tccttgacgg ctaccaaaat     2640
gacctaggga gacactactc tagctattat tactacaacc taagaaccgt tatgggacta     2700
tcaagtgagc aagacattga aaaacactat gaagagctta gaacaagtt acatgatatg      2760 tacaatcatt atgcggccgc actcgagcac caccaccacc accac                     2805
```

<210> SEQ ID NO 131
<211> LENGTH: 935
<212> TYPE: PRT
<213> ORGANISM: Streptococcus pyogenes

<400> SEQUENCE: 131

Met Ser Val Gly Val Ser His Gln Val Lys Ala Asp Asp Arg Ala Ser
1               5                   10                  15

Gly Glu Thr Lys Ala Ser Asn Thr His Asp Asp Ser Leu Pro Lys Pro

-continued

```
                20                  25                  30
Glu Thr Ile Gln Glu Ala Lys Ala Thr Ile Asp Ala Val Glu Lys Thr
                35                  40                  45
Leu Ser Gln Gln Lys Ala Glu Leu Thr Glu Leu Ala Thr Ala Leu Thr
 50                  55                  60
Lys Thr Thr Ala Glu Ile Asn His Leu Lys Glu Gln Gln Asp Asn Glu
 65                  70                  75                  80
Gln Lys Ala Leu Thr Ser Ala Gln Glu Ile Tyr Thr Asn Thr Leu Ala
                85                  90                  95
Ser Ser Glu Glu Thr Leu Leu Ala Gln Gly Ala Glu His Gln Arg Glu
                100                 105                 110
Leu Thr Ala Thr Glu Thr Glu Leu His Asn Ala Gln Ala Asp Gln His
                115                 120                 125
Ser Lys Glu Thr Ala Leu Ser Glu Gln Lys Ala Ser Ile Ser Ala Glu
                130                 135                 140
Thr Thr Arg Ala Gln Asp Leu Val Glu Gln Val Lys Thr Ser Glu Gln
145                 150                 155                 160
Asn Ile Ala Lys Leu Asn Ala Met Ile Ser Asn Pro Asp Ala Ile Thr
                165                 170                 175
Lys Ala Ala Gln Thr Ala Asn Asp Asn Thr Lys Ala Leu Ser Ser Glu
                180                 185                 190
Leu Glu Lys Ala Lys Ala Asp Leu Glu Asn Gln Lys Ala Lys Val Lys
                195                 200                 205
Lys Gln Leu Thr Glu Glu Leu Ala Ala Gln Lys Ala Ala Leu Ala Glu
                210                 215                 220
Lys Glu Ala Glu Leu Ser Arg Leu Lys Ser Ser Ala Pro Ser Thr Gln
225                 230                 235                 240
Asp Ser Ile Val Gly Asn Asn Thr Met Lys Ala Pro Gln Gly Tyr Pro
                245                 250                 255
Leu Glu Glu Leu Lys Lys Leu Glu Ala Ser Gly Tyr Ile Gly Ser Ala
                260                 265                 270
Ser Tyr Asn Asn Tyr Tyr Lys Glu His Ala Asp Gln Ile Ile Ala Lys
                275                 280                 285
Ala Ser Pro Gly Asn Gln Leu Asn Gln Tyr Gln Asp Ile Pro Ala Asp
                290                 295                 300
Arg Asn Arg Phe Val Asp Pro Asp Asn Leu Thr Pro Glu Val Gln Asn
305                 310                 315                 320
Glu Leu Ala Gln Phe Ala Ala His Met Ile Asn Ser Val Arg Arg Gln
                325                 330                 335
Leu Gly Leu Pro Pro Val Thr Val Thr Ala Gly Ser Gln Glu Phe Ala
                340                 345                 350
Arg Leu Leu Ser Thr Ser Tyr Lys Lys Thr His Gly Asn Thr Arg Pro
                355                 360                 365
Ser Phe Val Tyr Gly Gln Pro Gly Val Ser Gly His Tyr Gly Val Gly
                370                 375                 380
Pro His Asp Lys Thr Ile Ile Glu Asp Ser Ala Gly Ala Ser Gly Leu
385                 390                 395                 400
Ile Arg Asn Asp Asp Asn Met Tyr Glu Asn Ile Gly Ala Phe Asn Asp
                    405                 410                 415
Val His Thr Val Asn Gly Ile Lys Arg Gly Ile Tyr Asp Ser Ile Lys
                420                 425                 430
Tyr Met Leu Phe Thr Asp His Leu His Gly Asn Thr Tyr Gly His Ala
                435                 440                 445
```

-continued

```
Ile Asn Phe Leu Arg Val Asp Lys His Asn Pro Asn Ala Pro Val Tyr
    450                 455                 460

Leu Gly Phe Ser Thr Ser Asn Val Gly Ser Leu Asn Glu His Phe Val
465                 470                 475                 480

Met Phe Pro Glu Ser Asn Ile Ala Asn His Gln Arg Phe Asn Lys Thr
                    485                 490                 495

Pro Ile Lys Ala Val Gly Ser Thr Lys Asp Tyr Ala Gln Arg Val Gly
                500                 505                 510

Thr Val Ser Asp Thr Ile Ala Ala Ile Lys Gly Lys Val Ser Ser Leu
            515                 520                 525

Glu Asn Arg Leu Ser Ala Ile His Gln Glu Ala Asp Ile Met Ala Ala
530                 535                 540

Gln Ala Lys Val Ser Gln Leu Gln Gly Lys Leu Ala Ser Thr Leu Lys
545                 550                 555                 560

Gln Ser Asp Ser Leu Asn Leu Gln Val Arg Gln Leu Asn Asp Thr Lys
                565                 570                 575

Gly Ser Leu Arg Thr Glu Leu Leu Ala Ala Lys Ala Lys Gln Ala Gln
                580                 585                 590

Leu Glu Ala Thr Arg Asp Gln Ser Leu Ala Lys Leu Ala Ser Leu Lys
            595                 600                 605

Ala Ala Leu His Gln Thr Glu Ala Leu Ala Glu Gln Ala Ala Ala Arg
610                 615                 620

Val Thr Ala Leu Val Ala Lys Lys Ala His Leu Gln Tyr Leu Arg Asp
625                 630                 635                 640

Phe Lys Leu Asn Pro Asn Arg Leu Gln Val Ile Arg Glu Arg Ile Asp
                645                 650                 655

Asn Thr Lys Gln Asp Leu Ala Lys Thr Thr Ser Ser Leu Leu Asn Ala
                660                 665                 670

Gln Glu Ala Leu Ala Ala Leu Gln Ala Lys Gln Ser Ser Leu Glu Ala
            675                 680                 685

Thr Ile Ala Thr Thr Glu His Gln Leu Thr Leu Leu Lys Thr Leu Ala
690                 695                 700

Asn Glu Lys Glu Tyr Arg His Leu Asp Glu Asp Ile Ala Thr Val Pro
705                 710                 715                 720

Asp Leu Gln Val Ala Pro Pro Leu Thr Gly Val Lys Pro Leu Ser Tyr
                725                 730                 735

Ser Lys Ile Asp Thr Thr Pro Leu Val Gln Glu Met Val Lys Glu Thr
                740                 745                 750

Lys Gln Leu Leu Glu Ala Ser Ala Arg Leu Ala Ala Glu Asn Thr Ser
            755                 760                 765

Leu Val Ala Glu Ala Leu Val Gly Gln Thr Ser Glu Met Val Ala Ser
770                 775                 780

Asn Ala Ile Val Ser Lys Ile Thr Ser Ser Ile Thr Gln Pro Ser Ser
785                 790                 795                 800

Lys Thr Ser Tyr Gly Ser Gly Ser Ser Thr Thr Ser Asn Leu Ile Ser
                805                 810                 815

Asp Val Asp Glu Ser Thr Gln Arg Ala Ser Gly Gly Ser Met Ala
                820                 825                 830

Phe Asn Thr Ser Gln Ser Val Ser Ala Gln Val Tyr Ser Asn Glu Gly
            835                 840                 845

Tyr His Gln His Leu Thr Asp Glu Lys Ser His Leu Gln Tyr Ser Lys
850                 855                 860

Asp Asn Ala Gln Leu Gln Leu Arg Asn Ile Leu Asp Gly Tyr Gln Asn
865                 870                 875                 880
```

Asp Leu Gly Arg His Tyr Ser Ser Tyr Tyr Tyr Asn Leu Arg Thr
            885                 890                 895

Val Met Gly Leu Ser Ser Glu Gln Asp Ile Glu Lys His Tyr Glu Glu
        900                 905                 910

Leu Lys Asn Lys Leu His Asp Met Tyr Asn His Tyr Ala Ala Ala Leu
            915                 920                 925

Glu His His His His His His
    930                 935

<210> SEQ ID NO 132
<211> LENGTH: 2805
<212> TYPE: DNA
<213> ORGANISM: Streptococcus pyogenes

<400> SEQUENCE: 132

```
atggccttta acacaagcca gagtgtcagt gcacaagttt atagcaatga agggtatcac      60
cagcatttga ctgatgaaaa atcacacctg caatatagta aagacaacgc acaacttcaa     120
ttgagaaata tccttgacgg ctaccaaaat gacctaggga cacactactc tagctattat     180
tactacaacc taagaactgt tatgggacta tcaagtgagc aagacattga aaaacactat     240
gaagagctta agaacaagtt acatgatatg tacaatcatt atgctagcgg tggcggatcc     300
atgagtgtag gcgtatctca ccaagtcaaa gcagatgata gagcctcagg agaaacgaag     360
gcgagtaata ctcacgacga tagtttacca aaaccagaaa caattcaaga ggcaaaggca     420
actattgatg cagttgaaaa aactctcagt caacaaaaag cagaactgac agagcttgct     480
accgctctga caaaaactac tgctgaaatc aaccacctaa aagagcagca agataatgaa     540
caaaaagctt taacctctgc acaagaaatt tacactaata ctcttgcaag tagtgaggag     600
acgctattag cccaaggagc cgaacatcaa agagagttaa cagctactga aacagagctt     660
cataatgctc aagcagatca acattcaaaa gagactgcat tgtcagaaca aaaagctagc     720
atttcagcag aaactactcg agctcaagat ttagtggaac aagtcaaaac gtctgaacaa     780
aatattgcta agctcaatgc tatgattagc aatcctgatg ctatcactaa agcagctcaa     840
acggctaatg ataatacaaa agcattaagc tcagaattgg agaaggctaa agctgactta     900
gaaaatcaaa aagctaaagt taaaagcaa ttgactgaag agttggcagc tcagaaagct     960
gctctagcag aaaagaggc agaacttagt cgtcttaaat cctcagctcc gtctactcaa    1020
gatagcattg tgggtaataa taccatgaaa gcaccgcaag gctatcctct tgaagaactt    1080
aaaaaattag aagctagtgg ttatattgga tcagctagtt acaataatta ttacaaagag    1140
catgcagatc aaattattgc caaagctagt ccaggtaatc aattaaatca ataccaagat    1200
attccagcag atcgtaatcg ctttgttgat cccgataatt tgacaccaga agtgcaaaat    1260
gggctagcgc agtttgcagc tcacatgatt aatagtgtaa aagacaatt aggtctacca    1320
ccagttactg ttacagcagg atcacaagaa tttgcaagat tacttagtac cagctataag    1380
aaaactcatg gtaatacaag accatcattt gtctacggac agccaggggt atcagggcat    1440
tatggtgttg ggcctcatga taaaactatt attgaagact ctgccggagc gtcagggctc    1500
attcgaaatg atgataacat gtacgagaat atcggtgctt taacgatgt gcatactgtg    1560
aatggtatta acgtggtat ttatgacagt atcaagtata tgctctttac agatcatta    1620
cacggaaata catacggcca tgctattaac ttttacgtg tagataaaca taccctaat    1680
gcgcctgttt accttggatt ttcaaccagc aatgtaggat ctttgaatga cacttttgta    1740
atgtttccag agtctaacat tgctaaccat caacgcttta ataagacccc tataaaagcc    1800
```

```
gttggaagta caaaagatta tgcccaaaga gtaggcactg tatctgatac tattgcagcg   1860
atcaaaggaa aagtaagctc attagaaaat cgtttgtcgg ctattcatca agaagctgat   1920
attatggcag cccaagctaa agtaagtcaa cttcaaggta aattagcaag cacacttaag   1980
cagtcagaca gcttaaatct ccaagtgaga caattaaatg atactaaagg ttctttgaga   2040
acagaattac tagcagctaa agcaaaacaa gcacaactcg aagctactcg tgatcaatca   2100
ttagctaagc tagcatcgtt gaaagccgca ctgcaccaga cagaagcctt agcagagcaa   2160
gccgcagcca gagtgacagc actggtggct aaaaaagctc atttgcaata tctaagggac   2220
tttaaattga atcctaaccg ccttcaagtg atacgtgagc gcattgataa tactaagcaa   2280
gatttggcta aaactacctc atctttgtta aatgcacaag aagctttagc agccttacaa   2340
gctaaacaaa gcagtctaga agctactatt gctaccacag aacaccagtt gactttgctt   2400
aaaaccttag ctaacgaaaa ggaatatcgc cacttagacg aagatatagc tactgtgcct   2460
gatttgcaag tagctccacc tcttacgggc gtaaaaccgc tatcatatag taagatagat   2520
actactccgc ttgttcaaga aatggttaaa gaaacgaaac aactattaga agcttcagca   2580
agattagctg ctgaaaatac aagtcttgta gcagaagcgc ttgttggcca aacctctgaa   2640
atggtagcaa gtaatgccat tgtgtctaaa atcacatctt cgattactca gccctcatct   2700
aagacatctt atggctcagg atcttctaca acgagcaatc tcatttctga tgttgatgaa   2760
agtactcaac gtgcggccgc actcgagcac caccaccac ccac            2805

<210> SEQ ID NO 133
<211> LENGTH: 935
<212> TYPE: PRT
<213> ORGANISM: Streptococcus pyogenes

<400> SEQUENCE: 133

Met Ala Phe Asn Thr Ser Gln Ser Val Ser Ala Gln Val Tyr Ser Asn
 1               5                  10                  15

Glu Gly Tyr His Gln His Leu Thr Asp Glu Lys Ser His Leu Gln Tyr
                20                  25                  30

Ser Lys Asp Asn Ala Gln Leu Gln Leu Arg Asn Ile Leu Asp Gly Tyr
            35                  40                  45

Gln Asn Asp Leu Gly Arg His Tyr Ser Ser Tyr Tyr Tyr Tyr Asn Leu
        50                  55                  60

Arg Thr Val Met Gly Leu Ser Ser Glu Gln Asp Ile Glu Lys His Tyr
65                  70                  75                  80

Glu Glu Leu Lys Asn Lys Leu His Asp Met Tyr Asn His Tyr Ala Ser
                85                  90                  95

Gly Gly Gly Ser Met Ser Val Gly Val Ser His Gln Val Lys Ala Asp
                100                 105                 110

Asp Arg Ala Ser Gly Glu Thr Lys Ala Ser Asn Thr His Asp Asp Ser
            115                 120                 125

Leu Pro Lys Pro Glu Thr Ile Gln Glu Ala Lys Ala Thr Ile Asp Ala
        130                 135                 140

Val Glu Lys Thr Leu Ser Gln Gln Lys Ala Glu Leu Thr Glu Leu Ala
145                 150                 155                 160

Thr Ala Leu Thr Lys Thr Thr Ala Glu Ile Asn His Leu Lys Glu Gln
                165                 170                 175

Gln Asp Asn Glu Gln Lys Ala Leu Thr Ser Ala Gln Glu Ile Tyr Thr
            180                 185                 190

Asn Thr Leu Ala Ser Ser Glu Glu Thr Leu Leu Ala Gln Gly Ala Glu
```

```
                195                 200                 205
    His Gln Arg Glu Leu Thr Ala Thr Glu Thr Glu Leu His Asn Ala Gln
        210                 215                 220

Ala Asp Gln His Ser Lys Glu Thr Ala Leu Ser Glu Gln Lys Ala Ser
    225                 230                 235                 240

Ile Ser Ala Glu Thr Thr Arg Ala Gln Asp Leu Val Glu Gln Val Lys
                        245                 250                 255

Thr Ser Glu Gln Asn Ile Ala Lys Leu Asn Ala Met Ile Ser Asn Pro
                    260                 265                 270

Asp Ala Ile Thr Lys Ala Ala Gln Thr Ala Asn Asp Asn Thr Lys Ala
                275                 280                 285

Leu Ser Ser Glu Leu Glu Lys Ala Lys Ala Asp Leu Glu Asn Gln Lys
            290                 295                 300

Ala Lys Val Lys Lys Gln Leu Thr Glu Glu Leu Ala Ala Gln Lys Ala
    305                 310                 315                 320

Ala Leu Ala Glu Lys Glu Ala Glu Leu Ser Arg Leu Lys Ser Ser Ala
                        325                 330                 335

Pro Ser Thr Gln Asp Ser Ile Val Gly Asn Asn Thr Met Lys Ala Pro
                    340                 345                 350

Gln Gly Tyr Pro Leu Glu Glu Leu Lys Lys Leu Glu Ala Ser Gly Tyr
                355                 360                 365

Ile Gly Ser Ala Ser Tyr Asn Asn Tyr Lys Glu His Ala Asp Gln
    370                 375                 380

Ile Ile Ala Lys Ala Ser Pro Gly Asn Gln Leu Asn Gln Tyr Gln Asp
    385                 390                 395                 400

Ile Pro Ala Asp Arg Asn Arg Phe Val Asp Pro Asp Asn Leu Thr Pro
                        405                 410                 415

Glu Val Gln Asn Gly Leu Ala Gln Phe Ala Ala His Met Ile Asn Ser
                    420                 425                 430

Val Arg Arg Gln Leu Gly Leu Pro Pro Val Thr Val Thr Ala Gly Ser
                435                 440                 445

Gln Glu Phe Ala Arg Leu Leu Ser Thr Ser Tyr Lys Lys Thr His Gly
    450                 455                 460

Asn Thr Arg Pro Ser Phe Val Tyr Gly Gln Pro Gly Val Ser Gly His
    465                 470                 475                 480

Tyr Gly Val Gly Pro His Asp Lys Thr Ile Ile Glu Asp Ser Ala Gly
                        485                 490                 495

Ala Ser Gly Leu Ile Arg Asn Asp Asp Asn Met Tyr Glu Asn Ile Gly
                    500                 505                 510

Ala Phe Asn Asp Val His Thr Val Asn Gly Ile Lys Arg Gly Ile Tyr
                515                 520                 525

Asp Ser Ile Lys Tyr Met Leu Phe Thr Asp His Leu His Gly Asn Thr
    530                 535                 540

Tyr Gly His Ala Ile Asn Phe Leu Arg Val Asp Lys His Asn Pro Asn
    545                 550                 555                 560

Ala Pro Val Tyr Leu Gly Phe Ser Thr Ser Asn Val Gly Ser Leu Asn
                        565                 570                 575

Glu His Phe Val Met Phe Pro Glu Ser Asn Ile Ala Asn His Gln Arg
                    580                 585                 590

Phe Asn Lys Thr Pro Ile Lys Ala Val Gly Ser Thr Lys Asp Tyr Ala
                595                 600                 605

Gln Arg Val Gly Thr Val Ser Asp Thr Ile Ala Ala Ile Lys Gly Lys
    610                 615                 620
```

```
Val Ser Ser Leu Glu Asn Arg Leu Ser Ala Ile His Gln Glu Ala Asp
625                 630                 635                 640

Ile Met Ala Ala Gln Ala Lys Val Ser Gln Leu Gln Gly Lys Leu Ala
            645                 650                 655

Ser Thr Leu Lys Gln Ser Asp Ser Leu Asn Leu Gln Val Arg Gln Leu
        660                 665                 670

Asn Asp Thr Lys Gly Ser Leu Arg Thr Glu Leu Leu Ala Ala Lys Ala
            675                 680                 685

Lys Gln Ala Gln Leu Glu Ala Thr Arg Asp Gln Ser Leu Ala Lys Leu
690                 695                 700

Ala Ser Leu Lys Ala Ala Leu His Gln Thr Glu Ala Leu Ala Glu Gln
705                 710                 715                 720

Ala Ala Ala Arg Val Thr Ala Leu Val Ala Lys Lys Ala His Leu Gln
                725                 730                 735

Tyr Leu Arg Asp Phe Lys Leu Asn Pro Asn Arg Leu Gln Val Ile Arg
            740                 745                 750

Glu Arg Ile Asp Asn Thr Lys Gln Asp Leu Ala Lys Thr Thr Ser Ser
        755                 760                 765

Leu Leu Asn Ala Gln Glu Ala Leu Ala Ala Leu Gln Ala Lys Gln Ser
770                 775                 780

Ser Leu Glu Ala Thr Ile Ala Thr Thr Glu His Gln Leu Thr Leu Leu
785                 790                 795                 800

Lys Thr Leu Ala Asn Glu Lys Glu Tyr Arg His Leu Asp Glu Asp Ile
                805                 810                 815

Ala Thr Val Pro Asp Leu Gln Val Ala Pro Pro Leu Thr Gly Val Lys
            820                 825                 830

Pro Leu Ser Tyr Ser Lys Ile Asp Thr Thr Pro Leu Val Gln Glu Met
        835                 840                 845

Val Lys Glu Thr Lys Gln Leu Leu Glu Ala Ser Ala Arg Leu Ala Ala
850                 855                 860

Glu Asn Thr Ser Leu Val Ala Glu Ala Leu Val Gly Gln Thr Ser Glu
865                 870                 875                 880

Met Val Ala Ser Asn Ala Ile Val Ser Lys Ile Thr Ser Ser Ile Thr
                885                 890                 895

Gln Pro Ser Ser Lys Thr Ser Tyr Gly Ser Gly Ser Ser Thr Thr Ser
            900                 905                 910

Asn Leu Ile Ser Asp Val Asp Glu Ser Thr Gln Arg Ala Ala Ala Leu
        915                 920                 925

Glu His His His His His His
    930                 935

<210> SEQ ID NO 134
<211> LENGTH: 1230
<212> TYPE: DNA
<213> ORGANISM: Streptococcus pyogenes

<400> SEQUENCE: 134 atggcctta acacaagcca gagtgtcagt gcacaagttt atagcaatga agggtatcac      60
cagcatttga ctgatgaaaa atcacacctg caatatagta aagacaacgc acaacttcaa     120
ttgagaaata tccttgacgg ctaccaaaat gacctaggga cactactctc tagctattat     180
tactacaacc taagaaccgt tatgggacta tcaagtgagc aagacattga aaacactat      240 gaagagctta agaacaagtt acatgatatg tacaatcatt atgctagcgg tggcggatcc     300
atgagtgtag gcgtatctca ccaagtcaaa gcagatgata gagcctcagg agaaacgaag     360
```

```
gcgagtaata ctcacgacga tagtttacca aaaccagaaa caattcaaga ggcaaaggca    420
actattgatg cagttgaaaa aactctcagt caacaaaaag cagaactgac agagcttgct    480
accgctctga caaaaactac tgctgaaatc aaccacttaa aagagcagca agataatgaa    540
caaaaagctt taacctctgc acaagaaatt tacactaata ctcttgcaag tagtgaggag    600
acgctattag cccaaggagc cgaacatcaa agagagttaa cagctactga aacagagctt    660
cataatgctc aagcagatca acattcaaaa gagactgcat tgtcagaaca aaaagctagc    720
atttcagcag aaactactcg agctcaagat ttagtggaac aagtcaaaac gtctgaacaa    780
aatattgcta agctcaatgc tatgattagc aatcctgatg ctatcactaa agcagctcaa    840
acggctaatg ataatacaaa agcattaagc tcagaattgg agaaggctaa agctgactta    900
gaaaatcaaa aagctaaagt taaaaagcaa ttgactgaag agttggcagc tcagaaagct    960
gctctagcag aaaaagaggc agaacttagt cgtcttaaat cctcagctcc gtctactcaa   1020
gatagcattg tgggtaataa taccatgaaa gcaccgcaag gctatcctct tgaagaactt   1080
aaaaaattag aagctagtgg ttatattgga tcagctagtt acaataatta ttacaaagag   1140
catgcagatc aaattattgc caaagctagt ccaggtaatc aattaaatca ataccaagcg   1200
gccgcactcg agcaccacca ccaccaccac                                   1230
```

<210> SEQ ID NO 135
<211> LENGTH: 410
<212> TYPE: PRT
<213> ORGANISM: Streptococcus pyogenes

<400> SEQUENCE: 135

```
Met Ala Phe Asn Thr Ser Gln Ser Val Ser Ala Gln Val Tyr Ser Asn
 1               5                  10                  15

Glu Gly Tyr His Gln His Leu Thr Asp Glu Lys Ser His Leu Gln Tyr
             20                  25                  30

Ser Lys Asp Asn Ala Gln Leu Gln Leu Arg Asn Ile Leu Asp Gly Tyr
         35                  40                  45

Gln Asn Asp Leu Gly Arg His Tyr Ser Ser Tyr Tyr Tyr Asn Leu
     50                  55                  60

Arg Thr Val Met Gly Leu Ser Ser Glu Gln Asp Ile Glu Lys His Tyr
 65                  70                  75                  80

Glu Glu Leu Lys Asn Lys Leu His Asp Met Tyr Asn His Tyr Ala Ser
                 85                  90                  95

Gly Gly Gly Ser Met Ser Val Gly Val Ser His Gln Val Lys Ala Asp
            100                 105                 110

Asp Arg Ala Ser Gly Glu Thr Lys Ala Ser Asn Thr His Asp Asp Ser
        115                 120                 125

Leu Pro Lys Pro Glu Thr Ile Gln Glu Ala Lys Ala Thr Ile Asp Ala
    130                 135                 140

Val Glu Lys Thr Leu Ser Gln Gln Lys Ala Glu Leu Thr Glu Leu Ala
145                 150                 155                 160

Thr Ala Leu Thr Lys Thr Thr Ala Glu Ile Asn His Leu Lys Glu Gln
                165                 170                 175

Gln Asp Asn Glu Gln Lys Ala Leu Thr Ser Ala Gln Glu Ile Tyr Thr
            180                 185                 190

Asn Thr Leu Ala Ser Ser Glu Glu Thr Leu Leu Ala Gln Gly Ala Glu
        195                 200                 205

His Gln Arg Glu Leu Thr Ala Thr Glu Thr Glu Leu His Asn Ala Gln
    210                 215                 220
```

```
Ala Asp Gln His Ser Lys Glu Thr Ala Leu Ser Gln Lys Ala Ser
225                 230                 235                 240

Ile Ser Ala Glu Thr Thr Arg Ala Gln Asp Leu Val Glu Gln Val Lys
                245                 250                 255

Thr Ser Glu Gln Asn Ile Ala Lys Leu Asn Ala Met Ile Ser Asn Pro
            260                 265                 270

Asp Ala Ile Thr Lys Ala Ala Gln Thr Ala Asn Asp Asn Thr Lys Ala
        275                 280                 285

Leu Ser Ser Glu Leu Glu Lys Ala Lys Ala Asp Leu Glu Asn Gln Lys
    290                 295                 300

Ala Lys Val Lys Gln Leu Thr Glu Glu Leu Ala Ala Gln Lys Ala
305                 310                 315                 320

Ala Leu Ala Glu Lys Glu Ala Glu Leu Ser Arg Leu Lys Ser Ser Ala
                325                 330                 335

Pro Ser Thr Gln Asp Ser Ile Val Gly Asn Asn Thr Met Lys Ala Pro
            340                 345                 350

Gln Gly Tyr Pro Leu Glu Glu Leu Lys Lys Leu Glu Ala Ser Gly Tyr
        355                 360                 365

Ile Gly Ser Ala Ser Tyr Asn Asn Tyr Tyr Lys Glu His Ala Asp Gln
    370                 375                 380

Ile Ile Ala Lys Ala Ser Pro Gly Asn Gln Leu Asn Gln Tyr Gln Ala
385                 390                 395                 400

Ala Ala Leu Glu His His His His His His
                405                 410

<210> SEQ ID NO 136
<211> LENGTH: 8
<212> TYPE: DNA
<213> ORGANISM: Streptococcus pyogenes

<400> SEQUENCE: 136 agttggta                                                            8

<210> SEQ ID NO 137
<211> LENGTH: 84
<212> TYPE: DNA
<213> ORGANISM: Artificial Sequence
<220> FEATURE:
<223> OTHER INFORMATION: primer

<400> SEQUENCE: 137
gatcccatat ggctagcccg gggaattcgt ccatggagtg agtcgactga ctcgagtgat    60
cgagctcctg agcggccgca tgaa                                          84

<210> SEQ ID NO 138
<211> LENGTH: 84
<212> TYPE: DNA
<213> ORGANISM: Artificial Sequence
<220> FEATURE:
<223> OTHER INFORMATION: primer

<400> SEQUENCE: 138
ggtataccga tcgggcccct taagcaggta cctcactcag ctgactgagc tcactagctc    60
gaggactcgc cggcgtactt tcga                                          84

<210> SEQ ID NO 139
<211> LENGTH: 48
<212> TYPE: DNA
<213> ORGANISM: Artificial Sequence
<220> FEATURE:
```

-continued

<223> OTHER INFORMATION: primer

<400> SEQUENCE: 139
tcgacaagct tgcggccgca ctcgagcatc accatcacca tcactgat        48

<210> SEQ ID NO 140
<211> LENGTH: 48
<212> TYPE: DNA
<213> ORGANISM: Artificial Sequence
<220> FEATURE:
<223> OTHER INFORMATION: primer

<400> SEQUENCE: 140
gttcgaacgc cggcgtgagc acgtagaggt agtggtagtg actatcga        48

<210> SEQ ID NO 141
<211> LENGTH: 12
<212> TYPE: DNA
<213> ORGANISM: Artificial Sequence
<220> FEATURE:
<223> OTHER INFORMATION: primer

<400> SEQUENCE: 141
gtgcgtcata tg        12

<210> SEQ ID NO 142
<211> LENGTH: 12
<212> TYPE: DNA
<213> ORGANISM: Artificial Sequence
<220> FEATURE:
<223> OTHER INFORMATION: primer

<400> SEQUENCE: 142
gtgcgtgcta gc        12

<210> SEQ ID NO 143
<211> LENGTH: 12
<212> TYPE: DNA
<213> ORGANISM: Artificial Sequence
<220> FEATURE:
<223> OTHER INFORMATION: primer

<400> SEQUENCE: 143
gtgcgtacta gt        12

<210> SEQ ID NO 144
<211> LENGTH: 9
<212> TYPE: DNA
<213> ORGANISM: Artificial Sequence
<220> FEATURE:
<223> OTHER INFORMATION: primer

<400> SEQUENCE: 144 gcgtctgag        9

<210> SEQ ID NO 145
<211> LENGTH: 16
<212> TYPE: DNA
<213> ORGANISM: Artificial Sequence
<220> FEATURE:
<223> OTHER INFORMATION: primer

<400> SEQUENCE: 145
actcgctagc ggccgc        16

<210> SEQ ID NO 146

```
<211> LENGTH: 10
<212> TYPE: DNA
<213> ORGANISM: Artificial Sequence
<220> FEATURE:
<223> OTHER INFORMATION: primer

<400> SEQUENCE: 146
gcgtaagctt                                                          10
```